(12) United States Patent
Monaghan et al.

(10) Patent No.: US 6,326,359 B1
(45) Date of Patent: Dec. 4, 2001

(54) ADENOSINE A2A RECEPTOR AGONISTS AS ANTIINFLAMMATORY AGENTS

(75) Inventors: Sandra M. Monaghan; Simon J. Mantell, both of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/419,482

(22) Filed: Oct. 15, 1999

Related U.S. Application Data

(63) Continuation of application No. PCT/IB99/01629, filed on Oct. 5, 1999.

(30) Foreign Application Priority Data

Oct. 16, 1998 (GB) .................................................. 9822702
Nov. 19, 1998 (GB) .................................................. 9825383
Apr. 19, 1999 (GB) .................................................. 9908931

(51) Int. Cl.[7] ........................ A61K 31/70; C07H 19/167; C07H 19/173
(52) U.S. Cl. ................ 514/46; 514/45; 514/47; 536/27.6; 536/27.61; 536/27.62; 536/27.63; 536/27.7
(58) Field of Search .................. 514/45, 46, 47, 514/825, 861, 863, 866, 925; 536/27.6, 27.61, 27.62, 27.63, 27.7

(56) References Cited

U.S. PATENT DOCUMENTS

| | | | |
|---|---|---|---|
| 5,599,671 | * | 2/1997 | Jacobson et al. . |
| 5,859,019 | * | 1/1999 | Liang et al. . |
| 5,877,180 | * | 2/1999 | Linden et al. . |
| 6,180,615 | * | 1/2001 | Zablocki et al. . |
| 6,211,165 | * | 4/2001 | Liang et al. . |
| 6,214,807 | * | 4/2001 | Zablocki et al. . |
| 6,232,297 | * | 5/2001 | Linden et al. . |

FOREIGN PATENT DOCUMENTS

| | | | |
|---|---|---|---|
| 99/34804 | * | 7/1999 | (WO) . |
| 99/67266 | * | 12/1999 | (WO) . |
| 00/77018 | * | 12/2000 | (WO) . |
| 00/78776 | * | 12/2000 | (WO) . |

* cited by examiner

*Primary Examiner*—James O. Wilson
(74) *Attorney, Agent, or Firm*—Peter C. Richardson; Paul H. Ginsburg; Raymond M. Speer

(57) ABSTRACT

The present invention provides compounds of formula (I):

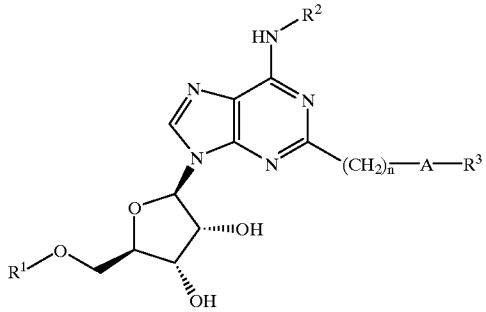

and pharmaceutically acceptable salts and solvates thereof, together with processes for the preparation of, compositions containing, uses of and intermediates used in the preparation of such compounds that have A2a receptor agonist activity.

28 Claims, No Drawings

ADENOSINE A2A RECEPTOR AGONISTS AS ANTIINFLAMMATORY AGENTS

REFERENCE TO COPENDING APPLICATIONS

This application is a continuation of copending prior filed international application designating the U.S. Ser. No. PCT/IB99/01629 filed Oct. 5, 1999, the benefit of the filing date of which is claimed, and which is incorporated herein by reference in its entirety; and corresponds to copending prior filed foreign applications Great Britain Serial No. 9822702.8 filed Oct. 16, 1998; Great Britain Serial No. 9825383.4 filed Nov. 19, 1998; and Great Britain Serial No. 9908931.0 filed Apr. 19, 1999, the benefit of the filing dates of which is claimed, and which are incorporated herein by reference in their entireties.

The present invention relates to certain adenine derivatives that are selective, functional agonists of the human adenosine A2a receptor, to their preparation, and to compositions and uses thereof. The compounds and compositions may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, such as superoxide anion radicals ($O_2^-$), and granule products, such as human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$ and HNE adversely affect pulmonary extracellular matrix. The A2 receptor subtype mediating many of these responses ($O_2^-$ and $LTB_4$/HNE release and cell adhesion) is established as A2a. The A2 subtype (A2a or A2b) mediating the other effects remains to be established.

Selective agonist activity at the A2a receptor is considered to offer greater therapeutic benefit than non-selective adenosine receptor agonists because interaction with other receptor subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over this receptor is also advantageous.

We have now surprisingly found the present adenine derivatives inhibit neutrophil function and are selective agonists of the adenosine A2a receptor.

The present compounds may be used to treat any disease for which an adenosine A2a receptor agonist is indicated. They can be used to treat a disease where leukocyte (e.g. neutrophil, eosinophil, basophil, lymphocyte, macrophage)-induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischemia, peripheral vascular disease, post-ischaemic reperfrision injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastro-intestinal tract or a psychotic disorder, or for wound healing.

Accordingly, in one aspect the present invention provides a compound of formula (I):

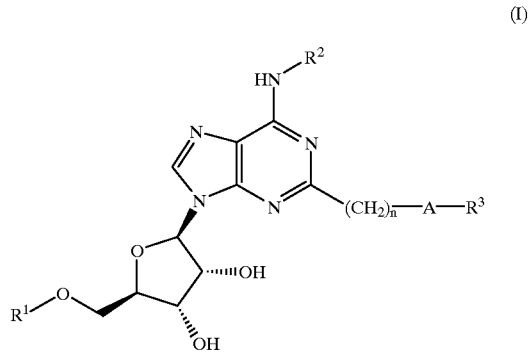

wherein
$R^1$ is alkyl or cyclopropylmethyl;
$R^2$ is phenyl-alkylene or naphthyl-alkylene, said alkylene chain being optionally further substituted by phenyl or naphthyl, each phenyl or naphthyl being optionally substituted by one or more substituents each independently selected from alkyl, alkoxy, halo and cyano;
n is 1 or 2;
A is $NR^a$, $NR^aC(O)$, $NR^aC(O)NR^a$, $NR^aC(O)O$, $OC(O)NR^a$, $C(O)NR^a$, $NR^aSO_2$, $SO_2NR^a$, O, S or $SO_2$;
$R^a$ is H, alkyl or benzyl optionally ring-substituted by one or more substituents each independently selected from alkyl, alkoxy, halo and cyano;
$R^3$ is a group of the formula $—(CH_2)_p—R^P—B$;
p is 0, 1 or 2;
$R^P$ is a bond, alkylene, cycloalkylene, phenylene or naphthylene, said cycloalkylene, phenylene and naphthylene each being optionally substituted by one or more substituents each independently selected from alkyl, alkoxy, halo and alkoxyalkylene;
B is
(i) H $—NR^bR^b$, $R^bR^bN$-alkylene, $—OR^b$, $—COOR^b$, $—OCOR^b$, $—SO_2R^b$, $—CN$, $—SO_2NR^bR^b$, $—NR^bCOR^b$, $—NR^bSO_2R^b$ or $—CONR^bR^b$, in which each $R^b$ is the same or different and is selected from H, alkyl, phenyl and benzyl, provided that,
(a) when B is $—OCOR^b$, $—SO_2R^b$, $—NR^bCOR^b$ or $—NR^bSO_2R^b$, then the terminal $R^b$ is not H, and,
(b) $R^P$ is a bond, p is 0 and B is H only when A is $NR^a$, $NR^aC(O)NR^a$, $OC(O)NR^a$, $C(O)NR^a$, $SO_2NR^a$, O or S,
(ii) an optionally-substituted, fully- or partially-saturated or -unsaturated, mono- or bicyclic, heterocyclic group, which is linked to $R^P$ by a ring carbon atom, or (iii) N-linked azetidinyl, pyrrolidinyl, piperidinyl, piperazinyl or morpholinyl, each optionally substituted by one or more alkyl substituents, with the proviso that —$(CH_2)_p$—$R^p$— is not —$CH_2$—; and where A is $NR^a$, $C(O)NR^a$, $OC(O)NR^a$ or $SO_2NR^a$, $R^a$ and $R^3$ taken together with the nitrogen atom to which they are attached can form an azetidine, pyrrolidine, piperidine or piperazine ring, optionally substituted by one or more alkyl substituents:

and pharmaceutically acceptable salts and solvates thereof.

In a second aspect the present invention provides a compound of the formula (I) wherein $R^1$ is $C_1$–$C_6$ alkyl or cyclopropylmethyl;

$R^2$ is phenyl-($C_1$–$C_6$)-alkylene or naphthyl-($C_1$–$C_6$)-alkylene, said $C_1$–$C_6$ alkylene chain being optionally further substituted by phenyl or naphthyl, each phenyl or naphthyl being optionally substituted by one or more substituents each independently selected from $C_1$–$C_6$ alkyl, $C_1$–$C_6$ alkoxy, halo and cyano;

n is 1 or 2;

A is $NR^a$, $NR^aC(O)$, $NR^aC(O)NR^a$, $NR^aC(O)O$, $OC(O)NR^a$, $C(O)NR^a$, $NR^aSO_2$, $SO_2NR^a$, O, S or $SO_2$;

$R^a$ is H, $C_1$–$C_6$ alkyl or benzyl optionally ring-substituted by one or more substituents each independently selected from $C_1$–$C_6$ alkyl, $C_1$–$C_6$ alkoxy, halo and cyano;

$R^3$ is a group of the formula —$(CH_2)_p$—$R^p$—B;

p is 0, 1 or 2;

$R^p$ is a bond, $C_1$–$C_6$ alkylene, $C_3$–$C_7$ cycloalkylene, phenylene or naphthylene, said $C_3$–$C_7$ cycloalkylene, phenylene and naphthylene each being optionally substituted by one or more substituents each independently selected from $C_1$–$C_6$ alkyl, $C_1$–$C_6$ alkoxy, halo and $C_1$–$C_6$ alkoxy-$C_1$–$C_6$-alkylene;

B is (i) H, —$NR^bR^b$, $R^bR^bN$—$(C_1$–$C_6)$-alkylene, —$OR^b$, —$COOR^b$, —$OCOR^b$, —$SO_2R^b$, —CN, —$SO_2NR^bR^b$, —$NR^bCOR^b$, —$NR^bSO_2R^b$ or —$CONR^bR^b$, in which each $R^b$ is the same or different and is selected from H, $C_1$–$C_6$ alkyl, phenyl and benzyl, provided that, (a) when B is —$OCOR^b$, —$SO_2R^b$, —$NR^bCOR^b$ or —$NR^bSO_2R^b$, then the terminal $R^b$ is not H, and, (b) $R^p$ is a bond, p is 0 and B is H only when A is $NR^a$, $NR^aC(O)NR^a$, $OC(O)NR^a$, $C(O)NR^a$, $SO_2NR^a$, O or S, (ii) an optionally-substituted, fully- or partially-saturated or -unsaturated, mono- or bicyclic, heterocyclic group, which is linked to $R^p$ by a ring carbon atom, or (iii) N-linked azetidinyl, pyrrolidinyl, piperidinyl, piperazinyl or morpholinyl, each optionally substituted by one or more $C_1$–$C_6$ alkyl substituents, with the proviso that —$(CH_2)_p$—$R^p$— is not —$CH_2$—; and where A is $NR^a$, $C(O)NR^a$, $OC(O)NR^a$ or $SO_2NR^a$, $R^a$ and $R^3$ taken together with the nitrogen atom to which they are attached can form an azetidine, pyrrolidine, piperidine or piperazine ring, each optionally substituted by one or more $C_1$–$C_6$ alkyl substituents:

and pharmaceutically acceptable salts and solvates thereof.

In a third aspect the present invention provides a compound of the formula (I) wherein $R^1$ is alkyl or cyclopropylmethyl;

$R^2$ is phenyl-alkylene or naphthyl-alkylene where the alkylene chain may be substituted with methyl, ethyl, phenyl or naphthyl;

n is 1 or 2; and

A is $NR^a$, $NR^aC(O)$, $NR^aC(O)NR^a$, $NR^aC(O)O$, $OC(O)NR^a$, $C(O)NR^a$, $NR^aSO_2$, $SO_2NR^a$, O, S or $SO_2$, in which $R^a$ is H or alkyl;

$R^3$ is a group of the formula —$(CH_2)_p$—$R^p$—B, wherein p is 0, 1 or 2;

$R^p$ is a bond, or is alkylene, optionally alkyl-substituted cycloalkylene, phenylene or naphthylene; and B is (i) H, —$NR^bR^b$, —$OR^b$, —$COOR^b$, —$OCOR^b$, —$SO_2R^b$, —CN, —$SO_2NR^bR^b$, —$NR^bCOR^b$ or —$CONR^bR^b$, in which each $R^b$ is the same or different and is selected from H and alkyl, provided that, (a) when B is —$SO_2R^b$ or —$NR^bCOR^b$, then the terminal $R^b$ is other than H, and, (b) $R^p$ is a bond, p is 0 and B is H only when A is $NR^a$, $NR^aC(O)NR^a$, $C(O)NR^a$, $SO_2NR^a$, O or S, or (ii) B is an optionally-substituted, fully or partially saturated or unsaturated mono- or bicyclic heterocyclic group, each of which is linked through a ring carbon atom;

and pharmaceutically acceptable salts and solvates thereof.

In the above definitions, halo means fluoro, chloro, bromo or iodo. Alkyl, alkoxy and alkylene groups containing the requisite number of carbon atoms can be unbranched- or branched-chain. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl. Examples of cycloalkylene include cyclopropylene, cyclobutylene, cyclopentylene, cyclohexylene and cycloheptylene.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of the formula (I) include the hydrates thereof.

Also included within the present scope of the compounds of the formula (I) are polymorphs thereof.

A compound of the formula (I) may contain one or more additional asymmetric carbon atoms and therefore exist in two or more stereoisomeric forms. The present invention includes the individual stereoisomers of the compounds of the formula (I) together with mixtures thereof.

Separation of diastereoisomers and cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

In the definition of B, said optionally-substituted, fully- or partially-saturated or -unsaturated, mono- or bicyclic, heterocyclic group, which is linked to $R^p$ by a ring carbon atom, preferably has from 4 to 12 ring atoms, preferably from 4 or 5 to 10 ring atoms, each independently selected from C, N, O and S. More preferably, said group has ring atoms selected from 1 to 4 N atoms, 1 or 2 O and 1 or 2 S atoms, with the remaining ring atoms being C atoms. Most preferably, said group has from 1 to 4 ring N atoms, or 1 or 2 ring N atoms and 1 O or 1 S ring atom, or 1 O or 1 S ring atom, with the remaining ring atoms being C atoms.

Examples of fully-unsaturated, that is heteroaryl, groups include imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, benzoxazolyl and quinoxalinyl.

Examples of partially-saturated or -unsaturated heterocyclic groups include 1,2-dihydroisoquinolinyl, 3,4-dihydroisoquinolinyl and 1,2,3,4-tetrahydroisoquinolinyl.

Examples of fully-saturated heterocyclic groups include azetidinyl, pyrrolidinyl, piperidinyl, tetrahydropyranyl, tetrahydrothiopyranyl, 1,1-dioxotetrahydrothiopyranyl, morpholinyl and piperazinyl.

Said heterocyclic groups can be optionally substituted by one or more substituents each independently selected from $R^5$, $-OR^5$, halo, oxo, hydroxy, cyano, $-COR^5$, $-COOH$, $-COOR^5$, $-CONH_2$, $-CONHR^5$, $-CONR^5R^5$, amino, $-NHR^5$, $-NR^5R^5$, $-SO_2R^5$, $-SO_2NH_2$, $-SO_2NHR^5$, $-SO_2NR^5R^5$, $-NHCOR^5$, $-NR^5COR^5$, $-NHSO_2R^5$, $-NR^5SO_2R^5$ and pyridinyl, wherein $R^5$ is $C_1$–$C_6$ alkyl, $C_3$–$C_7$ cycloalkyl, phenyl or naphthyl, each optionally substituted by $C_3$–$C_7$ cycloalkyl, $C_1$–$C_6$ alkoxy, halo, phenyl, naphthyl or benzylamino.

Preferably, $R^1$ is $C_1$–$C_6$ alkyl.

Preferably, $R^1$ is methyl.

Preferably, $R^2$ is phenyl-($C_1$–$C_6$)-alkylene, said $C_1$–$C_6$ alkylene chain being optionally further substituted by phenyl.

Preferably, $R^2$ is 2-phenylethyl, said ethyl chain being optionally further substituted by phenyl.

Preferably, $R^2$ is 2-phenylethyl or 2,2-diphenylethyl.

Preferably, $R^2$ is 2,2-diphenylethyl.

Preferably, A is $NR^a$, $NR^aC(O)$, $NR^aC(O)O$, $C(O)NR^a$, $NR^aSO_2$, $SO_2NR^a$, O, S or $SO_2$.

Preferably, A is $NR^a$ or $NR^aSO_2$.

Preferably, $R^a$ is H, $C_1$–$C_6$ alkyl or benzyl optionally ring-substituted by one or more $C_1$–$C_6$ alkoxy substituents.

Preferably, $R^a$ is H, methyl, 2-methylprop-1-yl or methoxybenzyl.

Preferably, $R^a$ is H, methyl, 2-methylprop-1-yl or 2-methoxybenzyl.

Preferably, $R^3$ is

H, $C_1$–$C_6$ alkyl optionally substituted by $C_3$–$C_7$ cycloalkyl, $C_1$–$C_6$ alkoxy, amino, $-NH(C_1$–$C_6$ alkyl), $-N(C_1$–$C_6$ alkyl)$_2$, $-CONH_2$, $-CONH(C_1$–$C_6$ alkyl), $-CON(C_1$–$C_6$ alkyl)$_2$, phenyl (optionally substituted by halo, $C_1$–$C_6$ alkoxy, $C_1$–$C_6$ alkoxy-($C_1$–$C_6$)-alkylene, amino-($C_1$–$C_6$ -alkylene, cyano or piperidinyl (optionally substituted by $C_1$–$C_6$ alkyl, halo-($C_1$–$C_6$)-alkyl or halo-($C_1$–$C_6$)-alkanoyl)), piperidinyl or tetrahydropyranyl, $C_3$–$C_7$ cycloalkyl optionally substituted by $C_1$–$C_6$ alkyl, $C_1$–$C_6$ alkoxy, benzylamino or $C_1$–$C_6$ alkanesulphonamido, phenyl optionally substituted by halo, $C_1$–$C_6$ alkoxy, $C_1$–$C_6$ alkoxy-($C_1$–$C_6$)-alkylene, amino-($C_1$–$C_6$)-alkylene or piperidinyl (optionally substituted by $C_1$–$C_6$ alkyl, halo-($C_1$–$C_6$)-alkyl or halo-($C_1$–$C_6$)-alkanoyl), or azetidinyl, pyridinyl, piperidinyl, tetrahydrothiopyranyl or 1,2,3,4-tetrahydroisoquinolinyl, each optionally substituted by $C_1$–$C_6$ alkyl, benzhydryl, halo-($C_1$–$C_6$)-alkanoyl, oxo, hydroxy, cyano, $C_1$–$C_6$ alkoxycarbonyl, benzoyl or pyridinyl.

Preferably, $R^3$ is H, methyl, n-propyl, i-propyl, 2-methylprop-1-yl, 2,2-dimethylprop-1-yl, n-butyl, t-butyl, pentan-3-yl, cyclopentyl, cyclohexyl, 4-(isopropyl) cyclohexyl, cyclopropylmethyl, cyclohexylmethyl, 2-methoxyethyl, 2-dimethylaminoethyl, 2-(N,N-dimethylcarbamoyl)ethyl, N,N-(diisopropyl) carbamoylmethyl, 2-(N-t-butylcarbamoyl)ethyl, phenyl, benzyl, 4-chlorobenzyl, 2-methoxybenzyl, 3,4-dimethoxybenzyl, 4-(isopropoxy)benzyl, 2-methoxymethylbenzyl, 4-aminomethylbenzyl, 4-cyanobenzyl, 4,4-dimethylcyclohexyl, 4-methoxycyclohexyl, 4-benzylaminocyclohexyl, 4-methanesulphonamidocyclohexyl, 2-piperidinoethyl, 4-(piperidin-4-yl)phenyl, 4-(1-trifluoroacetylpiperidin-4-yl) phenyl, 1-benzhydrylazetidin-3-yl, 2,6-dimethylpyridin-3-yl, 5-cyanopyridin-2-yl, 1-methylpiperidin-4-yl, 1-(isopropyl)piperidin-4-yl, 1-t-butoxycarbonylpiperidin-4-yl, 1-benzoylpiperidin-4-yl, 1-(2-pyridinyl)piperidin-4-yl, 1,1-dioxotetrahydrothiopyran-4-yl, tetrahydropyran-4-ylmethyl, 5-methyl-1,2,3,4-tetrahydroisoquinolin-8-yl or 5-methyl-2-trifluoroacetyl-1,2,3,4-tetrahydroisoquinolin-8-yl. Preferably, $R^3$ is phenyl, cyclohexyl, 5-methyl-1,2,3,4-tetrahydroisoquinolin-8-yl, 2-methylprop-1-yl, i-propyl, 2-methoxybenzyl or N,N-(diisopropyl)carbamoylmethyl.

Preferably, $-A-R^3$ is amino, isopropylamino, pentan-3-ylamino, 2-methylprop-1-ylamino, di(2-methylprop-1-yl) amino, N-cyclohexyl-N-methylamino, 2-methoxyethylamino, 2-(N,N-dimethylcarbamoyl) ethylamino, N,N-(diisopropyl)carbamoylmethylamino, 2-(N-t-butylcarbamoyl)ethylamino, cyclopentylamino, cyclohexylamino, 4,4dimethylcyclohexylamino, 4-(isopropyl)cyclohexylamino, 4-methoxycyclohexylamino, cis-4-methoxycyclohexylamino, trans-4-methoxycyclohexylamino, 4-benzylaminocyclohexylamino, trans-4-benzylaminocyclohexylamino, 4-methanesulphonamidocyclohexylamino, trans-4-methanesulphonamidocyclohexylamino, cyclopropylmethylamino, cyclohexylmethylamino, benzylamino, 4-chlorobenzylamino, 2-methoxybenzylamino, di(2-methoxybenzyl)amino, 4-(isopropoxy)benzylamino, 3,4-dimethoxybenzylamino, 2-methoxymethylbenzylamino, 4-aminomethylbenzylamino, 4-cyanobenzylamino, 1-benzhydrylazetidin-3-ylamino, 2,6-dimethylpyridin-3-ylamino, 5-cyanopyridin-2-ylamino, 1-methylpiperidin-4-ylamino, 1-(isopropyl)piperidin-4-ylamino, 1-(t-butoxycarbonyl)piperidin-4-ylamino, 1-benzoylpiperidin-4-ylamino, 1-(pyridin-2-yl)piperidin-4-ylamino, 2-piperidinoethylamino, 1,1-dioxotetrahydrothiopyran-4-ylamino, benzamido, phenylacetamido, t-butoxycarbonylamino, methanesulphonamido, n-propylsulphonylamido, i-propylsulphonylamido, n-butylsulphonamido, 2-methylprop-1-ylsulphonamido, 2,2-dimethylprop-1-ylsulphonamido, 2-methoxyethylsulphonamido, phenylsulphonylamido, benzylsulphonamido, 4-(piperidin-4-yl) phenylsulphonylamido, 4-(1-trifluoroacetylpiperidin-4-yl) phenylsulphonylamido, tetrahydropyran-4-ylmethylsulphonamido, 5-methyl-1,2,3,4-tetrahydroisoquinolin-8-ylsulphonylamido, 5-methyl-2-trifluoroacetyl-1,2,3,4-tetrahydroisoquinolin-8-ylsulphonylamido, benzylaminosulphonyl, 2-(N,N-dimethylamino)ethoxy, benzyloxy, 2-piperidinoethoxy, 1-methylpiperidin-4-yloxy, phenylthio, benzylthio or benzylsulphonyl, or is 4-isopropylpiperidinocarbonyl. Preferably, —A—$R^3$ is phenylsulphonamido, cyclohexylamino, 5-methyl-1,2,3,4-tetrahydroisoquinolin-8-ylsulphonylamido, 2-methylprop-1-ylamino, i-propylamino, 2-methoxybenzylamino, N,N-(diisopropyl) carbamoylmethylamino or 2-methyl prop-1-ylsulphonamido.

Preferred examples of compounds of the formula (I) include those of the Examples section hereafter, including any pharmaceutically acceptable salts thereof.

The compounds of the formula (I) can be prepared by conventional routes such as by the procedures described in the general methods presented below or by the specific methods described in the Examples section, or by similar methods thereto. The present invention also encompasses any one or more of these processes for preparing the compounds of formula (I), in addition to any novel intermediates used therein. In the general methods described, $R^1$, $R^2$, $R^3$, A and n are as previously described for a compound of the formula (I) unless otherwise stated.

Compounds of formula (I) may be prepared by reduction of the corresponding compound of formula (IIA):

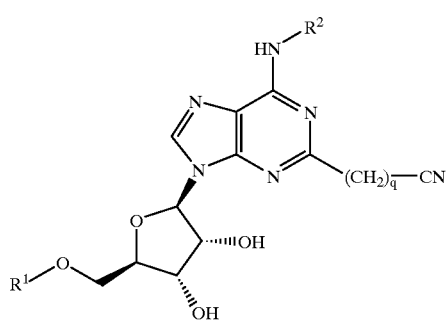

(IIA)

wherein q is n-1, using a reducing agent, such as by catalytic hydrogenation (e.g. with palladium-on-carbon), in a suitable solvent such as an alcohol (e.g. ethanol), optionally in the presence of ammonia, to form the corresponding compound of formula (IA), which is a compound of formula (I) wherein A is —NH and $R^3$ is —H:

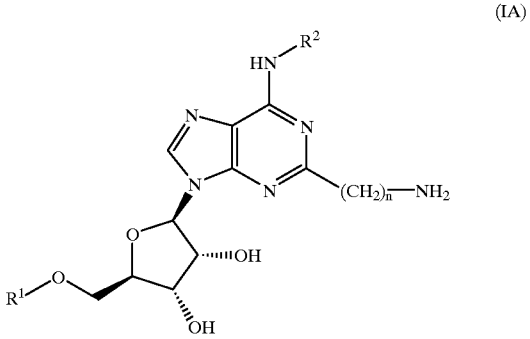

(IA)

and thereafter optionally converting the compound of formula (IA) so prepared to another compound of formula (I) or salt thereof. Conversion of the —$(CH_2)_n NH_2$ group of formula (IA) may take place by methods known to those skilled in the art. A suitable method to prepare compounds of formula (I) wherein A is —NHCO— or —$NHSO_2$ comprises reaction of the corresponding compound of formula (IA) with a compound of formula X—(CO or $SO_2$)—$R^3$ wherein X is a leaving group, such as halo (especially chloro), in the presence of an acid acceptor, such as triethylamine, and in a suitable inert solvent, such as tetrahydrofuran (THF) or dichloromethane. Alternatively, where a compound of the formula (I) wherein A is $NHSO_2$ is required, 2,6-lutidine may be utilised as both the acid acceptor and the solvent. Other standard methods may be used to convert the $(CH_2)_n$—$NH_2$ group to those wherein A is —$NR^a$ (e.g., using a compound of the formula halo-$R^3$, where halo is preferably chloro, or where p is 2, $R^P$ is a bond and B is —$CONR^b R^b$, a suitable acrylamide derivative), —$NR^a CO$, —$NR^a CONR^a$, —$NR^a COO$ (e.g., by reaction with a suitable dicarbonate derivative) and —$NR^a SO_2$.

Alternatively, the corresponding compound of formula (IIA) may be subjected to nitrile hydrolysis, using standard methods, followed by protection of the reactive hydroxy/carboxyl groups to form the corresponding protected ester of formula (IIB):

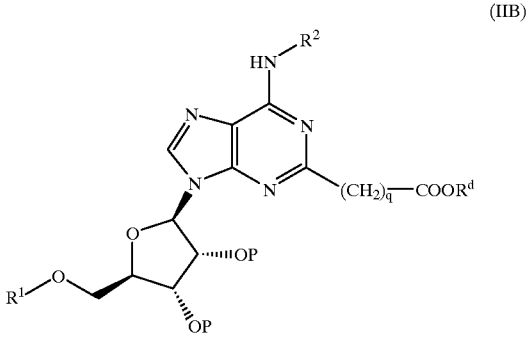

(IIB)

wherein P is a protecting group, preferably tert-butyldimethylsilyl chloride (TBDMS);

$R^d$ is H or alkyl; and q is as defined for formula (IIA).

Thereafter, the compound of formula (IIB) may be reduced using a reducing agent, such as a metal hydride (e.g. lithium borohydride), to form the corresponding compound of formula (IB), which is a protected compound of formula (I) wherein A is —O— and $R^3$ is H:

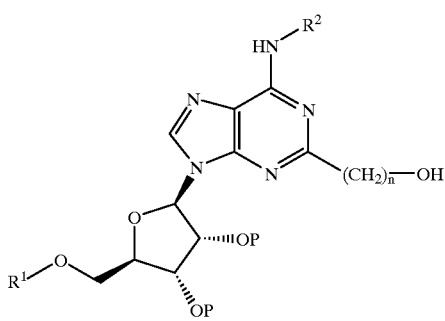

(IB)

wherein P is as hereinbefore defined;

and thereafter, either prior to or after deprotection, optionally converting the compound of formula (IB) so prepared to another compound of formula (I) or salt thereof.

Conversion of the —$(CH_2)_n$OH group of formula (IB) may take place by methods known to those skilled in the art. For example, standard methods may be used to prepare compounds of formula (I) wherein A is —$OCONR^a$ or —$AR^3$ is $OR^3$ wherein $R^3$ is not H from the corresponding compound of formula (IB).

A method to prepare compounds of formula (IIA) where q is 1, comprises reacting the corresponding compound of formula (IB) wherein n is 1 with methanesulphonyl chloride in the presence of triethylamine to produce the corresponding methanesulphonate of formula (XII):

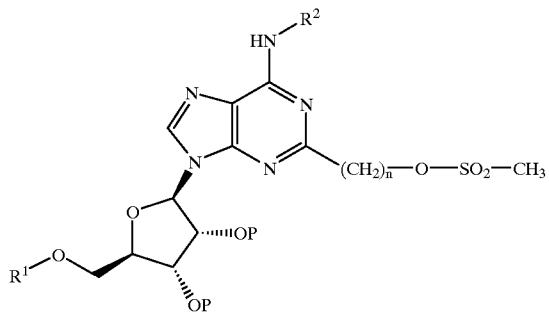

(XII)

wherein n is 1, which can thereafter be reacted with an alkali metal cyanide to produce the compound of formula (IIA) wherein q is 1.

Alternatively, the methanesulphonate of formula (XII) wherein n is 1 or 2 (prepared similarly from a compound of the formula (IB) wherein n is 2) may be reacted with a compound of formula $R^3A^2M$, wherein $A^2$ is O or S and M is a metal, such as sodium, to produce (after deprotection) the corresponding compound of formula (I) wherein A is O or S. The sulphide (i.e. wherein A=S) may then be oxidised (as described below for the oxidation of the intermediate of formula (VI)) to the corresponding sulphone (wherein A=$SO_2$). Alternatively, the unprotected methanesulphonate intermediate may be reacted with a) a metal salt of a suitable sulphonamide to form a compound of the formula (I) wherein A is $NR^aSO_2$, b) a suitable amine, optionally in the presence of a suitable acid acceptor (e.g. triethylamine or diisopropylethylamine), to form a compound of the formula (I) wherein A is $NR^a$, c) a suitable alkoxide to form a compound of the formula (I) wherein A is O, or d) a suitable thiol in the presence of a suitable acid acceptor, e.g. triethylamine, to form a compound of the formula (I) wherein A is S.

A suitable method to prepare compounds of formula (I) wherein A is —NH but $R^3$ is other than H is by reductive amination, which comprises reaction of the corresponding compound of formula (IA) with a suitable aldehyde or ketone precursor for the group $R^3$ in the presence of a suitable reducing agent such as sodium triacetoxyborohydride, optionally in the presence of acetic acid, and in an inert solvent, such as THF or dichloromethane.

The compound of formula (IIA) wherein q is 0 (i.e. n is 1) may be prepared by reaction of the corresponding compound of formula (III):

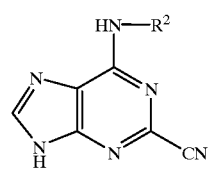

(III)

with a protected ester of formula (IV):

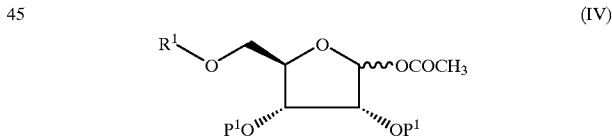

(IV)

wherein $P^1$ is a protecting group, preferably —C(O)Ph.

Suitable de-protection, such as de-esterification, methods include (a) enzymatic de-esterification with an esterase; and (b) chemical de-esterification with a base, such as sodium methoxide, sodium carbonate or ammonia, in a suitable solvent, e.g. methanol or ethanol.

Alterative deprotection methods are well-known to those skilled in the art and include those described in "Protective Groups in Organic Synthesis" by Greene et al (Second Edition, Wiley-lnterscience). In all the following methods, appropriate protection and/or deprotection steps may be taken.

The compound of formula (III) may be prepared from the corresponding protected compound of formula (V):

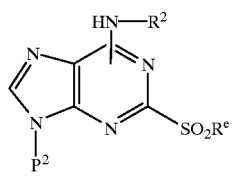

(V)

wherein P² is a protecting group, such as tetrahydropyranyl (THP) and $R^e$ is alkyl with a suitable cyanide derivative, such as an alkali metal cyanide such as KCN, followed by deprotection, such as with a mineral acid, e.g. aqueous HCl, in an alcoholic solvent, e.g. ethanol.

The compound of formula (V) may itself be prepared from the corresponding compound of formula (VI):

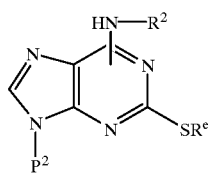

(VI)

wherein P² and $R^e$ are as defined in formula (V), by reaction with an oxidising agent, such as potassium peroxymonosulphate (OXONE (trade mark)).

The compound of formula (VI) may itself be prepared from the corresponding halide of formula (VII):

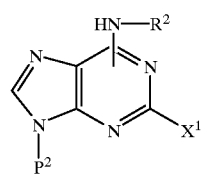

(VII)

wherein P² is as defined in formula (VI), and $X^1$ is halo, preferably chloro, by reaction with a corresponding thioalkoxide, such as sodium thiomethoxide.

The compound of formula (VII) may be prepared from the protected starting material of formula (VIII):

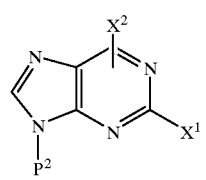

(VIII)

wherein P² and $X^1$ are as previously defined, and $X^2$ is a leaving group, such as halo, preferably chloro)by reaction with an amine of formula $R^2NH_2$. The protected starting material of formula (VIII) may itself be prepared by standard protecting methods from a 2,6-dihalopurine, such as by reaction with 2,3-dihydropyran in the presence of catalytic 4-toluenesulphonic acid.

The compound of formula (IV) may be prepared from the corresponding ether of formula (IX):

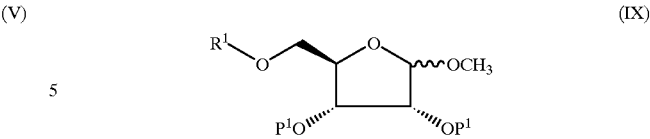

(IX)

wherein $P^1$ is as defined in formula (IV), by standard methods, such as by reaction with acetic acid/acetic anhydride in the presence of sulphuric acid.

The protected ether of formula (IX) may itself be prepared from the compound of formula (X):

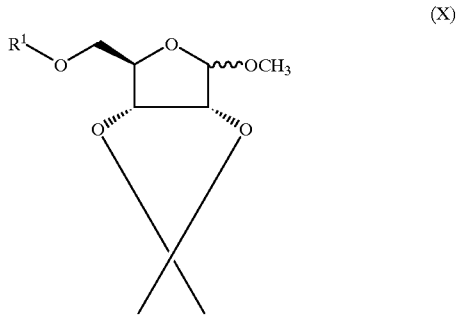

(X)

by reaction with an acid, e.g. aqueous HCl, in a polar solvent, e.g. methanol, followed by protection of the reactive hydroxyl groups, as hereinbefore described, such as by using benzoyl chloride in the presence of an acid acceptor, e.g. pyridine.

The compound of formula (X) may be prepared from the corresponding alcohol of formula (XI):

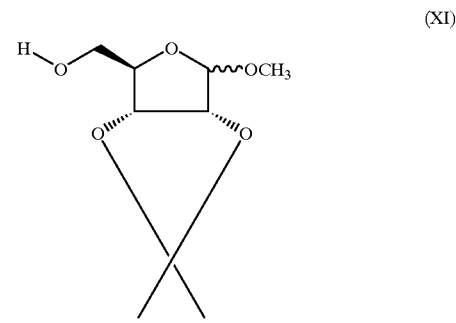

(XI)

by standard methods, such as by the formation of an alkoxide ion by reaction with sodium hydride, and then reaction with a compound of formula $R^1$—$X^3$ wherein $X^3$ is a leaving group such as halo, preferably iodo.

The compound of formula (XI) is obtainable from D-ribose as described in J. Het. Chem., 13, 485 (1966).

All the compounds of the formula (I) may be prepared by deprotection of the corresponding compound (XIII) wherein the 3- and 4-hydroxy groups on the pendant tetrahydrofuran ring are suitably protected, e.g. by t-butyldimethylsilyl groups, under suitable conditions, e.g. using tetra-n-butylammonium fluoride in THF. Other suitable protecting groups and deprotection conditions are well-known to the skilled person such as from the Greene reference mentioned above.

Compounds of the formula (I) wherein A is $C(O)NR^a$ may be prepared from the corresponding carboxylic acid (e.g. a compound of the formula (IIB)) by condensation with a suitable amine of the formula $NHR^3R^a$. Suitable condensation conditions include using N,N-dicyclohexylcarbodiimide, 1H-1,2,3-benzotriazol-1-ol monohydrate, diisopropylethylamine and dichloromethane.

Compounds of the formula (I) can also be interconverted using conventional functional group interconversion techniques.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intra-arterially, intraperitoneally, intrathecally, intraventricularly, intrastemally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.01 to 100 mg/kg, body weight of the subject to be treated, preferably from 0.1 to 100 mg/kg (in single or divided doses).

Thus tablets or capsules of the compound of the formula (I) may contain from 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 to 4000 $\mu$g of a compound of the formula (I) for delivery to the patient. The overall daily dose with an aerosol will be in the range of from 20 $\mu$g to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment, gel, suspension, dusting powder, spray or drug-incorporated dressing (e.g. a tulle dressing, a white soft paraffin or polyethylene glycol impregnated gauze dressing, or a hydrogel, hydrocolloid, alginate or film dressing). The compounds of the formula (I) may also be transdermally administered, for example, by the use of a skin patch.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. They can also be formulated as a hydrogel with cellulose or polyacrylate derivatives or other viscosity modifiers.

It is to be appreciated that all references herein to treatment include curative, palliative and prophylactic treatment.

Thus the invention provides:

(i) a compound of the formula (I) or a pharmaceutically acceptable salt or solvate thereof;

(ii) processes for the preparation of a compound of the formula (I) or a pharmaceutically acceptable salt or solvate thereof;

(iii) a pharmaceutical composition including a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament to treat a disease for which a A2a receptor agonist is indicated;

(vi) the use of a compound of the formula (I) or of a pharmaceutically acceptable salt, solvate or composition thereof, for the manufacture of an anti-inflammatory agent;

(vii) the use of a compound of the formula (I) or of a pharmaceutically acceptable salt, solvate or composition thereof, for the manufacture of a medicament for the treatment of a respiratory disease;

(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) the use of a compound of the formula (I) or of a pharmaceutically acceptable salt, solvate or composition thereof, for the manufacture of a medicament for the treatment of septic shock, male erectile dysfunction, hypertension, stroke, epilepsy, cerebral ischemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastrointestinal tract or a psychotic disorder, or for wound healing;

(x) a method of treatment of a mammal, including a human being, to treat a disease for which a A2a receptor agonist is indicated including treating said mammal with an effective amount of a compound of the formula (I) or with a pharmaceutically acceptable salt, solvate or composition thereof;

(xi) a method of treatment of a mammal, including a human being, to treat an inflammatory disease including treating said mammal with an effective amount of a compound of the formula (I) or with a pharmaceutically acceptable salt, solvate or composition thereof;

(xii) a method of treatment of a mammal, including a human being, to treat a respiratory disease including treating said mammal with an effective amount of a compound of the formula (I) or with a pharmaceutically acceptable salt, solvate or composition thereof;

(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) a method of treatment of a mammal, including a human being, to treat septic shock, male erectile dysfunction, hypertension, stroke, epilepsy, cerebral ischemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastro-intestinal tract or a psychotic disorder, or for wound healing, including treating said mammal with an effective amount of a compound of the formula (I) or with a pharmaceutically acceptable salt, solvate or composition thereof; and (xv) an intermediate of the formula (IIA), (IIB), (IB), (XII) or (XIII).

The following Examples illustrate the preparation of the compounds of the formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded in the thermospray ionisation mode. The following abbreviations have been used for common solvents: EtOAc, ethyl acetate; $CH_2Cl_2$, dichloromethane; $CDCl_3$, deuterochloroform; DMSO, dimethylsulphoxide. The abbreviation TBDMS means tert-butyldimethylsilyl and psi means pounds per square inch. Where thin layer chromatography has used it refers to silica gel TLC using silica gel 60 $F_{254}$ plates, $R_f$ is the distance travelled by a compound divided by the distance travelled by the solvent front on a TLC plate.

EXAMPLES

Example 1

(2R,3R,4S,5R)-2-{2-(Aminomethyl)-6-[(2,2-diphenylethyl)amino]-9H-purin-9-yl}-5-(methoxymethyl)tetrahydro-3,4-furandiol

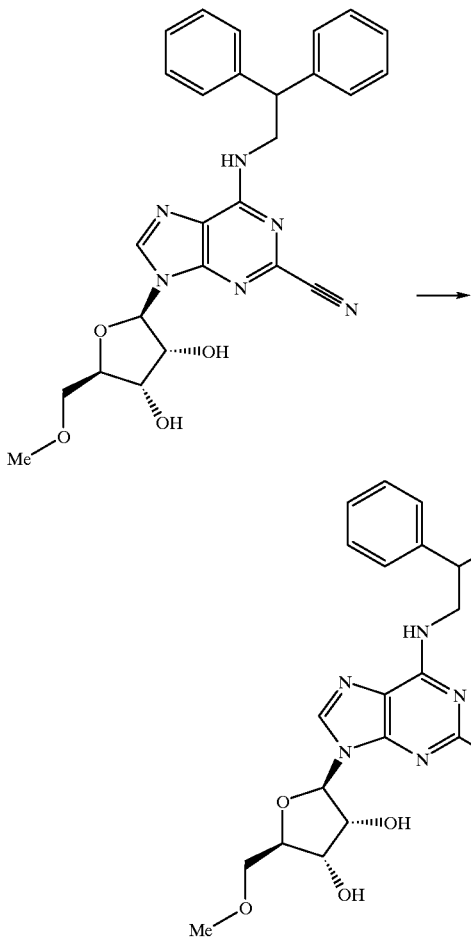

A solution of 9-[(2R,3R,4S,5R)-3,4-dihydroxy-5-(methoxymethyl)tetrahydro-2-furanyl]-6-[(2,2-diphenylethyl)amino]-9H-purine-2-carbonitrile (preparation 12) (2.15 g, 4.42 mmol) in ethanol (120 ml) saturated with ammonia gas was treated with 5% palladium on charcoal (1 g), pressurised to 1034 kPa (150 psi) with hydrogen in a sealed vessel and stirred at room temperature for 24 hr. The mixture was then filtered through Arbocel (trade mark) and the residue washed with ethanol. The solvent was removed under reduced pressure from the filtrate, the residue dissolved in ethanol and the solvent again removed under reduced pressure. A solid precipitated on re-evaporation which was then dissolved in hot ethanol (100 ml) and the solution cooled and filtered. The residue was washed with ethanol then diethyl ether and dried to give the title compound as an off white solid (1.05 g, 48%). The filtrate and washings were combined and the solvent removed under reduced pressure to give a residue which was then triturated with dichloromethane and a few drops of ethanol and filtered to afford a further portion of product (0.45 g). MS: 491 (MH$^+$).

$^1$H-NMR (d$_6$ DMSO) δ=8.20 (1H, s), 7.70–7.60 (1H, br s), 7.40–7.20 (8H, m), 7.20–7.10 (2H, m), 5.95–5.80 (1H, m), 5.40 (1H, d), 5.20 (1H, d), 4.70–4.50 (2H, m), 4.40–4.05 (2H, m), 4.05–3.95 (1H, m), 3.75 (1H, s), 3.60–3.40 (2H, m), 3.30 (3H, s), 1.95–1.80 (2H, br s). Analysis: Found C, 63.16, H, 6.12, N, 16.99; C$_{26}$H$_{30}$N$_6$O$_4$.0.25H$_2$O requires C, 63.08, H, 6.21, N, 16.98%.

Example 2

N-{[9-[(2R,3R,4S,5R)-3,4-Dihydroxy-5-(methoxymethyl)tetrahydro-2-furanyl]-6-[(2,2-diphenylethyl)amino]-9H-purin-2-yl]methyl}-2-phenylacetamide

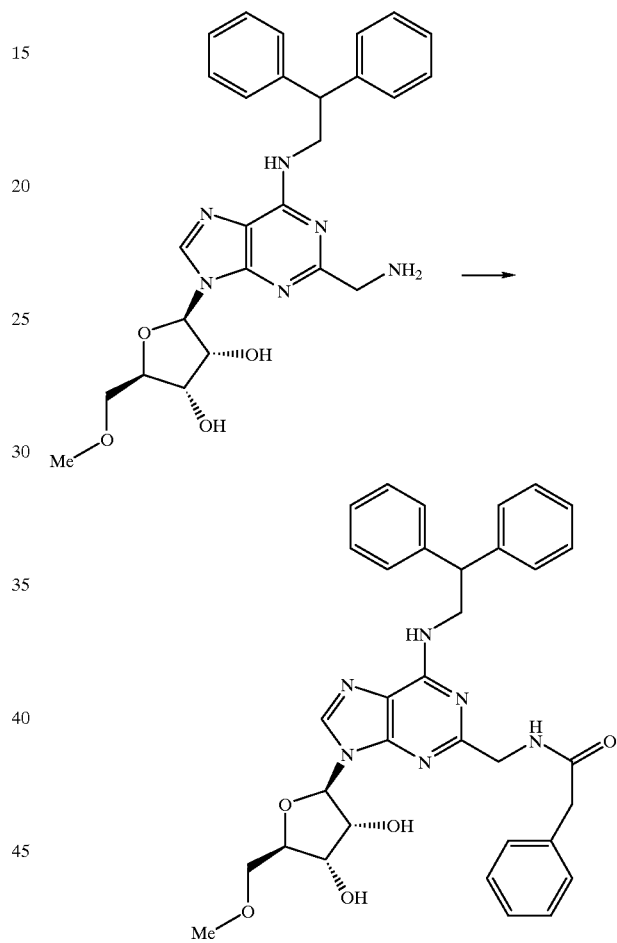

A stirred solution of (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (220 mg, 0.45 mmol) in dichloromethane (10 ml) was treated with triethylamine (0.38 ml, 2.70 mmol) and phenylacetylchloride (280 mg, 1.80 mmol) at 0° C. and the resultant mixture stirred for 15 min. The mixture was then stirred at room temperature for 72 hr. The solvent was removed under reduced pressure and methanol (20 ml), saturated with ammonia gas, added. The resultant mixture was stirred at room temperature for 2 hr, treated with 2 molar aqueous sodium hydroxide (10 ml) and then left standing at room temperature for 24 hr. The methanol was removed under reduced pressure and the aqueous layer extracted with dichloromethane (×3). The combined organic layers were washed with water (×2), dried with anhydrous magnesium sulfate, filtered and the solvent removed under reduced pressure. The residue was dissolved in 1,4-dioxan (6 ml), 0.88 aqueous ammonia solution (8 ml) added and the mixture stirred at room temperature for 10 days. The 1,4-dioxan was removed under reduced pressure and the aqueous layer extracted with dichloromethane (×3).

The combined organic extracts were dried with anhydrous magnesium sulfate, filtered and the solvent removed under reduced pressure. The residue was purified by column chromatography on silica gel eluting with a solvent system of dichloromethane:methanol (97.5:2.5), to give the product which was azeotroped with dichloromethane to afford the title compound as a foam (115 mg). MS: 631 (MNa$^+$).

$^1$H-NMR (d$_6$ DMSO) δ=8.40–8.22 (1H, m), 8.22–8.10 (1H, m), 7.78–7.60 (1H, m), 7.40–7.0 (14H, m), 6.00–5.80 (1H, m), 5.50–5.40 (1H, m), 5.30–5.20 (1H, m), 4.70–4.42 (2H, m), 4.42–4.22 (2H, m), 4.22–3.90 (4H, m), 3.70–3.40 (4H, m), 3.40–3.10 (3H, m). Analysis: Found C, 65.06, H, 5.79, N, 13.29; C$_{34}$H$_{36}$N$_6$O$_5$.0.17CH$_2$Cl$_2$.0.5H$_2$O requires C, 64.96, H, 5.96, N, 13.30%.

mg, 0.22 mmol) in dry tetrahydrofuran (20 ml) was treated with triethylamine (0.1 ml, 0.72 mmol) and the mixture heated gently until all components had dissolved. The solution was then cooled to room temperature, treated with a solution of benzoyl chloride (28 mg, 0.20 mmol) in dry tetrahydrofuran (2 ml) and the mixture stirred for 1.5 hr. The solvent was removed under reduced pressure and the residue purified by column chromatography on silica gel eluting with a solvent system of dichloromethane:methanol (95:5), to give the product which was then triturated with a mixture of diethyl ether and pentane, filtered off and dried to afford the title compound as a solid (80 mg). MS: 595 (MH$^+$).

$^1$H-NMR (CDCl$_3$) δ=7.95 (1H, s), 7.80 (2H, d), 7.60–7.50 (1H, br s), 7.45 (1H, m), 7.40–7.20 (12H, m), 5.95 (1H, d), 5.95–5.80 (1H, br s), 5.80–5.60 (1H, br s), 4.70 (2H, d), 4.55 (1H, t), 4.50–4.20 (4H, m), 3.70–3.50 (2H, m), 3.40–3.25 (3H, m). Analysis: Found C, 66.06, H, 5.75, N, 13.97; C$_{33}$H$_{34}$N$_6$O$_5$.0.25H$_2$O requires C, 66.15, H, 5.80, N, 14.03%.

Example 3

N-{[9-[(2R,3R,4S,5R)-3,4-Dihydroxy-5-(methoxymethyl)tetrahydro-2-furanyl]-6-[(2,2-diphenylethyl)amino]-9H-purin-2-yl]methyl}benzamide

Example 4

N-{[9-[(2R,3R,4S,5R)-3,4-Dihydroxy-5-(methoxymethyl)tetrahydro-2-furanyl]-6-[(2,2-diphenylethyl)amino]-9H-purin-2-yl]methyl}benzenesulfonamide

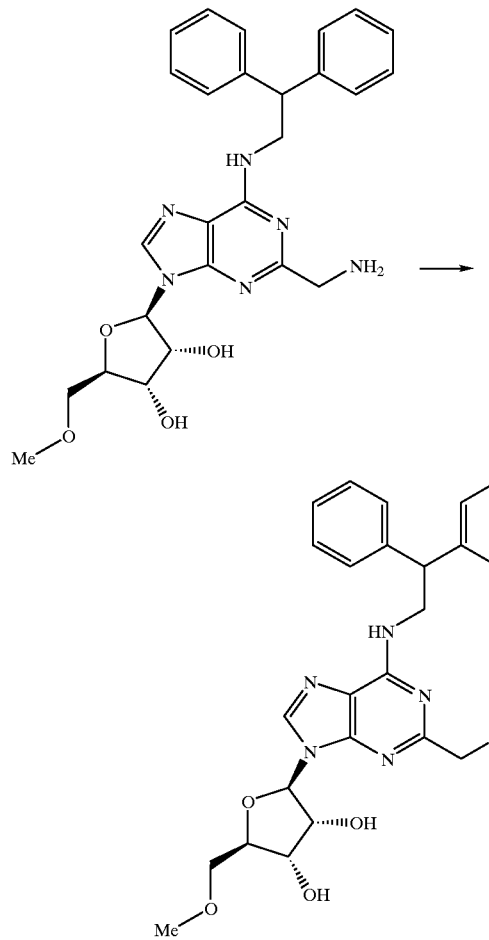

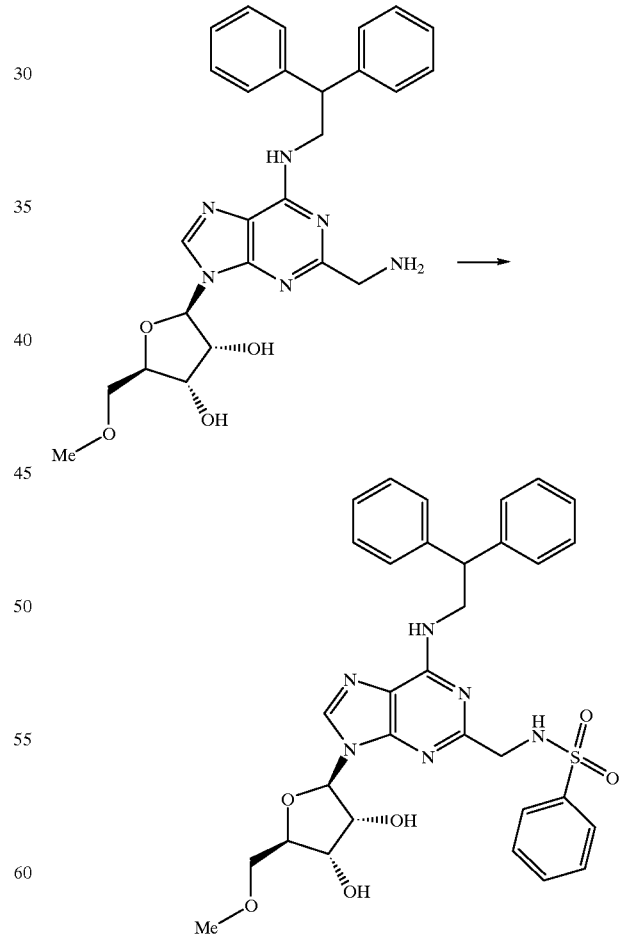

A stirred solution of (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (110

The title compound was prepared by a similar method to example 3 from (2R,3R,4S,5R)-2-{2-(aminomethyl)-6-[(2,2-diphenylethyl)amino]-9H-purin-9-yl}-5-

(methoxymethyl)-tetrahydro-3,4-furandiol (example 1) (110 mg, 0.22 mmol), benzenesulfonyl chloride (36 mg, 0.20 mmol) and triethylamine (0.1 ml, 0.72 mmol) to afford the title compound as a solid (100 mg). MS: 631 (MH+).

$^1$H-NMR (CDCl$_3$) δ=7.90 (1H, s), 7.85 (2H, d), 7.45 (1H, m), 7.40–7.20 (12H, m), 5.90 (1H, d), 5.80–5.70 (2H, m), 5.95–5.85 (1H, br s), 4.50 (2H, m), 4.40–4.10 (6H, m), 3.65–3.55 (2H, m), 3.30 (3H, s), 3.00 (1H, s). Analysis: Found C, 60.46, H, 5.44, N, 13.25; C$_{32}$H$_{34}$N$_6$O$_6$S.0.25H$_2$O requires C, 60.51, H, 5.47, N, 13.23%.

Example 5

(2R,3R,4S,5R)-2-[2-[(Benzylamino)methyl]-6-[(2,2-diphenylethyl)amino]-9H-purin-9-yl]-5-(methoxymethyl)tetrahydro-3,4-furandiol under reduced pressure. The residue was purified by column chromatography on silica gel eluting with a solvent system of dichloromethane:methanol (92:8) to afford the title compound as a solid (67 mg). MS: 581 (MH+).

$^1$H-NMR (CDCl$_3$) δ=7.95 (1H, s), 7.40–7.20 (15H, m), 6.90 (1H, d), 5.90–5.70 (1H, br s), 4.40–4.20 (6H, m), 4.00–3.80 (4H, m), 3.65–3.55 (2H, m), 3.35 (3H, s). Analysis: Found C, 67.43, H, 6.29, N, 14.29; C$_{33}$H$_{36}$N$_6$O$_4$.0.5H$_2$O requires C, 67.22, H, 6.32, N, 14.25%.

Example 6

(2R,3R,4S,5R)-2-[2-[(Cyclohexylamino)methyl]-6-[(2,2-diphenylethyl)amino]-9H-purin-9-yl]-5-(methoxymethyl)tetrahydro-3,4-furandiol

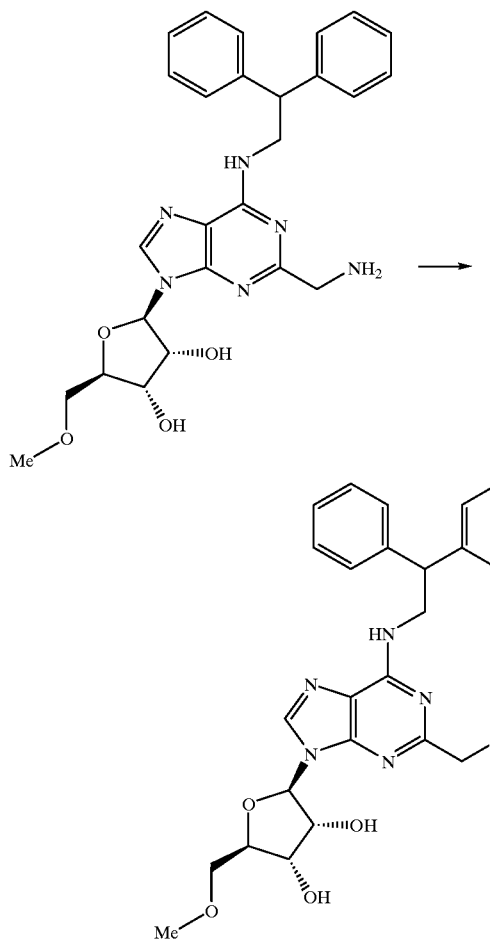
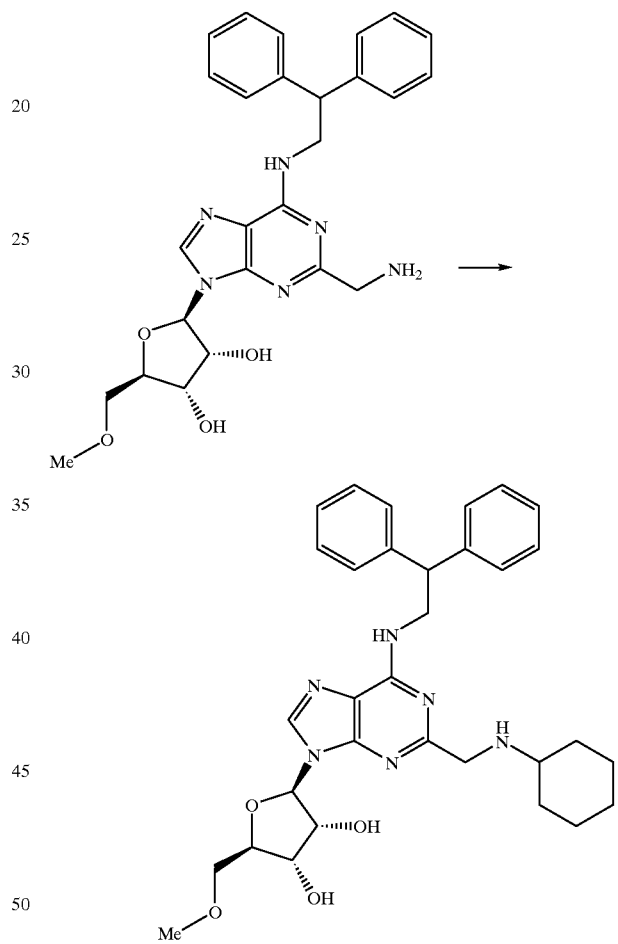

(2R,3R,4S,5R)-2-{2-(Aminomethyl)-6-[(2,2-diphenylethyl)amino]-9H-purin-9-yl}-5-(methoxymethyl) tetrahydro-3,4-furandiol (example 1) (110 mg, 0.22 mmol) was dissolved (using gentle heating) in dry tetrahydrofuran (15 ml). The stirred solution was then cooled to room temperature and treated with a solution of benzaldehyde (21 mg, 0.20 mmol) in dry tetrahydrofuran (2 ml) followed by addition of sodium triacetoxyborohydride (70 mg, 0.33 mmol). The resultant mixture was stirred at room temperature for 24 hr, diluted with ethyl acetate and then washed sequentially with saturated aqueous sodium hydrogen carbonate and brine. The organic solution was then dried with anhydrous magnesium sulfate and the solvent removed (2R,3R,4S,5R)-2-{2-(Aminomethyl)-6-[(2,2-diphenylethyl)amino]-9H-purin-9-yl}-5-(methoxymethyl) tetrahydro-3,4-furandiol (example 1) (110 mg, 0.22 mmol) was dissolved (using gentle heating) in dry tetrahydrofuran (20 ml) and the stirred solution treated with a solution of cyclohexanone (22 mg, 0.22 mmol) in dry tetrahydrofuran (2 ml) followed by addition of sodium triacetoxyborohydride (70 mg, 0.33 mmol) and a solution of acetic acid (0.14 ml, 0.25 mmol) in dry tetrahydrofuran (2 ml). The mixture was then stirred at room temperature for 24 hr. The reaction mixture was diluted with diethyl ether, washed with saturated aqueous sodium hydrogen carbonate, brine, dried with anhydrous magnesium sulfate and the solvent removed under reduced pressure. The residue was purified by column chromatography on silica gel eluting with a gradient system of dichloromethane:methanol:ammonia (95:5:0.5) changing to dichloromethane:methanol:ammonia (90:10:1) to afford the title compound as a solid (80 mg). MS: 573 (MH$^+$).

$^1$H-NMR (CDCl$_3$) δ=7.90 (1H, s), 7.40–7.20 (10H, m), 5.90 (1H, d), 5.85–5.70 (1H, br s), 4.40–4.35 (4H, m), 4.35–4.20 (2H, m), 3.95 (2H, s), 3.65–3.55 (2H, m), 3.35 (3H, s), 2.60–2.45 (1H, m), 2.00–1.95 (2H, m), 1.80–1.70 (2H, m), 1.70–1.60 (1H, m), 1.30–1.10 (5H, m). Analysis: Found C, 66.14, H, 7.08, N, 14.45; C$_{32}$H$_{40}$N$_6$O$_4$.0.5H$_2$O requires C, 66.07, H, 7.10, N, 14.45%.

Example 7

(2R,3R,4S,5R)-2-[2-{[(Cyclohexylmethyl)amino]methyl}-6-[(2,2-diphenylethyl)amino]-9H-purin-9-yl]-5-(methoxymethyl)tetrahydro-3,4-furandiol

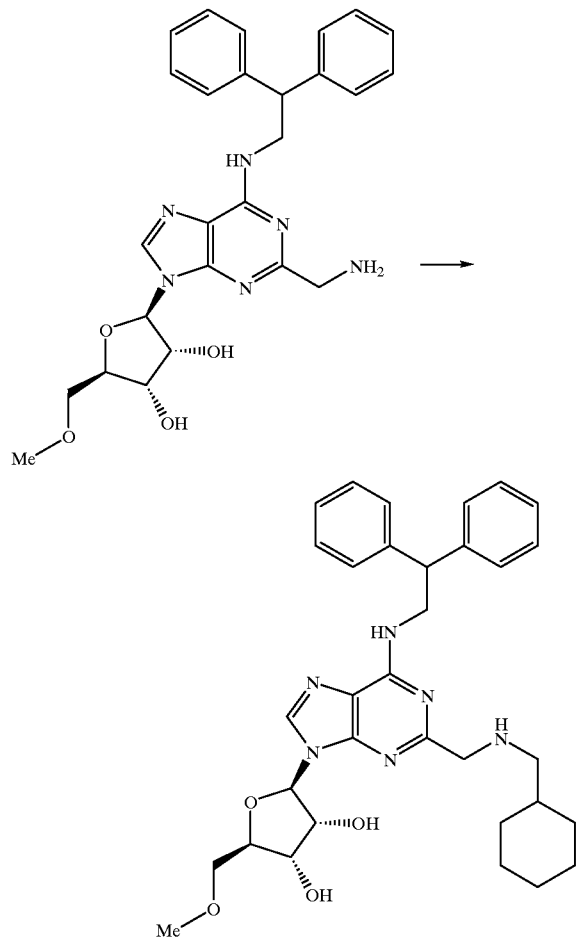

The title compound was prepared by a similar method to example 5 from (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (110 mg, 0.22 mmol), cyclohexanecarboxaldehyde (22 mg, 0.20 mmol) and sodium tnacetoxyborohydnde (70 mg, 0.33 mmol) to afford the title compound as a solid (55 mg). MS: 587 (MH$^+$).

$^1$H-NMR (CDCl$_3$) δ=8.00 (1H, s), 7.40–7.20 (10H, m), 6.00 (1H, d), 5.90–5.70 (1H, brs), 4.50–4.40 (1H, m), 4.40–4.20 (5H, m), 4.10–3.90 (2H, m), 3.75–3.55 (2H, m), 3.35 (3H, s), 2.70–2.55 (2H, m), 1.90–1.75 (2H, m), 1.75–1.55 (4H, m), 1.40–1.05 (4H, m), 1.05–0.80 (2H, m). Analysis: Found C, 65.40, H, 7.18, N, 13.62; C$_{33}$H$_{42}$N$_6$O$_4$.H$_2$O requires C, 65.54, H, 7.33, N, 13.90%.

Example 8

(2R,3R,4S,5R)-2-[2-[(Cyclopentylamino)methyl]-6-[(2,2-diphenylethyl)amino]-9H-purin-9-yl]-5-(methoxymethyl)tetrahydro-3,4-furandiol

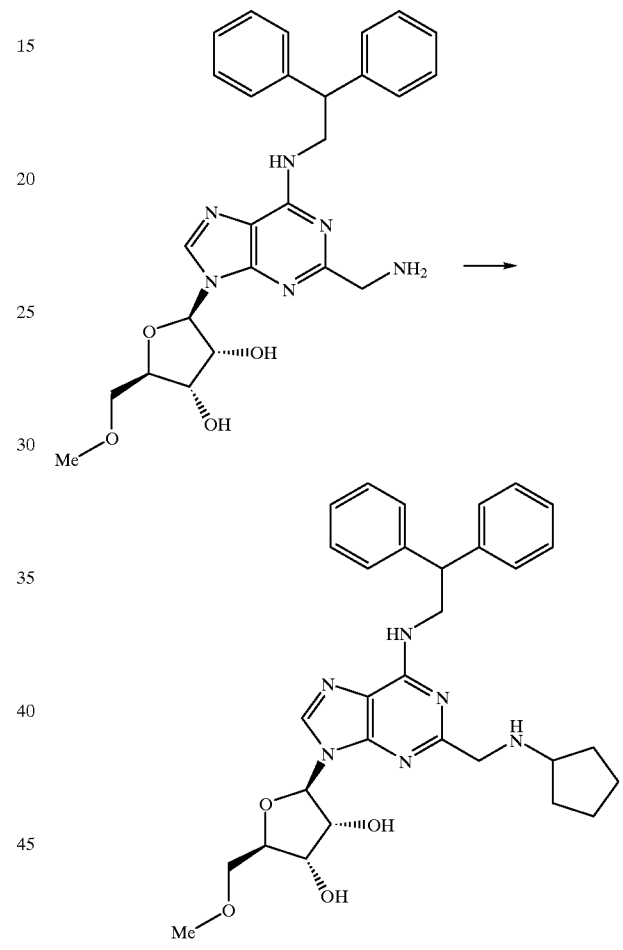

The title compound was prepared by a similar method to example 6 from (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (110 mg, 0.22 mmol), cyclopentanone (18 mg, 0.21 mmol), sodium triacetoxyborohydride (70 mg, 0.33 mmol) and acetic acid (0.14 ml, 0.25 mmol) to afford the title compound as a solid (48 mg). MS: 559 (MH$^+$).

$^1$H-NMR (CDCl$_3$) δ=8.00 (1H, s), 7.40–7.20 (10H, m), 6.00 (1H, d), 5.85–5.70 (1H, br s), 4.50–4.40 (1H, m), 4.40–4.20 (5H, m), 4.20–3.95 (2H, m), 3.75–3.55 (2H, m), 3.45–3.40 (1H, br s), 3.35 (3H, s), 2.00–1.90 (2H, m), 1.90–1.65 (4H, m), 1.65–1.45 (2H, m), 1.25 (1H, s).

Example 9

N-{[9-[(2R,3R,4S,5R)-3,4-Dihydroxy-5-(methoxymethyl)tetrahydro-2-furanyl]-6-[(2,2-diphenylethyl)amino]-9H-purin-2-yl]methyl}-1-propanesulfonamide

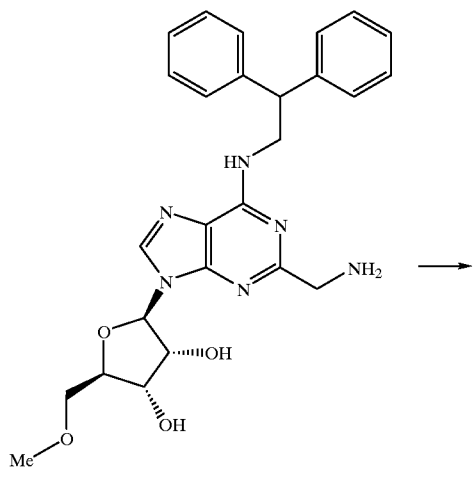

The title compound was prepared by a similar method to example 3 from (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (110 mg, 0.22 mmol), 1-propanesulphonyl chloride (28 mg, 0.19 mmol) and triethylamine (0.1 ml, 0.72 mmol). The residue was purified by column chromatography on silica gel eluting with a gradient system of dichloromethane:methanol (98:2) gradually changing to dichloromethane:methanol (95:5) to afford the title compound as a solid (50 mg). MS: 597 (MH$^+$).

$^1$H-NMR (CDCl$_3$) δ=7.95 (1H, s), 7.40–7.20 (10H, m), 5.95 (1H, d), 5.90–5.80 (1H, br s), 5.50–5.40 (1H, m), 5.00–4.85 (1H, br s), 4.55 (2H, m), 4.40–4.20 (6H, m), 3.70–3.55 (2H, m), 3.35 (3H, s), 3.20–3.10 (1H, br s), 3.00 (2H, t), 1.95–1.80 (2H, m), 1.00 (3H, t).

Example 10

(2R,3R,4S,5R)-2-{6-[(2,2-Diphenylethyl)amino]-2-[(isopropylamino)methyl]-9H-purin-9-yl}-5-(methoxymethyl)tetrahydro-3,4-furandiol

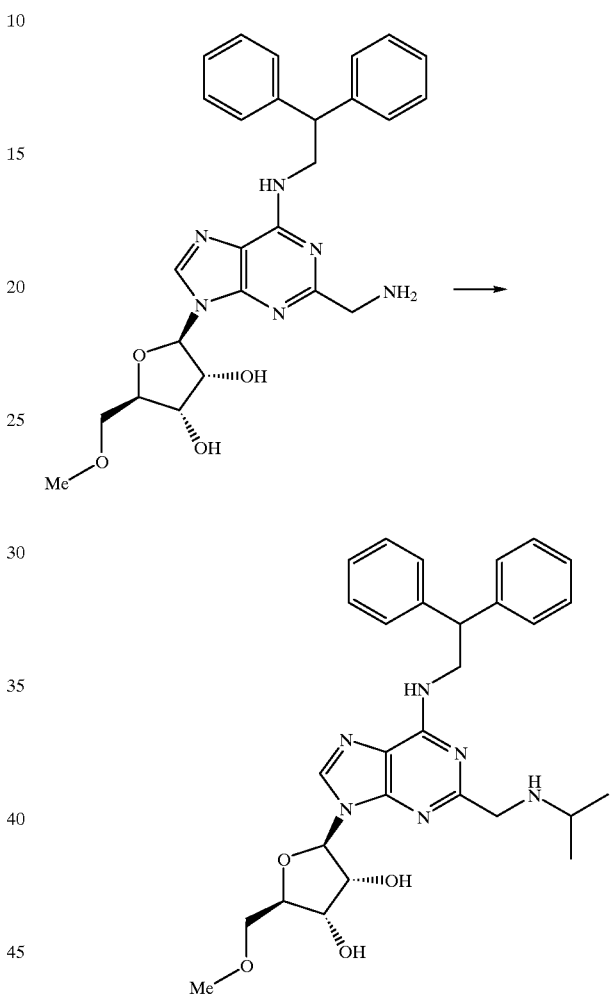

The title compound was prepared by a similar method to example 6 from (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (100 mg, 0.20 mmol), acetone (12 mg, 0.21 mmol), sodium triacetoxyborohydride (70 mg, 0.33 mmol) and acetic acid (0.14 ml, 0.25 mmol) to afford the title compound (63 mg). MS: 533 (MH$^+$).

$^1$H-NMR (CDCl$_3$) δ=7.95 (1H, s), 7.35–7.20 (10H, m), 5.95 (1H, d), 5.90–5.70 (1H, br s), 4.40–4.30 (4H, m), 4.30–4.20 (2H, m), 3.90 (2H, s), 3.65–3.55 (2H, m), 3.30 (3H, s), 2.95–2.85 (1H, m), 1.20–1.10 (6H, m).

Example 11

(2R,3R,4S,5R)-2-{2-(2-Aminoethyl)-6-[(2,2-diphenylethyl)amino]-9H-purin-9-yl}-5-(methoxymethyl)tetrahydro-3,4-furandiol

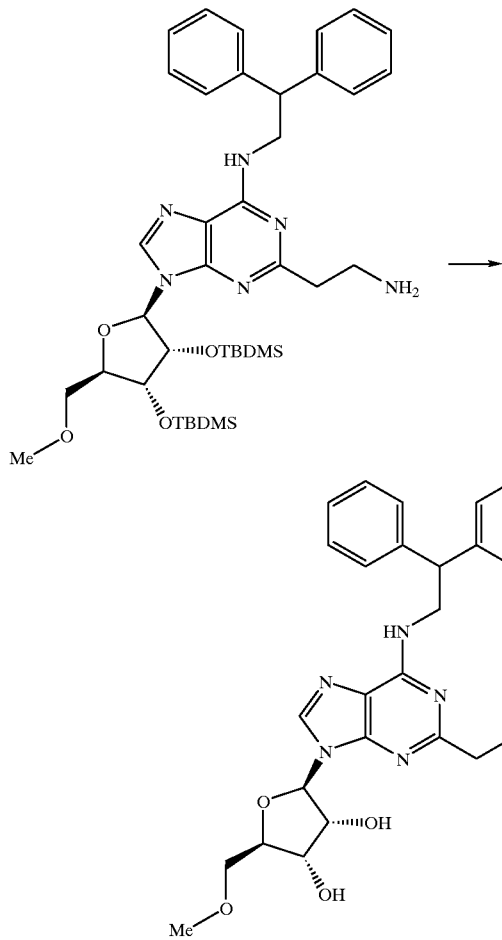

N-{2-(2-Aminoethyl)-9-[(2R,3R,4R,5R)-3,4-bis{[tert-butyl(dimethyl)silyl]oxy}-5-(methoxymethyl)tetrahydro-2-furanyl]-9H-purin-6-yl}-N-(2,2-diphenylethyl)amine (1.07 g, 1.46 mmol) (preparation 18) was dissolved in dry tetrahydrofuran (4 ml), a 1M solution of tetra-n-butylammonium fluoride in tetrahydrofuran (6 ml, 6 mmol) added and the mixture stirred at room temperature for 2.5 hr. The solvent was removed under reduced pressure and the residue dissolved in dichloromethane. The solvent was again removed under reduced pressure and the residue purified by column chromatography on silica gel eluting with a solvent system of dichloromethane:methanol:ammonia (90:10:1), to give the product as a foam (760 mg). MS: 505 (MH$^+$).

$^1$H-NMR (CDCl$_3$) δ=7.95 (1H, s), 7.20–7.36(10H, m), 5.94 (1H, d), 5.75 (1H, br s), 4.24–4.44 (5H, m), 3.56–3.68 (2H, m), 3.34 (3H, s), 3.19 (2H, brt), 2.95 (2H, br s).

Example 12

(2R,3R,4S,5R)-2-{2-[2-(Cyclohexylamino)ethyl]-6-[(2,2-diphenyl ethyl)amino]-9H-purin-9-yl}-5-(methoxymethyl)tetrahydro-3,4-furandiol

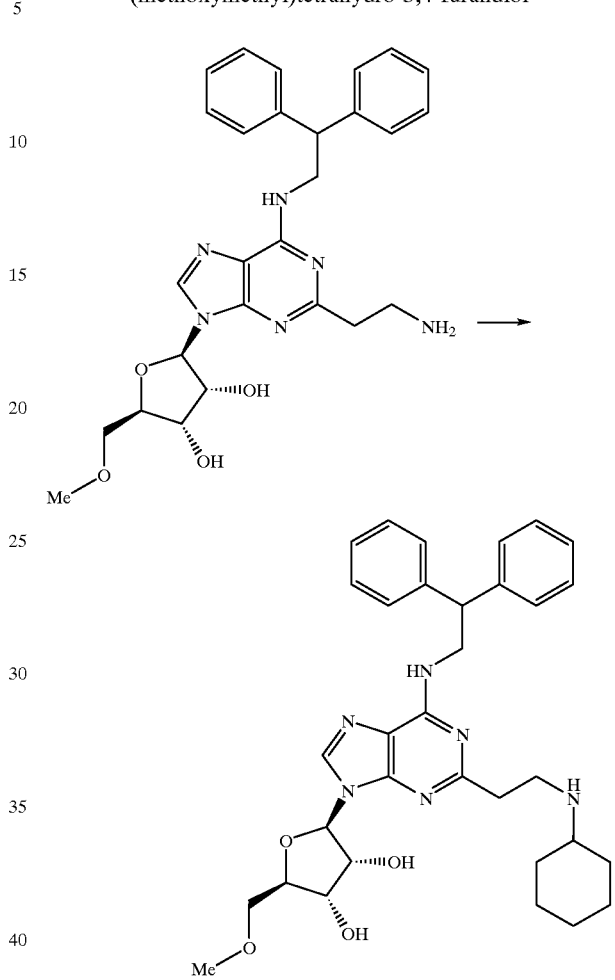

Sodium triacetoxyborohydride (75 mg, 0.35 mmol) and acetic acid (16 mg, 0.27 mmol) were added sequentially to a stirred solution of (2R,3R,4S,5R)-2-{2-(2-aminoethyl)-6-[(2,2-diphenylethyl)amino]-9H-purin-9-yl}-5-(methoxymethyl)tetrahydro-3,4-furandiol (example 11) (120 mg, 0.24 mmol) and cyclohexanone (23 mg, 0.235 mmol) in dichloromethane (15 ml). The resulting mixture was stirred at room temperature for 24 hr, diluted with dichloromethane and washed sequentially with a saturated aqueous solution of sodium hydrogen carbonate, water and brine. The organic phase was dried with anhydrous sodium sulfate, the solvent removed under reduced pressure and the residue purified by column chromatography on silica gel eluting with a gradient system of dichloromethane:methanol:ammonia (95:5:0.5) changing to dichloromethane:methanol:ammonia (90:10:1) to afford the title compound as a solid (78 mg). MS: 587 (MH$^+$).

$^1$H-NMR (CDCl$_3$) δ=7.92 (1H, s), 7.20–7.36 (10H, m), 5.91 (1H, d), 5.69 (1H, br s), 4.20–4.46 (6H, m), 3.57–3.68 (2H, m), 3.37 (3H, s), 3.10 (2H, brt), 2.99 (2H, br s), 2.51 (1H, m), 1.90 (2H, br s), 1.57–1.75 (3H, m), 1.05–1.29 (5H, m). Analysis: Found C, 66.18, H, 7.25, N, 13.89; C$_{33}$H$_{42}$N$_6$O$_4$.0.75H$_2$O requires C, 66.03, H, 7.30, N, 14.00%.

Example 13

N-(2-{9-[(2R,3R,4S,5R)-3,4-Dihydroxy-5-(methoxymethyl)tetrahydro-2-furanyl]-6-[(2,2-diphenylethyl)amino]-9H-purin-2-yl}ethyl)benzenesulfonamide

Example 14

(2R,3R,4S,5R)-2-{6-[(2,2-diphenylethyl)amino]-2-[2-(isopropylamino)ethyl]-9H-purin-9-yl}-5-(methoxymethyl)tetrahydro-3,4-furandiol

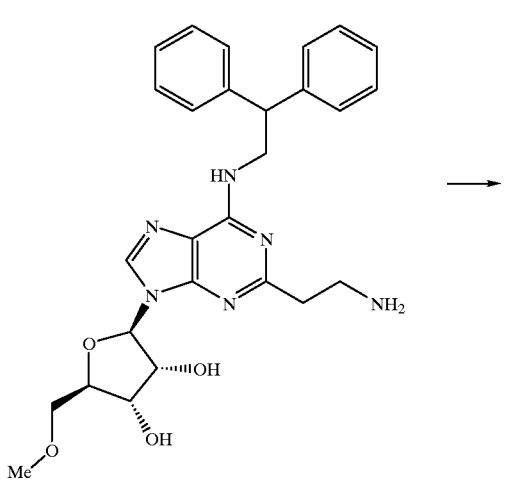

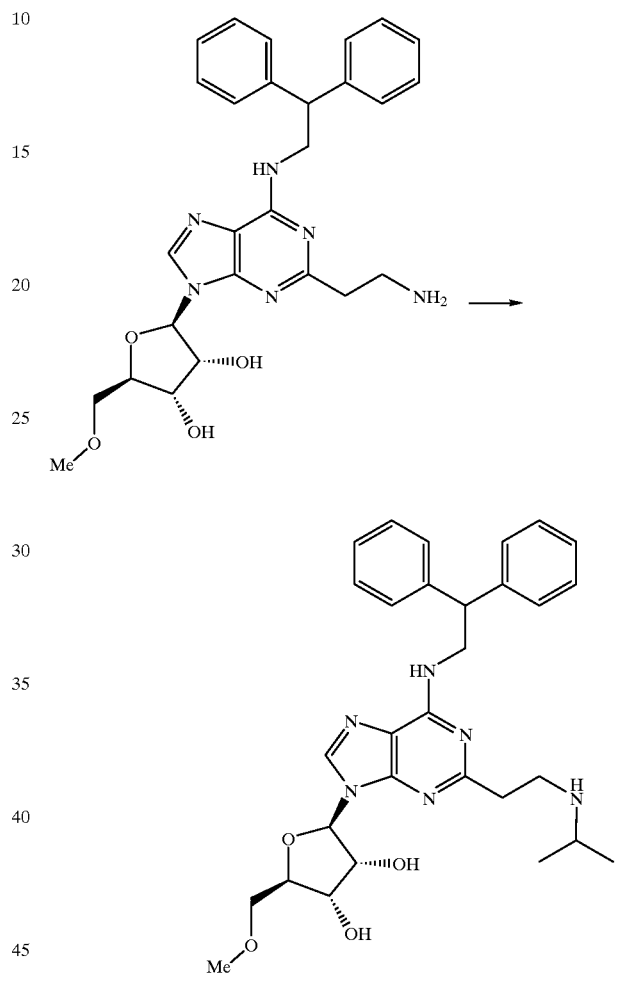

The title compound was prepared by a similar method to example 3 using (2R,3R,4S,5R)-2-{2-(2-aminoethyl)-6-[(2,2-diphenylethyl)amino]-9H-purin-9-yl}-5-(methoxymethyl)tetrahydro-3,4-furandiol (example 11) (200 mg, 0.40 mmol), benzenesulphonyl chloride (70 mg, 0.40 mmol) and triethylamine (0.15 ml, 1.08 mmol) to afford the title compound as a solid (145 mg). MS: 645 (MH$^+$).

$^1$H-NMR (CDCl$_3$) δ=7.91 (1H, s), 7.80 (2H, d), 7.20–7.55 (13H, m), 6.40 (1H, br t), 5.90 (1H, d), 5.74 (1H, br s), 4.20–4.50 (5H, m), 3.58–3.70 (2H, m), 3.32–3.45 (5H, m), 3.14 (1H, d), 2.92 (2H, br t). Analysis: Found C, 60.75, H, 5.64, N, 12.91; C$_{33}$H$_{36}$N$_6$O$_6$S.0.25H$_2$O requires C, 61.05, H, 5.67, N, 12.94%.

The title compound was prepared by a similar method to example 12 using (2R,3R,4S,5R)-2-{2-(2-aminoethyl)-6-[(2,2-diphenylethyl)amino]-9H-purin-9-yl}-5-(methoxymethyl)tetrahydro-3,4-furandiol (example 11) (120 mg, 0.24 mmol), acetone (14 mg, 0.24 mmol), acetic acid (16 mg, 0.27 mmol) and sodium triacetoxyborohydride (75 mg, 0.35 mmol) to afford the title compound as a solid (55 mg). MS: 547 (MH$^+$).

$^1$H-NMR (CDCl$_3$) δ=7.90(1H, s), 7.20–7.39 (10H, m), 5.90 (1H, d), 5.72 (1H, br s), 4.20–4.48 (5H, m), 3.55–3.66 (2H, m), 3.32 (3H, s), 2.80–3.10 (5H, m), 1.00–1.05 (6H, m). Analysis: Found C, 64.66, H, 7.05, N, 15.00; C$_{30}$H$_{38}$N$_6$O$_4$.0.5H$_2$O requires C, 64.85, H, 7.07, N, 15.12%.

Example 15

N-({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)-2-methyl-1-propanesulfonamide

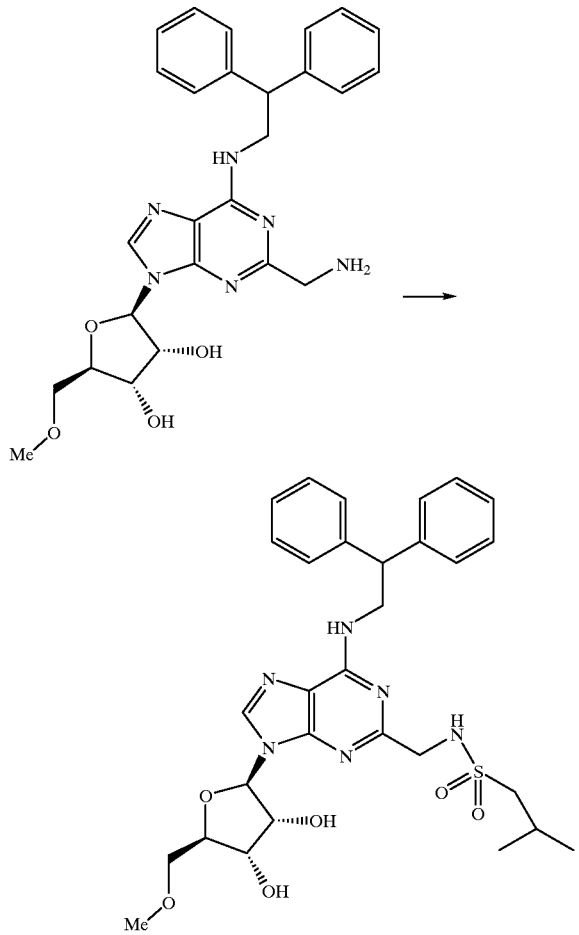

Example 16

(2R,3R,4S,5R)-2-(6-[(2,2-Diphenylethyl)amino]-2-{[(1-isopropyl-4-piperidinyl)amino]methyl}- 9H-purin-9-yl)-5-(methoxymethyl)tetrahydro-3,4-furandiol

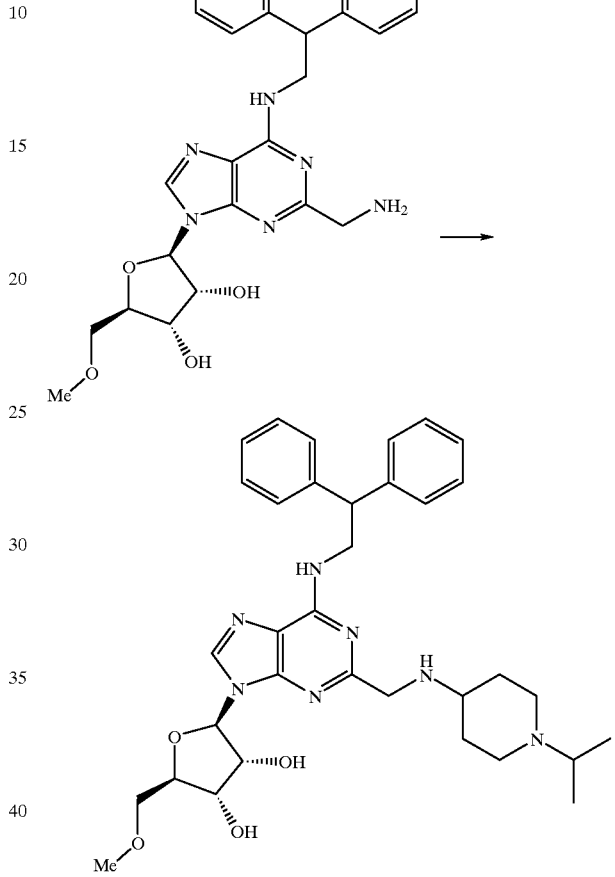

(2R,3R,4S,5R)-2-{2-(Aminomethyl)-6-[(2,2-diphenylethyl)amino]-9H-purin-9-yl}-5-(methoxymethyl)tetrahydro-3,4-furandiol (example 1) (300 mg, 0.61 mmol) was dissolved in dry tetrahydrofuran (20 ml) (using gentle heating), a solution of 2-methyl-1-propanesulphonyl chloride (50 mg, 0.32 mmol) in dry tetrahydrofuran (2.5 ml) added and the mixture stirred at room temperature for 18 hr under a nitrogen atmosphere. A solution of triethylamine (100 mg, 0.98 mmol) and 2-methyl-1-propanesulphonyl chloride (50 mg, 0.32 mmol) in dry tetrahydrofuran (5 ml) was added and the resulting mixture stirred for a further 5 hr. The solvent was then removed under reduced pressure and the residue purified by column chromatography on silica gel eluting with a solvent system of dichloromethane:methanol (97:3), to give the product as a foam (117 mg). MS: 611 (MH$^+$).

$^1$H-NMR (CDCl$_3$) δ=7.96 (1H, s), 7.20–7.40 (10H, m), 5.95 (1H, d), 5.50 (1H, t), 5.03 (1H, br s), 4.55 (2H, s), 4.20–4.42 (6H, m), 3.56–3.70 (2H, m), 3.38 (3H, s), 2.96 (2H, d), 2.20–2.35 (1H, m), 1.08 (6H, d). Analysis: Found C, 58.22, H, 6.29, N, 13.45; C$_{30}$H$_{38}$N$_6$O$_6$S.0.1CH$_2$Cl$_2$ requires C, 58.38, H, 6.22, N, 13.57%.

(2R,3R,4S,5R)-2-{2-(Aminomethyl)-6-[(2,2-diphenylethyl)amino]-9H-purin-9-yl}-5-(methoxymethyl)tetrahydro-3,4-furandiol (example 1) (310 mg, 0.63 mmol) was dissolved (using gentle heating) in dry tetrahydrofuran (20 ml). The resulting solution was cooled to room temperature and, with stirring, treated with a solution of 1-isopropyl-4-piperidinone (90 mg, 0.63 mmol) and acetic acid (45 mg) in dry tetrahydrofuran (5 ml). The mixture was stirred for 1 hr, sodium triacetoxyborohydride (200 mg, 0.94 mmol) added and stirring continued for a further 18 hr. The solvent was then removed under reduced pressure and the residue partitioned between a saturated aqueous solution of sodium hydrogen carbonate and ethyl acetate. The organic phase was separated and the solvent removed under reduced pressure. The residue was purified by column chromatography on silica gel eluting with a gradient system of dichloromethane:methanol:ammonia (90:10:0.5) changing to dichloromethane:methanol:ammonia (85:15:0.75) to afford the title compound as a foam (140 mg). MS: 616 (MH$^+$).

$^1$H-NMR (CDCl$_3$) δ=7.90 (1H, s), 7.19–7.38 (10H, m), 5.94 (1H, d), 5.81 (1H, br s), 4.21–4.44 (6H, m), 3.88 (2H, s), 3.53–3.70 (2H, m), 3.36 (3H, s), 2.70–2.90 (3H, m), 2.57 (1H, m), 2.20 (4H, t), 1.94 (3H, br d), 1.52 (2H, m), 1.06

(6H, d). Analysis: Found C, 62.93, H, 7.48, N, 14.95; $C_{34}H_{45}N_7O_4 \cdot H_2O \cdot 0.16CH_2Cl_2$ requires C, 63.33, H, 7.36, N, 15.13%.

Example 17

Cis-(2R,3R,4S,5R)-2-(6-[(2,2-diphenylethyl)amino]-2-{[(4-isopropylcyclohexyl)amino]methyl}-9H-purin-9-yl)-5-(methoxymethyl)tetrahydro-3,4-furandiol and trans-(2R,3R,4S,5R)-2-(6-[(2,2-diphenylethyl)amino]-2-{[(4-isopropylcyclohexyl)amino]methyl}-9H-purin-9-yl)-5-(methoxymethyl)tetrahydro-3,4-furandiol

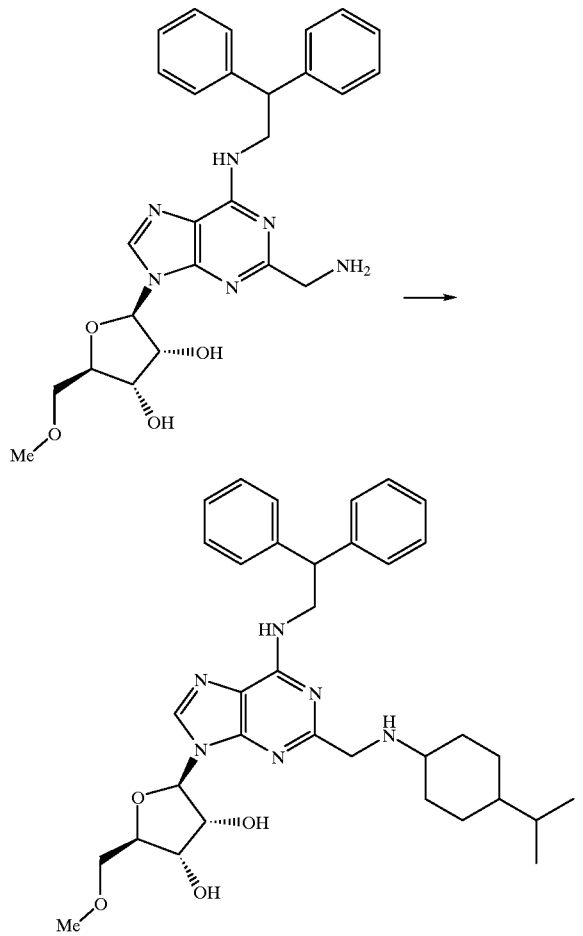

(2R,3R,4S,5R)-2-{2-(Aminomethyl)-6-[(2,2-diphenylethyl)amino]-9H-purin-9-yl}-5-(methoxymethyl)tetrahydro-3,4-furandiol (example 1) (300 mg, 0.61 mmol) was dissolved (using gentle heating) in dry tetrahydrofuran (20 ml). The resulting solution was cooled to room temperature and, with stirring, treated with a solution of 4-isopropylcyclohexanone (85 mg, 0.61 mmol) and acetic acid (44 mg) in dry tetrahydrofuran (5 ml), followed by addition of solid sodium triacetoxyborohydride (194 mg, 0.91 mmol). The resulting mixture was then stirred at room temperature for 18 hr before removal of the solvent under reduced pressure and partitioning of the residue between a saturated aqueous solution of sodium hydrogen carbonate and ethyl acetate. The organic phase was separated and the solvent removed under reduced pressure. The residue was purified by column chromatography on silica gel eluting with a solvent system of dichloromethane:methanol:ammonia (94:6:0.3) to afford the title compound as a foam and as a mixture of cis and trans isomers (170 mg). MS: 615 (MH$^+$).

$^1$H-NMR (CDCl$_3$) δ=7.89 (1H, s), 7.18–7.38 (10H, m), 5.84–5.97 (2H, m), 4.20–4.42 (6H, m), 3.89 (2H, d), 3.50–3.70 (2H, m), 3.31 (1H, s), 2.80 (1H, br s), 2.48 (1H, br t), 2.00 (1H, br t), 0.98–1.79 (9H, m), 0.84 (6H, d).

Example 18

(2R,3R,4S,5R)-2-(6-[(2,2-Diphenylethyl)amino]-2-{2-[(1-ethylpropyl)amino]ethyl}-9H-purin-9-yl)-5-(methoxymethyl)tetrahydro-3,4-furandiol

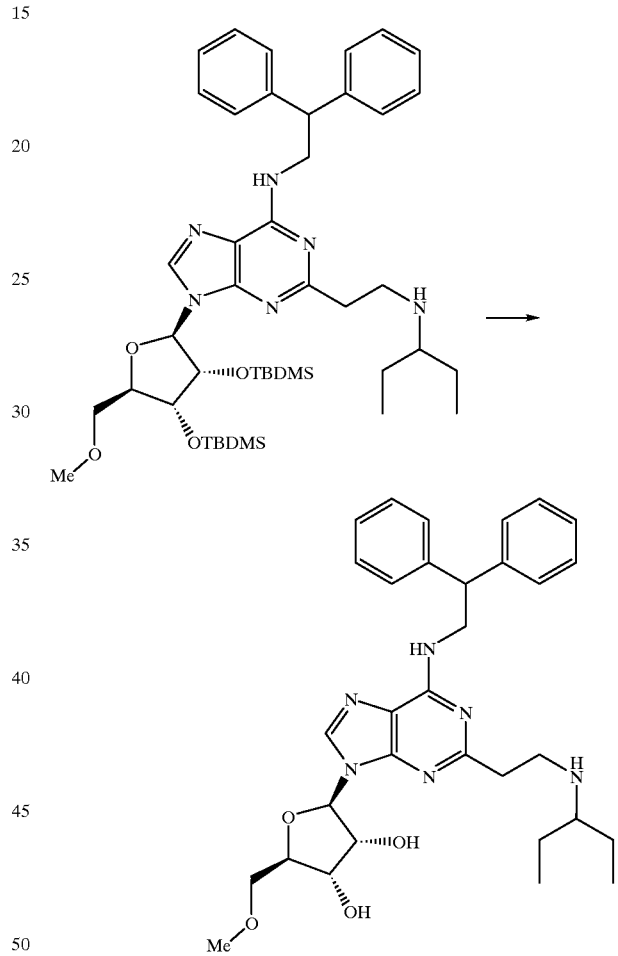

N-(2-{9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}ethyl)-N-(1-ethylpropyl)amine (250 mg, 0.31 mmol) (preparation 19) was dissolved in dry tetrahydrofuran (1 ml), a 1M solution of tetra-n-butylammonium fluoride in tetrahydrofuran (1 ml, 1 mmol) added and the mixture stirred at room temperature for 3 days. The solvent was removed under reduced pressure and the residue purified by column chromatography eluting with a gradient system of dichloromethane:methanol:ammonia (94:6:0.6) changing to dichloromethane:methanol:ammonia (90:10:1) to give the crude product as a foam. This was dissolved in ethyl acetate (15 ml) and the solution washed sequentially with dilute aqueous sodium hydroxide solution, brine and water, then dried with anhydrous sodium sulfate. The solvent removed under reduced pressure to give the title compound as a powder (100 mg). MS: 575 (MH⁺)

¹H-NMR (CDCl₃) δ=7.85 (1H, s), 7.18–7.36 (10H, m), 5.92 (1H, d), 5.70 (1H, br s), 4.20–4.48 (6H, m), 3.55–3.67 (2H, m), 3.33 (3H, s), 3.00–3.20 (4H, m), 2.52 (1H, br t), 1.43–1.54 (4H, m), 0.85–0.92 (6H, m). Analysis: Found C, 64.77, H, 7.32, N, 14.03; $C_{32}H_{42}N_6O_4 \cdot H_2O$ requires C, 64.84, H, 7.48, N, 14.18%

Example 19

N-({9-[2R,3R,4S,5R)-3,4-Dihydroxy-5-(methoxymethyl)tetrahydro-2-furanyl]-6-[(2,2-diphenylethyl)amino]- 9H-purin-2-yl}methyl)-5-methyl-2-(2,2,2-trifluoroacetyl)-1,2,3,4-tetrahydro-8-isoquinolinesulfonamide

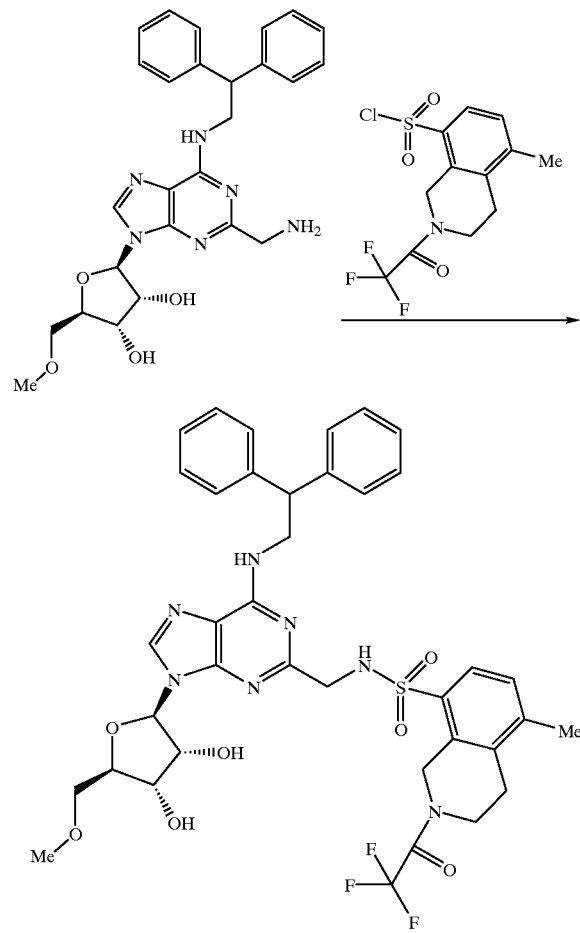

The title compound was prepared by a similar method to example 3 using (2R,3R,4S,5R)-2-{2-(Aminomethyl)-6-[(2,2-diphenylethyl)amino}-9H-purin-9-yl}-5-(methoxymethyl)tetrahydro-3,4-furandiol (example 1) (240 mg, 0.49 mmol), 5-methyl-2-(2,2,2-trifluoroacetyl)-1,2,3,4-tetrahydro-8-isoquinolinesulfonyl chloride (prepared as described in WO-95/13274) (140 mg, 0.41 mmol) and triethylamine (15 mg, 0.15 ml) to give title compound (340 mg) as a solid. $R_f$ 0.65 in dichloromethane:methanol:ammonia (80:20:1).

¹H NMR (CDCl₃) δ=8.00 (1H, s), 7.95–7.90 (1H, m), 7.35–7.20 (12H, m), 6.30–6.20 (1H, m), 6.05–6.00 (1H, m), 5.80–5.75 (1H, m), 5.40–5.30 (1H, m), 5.25–5.15 (1H, m), 4.60–4.50 (2H, m), 4.40–4.05 (6H, m), 4.00–3.80 (2H, m), 3.80–3.60 (2H, m), 3.40 (3H, s), 3.30–3.20 (1H, m), 2.90–2.80 (2H, m), 2.30 (3H, s).

Example 20

N-({9-[2R,3R,4S,5R)-3,4-Dihydroxy-5-(methoxymethyl)tetrahydro-2-furanyl]-6-[(2,2-diphenylethyl)amino]-9H-purin-2-yl})-5-methyl-1,2,3,4-tetrahydro-8-isoquinolinesulfonamide

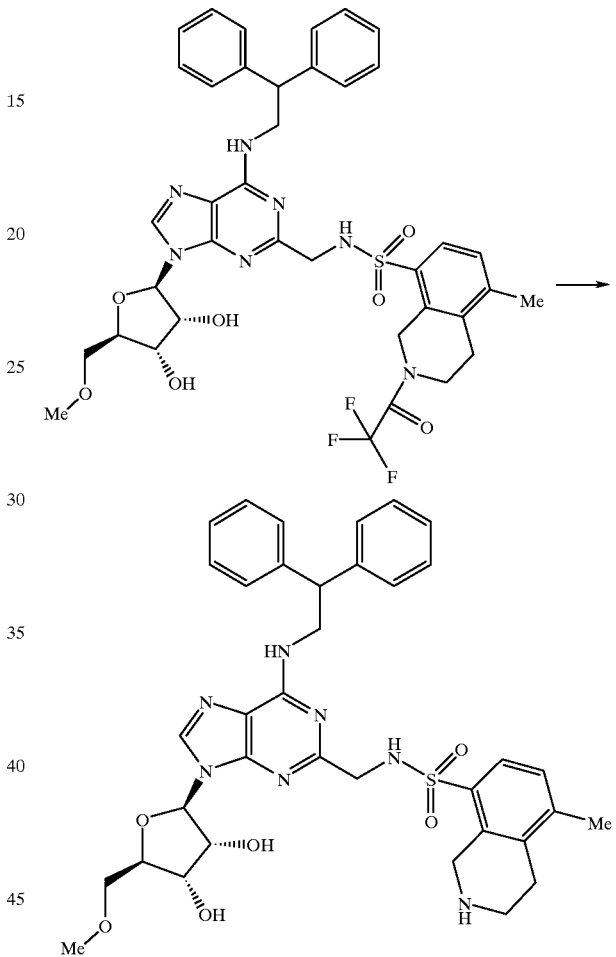

N-({9-[2R,3R,4S,5R)-3,4-dihydroxy-5-(methoxymethyl)tetrahydro-2-furanyl]-6-[(2,2-diphenylethyl)amino]-9H-purin-2-yl}methyl)-5-methyl-2-(2,2,2-trifluoroacetyl)-1,2,3,4-tetrahydro-8-isoquinolinesulfonamide (example 19) (290 mg, 0.36 mmol) was dissolved in a saturated methanolic solution of ammonia (20 ml) and the solution stirred for 24 hr. The solvent was then removed under reduced pressure and the residue dissolved in ethyl acetate (25 ml) to give a solution which was then washed with water (2×10 ml) followed by brine (10 ml). The solvent was removed under reduced pressure and the residue triturated with diethyl ether and dried. This gave the title compound (179 mg) as a solid. MS: 701 (MH⁺).

¹H NMR (CDCl₃) δ=8.15 (1H, s), 7.85 (1H, d), 7.5–7.15 (10H, m), 7.1 (1H, d), 6.05 (1H, s), 5.80 (1H, br s), 4.80–4.60 (2H, m), 4.50–4.40 (1H, m), 4.35–4.05 (7H, m), 3.85–3.75 (1H, m), 3.70–3.60 (1H, m), 3.45 (3H, s), 3.25–3.15 (1H, m), 2.95–2.85 (1H, m), 2.70–2.60 (2H, m),

Example 21

N-({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)-4-[1-(2,2,2-trifluoroacetyl)-4-piperidinyl]benzenesulfonamide

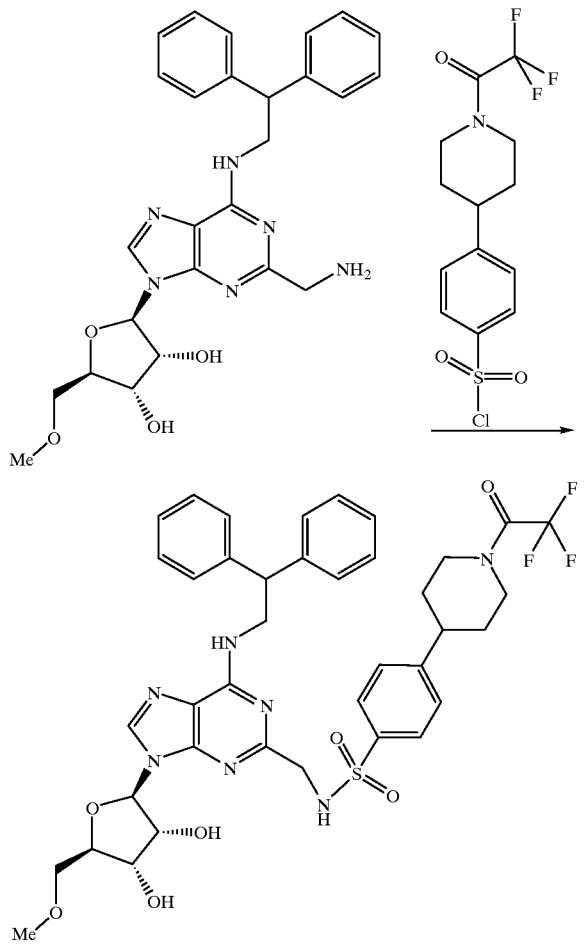

The title compound was prepared by a similar method to example 3 using (2R,3R,4S,5R)-2-{2-(aminomethy)-6-[(2,2-diphenylethyl)amino}-9H-purin-9-yl}-5-(methoxymethyl)tetrahydro-3,4-furandiol (example 1) (250 mg, 0.51 mmol), 4-[1-(2,2,2-trifluoroacetyl)-4-pipendinyl]benzenesulfonyl chloride (preparation 20) (157 mg, 0.48 mmol) and triethylamine (155 mg, 1.53 mmol) in tetrahydrofuran (25 ml). This gave the title compound as a solid (300 mg). MS: 811 (MH$^+$)

$^1$H NMR (CDCl$_3$) δ=7.90 (1H, s), 7,80–7.75 (2H, m), 7.40–7.10 (12H, m), 5.90–5.85 (1H, m), 5.85–5.75 (2H, m), 4.90 (1H, br s), 4.70–4.60 (1H, m), 4.50 (2H, s), 4.35–4.05 (6H, m), 3.70–3.55 (2H, m), 3.35 (3H, s), 3.25–3.10 (2H, m), 2.85–2.70 (2H, m), 1.90–1.80 (2H, m), 1.70–1.45 (2H partially obscured by H$_2$O).

Example 22

N-({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)-4-(4-piperidinyl)benzenesulfonamide

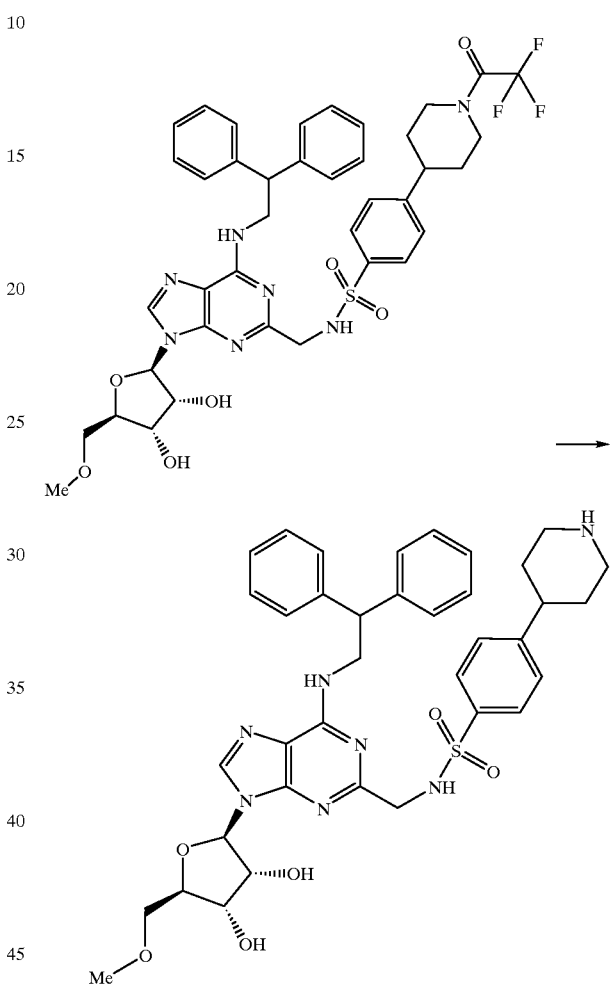

The title compound was prepared by a similar method to example 20 using N-({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)-4-[1-(2,2,2-trfluoroacetyl)-4-piperidinyl]benzenesulfonamide (0.26 g, 0.32 mmol) (example 21) and a saturated methanolic solution of ammonia (20 ml). This gave the title compound (180 mg) as a solid. MS: 715 (MH$^+$)

$^1$H NMR (CDCl$_3$) δ=7.95 (1H, s), 7.75–7.5 (2H, m), 7.35–7.20 (10H, m), 7.15–7.05 (2H, m), 5.90–5.75 (2H, m), 4.50–4.40 (2H, m), 4.35–4.10 (7H, m), 3.70–3.55 (2H, m), 3.35 (3H, s), 3.20–3.05 (2H, m), 2.70–2.60 (2H, m), 2.60–2.45 (1H, m) 1.75–1.25 (4H, m).

2.20 (3H, s). Analysis: Found C, 58.96, H, 5.74, N, 13.54; C$_{36}$H$_{41}$N$_7$O$_6$S.2H$_2$O requires C, 58.77, H, 6.17, N, 13.33%

Example 23

N-({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)-2-methoxy-1-ethanesulfonamide

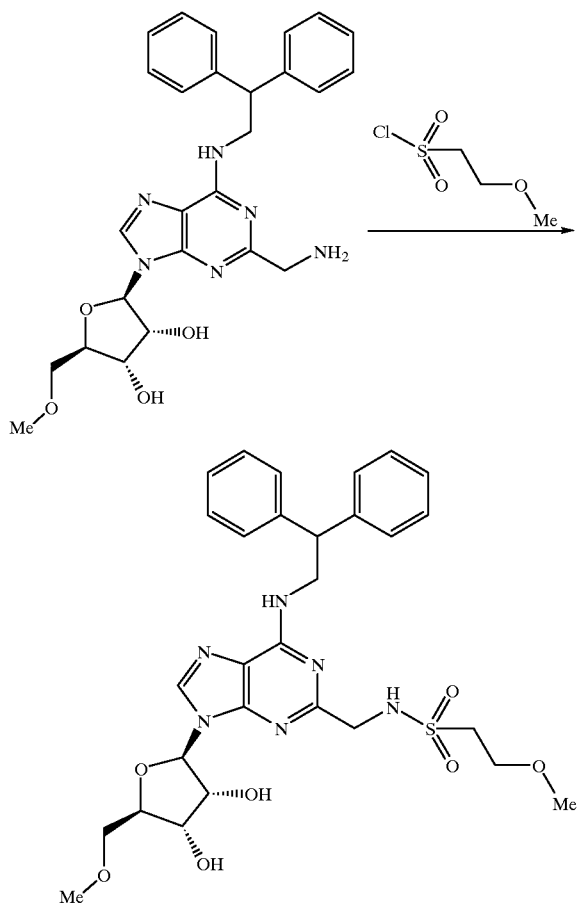

The title compound was prepared by a similar method to example 3 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (250 mg, 0.49 mmol), 2-methoxy-1-ethanesulfonyl chloride (J. Org. Chem. 2633, 26, 1961) (77 mg, 0.49 mmol), triethylamine (150 mg, 1.5 mmol) in tetrahydrofuran (23 ml). The crude product was purified by column chromatography on silica gel eluting with a solvent system of dichloromethane:methanol:ammonia (96:4:0.2) gave the title compound (225 mg) as an oil. MS: 614 (MH$^+$).

$^1$H NMR (CDCl$_3$) δ=7.95 (1H, s), 7.35–2.20 (10H, m), 6.00–5.95 (1H, m), 5.90–5.75 (1H, m), 5.55–5.50 (1H, m), 5.10 (1H, br s), 4.50 (2H, s), 4.40–4.20 (6H, m), 3.85–3.75 (2H, m), 3.45–3.35 (5H, m), 3.30 (3H, s), 3.05 (1H, s). Analysis: Found C, 55.92, H, 5.80, N, 13.42; C$_{29}$H$_{36}$N$_6$O$_7$S.0.167CH$_2$Cl$_2$ requires C, 55.89, H, 5.84, N, 13.41%.

Example 24

N-({9-[(2R,3R,4S,5R)-3,4-Dihydroxy-5-(methoxymethyl)tetrahydro-2-furanyl]-6-[(2,2-diphenylethyl)amino]-9H-purin-2-yimethyl)(tetrahydro-2H-pyran-4-yl)methanesulfonamide

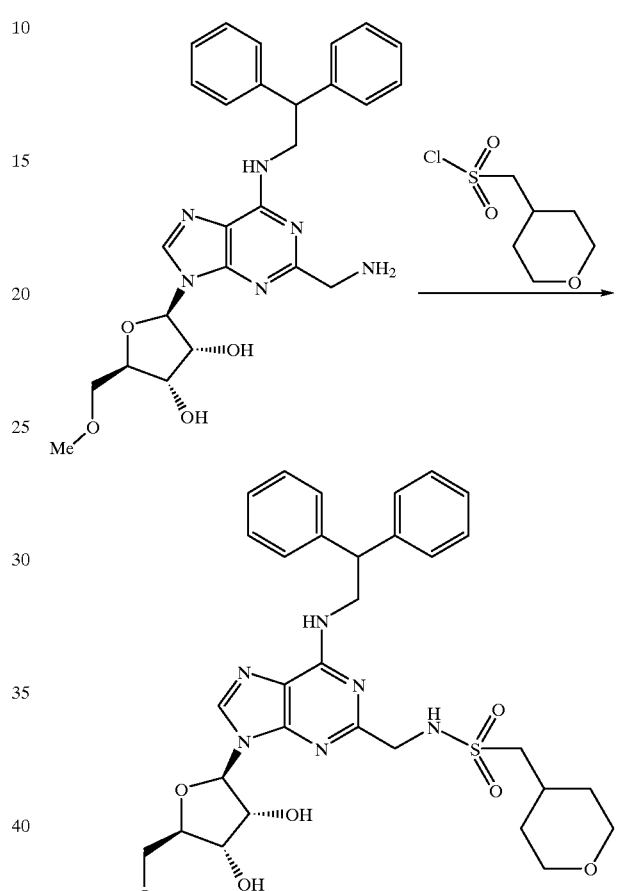

The title compound was prepared by a similar method to example 3 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (245 mg, 0.48 mmol), tetrahydro-2H-pyran-4-ylmethanesulfonyl chloride (preparation 21) (95 mg, 0.48 mmol), triethylamine (145 mg, 1.44 mmol) in tetrahydrofuran (23 ml). Purification by column chromatography on silica gel eluting with a solvent system of dichloromethane:methanol:ammonia (95:5:0.25) gave the title compound as an oil (118 mg). MS: 654 (MH$^+$).

$^1$H NMR (CDCl$_3$) δ=7.90 (1H, s), 7.35–7.20 (10H, m), 5.95–5.90 (1H, m), 5.90–5.75 (1H, br s), 5.50–5.45 (1H, m), 4.90–4.80 (1H, br s), 4.60–4.50 (2H, m), 4.40–4.20 (6H, m), 3.95–3.90 (2H, m), 3.70–3.55 (2H, m), 3.45–3.30 (5H, m), 3.10 (1H, br s), 3.05–2.95 (2H, m), 2.30–2.15 (1H, m), 1.85–1.75 (2H, m), 1.50–1.30 (2H, m).

Example 25

N-({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)-2-propanesulfonamide

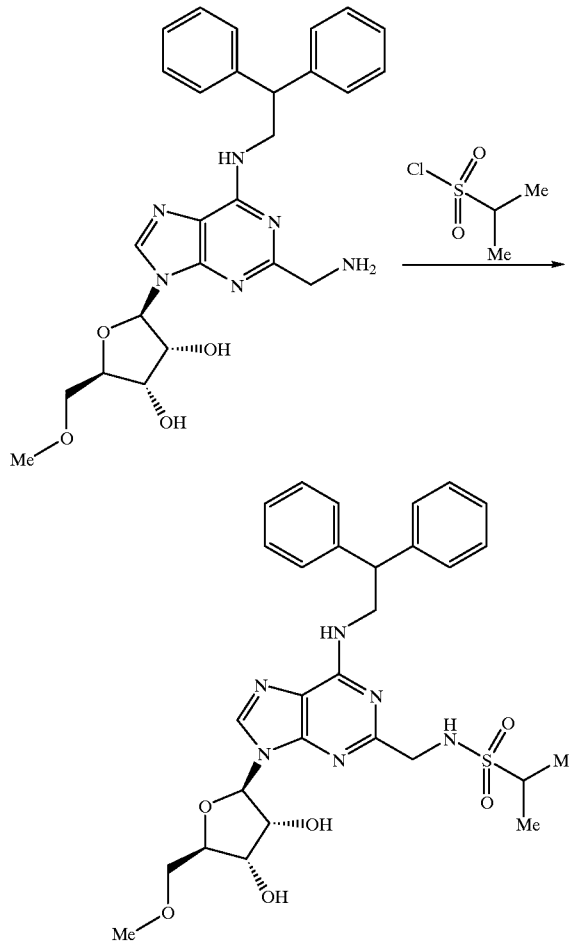

Example 26

N-({9-[(2R,3R,4S,5R)-3,4-Dihydroxy-5-(methoxymethyl)tetrahydro-2furanyl]-6-[(2,2-diphienylethyl)amino]-9H-purin-2-yl}methyl)-2,2-dimethyl-1-propanesulfonamide

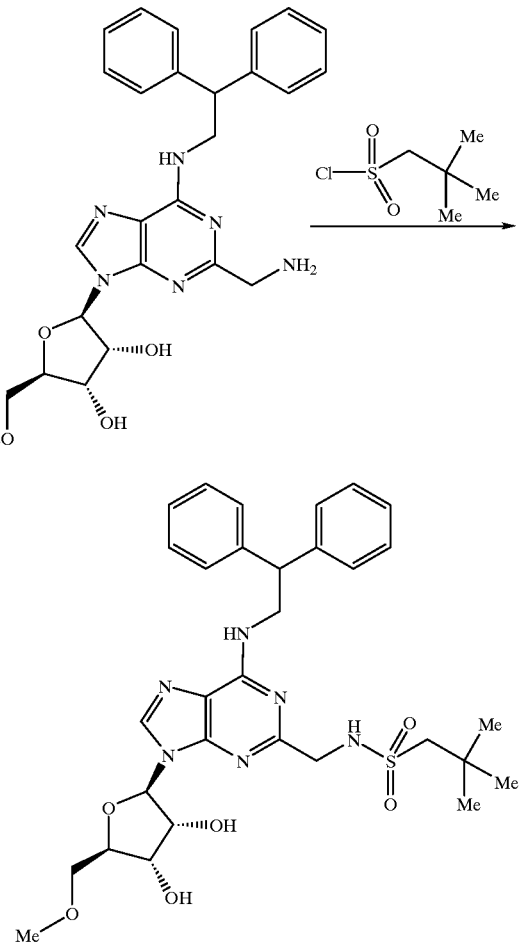

Isopropylsulphonyl chloride (120 mg, 0.84 mmol) was added to a stirred solution of (2R,3R,4S,5R)-2-{2-(aminomethyl)-6-[(2,2-diphenylethyl)amino}-9H-purin-9-yl}-5-(methoxymethyl)tetrahydro-3,4-furandiol (408 mg, 0.8 mmol) (example 1) in 2,6-lutidine (10 ml). The mixture was stirred at room temperature for 24 hr followed by stirring at 50° C. for a further 5 days. A second portion of isopropylsulphonyl chloride (120 mg, 0.84 mmol) and lutidine (4 ml) were added and the reaction stirred at 50° C. for 24 hr. A third portion of isopropylsulphonyl chloride (120 mg, 0.84 mmol) was added and heating at 50° C. continued for a further 24 hr. At the end of this period the solvent was removed under reduced pressure and the residue partitioned between ethyl acetate and aqueous ammonia. The organic phase was separated and the solvent removed under reduced pressure to give a residue which was purified by column chromatography on silica gel eluting with a solvent system of dichloromethane:methanol:ammonia (98:2:0.1) increasing to dichloromethane:methanol:ammonia (96:4:0.2). This gave the title compound (118 mg) as an oil. MS: 597 (MH$^+$).

$^1$H NMR (CDCl$_3$) mixture of rotamers δ=7.90 (1H, s), 7.35–7.20 (10H, m), 5.95–5.90 (1H, m), 5.85–5.70 (1H, brs), 4.90 (1H, brs), 4.60–4.15 (8H, m), 3.70–3.55 (2H, m), 3.30 (3H, s), 3.25–3.10 (2H, m), 1.80 (1H, d), 1.40 (5H, d).

A solution of 2,2-dimethyl-1-propanesulfonyl chloride (80 mg, 0.47 mmol) (Synthesis 489, 7, 1974) in tetrahydrofuran (5 ml) was added to a stirred solution of (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (450 mg, 0.92 mmol) in tetrahydrofuran (30 ml) and the mixture stirred for 24 hr at room temperature. The solvent was then removed under reduced pressure and the residue partitioned between ethyl acetate and aqueous ammonia. The organic phase was separated and the solvent removed under reduced pressure to give a residue which was purified by column chromatography on silica gel eluting with a solvent system of dichloromethane:methanol (19:1) to give title compound (40 mg) as an oil. MS: 625 (MH$^+$).

$^1$H NMR (CDCl$_3$) δ=7.95 (1H, s), 7.35–7.15 (10H, m), 6.00–5.95 (2H, m), 5.60–5.55 (1H, m), 5.10 (1H, br s), 4.55–4.45 (2H, m), 4.40–4.20 (6H, m), 3.70–3.55 (2H, m), 3.4 (1H, brs), 3.35 (3H, s), 3.00 (2H, s), 1.15 (9H, s).

Example 27

N-({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)(phenyl)methanesulfonamide

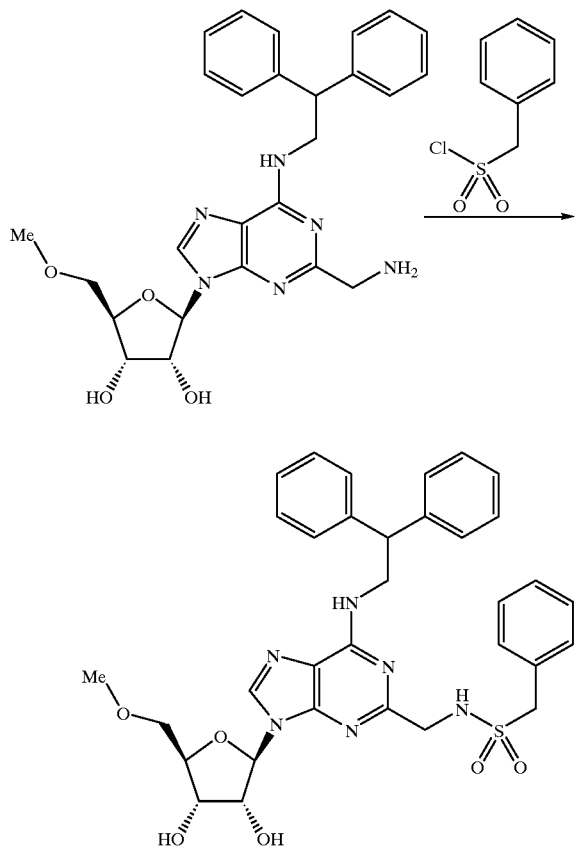

The title compound was prepared by a similar method to example 3 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (265 mg, 0.54 mmol), phenylmethanesulfonyl chloride (98 mg, 0.51 mmol) and triethylamine (185 mg, 1.83 mmol) in dry tetrahydrofuran (23 ml). This gave the title compound (240 mg) as a gum. MS: 645 (MH$^+$).

$^1$H NMR (CDCl$_3$) δ=7.90 (1H, br s), 7.40–7.20 (15H, m), 5.90–5.80 (2H, m), 5.50–5.45 (1H, m), 4.90 (1H, br s), 4.55–4.45 (2H, m), 4.35–4.10 (8H, m), 3.65–3.50 (2H, m), 3.30 (3H, s), 3.15 (1H, s). Analysis: Found C, 60.09, H, 5.63, N, 12.24; C$_{33}$H$_{36}$N$_6$O$_6$S.0.5H$_2$O.0.1CH$_2$Cl$_2$ requires C, 60.04, H, 5.66, N, 12.69%.

Example 28

N-{9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)-1-butanesulfonamide

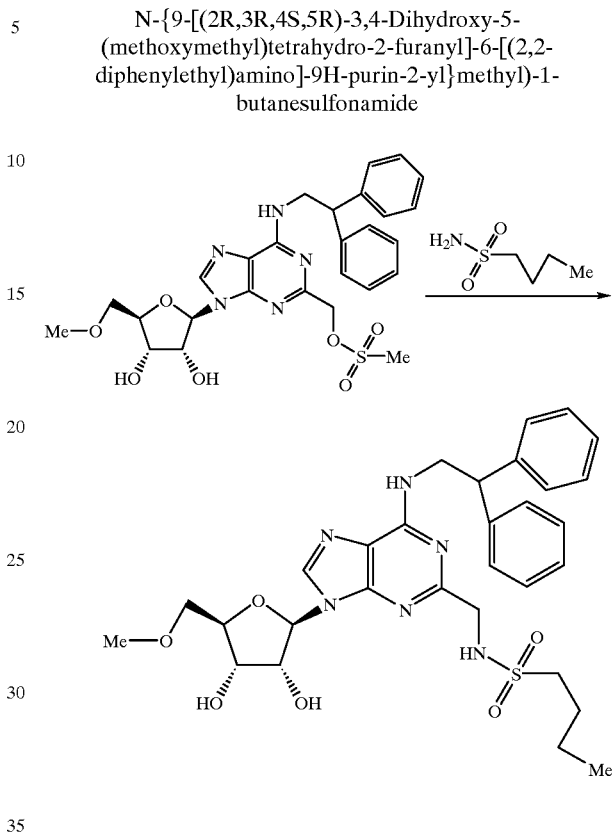

1-Butanesulphonamide (J. Am. Chem. Soc. 5512, 72, 1950) (280 mg, 2.1 mmol) was dissolved in stirred tetrahydrofuran (10 ml) and sodium hydride added (0.059 of 80% dispersion in mineral oil, 1.56 mmol). After effervesence had ceased the reaction mixture was cooled to 0° C. and a solution of {9-[(2R,3R,4S,5R)-3,4-dihydroxy-5-(methoxymethyl)tetrahydro-2-furanyl]-6-[(2,2-diphenylethyl)amino]-9H-purin-2-yl}methyl methanesulfonate (300 mg, 052 mmol) (preparation 25) in tetrahydrofuran (5 ml) added. The reaction mixture was stirred for 24 hr then quenched by the addition of methanol (0.5 ml). The solvent was removed under reduced pressure and the residue partitioned between water (50 ml) and dichloromethane (100 ml). The organic layer was separated and dried with anhydrous magnesium sulfate. The residue after solvent evaporation under reduced pressure was purified by column chromatography on silica gel eluting with a solvent system of ethyl acetate:hexane (1:1) followed by ethyl acetate followed by dichloromethane:methanol (19:1). This gave the title compound (60 mg) as a foam. MS: 612 (MH$^+$).

$^1$H NMR (CDCl$_3$) Mixture of rotamers δ=8.00 (0.3H, br s), 7.95 (0.7H, br s), 7.40–7.20 (10H, m), 5.95–5.90 (1H, m), 4.75–4.65 (2H, m), 4.55–4.20 (6H, m), 3.70–3.55 (2H, m), 3.35 (3H, s), 3.15 (0.6H, s), 3.10–3.00 (1.4H, m), 1.85–1.75 (1.4H, m), 1.60–1.55 (0.6H, m obscured by HOD), 1.50–1.35 (1.4H, m), 1.25 (0.6H, s), 0.95–0.85 (3H, m).

Example 29

(2R,3R,4S,5R)-2-{2-{[(4-Chlorobenzyl)amino]methyl}-6-[(2,2-diphenylethyl)amino]-9H-purin-9-yl}-5-(methoxymethyl)tetrahydro-3,4-furandiol

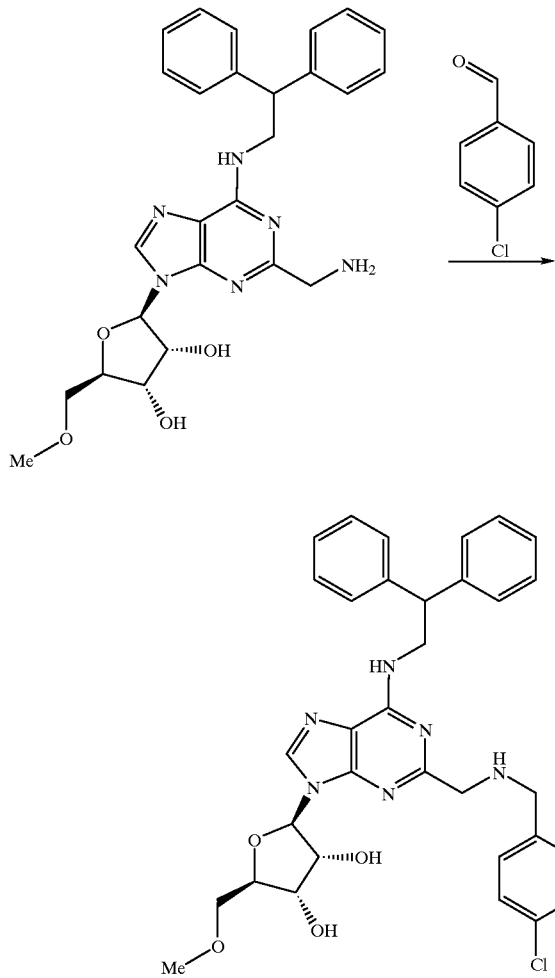

The title compound was prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (200 mg, 0.4 mmol), sodium triacetoxyborohydride (152 mg, 0.72 mmol) and 4-chlorobenzaldehyde (75 mg, 0.53 mmol). The product was purified by column chromatography on silica gel eluting with a solvent system of dichloromethane:methanol (98:2) gradually increasing polarity to dichloromethane:methanol (90:10), which gave the title compound (53 mg) as a foam. MS: 615 (MH$^+$).

$^1$H NMR (CDCl$_3$) δ=7.90 (1H, s), 7.35–7.20 (14H, m), 5.95–5.90 (1H, m), 5.80 (1H, br s), 4.45–4.20 (6H, m), 3.90–3.80 (4H, m), 3.65–3.50 (2H, m), 3.30 (3H, s). Analysis: Found C, 63.91, H, 5.71, N, 13.35; C$_{33}$H$_{35}$N$_6$O$_4$Cl.0.33H$_2$O requires C, 63.82, H, 5.79, N, 13.54%.

Example 30

(2R,3R,4S,5R)-2-(6-[(2,2-Diphenylethyl)amino]-2-{[(2-methoxybenzyl)amino]methyl}-9H-purin-9-yl)-5-(methoxymethyl)tetrahydro-3,4-furandiol

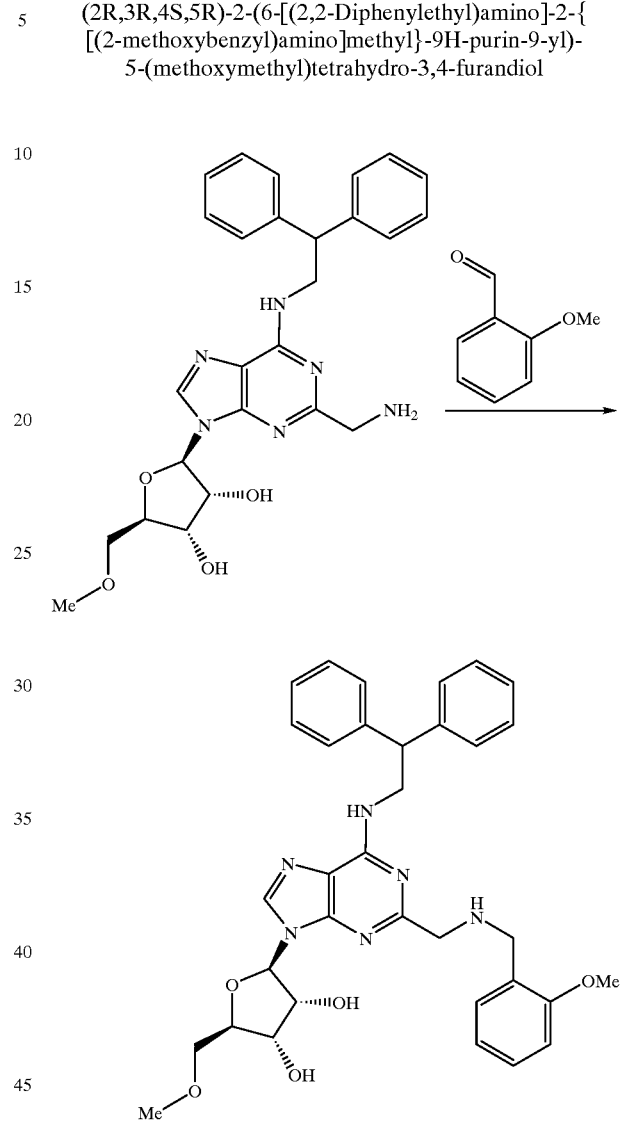

The title compound was prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (200 mg, 0.4 mmol), sodium triacetoxyborohydnde (152 mg, 0.72 mmol) and 2-methoxybenzaldehyde (75 mg, 0.53 mmol). The product was purified by column chromatography on silica gel eluting with a solvent system of dichloromethane:methanol:ammonia (95:5:0.5), which gave the title compound (53 mg) as a foam. MS: 611 (MH$^+$).

$^1$H NMR (CDCl$_3$) δ=7.85 (1H, br s), 7.30–7.10 (12H, m), 6.90–6.75 (2H, m), 6.10–5.90 (2H, m), 4.45–4.10 (6H, m), 3.90 (3H, s), 3.75–3.45 (4H, m), 3.30 (3H, s).

Example 31

(2R,3R,4S,5R)-2-{2-{[Bis(2-methoxybenzyl)amino]methyl}-6-[(2,2-diphenylethyl)amino]-9H-purin-9-yl}-5-(methoxymethyl)tetrahydro-3,4-furandiol

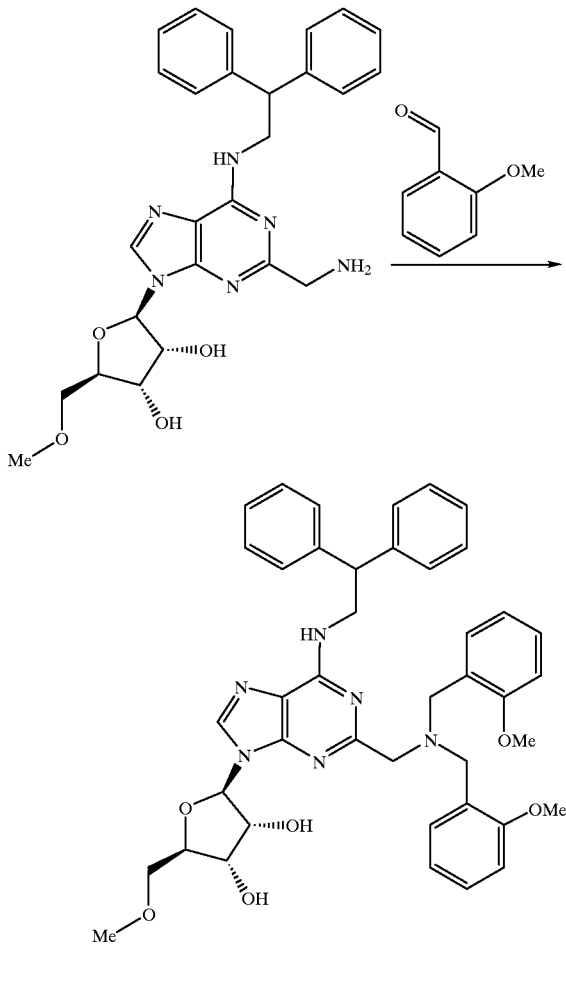

The title compound was prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (200 mg, 0.4 mmol), sodium triacetoxyborohydride (230 mg, 0.72 mmol) and 2-methoxybenzaldehyde (111 mg, 0.82 mmol). The product was purified by column chromatography on silica gel eluting with a solvent gradient of dichloromethane:methanol (98:2) increasing in polarity to dichloromethane:methanol (93:7). This gave the title compound (130 mg) as a foam. MS: 731 (MH$^+$).

$^1$H NMR (CDCl$_3$) δ=7.90 (1H, br s), 7.75–7.65 (2H, m), 7.30–7.15 (14H, m), 6.90–6.75 (4H, m), 5.90 (1H, br s), 5.70 (1H, br s), 4.45–4.25 (6H, m), 3.95–3.80 (6H, m), 3.70 (6H, s), 3.65–3.50 (3H, m), 3.30 (3H, s). Analysis: Found C, 67.48, H, 6.34, N, 11.26; C$_{42}$H$_{46}$N$_6$O$_6$.H$_2$O requires C, 67.38, H, 6.42, N, 11.23%.

Example 32

(2R,3R,4S,5R)-2-(6-[(2,2-Diphenylethyl)amino]-2-{[(4-isopropoxybenzyl)amino]methyl}-9H-purin-9-yl)-5-(methoxymethyl)tetrahydro-3,4-furandiol

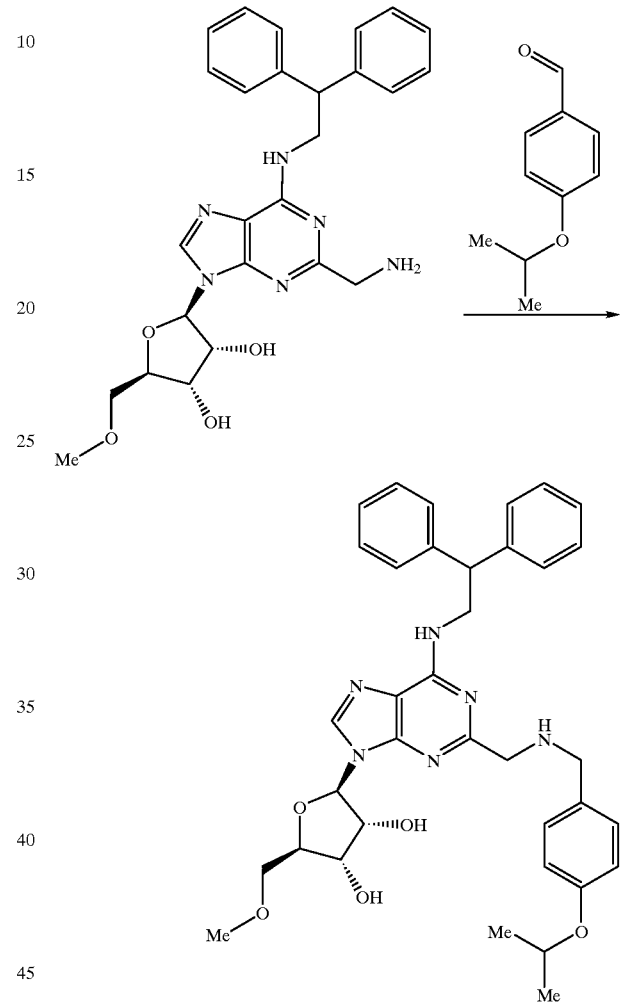

The title compound was prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (225 mg, 0.46 mmol), sodium triacetoxyborohydnde (212 mg, 1.0 mmol) and 4-isopropoxybenzaldehyde (84 mg, 0.51 mmol) in tetrahydrofuran (15 ml). The product was purified by column chromatography on silica gel eluting with a solvent system of dichloromethane:methanol:ammonia (95:5:0.5). This gave the title compound (53 mg) as a foam. MS: 639 (MH$^+$).

$^1$H NMR (CDCl$_3$) δ=7.90 (1H, br s), 7.35–7.15 (12H, m), 6.80 (2H, d), 6.00–5.90 (1H, m), 5.85 (1H, br s), 4.55–4.25 (6H, m), 3.90 (2H, s), 3.75 (2H, s), 3.65–3.50 (2H, m), 3.30 (3H, s), 1.30 (6H, d).

Example 33

(2R,3R,4S,5R)-2-{2-{[(3,4-Dimethoxybenzyl)amino]methyl}-6-[(2,2-diphenylethyl)amino]-9H-purin-9-yl}-5-(methoxymethyl)tetrahydro-3,4-furandiol

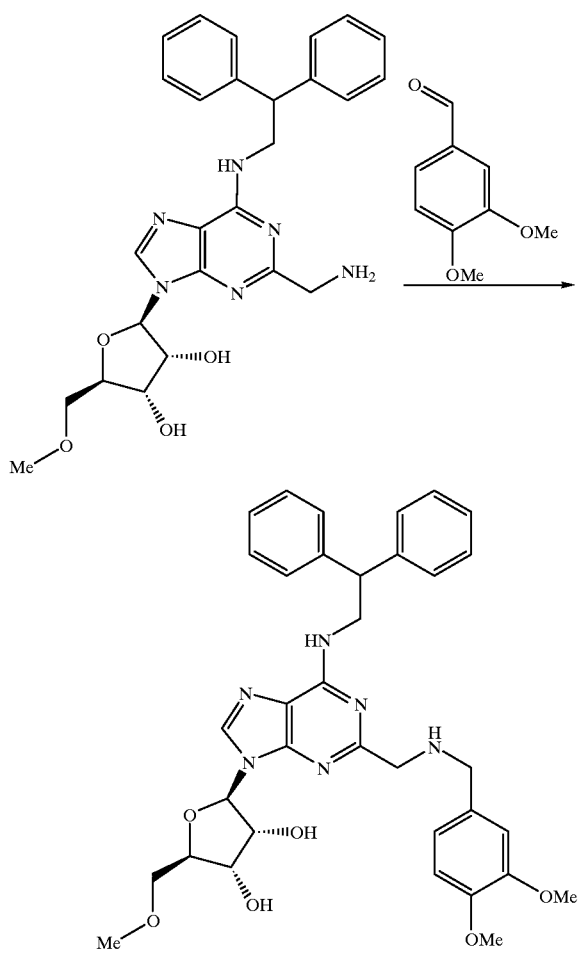

(2R,3R,4S,5R)-2-{2-(Aminomethyl)-6-[(2,2-diphenylethyl)amino}-9H-purin-9-yl}-5-(methoxymethyl)tetrahydro-3,4-furandiol (example 1) (200 mg, 0.4 mmol) was dissolved in stirred tetrahydrofuran (5 ml) and 3,4-dimethoxybenzaldehyde (130 mg, 0.8 mmol) added. The reagents were stirred together until everything had dissolved and then sodium triacetoxyborohydride (130 mg, 0.6 mmol) added. The reaction mixture was stirred for 24 hr and then quenched by the addition of methanol (1 ml). The solvent was removed under reduced pressure and the residue purified by column chromatography on silica gel eluting with a solvent gradient of dichloromethane:methanol:ammonia (95:5:0.5) increasing to (92:7:1). This gave the title compound (90 mg) as a foam. MS: 641 (MH+).

$^1$H NMR (CDCl$_3$) δ=7.90 (1H, s), 7.35–7.20 (10H, m), 6.95–6.70 (3H, m), 6.00–5.90 (1H, m), 5.85 (1H, br s), 4.40–4.20 (6H, m), 3.95–3.75 (10H, m), 3.65–3.50 (2H, m), 3.30 (3H, s).

Example 34

(2R,3R,4S,5R)-2-[6-[(2,2-Diphenylethyl)amino]-2-({[2-(methoxymethyl)benzyl]amino}methyl)-9H-purin-9-yl]-5-(methoxymethyl)tetrahydro-3,4-furandiol

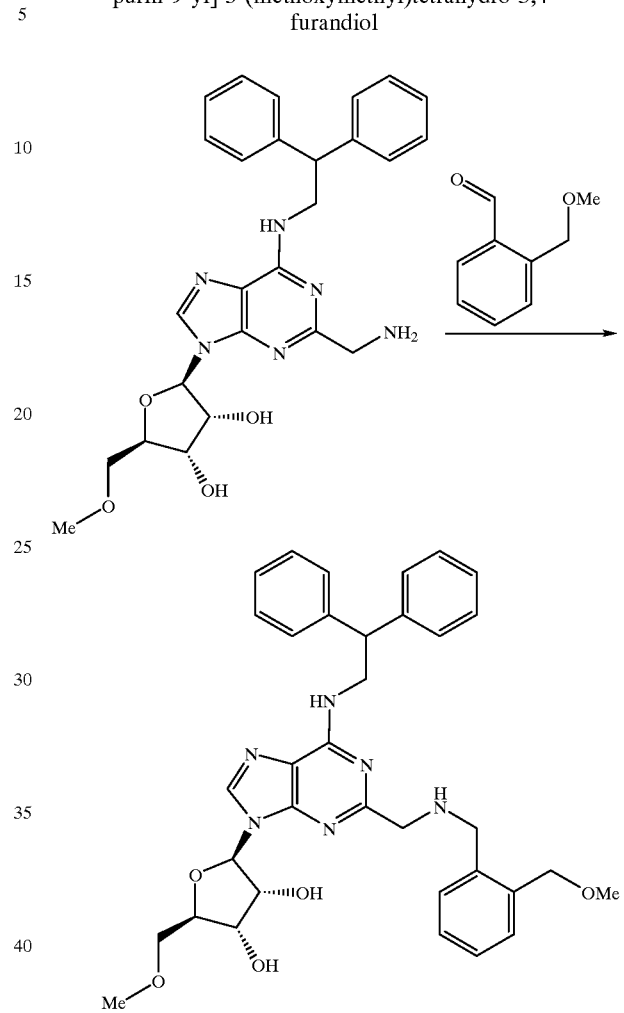

A solution of (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (323 mg, 0.66 mmol), 2-(methoxymethyl)benzaldehyde (109 mg, 0.73 mmol) (Tetrahedron 4739, 47, 1991) and 1 drop of acetic acid in tetrahydrofuran (15 ml) was stirred at room temperature for 24 hr. Sodium triacetoxyborohydride (310 mg, 1.45 mmol) was then added and the reaction mixture stirred for 1 hr. At this point the solvent was partially removed under reduced pressure and the residue partitioned between ethyl acetate and saturated aqueous sodium hydrogen carbonate solution. The solvent was removed from the organic layer under reduced pressure and the residue purified by column chromatography on silica gel eluting with a solvent system of dichloromethane:methanol (97:3) increasing in polarity to dichloromethane:methanol:ammonia (95:5:0.5). This gave the title compound (250 mg) as a foam. MS: 625 (MH+).

$^1$H NMR (CDCl$_3$) δ=7.95 (1H, s), 7.45–7.15 (14H, m), 6.00–5.90 (1H, m), 5.80 (1H, br s), 4.55 (2H, s), 4.45–4.25 (6H, m), 3.95 (4H, s), 3.70–3.50 (2H, m), 3.30 (6H, s). Analysis: Found C, 64.11, H, 6.24, N, 12.78; C$_{35}$H$_{40}$N$_6$O$_5$.1.5H$_2$O requires C, 64.51, H, 6.60, N, 12.90%.

Example 35

(2R,3R,4S,5R)-2-{2-({[4-(Aminomethyl)benzyl]amino}methyl)-6-[(2,2-diphenylethyl)amino]-9H-purin-9-yl}-5-(methoxymethyl)tetrahydro-3,4-furandiol

Example 36

(2R,3R,4S,5R)-2-{2-{2-[(Cyclohexylmethyl)amino]ethyl}-6-[(2,2-diphenylethyl)amino]-9H-purin-9-yl}-5-(methoxymethyl)tetrahydro-3,4-furandiol

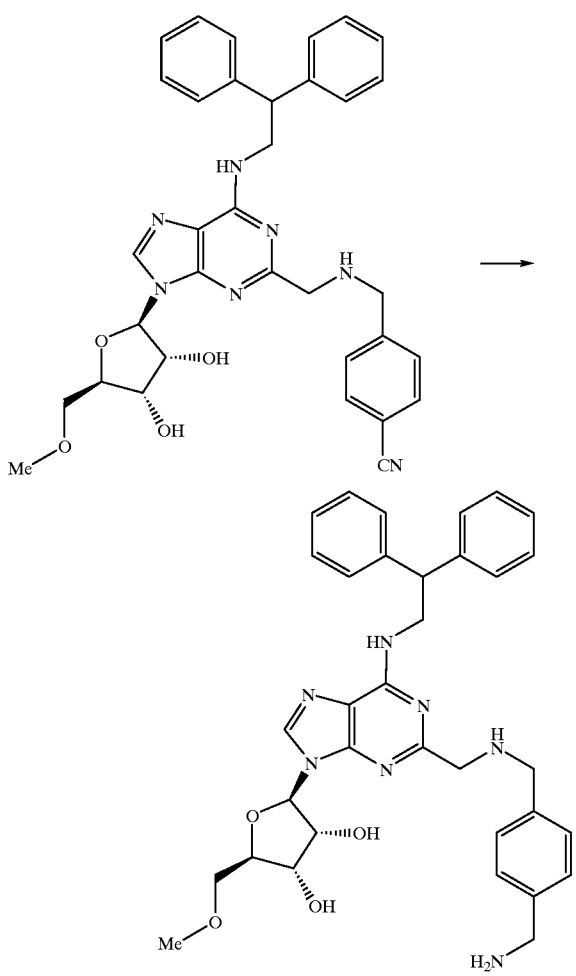

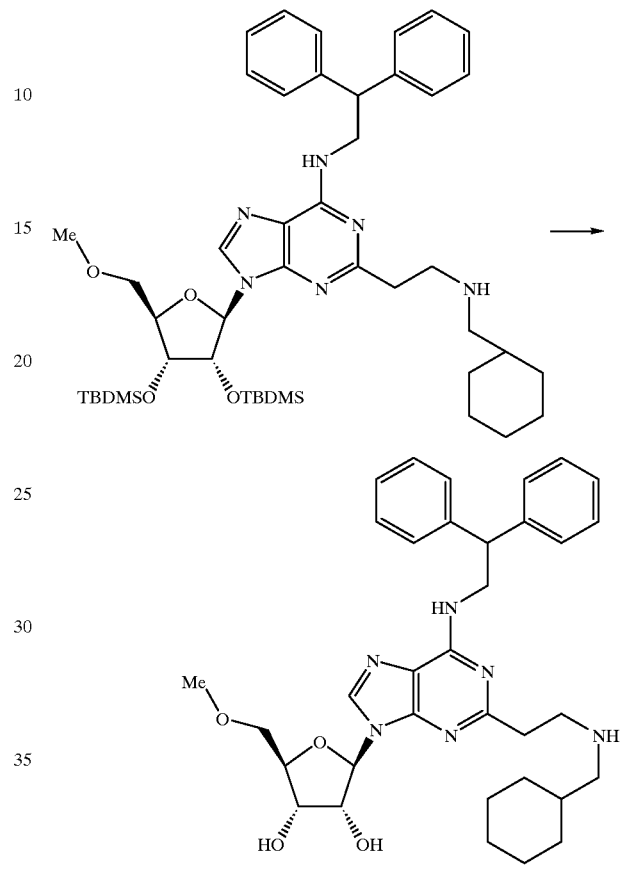

4-{[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]methyl}benzonitrle (example 42) (380 mg, 0.62 mmol) was dissolved in a stirred saturated ethanolic solution of ammonia (50 ml) and Raney Nickel (200 mg) added. The reaction mixture was stirred under an atmosphere of 414 kPa (60 psi) of hydrogen for 24 hr. The Raney Nickel was then filtered off through Arbocel (trade mark) and the solvent removed from the filtrate under reduced pressure to give a residue which was purified by column chromatography on silica gel eluting with a solvent gradient of dichloromethane:methanol (97:3) increasing in polarity to dichloromethane:methanol:ammonia (80:20:3). This gave the title compound (260 mg) as a gum. MS: 611 (MH$^+$).

$^1$H NMR (CDCl$_3$+drop d$_6$ DMSO) δ=7.85 (1H, s), 7.30–7.20 (10H, m), 7.20–7.10 (4H, m), 5.90 (1H, d), 5.75 (1H, br s), 4.45–4.40 (1H, m), 4.35–4.15 (6H, m), 3.85–3.75 (6H, m), 3.60–3.50 (2H, m), 3.30 (3H, s). Analysis: Found C, 65.24, H, 6.26, N, 15.62; C$_{34}$H$_{39}$N$_7$O$_4$.H$_2$O requires C, 65.07, H, 6.53, N, 15.62%.

N-(9-[(2R,3R,4R,5R)-3,4-Bis{[tert-butyl(dimethyl)silyl]oxy}-5-(methoxymethyl)tetrahydro-2-furanyl]-2-{2-[(cyclohexylmethyl)amino]ethyl}-9H-purin-6-yl)-N-(2,2-diphenylethyl)amine (210 mg, 0.25 mmol) (preparation 23) was dissolved in stirred tetrahydrofuran (1 ml) and a 1M solution of tetra-n-butylammonium fluoride in tetrahydrofuran (1 ml, 1 mmol) added. The reaction mixture was stirred at room temperature for 24 hr. The solvent was removed under reduced pressure and the residue partitioned between dilute aqueous sodium hydroxide solution and ethyl acetate. The organic layer was separated and the aqueous phase extracted with ethyl acetate. The ethyl acetate phases were combined and dried with anhydrous magnesium sulfate. The solvent was removed under reduced pressure and the residue purified by column chromatography on silica gel eluting with a solvent gradient of dichloromethane:methanol:ammonia (94:6:0.6) increasing in polarity to (91:9:0.9). This gave the title compound (70 mg) as a powder. MS: 601 (MH$^+$).

$^1$H NMR (CDCl$_3$) δ=8.00 (1H, s), 7.35–7.20 (10H, m), 6.00–5.95 (1H, m), 5.75–5.70 (1H, m), 4.50–4.45 (1H, m), 4.40–4.20 (5H, m), 3.70–3.55 (2H, m), 3.30 (3H, s), 3.20–3.05 (3H, m), 2.75–2.65 (2H, m), 1.85–1.75 (2H, m), 1.75–1.60 (4H, m), 1.30–1.10 (4H, m), 1.00–0.80 (3H, m). Analysis: Found C, 64.94, H, 7.33, N, 13.18; C$_{34}$H$_{44}$N$_6$O$_4$.1.5H$_2$O requires C, 65.05, H, 7.55, N, 13.39%.

Example 37

N-(2-{9-[(2R,3R,4S,5R)-3,4-Dihydroxy-5-(methoxymethyl)tetrahydro-2-furanyl]-6-[(2,2-diphenylethyl)amino]-9H-purin-2-yl}ethyl)methanesulfonamide

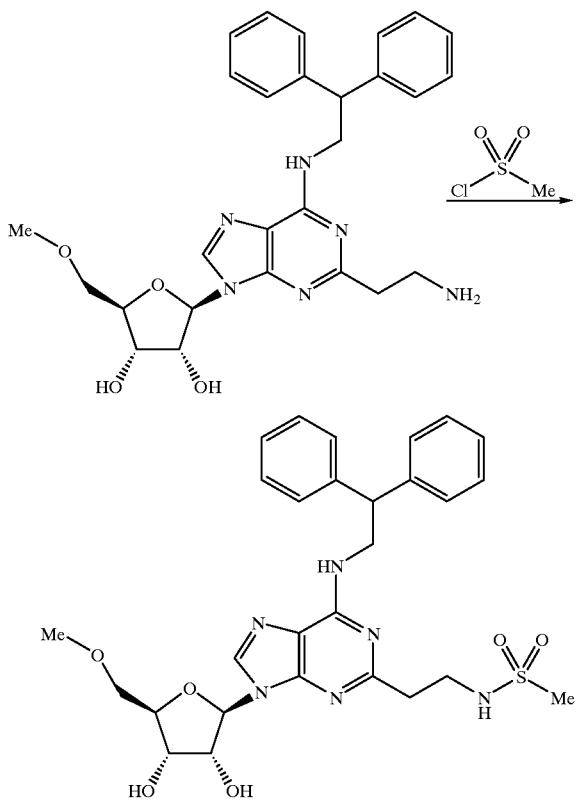

Methanesulfonyl chloride (27 mg, 0.22 mmol) was added to a stirred solution of (2R,3R,4S,5R)-2-{2-(2-aminoethyl)-6-[(2,2-diphenylethyl)amino]-9H-purin-9-yl}-5-(methoxymethyl)tetrahydro-3,4-furandiol (120 mg, 0.23 mmol) (Example 11) and triethylamine (0.1 ml, 0.72 mmol) in dichloromethane (10 ml). The reaction mixture was stirred at room temperature for 2 hr when the solvent was removed under reduced pressure. The residue was purified by column chromatography on silica gel eluting with a solvent gradient of dichloromethane:methanol (98:2) increasing in polarity to (95:5). This gave the title compound (87 mg) as a powder. MS: 583 (MH$^+$).

$^1$H NMR (CDCl$_3$) δ=7.95 (1H, s), 7.35–7.20 (10H, m), 6.10 (1H, s), 5.95–5.90 (1H, s), 5.75 (1H, s), 5.20 (1H, s), 4.50 (1H, br s), 4.45–4.20 (5H, m), 3.70–3.50 (4H, m), 3.35 (3H, s), 3.15–3.00 (3H, m), 2.90 (3H, s). Analysis: Found C, 56.86, H, 5.97, N, 14.15; C$_{28}$H$_{34}$N$_6$O$_6$S.0.5H$_2$O requires C, 56.84, H, 5.96, N, 14.20%.

Example 38

(2R,3R,4S,5R)-2-{2-[(Benzyloxy)methyl]-6-[(2,2-diphenylethyl)amino]-9H-purin-9-yl}-5-(methoxymethyl)tetrahydro-3,4-furandiol

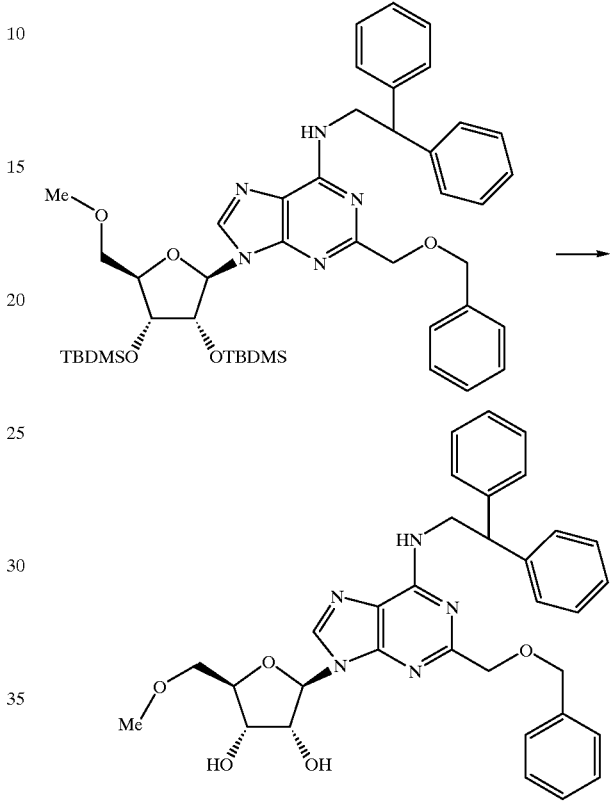

2-[(Benzyloxy)methyl]-9-[(2R,3R,4R,5R)-3,4-bis{[tert-butyl(dimethyl)silyl]oxy}-5-(methoxymethyl)tetrahydro-2-furanyl]-N-(2,2-diphenylethyl)-9H-purin-6-amine (65 mg, 0.08 mmol) (preparation 24) was dissolved in stirred tetrahydrofuran (10 ml) and a 1 molar solution of tetra-n-butylammonium fluoride in tetrahydrofuran (0.5 ml, 0.5 mmol) added. The reaction mixture was stirred at room temperature for 15 min. The solvent was removed under reduced pressure and the residue partitioned between saturated aqueous sodium hydrogen carbonate solution and ethyl acetate. The ethyl acetate layer was separated, washed with brine and dried with anhydrous sodium sulfate. The solvent was removed under reduced pressure to give a residue which was purified by column chromatography on silica gel eluting with a solvent system of ethyl acetate:hexane (3:1) increasing in polarity to ethyl acetate:methanol (97:3). This gave the title compound (25 mg) as a gum. MS: 604 (MNa$^+$).

1H NMR (CDCl$_3$) δ=8.00 (1H, s), 7.45–7.15 (15H, m), 6.50 (1H, br s), 6.05–6.00 (1H, m), 6.00–5.85 (1H, m), 4.70–4.55 (4H, m), 4.45–4.25 (6H, m), 3.65–3.50 (2H, m), 3.30 (3H, s).

Example 39

(2R,3R,4S,5R)-2-{2-[(Benzylsulfonyl)methyl]-6-[(2,2-diphenylethyl)amino]-9H-purin-9-yl}-5-(methoxymethyl)tetrahydro-3,4-furandiol

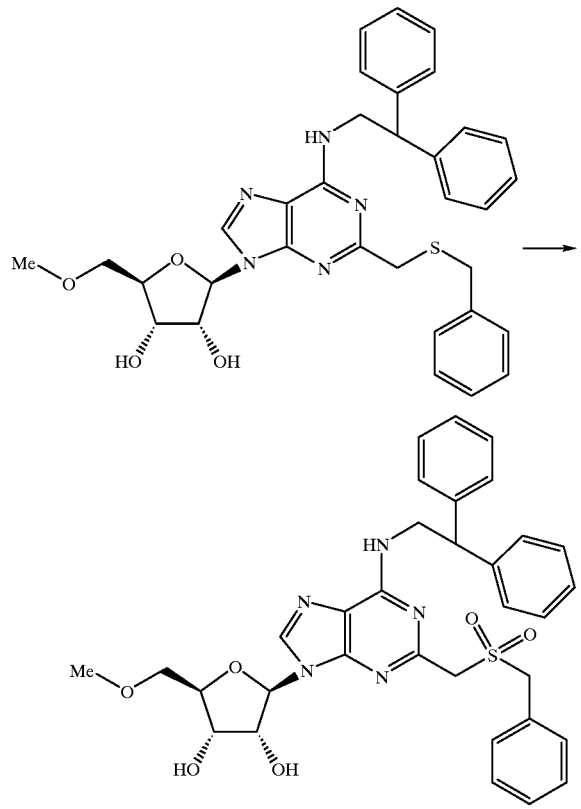

(2R,3R,4S,5R)-2-{2-[(Benzylsulfanyl)methyl]-6-[(2,2-diphenylethyl)amino]-9H-purin-9-yl}-5-(methoxymethyl)tetrahydro-3,4-furandiol (100 mg, 0.17 mmol) (example 76) was dissolved in stirred acetone (3 ml) and solid sodium hydrogen carbonate (100 mg, 1.2 mmol) added. A solution of Oxone (trade mark) (potassium peroxymonosulphate) (410 mg, 0.68 mmol) dissolved in water (2 ml) was then added dropwise to the original solution over the course of 30 min. Dichloromethane (2 ml) was also added and the reaction mixture stirred at room temperature for 60 hr. The reaction mixture was then diluted with ethyl acetate (100 ml) and water (50 ml). The organic layer was separated, dried with anhydrous magnesium sulfate and the solvent removed under reduced pressure to give a residue which was purified by column chromatography on silica gel eluting with a solvent gradient of ethyl acetate:hexane (4:1) increasing in polarity to ethyl acetate:methanol (96:4). This gave the title compound (50 mg) as a gum. MS: 630 (MH$^+$).

$^1$H NMR (CDCl$_3$) δ=8.05 (1H, s), 7.55–7.45 (2H, m), 7.35–7.15 (13H, m), 6.05–5.95 (2H, m), 5.25 (1H, s), 4.55–4.25 (10H, m), 3.70–3.55 (2H, m), 3.45 (1H, s), 3.35 (3H, s).

Example 40

(2R,3R,4S,5R)-2-{2-({[trans-4-(Benzylamino)cyclohexyl]amino}methyl)-6-[(2,2-diphenylethyl)amino]-9H-purin-9-yl}-5-(methoxymethyl)tetrahydro-3,4-furandiol

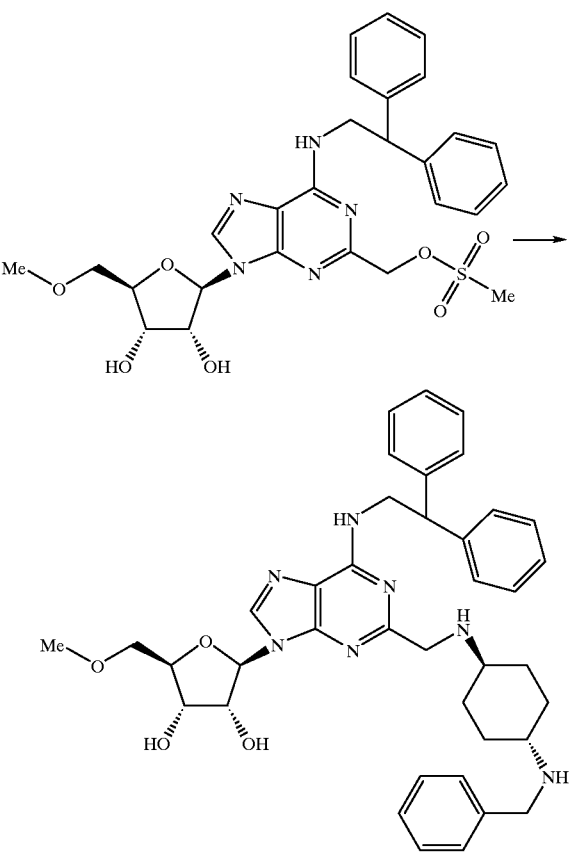

{9-[(2R,3R,4S,5R)-3,4-Dihydroxy-5-(methoxymethyl)tetrahydro-2-furanyl]-[(2,2-diphenylethyl)amino]-9H-purin-2-yl}methyl methanesulfonate (230 mg, 0.4 mmol) (preparation 25), N-(trans-4-aminocyclohexyl)benzylamine (preparation 27) (160 mg, 0.8 mmol) and N-ethyl-N-isopropyl-2-propanamine (100 mg, 0.8 mmol) were dissolved in a stirred mixture of ethanol (3 ml) and dichloromethane (12 ml) and the reaction mixture stirred for 48 hr at room temperature. The solvent was then removed under reduced pressure and the residue partitioned between ethyl acetate and water. The ethyl acetate layer was separated, washed with brine and then dried with anhydrous magnesium sulfate. The solvent was removed under reduced pressure and the residue purified by column chromatography on silica gel eluting with a solvent gradient of dichloromethane:methanol:ammonia (98:2:0.3) increasing in polarity to (90:10:1). The residue after solvent evaporation was triturated with diethyl ether to give the title compound (26 mg) as a solid. MS: 678 (MH$^+$).

$^1$H NMR (CDCl$_3$) δ=7.90 (1H, s), 7.35–7.15 (15H, m), 5.90–5.80 (2H, m), 4.40–4.20 (6H, m), 3.90 (2H, s), 3.80 (2H, s), 3.65–3.55 (2H, m), 3.30 (3H, s), 2.60–2.45 (2H, m), 2.05–1.90 (4H, m) 1.25–1.05 (4H, m).

Example 41

2-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]-N,N-diisopropylacetamide

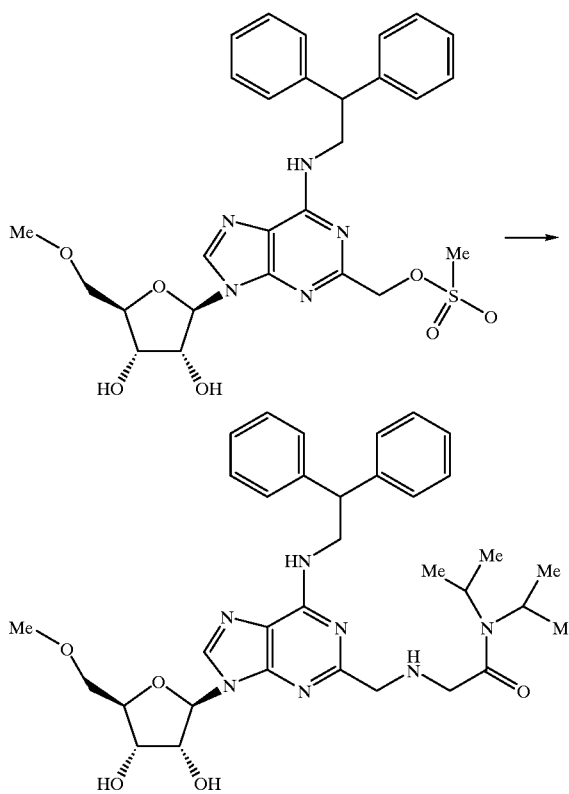

The title compound was prepared by a similar method to example 40 using {9-[(2R,3R,4S,5R)-3,4-dihydroxy-5-(methoxymethyl)tetrahydro-2-furanyl]-6-[(2,2-diphenylethyl)amino]-9H-purin-2-yl}methyl methanesulfonate (preparation 25) (374 mg, 0.66 mmol), 2-amino-N,N-diisopropylacetamide (520 mg, 3.3 mmol) (preparation 22) and N-ethyl-N-isopropyl-2-propanamine (170 mg, 1.32 mmol). The compound was purified by column chromatography on silica gel eluting with a solvent gradient of dichloromethane:methanol:ammonia (95:5:0.5) increasing in polarity to (90:10:1). The solvent was removed under reduced pressure to give a residue which was triturated with diethyl ether to give the title compound (47 mg) as a solid. MS: 632 (MH$^+$).

$^1$H NMR (CDCl$_3$) δ=7.90 (1H, s), 7.35–7.15 (10H, m), 5.95–5.90 (1H, m), 5.70 (1H, s), 4.70–4.65 (1H, m), 4.60–4.55 (1H, m), 4.40–4.25 (4H, m), 4.05–3.85 (3H, m), 3.70–3.65 (1H, m), 3.60–3.45 (5H, m), 3.35 (3H, s), 1.35 (6H, d), 1.20 (6H, d). Analysis: Found C, 62.51, H, 7.03, N, 14.85; C$_{34}$H$_{45}$N$_7$O$_5$.1.1H$_2$O requires C, 62.62, H, 7.24, N, 15.04%.

Example 42

4-{[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]methyl}benzonitrile

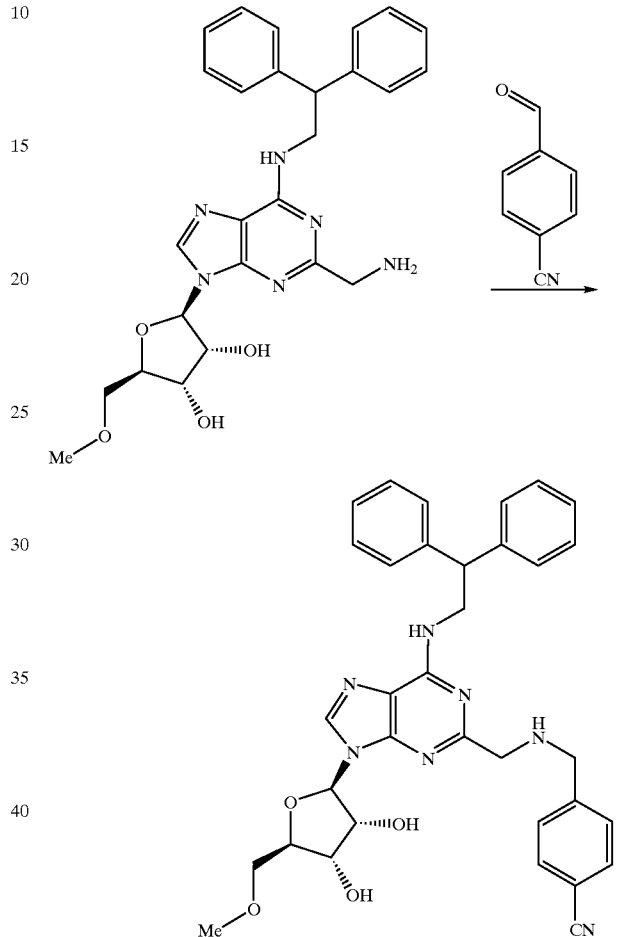

The title compound was prepared by a similar method to example 5 from (2R,3R,4S,5R)-2-{2-(aminomethyl)-6-[(2,2-diphenylethyl)amino}-9H-purin-9-yl}-5-(methoxymethyl)tetrahydro-3,4-furandiol (example 1) (400 mg, 0.82 mmol), sodium triacetoxyborohydride (260 mg, 1.22 mmol) and 4-cyanobenzaldehyde (120 mg, 0.9 mmol) The product was purified by column chromatography on silica gel eluting with a gradient system of dichloromethane:methanol:ammonia (92:7:1) gradually increasing polarity to dichloromethane:methanol:ammonia (90:10:1), which gave the title compound (210 mg) as a foam. MS: 606 (MH$^+$).

$^1$H NMR (CDCl$_3$) δ=7.95 (1H, s), 7.60–7.55 (2H, m), 7.55–7.45 (2H, m), 7.40–7.20 (10H, m), 5.95–5.90 (1H, m), 5.85 (1H, br s), 4.50–4.20 (6H, m), 3.95–3.85 (4H, m), 3.65–3.55 (2H, m), 3.35 (3H, s).

Example 43

(2R,3R,4S,5R)-2-(6-[(2,2-Diphenylethyl)amino]-2-{[2-(1-piperidinyl)ethoxy]methyl}- 9H-purin-9-yl)-5-(methoxymethyl)tetrahydro-3,4-furandiol

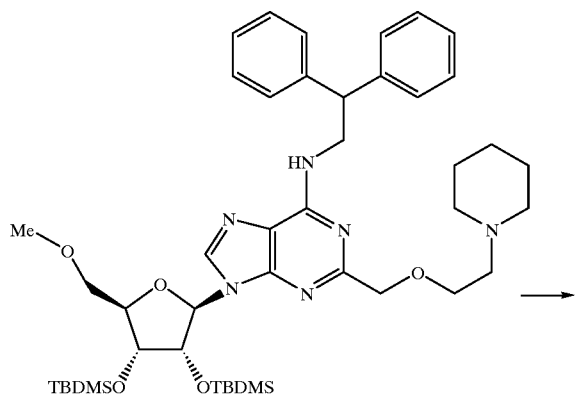

The title compound was prepared by a similar method to example 38 using N-(9-[(2R,3R,4R,5R)-3,4-bis{[tert-butyl(dimethyl)silyl]oxy}-5-(methoxymethyl)tetrahydro-2-furanyl]-2-{[2-(1-piperidinyl)ethoxy]methyl}-9H-purin-6-yl)-N-(2,2-diphenylethyl)amine (100 mg, 0.12 mmol) (preparation 29), and a 1M solution of tetra-n-butylammonium fluoride in tetrahydrofuran (0.5 ml, 0.5 mmol). The compound was purified by column chromatography on silica gel eluting with a solvent system of dichloromethane:methanol:ammonia (95:5:0.5) to give the title compound (22 mg) as a gum. MS: 604 (MH⁺).

¹H NMR (CDCl₃) δ=8.15 (1H, s), 7.35–7.20 (10H, m), 6.15 (1H, s), 5.70 (1H, br s), 4.70–4.55 (2H, m), 4.45–4.15 (6H, m), 3.90–3.75 (3H, m), 3.70–3.60 (1H, m), 3.45 (3H, s), 2.80–2.40 (6H, m), 1.75–1.65 (4H, m), 1.55–1.45 (2H, m).

Example 44

3-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]-N,N-dimethylpropanamide

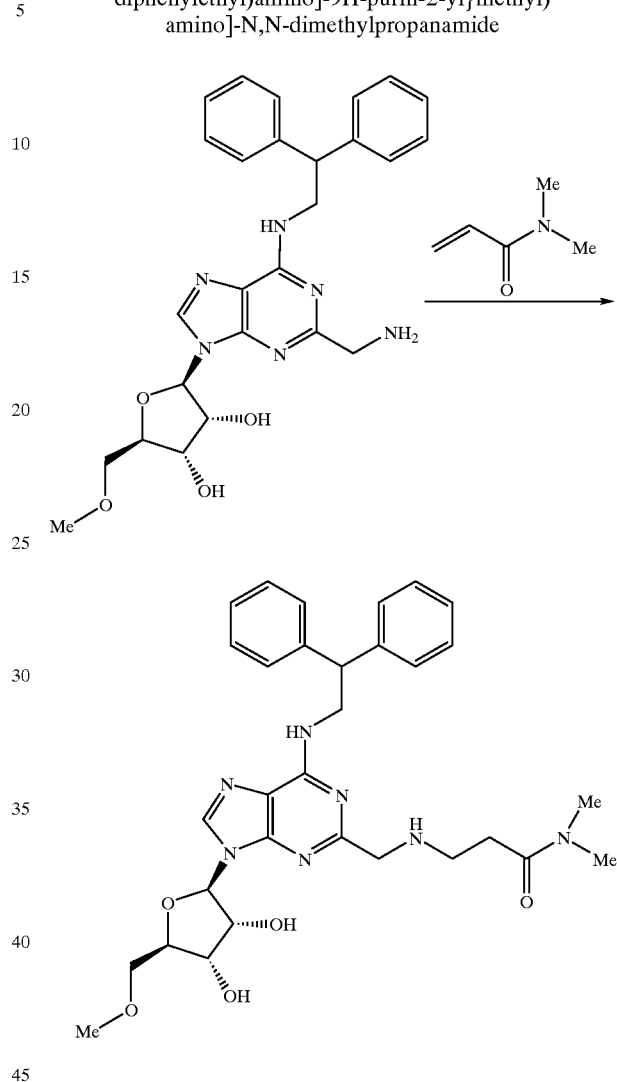

(2R,3R,4S,5R)-2-{2-(Aminomethyl)-6-[(2,2-diphenylethyl)amino]-9H-purin-9-yl}-5-(methoxymethyl)tetrahydro-3,4-furandiol (example 1) (200 mg, 0.39 mmol) was dissolved in stirred methanol (10 ml) and N,N-dimethylacrylamide (40 mg, 0.39 mmol) added. The reaction mixture was stirred for 120 hr at room temperature and then 50° C. for a further 24 hr. More N,N-dimethylacrylamide (9 mg, 0.1 mmol) was added and the reaction mixture was heated at 50° C. for 30 hr. A further portion of N,N-dimethylacrylamide (10 mg, 0.1 mmol) was added and the reaction mixture heated to 50° C. for a further 24 hr. The solvent was then removed under reduced pressure and the residue purified by column chromatography on silica gel eluting with a solvent system of dichloromethane:methanol:ammonia (94:4:0.2) increasing in polarity to (93:7:0.3) to give the title compound (100 mg) as a foam. MS: 590 (MH⁺).

¹H NMR (CDCl₃) δ=7.95 (1H, s), 7.35–7.20 (10H, m), 6.00 (1H, s), 5.60 (1H, br s), 4.65–4.60 (2H, m), 4.40–4.15 (4H, m), 4.05–3.90 (2H, m), 3.80–3.75 (1H, m), 3.65–3.60

(1H, m), 3.40 (3H, s), 3.05 (3H, s), 3.00–2.95 (5H, m), 2.75–2.55 (2H, m).

Example 45

(2R,3R,4S,5R)-2-{6-[(2,2-Diphenylethyl)amino]-2-[(phenylsulfanyl)methyl]-9H-purin-9-yl}-5(methoxymethyl)tetrahydro-3,4-furandiol

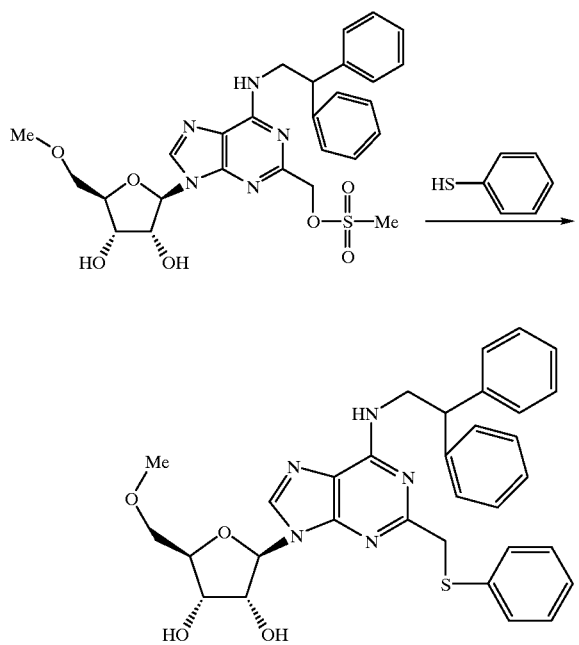

{9-[(2R,3R,4S,5R)-3,4-Dihydroxy-5-(methoxymethyl)tetrahydro-2-furanyl]-6-[(2,2-diphenylethyl)amino]-9H-purin-2-yl}methyl methanesulfonate (400 mg, 0.7 mmol) (Preparation 25), triethylamine (0.2 ml, 1.4 mmol) and thiophenol (100 mg, 0.9 mmol) were dissolved in tetrahydrofuran (3 ml) and the reaction mixture stirred for 24 hr at room temperature. The solvent was then removed under reduced pressure and the residue purified by column chromatography on silica gel eluting with a solvent gradient of dichloromethane:methanol (99:1) increasing in polarity to (95:5). This gave the title compound (150 mg) as a foam. MS: 584 (MH$^+$).

$^1$H NMR (CDCl$_3$) δ=7.90 (1H, s), 7.50–7.40 (2H, m), 7.40–7.10 (13H, m), 5.85–5.70 (2H, m), 4.45–4.20 (9H, m), 3.60–3.50 (2H, m), 3.30 (3H, s), 3.05 (1H, s).

Example 46

(2R,3R,4S,5R)-2-[6-[(2,2-Diphenylethyl)amino]-2-({[2-(1-piperidinyl)ethyl]amino}methyl)-9H-purin-9-yl]-5-(methoxymethyl)tetrahydro-3,4-furandiol

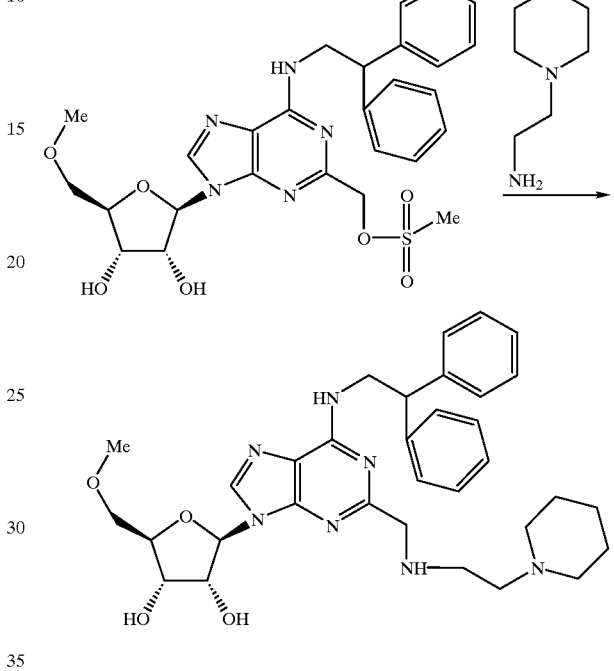

{9-[(2R,3R,4S,5R)-3,4-Dihydroxy-5-(methoxymethyl)tetrahydro-2-furanyl]-6-[(2,2-diphenylethyl)amino]-9H-purin-2-yl}methyl methanesulfonate (150 mg, 0.26 mmol) (Preparation 25) was dissolved in stirred dichloromethane (5 ml) and 2-(1-piperidinyl)ethylamine (0.2 ml, 1.3 mmol) added. The reaction mixture was stirred for 24 hr at room temperature. The solvent was removed from the reaction mixture under reduced pressure and the residue partitioned between dichloromethane (100 ml) and water (50 ml). The organic layer was separated and washed with water (50 ml), followed by removal of solvent under reduced pressure and purification of the residue by column chromatography on silica gel eluting with a solvent gradient of dichloromethane:methanol (95:5) increasing in polarity to dichloromethane:methanol:ammonia (90:10:1). This gave title compound (40 mg) as a gum. MS: 603 (MH$^+$).

$^1$H NMR (CDCl$_3$) δ=8.05 (0.15H, br s), 7.95 (0.85H, s), 7.35–7.15 (10H, m), 6.05–6.00 (1H, m), 5.70 (1H, br s), 4.50–3.85 (10H, m), 3.75–3.70 (1H, m), 3.60–3.55 (1H, m), 3.35 (3H, s), 2.95–2.75 (2H, m), 2.65–2.55 (0.3H, m), 2.55–2.45 (1.7H, m), 2.45–2.30 (4H, m), 1.60–1.55 (4H, m), 1.45–1.35 (2H, m).

Example 47

2-{9-[(2R,3R,4S,5R)-3,4-Dihydroxy-5-(methoxymethyl)tetrahydro-2-furanyl]-6-[(2,2-diphenylethyl)amino]-9H-purin-2-yl}-(4-isopropyl-1-piperidinyl)-1-ethanone

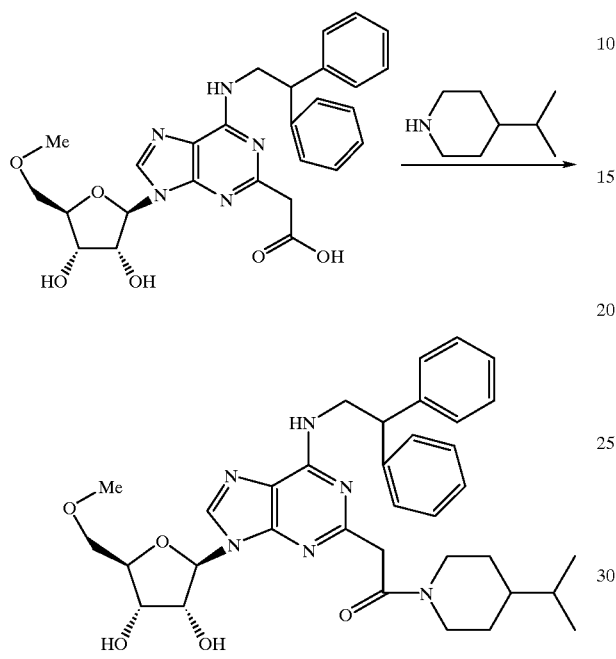

4-Isopropylpiperidine (J. Am. Chem. Soc. 2592, 68, 1946) (105 mg, 0.64 mmol) was added to a stirred solution of 2-{9-[(2R,3R,4S,5R)-3,4-dihydroxy-5-(methoxymethyl)tetrahydro-2-furanyl]-6-[(2,2-diphenylethyl)amino]-9H-purin-2-yl}acetic acid (300 mg, 0.58 mmol) (preparation 51), N,N'-dicyclohexylcarbodiimide (150 mg, 0.64 mmol), 1H-1,2,3-benzotriazol-1-ol monohydrate (110 mg, 0.71 mmol) and N-ethyl-N-isopropyl-2-propanamine (190 mg, 1.47 mmol) in dichloromethane (15 ml). The reaction mixture was stirred for 24 hr at room temperature. The solvent was then removed under reduced pressure, then the residue treated with ethyl acetate and the mixture filtered. The solid was washed with ethyl acetate and the combined ethyl acetate filtrates washed with saturated aqueous sodium hydrogen carbonate solution, brine and dried with anhydrous magnesium sulfate. The solvent was removed under reduced pressure and the residue purified by column chromatography on silica gel eluting with a solvent system of dichloromethane:methanol:ammonia (95:5:0.5) to give some pure and some impure material. The impure material was then re-purified by column chromatography on silica gel eluting with a solvent gradient of ethyl acetate increasing in polarity to ethyl acetate:methanol (95:5). The pure fractions from both columns were combined to give the title compound (285 mg) as a foam. MS: 629 (MH$^+$).

$^1$H NMR (CDCl$_3$) δ=7.90 (1H, br s), 7.35–7.20 (10H, m), 6.20–6.05 (1H, m), 5.95–5.90 (1H, m), 5.70 (1H, br s), 4.70–4.60 (1H, m), 4.45–4.40 (1H, m), 4.40–4.20 (5H, m), 4.05–3.85 (3H, m), 3.60–3.50 (3H, m), 3.35–3.30 (3H, m), 2.95–2.85 (1H, m), 2.55–2.45 (1H, m), 1.70–1.60 (1H, m), 1.60–1.55 (1H, m), 1.40–1.30 (1H, m), 1.20–1.10 (2H, m), 1.05–0.95 (1H, m), 0.85–0.75 (6H, m).

Example 48

(2R,3R,4S,5R)-2-{2-{[2-(Dimethylamino)ethoxy]methyl}-6-[(2,2-diphenylethyl)amino]-9H-purin-9-yl}-5-(methoxymethyl)tetrahydro-3,4-furandiol

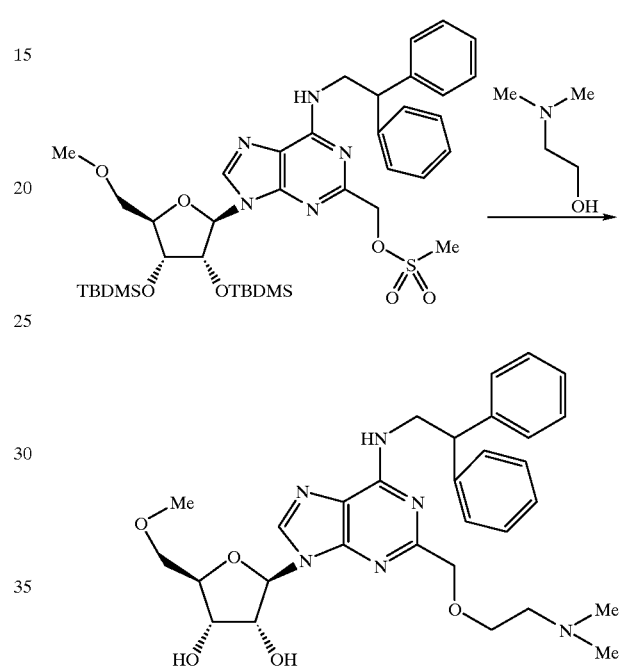

Potassium tert butoxide (112 mg, 1 mmol) was added to a stirred solution of {9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate (200 mg, 0.25 mmol) (preparation 16) and 2-(N,N-dimethylamino)ethanol (0.16 ml, 1.5 mmol) in N,N-dimethylformamide (3 ml). The reaction was quenched by the addition of saturated aqueous ammonium chloride solution (30 ml) after 30 min. The aqueous phase was extracted with dichloromethane (60 ml). The organic phase was separated, dried with anhydrous magnesium sulfate and the solvent removed under reduced pressure to give a residue that was azeotroped with toluene to remove traces of N,N-dimethylformamide. This was then purified by column chromatography on silica gel eluting with a solvent gradient of dichloromethane:methanol:ammonia (94:5:1) increasing in polarity to (84:14:2) to give the title compound (33 mg) as a foam. MS: 563 (MH$^+$).

$^1$H NMR (CDCl$_3$) δ=8.15 (1H, s), 7.35–7.20 (10H, m), 6.10 (1H, s), 5.85 (1H, br s), 4.70–4.55 (2H, m), 4.45–4.20 (8H, m), 3.85–3.80 (1H, m), 3.80–3.75 (2H, m), 3.65–3.60 (1H, m), 3.45 (3H, s), 2.75–2.60 (2H, m), 2.40 (6H, s).

Example 49

(2R,3R,4S,5R)-2-{2-{[(2,6-Dimethyl-3-pyridinyl)amino]methyl}-6-[(2,2-diphenylethyl)amino]-9H-purin-9-yl}-5-(methoxymethyl)tetrahydro-3,4-furandiol

Example 50

N-{4-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]trans-cyclohexyl}methanesulfonamide

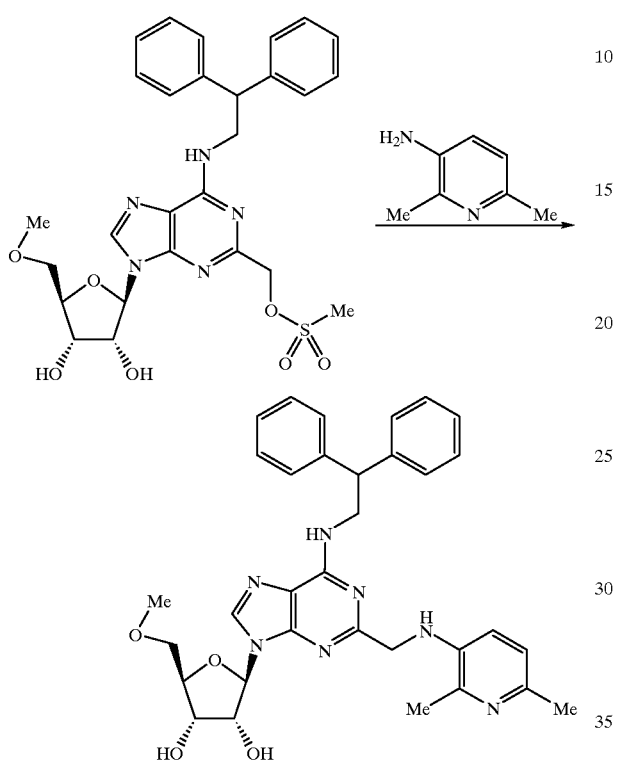

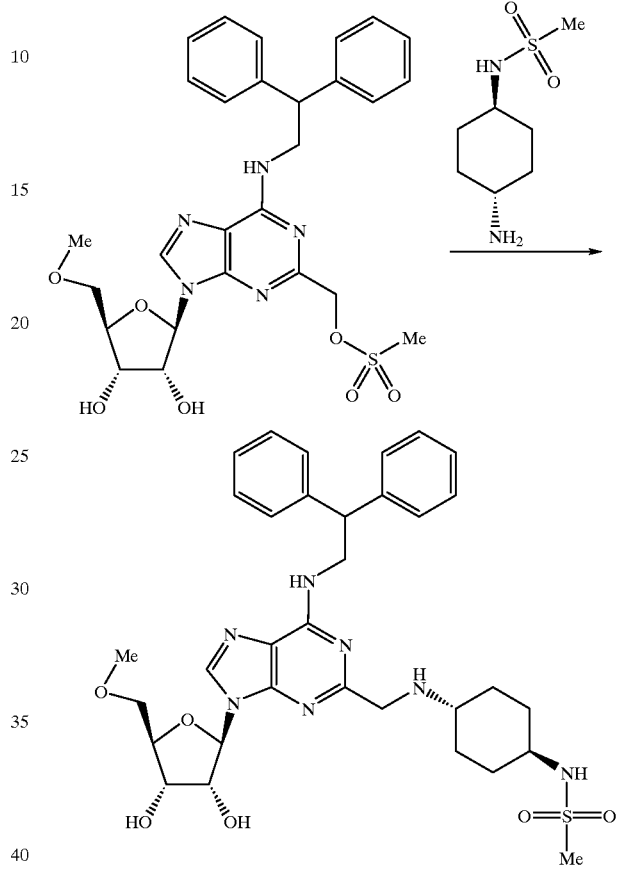

{9-[(2R,3R,4S,5R)-3,4-Dihydroxy-5-(methoxymethyl)tetrahydro-2-furanyl]-6-[(2,2-diphenylethyl)amino]-9H-purin-2-yl}methyl methanesulfonate (preparation 25) (75 mg, 0.13 mmol) was added to a solution of 2,6dimethyl-3-pyridinylamine (22 mg, 0.17 mmol) and triethylamine (0.036 ml, 0.26 mmol) in ethyl acetate (3 ml) and N,N-dimethylformamide (1 ml) in the reaction vessel of a Argonaut Quest 210 machine. The reaction mixture was agitated and heated to 60° C. for 12 hr. More 2,6-dimethyl-3-pyridinylamine (22 mg, 0.17 mmol) and triethylamine (0.036 ml, 0.26 mmol) were added and heating and agitation continued for a further 24 hr. The reaction mixture was then washed with water and the organic phase separated and dried with anhydrous magnesium sulfate. The solvent was removed under reduced pressure to give a residue which was purified by reverse phase HPLC using firstly a Lana $C_8$ (2) column and then a Magellan $C_{18}$ column eluting with 5 mM ammonium acetate in water:2 mM ammonium acetate in acetonitrile (90:10) decreasing in polarity to 5 mM ammonium acetate in water:2 mM ammonium acetate in acetonitrile (10:90) as eluant. This gave the title compound (9 mg) as a gum. MS: 596 (MH$^+$).

$^1$H NMR (CDCl$_3$) δ=7.95 (1H, s), 7.35–7.20 (10H, m), 6.85–6.70 (2H, m), 6.10–6.00 (1H, m), 5.95–5.90 (1H, m), 4.45–4.40 (1H, m), 4.40–4.25 (7H, m), 3.70–3.50 (2H, m), 3.35 (3H, s), 2.40–2.30 (6H, m).

N-(trans-4-Aminocyclohexyl)methanesulfonamide (183 mg, 0.8 mmol) (preparation 33) was added to a stirred solution of {9-[(2R,3R,4S,5R)-3,4-dihydroxy-5-(methoxymethyl)tetrahydro-2-furanyl]-6-[(2,2-diphenylethyl)amino]-9H-purin-2-yl}methyl methanesulfonate (230 mg, 0.4 mmol) (preparation 25) and N-ethyl-N-isopropyl-2-propanamine (210 mg, 1.6 mmol) in ethanol (3 ml) and dichloromethane (12 ml). The reaction mixture was stirred for 48 hr at room temperature. The solvent was then removed under reduced pressure and the residue partitioned between ethyl acetate and water. The ethyl acetate layer was separated, washed with brine and dried with anhydrous magnesium sulfate. The solvent was removed under reduced pressure to give a residue which was purified by column chromatography on silica gel eluting with a solvent gradient of dichloromethane:methanol:ammonia (98:2:0.3) increasing in polarity to (90:10:1) to give the title compound (50 mg) as a foam. MS: 667 (MH$^+$).

$^1$H NMR (CDCl$_3$) Mixture of Rotamers δ=8.00 (0.2H, s), 7.95 (0.8H, s), 7.35–7.20 (10H, m), 6.00–5.85 (2H, m), 4.40–4.20 (8H, m), 4.00–3.85 (2H, m), 3.70–3.55 (2H, m), 3.35 (0.6H, s), 3.30 (2.4H, s), 3.30–3.20 (1H, m), 2.95 (2.4H, s), 2.90 (0.6H, s), 2.65–2.50 (1H, m), 2.10–1.95 (4H, m), 1.35–1.15 (4H, m).

Example 51

(2R,3R,4S,5R)-2-(6-[(2,2-Diphenylethyl)amino]-2-{2-[(2-methoxyethyl)amino]ethyl}-9H-purin-9-yl)-5-(methoxymethyl)tetrahydro-3,4-furandiol

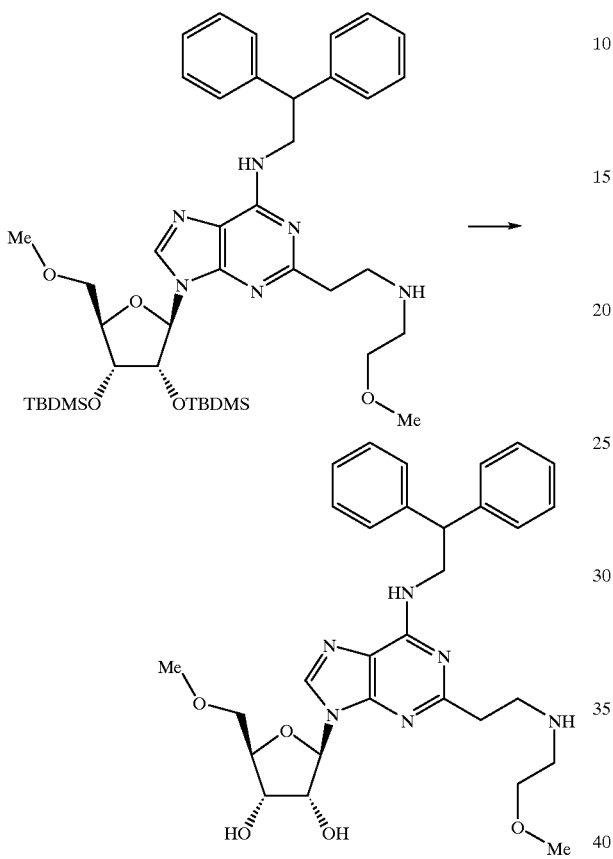

Example 52

(2R,3R,4S,5R)-2-{2-{[Cyclohexyl(methyl)amino]methyl}-6-[(2,2-diphenylethyl)amino]-9H-purin-9-yl}-5-(methoxymethyl)tetrahydro-3,4-furandiol

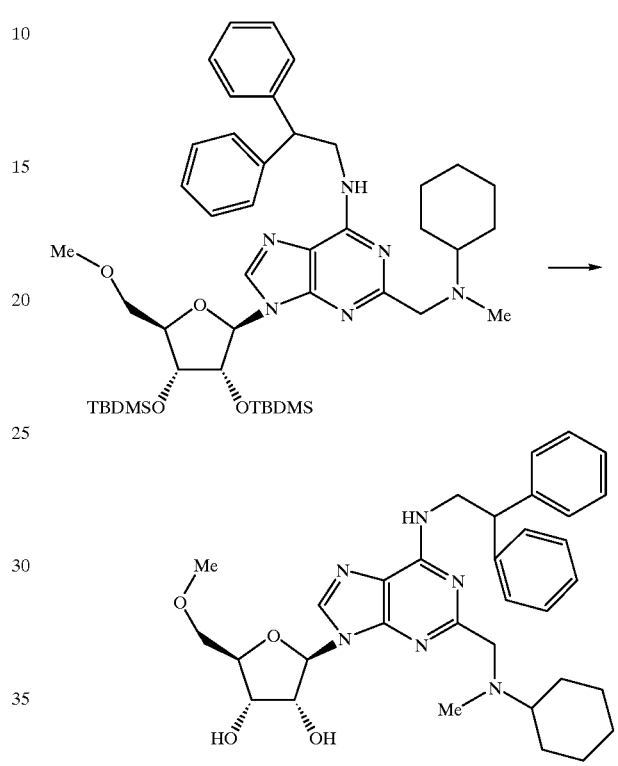

The title compound was prepared by a similar method to example 38 using N-(2-{9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}ethyl)-N-(2-methoxyethyl)amine (150 mg, 0.19 mmol) (preparation 34) and a 1 molar solution of tetra-n-butylammonium fluoride in tetrahydrofuran (0.5 ml, 0.5 mmol). The compound was purified by column chromatography on silica gel eluting with a solvent gradient of dichloromethane:methanol:ammonia (94:6:0.6) increasing in polarity to (90:10:1) to give the title compound (50 mg) as a foam. MS: 563 (MH$^+$).

$^1$H NMR (CDCl$_3$) δ=7.95 (1H, s), 7.35–7.20 (10H, m), 5.95–5.90 (1H, m), 5.65 (1H, br s), 4.50–4.45 (1H, m), 4.40–4.20 (5H, m), 3.70–3.65 (1H, m), 3.60–3.50 (3H, m), 3.35 (3H, s), 3.30 (3H, s), 3.15–3.00 (4H, m), 2.90–2.85 (2H, m). Analysis: Found C, 61.20, H, 6.79, N, 14.07; C$_{30}$H$_{38}$N$_6$O$_5$·1.5H$_2$O requires C, 61.10, H, 7.01, N, 14.25%.

N-(9-[(2R,3R,4R,5R)-3,4-Bis{[tert-butyl(dimethyl)silyl]oxy}-5-(methoxymethyl)tetrahydro-2-furanyl]-2-{[cyclohexyl(methyl)amino]methyl}-9H-purin-6-yl)-N-(2,2-diphenylethyl)amine (133 mg, 0.16 mmol) (preparation 35) was dissolved in stirred tetrahydrofuran (1 ml) and a 1 molar solution of tetra-n-butylammonium fluoride in tetrahydrofuran (1 ml, 1 mmol) was added. The reaction mixture was stirred for 1 hr, then the solvent was removed under reduced pressure. The residue was purified by column chromatography on silica gel eluting with a solvent system of dichloromethane:methanol:ammonia (95:5:0.5) to give the title compound (83 mg) as a foam. MS: 587 (MH$^+$).

$^1$H NMR (CDCl$_3$) δ=7.90 (1H, s), 7.35–7.20 (10H, m), 5.90–5.85 (1H, m), 5.65 (1H, br s), 4.45–4.25 (6H, m), 3.75 (2H, br s), 3.60–3.50 (2H, m), 3.30 (4H, s), 2.55–2.30 (4H, m), 1.95–1.85 (2H, m), 1.80–1.75 (2H, m), 1.65–1.60 (1H, m), 1.35–1.20 (5H, m). Analysis: Found C, 65.65, H, 7.09, N, 13.70; C$_{33}$H$_{42}$N$_6$O$_4$·H$_2$O requires C, 65.54, H, 7.33, N, 13.90%.

Example 53 tert-Butyl 4-[({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)amino]-1-piperidinecarboxylate

Example 54

(2R,3R,4S,5R)-2-[6-[(2,2-Diphenylethyl)amino]-2-({[1-(2-pyridinyl)-4-piperidinyl]amino}methyl)-9H-purin-9-yl]-5-(methoxymethyl)tetrahydro-3,4-furandiol

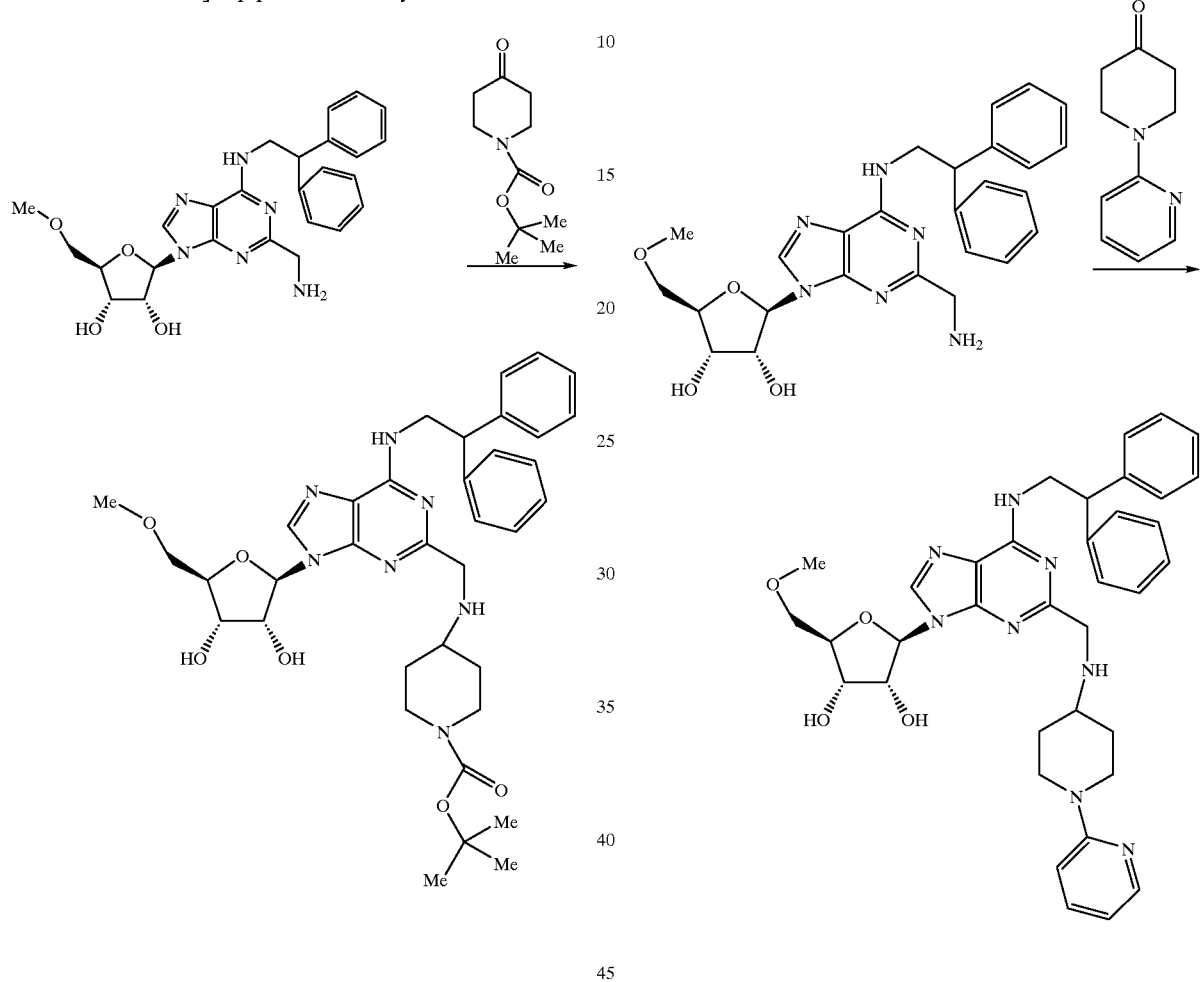

The title compound was prepared by a similar method to example 6 using (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (250 mg, 0.51 mmol), tert-butyl 4-oxo-1-piperidinecarboxylate (100 mg, 0.51 mmol), sodium triacetoxyborohydnde (162 mg, 0.75 mmol) and acetic acid (30 mg, 0.5 mmol) in tetrahydrofuran (20 ml). The product was purified by column chromatography on silica gel eluting with a solvent system of dichloromethane:methanol:ammonia (92.3:6.7:0.33) to give the title compound (260 mg) as a solid. R 0.66 in dichloromethane:methanol:ammonia (80:20:1).

$^1$H NMR (CDCl$_3$) δ=7.90 (1H, s), 7.35–7.20 (10H, m), 5.95–5.85 (2H, m), 4.45–4.25 (6H, m), 4.05–3.95 (2H, m), 3.90 (2H, s), 3.65–3.55 (2H, m), 3.35 (3H, s), 2.85–2.65 (3H, m), 1.90–1.60 (4H plus HOD in CDCl$_3$, m), 1.50 (9H, s), 1.40–1.25 (2H, m).

The title compound was prepared by a similar method to example 6 using (2R,3R,4S,5R)-2-{2-(aminomethyl)-6-[(2,2-diphenylethyl)amino]-9H-purin-9-yl}-5-(methoxymethyl)tetrahydro-3,4-furandiol (example 1) (300 mg, 0.6 mmol), acetic acid (45 mg, 0.72 mmol), sodium triacetoxyborohydride (200 mg, 0.91 mmol) and 1-(2-pyridinyl)-4-piperidinone (120 mg, 0.66 mmol) (preparation 37). The product was purified by column chromatography on silica gel eluting with a solvent system of dichloromethane:methanol:ammonia (96:4:0.2) increasing in polarity to (93:7:0.3) to give the title compound (199 mg) as a foam. MS: 653 (MH$^+$).

$^1$H NMR (CDCl$_3$) δ=8.20–8.15 (1H, m), 7.90 (1H, s), 7.50–7.40 (1H, s), 7.35–7.15 (10H, m), 6.65–6.60 (1H, m), 6.60–6.55 (1H, m), 5.95–5.90 (1H, m), 5.80 (1H, br s), 4.40–4.15 (8H, m), 3.95 (2H, s), 3.65–3.50 (2H, m), 3.30 (3H, s), 2.95–2.75 (3H, m), 2.00–1.90 (2H, m), 1.55–1.40 (2H, m). Analysis: Found C, 64.30, H, 6.38, N, 16.45; C$_{36}$H$_{42}$N$_8$O$_4$.0.5H$_2$O.0.14CH$_2$Cl$_2$ requires C, 64.60, H, 6.49, N, 16.68%.

Example 55 tert-Butyl {9-[(2R,3R,4S,5R)-3,4-dihydroxy-5-(methoxymethyl)tetrahydro-2-furanyl]-6-[(2,2-diphenylethyl)amino]-9H-purin-2-yl}methylcarbamate

Example 56

4-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]tetrahydro-1λ$^6$-thiopyran-1,1(2H)-dione

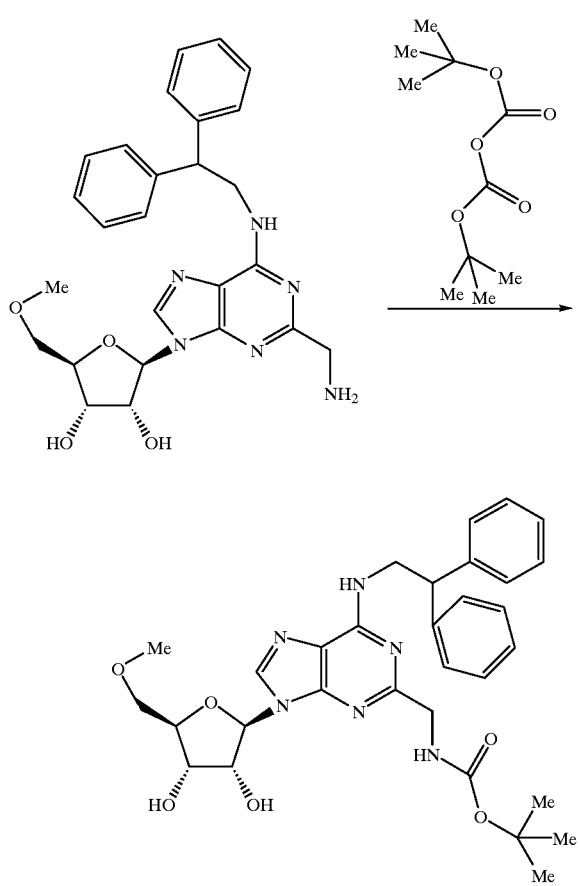

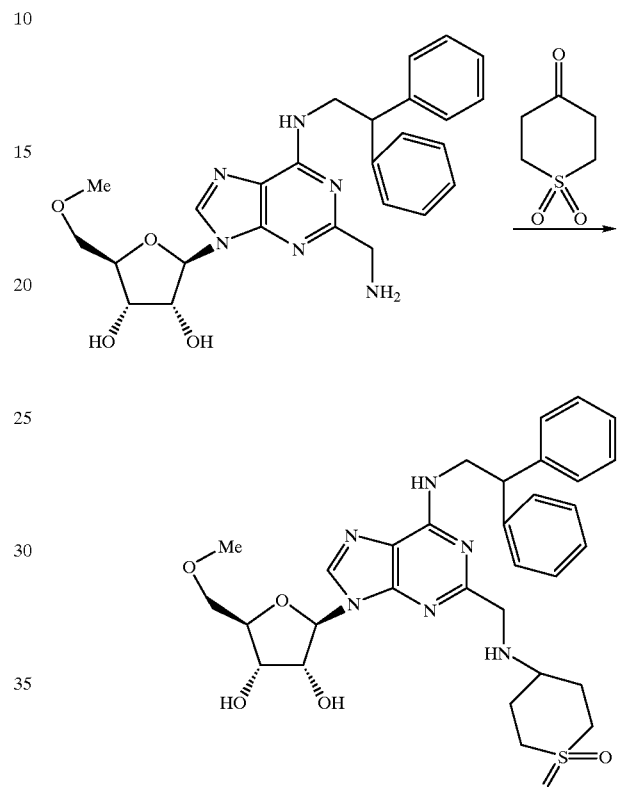

Di-tert-butyl dicarbonate (88 mg, 0.4 mmol) was added to a stirred solution of (2R,3R,4S,5R)-2-{2-(aminomethyl)-6-[(2,2-diphenylethyl)amino]-9H-purin-9-yl}-5-(methoxymethyl)-tetrahydro-3,4-furandiol (example 1) (210 mg, 0.43 mmol) in tetrahydrofuran (20 ml). The reaction mixture was stirred at room temperature for 30 min, the solvent was removed under reduced pressure and the residue purified by column chromatography on silica gel eluting with a solvent system of dichloromethane:methanol (95:5) to give the title compound (210 mg) as a foam. MS: 591 (MH$^+$).

$^1$H NMR (CDCl$_3$) δ=7.90 (1H, s), 7.35–7.20 (10H, m), 5.95–5.80 (2H, m), 5.50 (1H, br s), 4.50–4.25 (8H, m), 3.65–3.55 (2H, m), 3.35 (3H, s), 3.20 (1H, br s), 1.45 (9H, s). Analysis: Found C, 61.12, H, 6.30, N, 13.65; C$_{31}$H$_{37}$N$_6$O$_6$·0.5H$_2$O·0.1CH$_2$Cl$_2$ requires C, 61.52, H, 6.34, N, 13.84%.

The title compound was prepared by a similar method to example 6 using (2R,3R,4S,5R)-2-{2-(aminomethyl)-6-[(2,2-diphenylethyl)amino}-9H-purin-9-yl}-5-(methoxymethyl)tetrahydro-3,4-furandiol (305 mg, 0.60 mmol) (example 1), tetrahydro-1λ$^6$-thiopyran-1,1,4-trione (88 mg, 0.60 mmol), sodium triacetoxyborohydrde (200 mg, 0.90 mmol) and acetic acid (43 mg, 0.72 mmol). The product was purified by column chromatography on silica gel eluting with a solvent system of dichloromethane:methanol:ammonia (96:4:0.2) to give the title compound (160 mg) as a foam. MS: 623 (MH$^+$).

$^1$H NMR (CDCl$_3$) δ=7.90 (1H, s), 7.35–7.20 (10H, m), 6.10 (1H, br s), 5.95–5.90 (1H, m), 5.85 (1H, br s), 4.50–4.45 (1H, m), 4.40–4.20 (5H, m), 3.85 (2H, br s), 3.65–3.55 (2H, m), 3.40–3.30 (5H, m), 3.20 (1H, br s), 3.00–2.95 (1H, m), 2.85–2.75 (2H, m), 2.30–2.20 (2H, m), 2.15–2.00 (2H, m). Analysis: Found C, 56.26, H, 5.79, N, 12.48; C$_{31}$H$_{38}$N$_6$O$_6$S·0.5CH$_2$Cl$_2$ requires C, 55.98, H, 5.91, N, 12.63%.

Example 57

{4-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]-1-piperidinyl}(phenyl)methanone

Example 58

N-(2-{9-[(2R,3R,4S,5R)-3,4-Dihydroxy-5-(methoxymethyl)tetrahydro-2-furanyl]-6-[(2,2-diphenylethyl)amino]-9H-purin-2-yl}ethyl)benzenesulfonamide

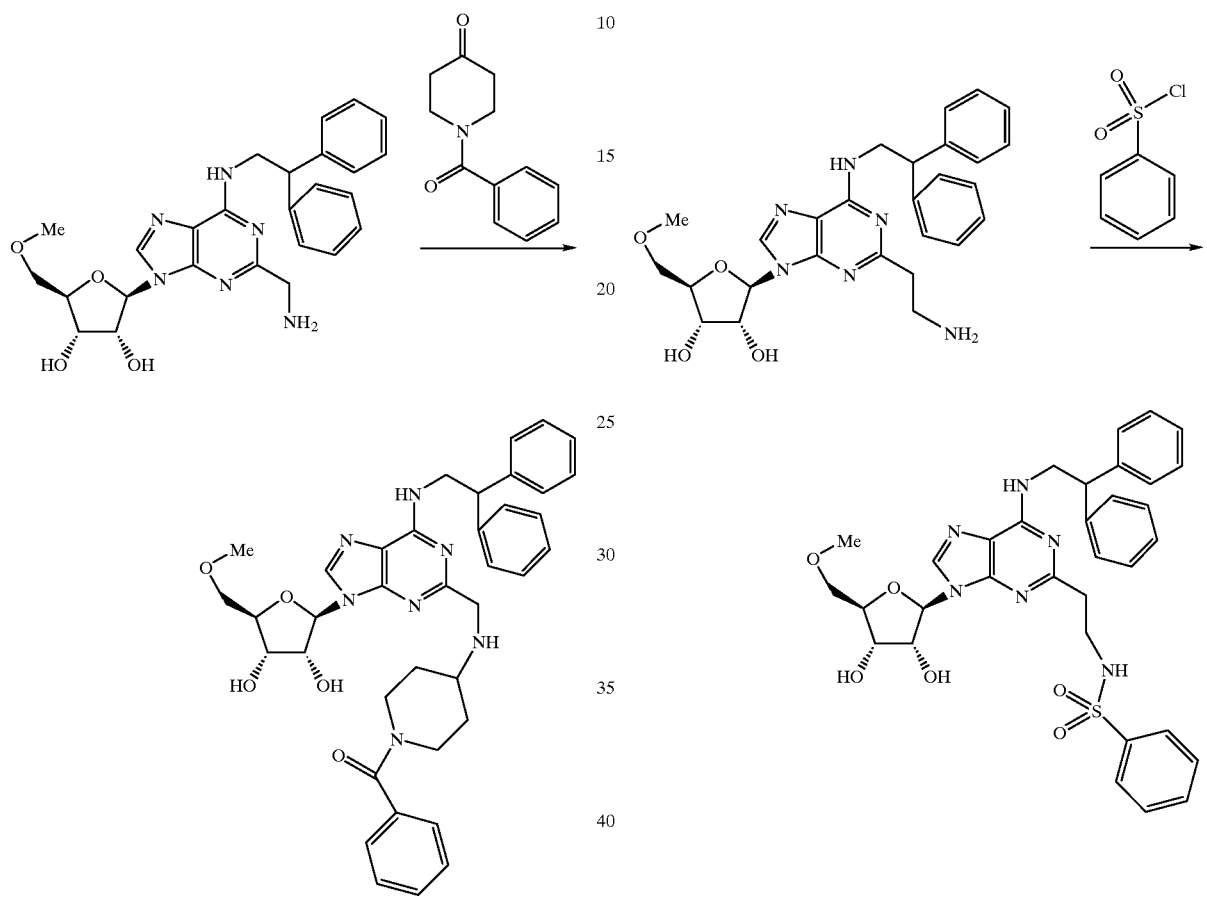

The title compound was prepared by a similar method to example 6 using (2R,3R,4S,5R)-2-{2-(aminomethyl)-6-[(2,2-diphenylethyl)amino)-9H-purin-9-yl}-5-(methoxymethyl)tetrahydro-3,4-furandiol (310 mg, 0.63 mmol) (example 1), 1-benzoyl-4-piperidinone (128 mg, 0.63 mmol), sodium triacetoxyborohydride (200 mg, 0.90 mmol) and acetic acid (45 mg, 0.74 mmol). The product was purified by column chromatography on silica gel eluting with a solvent system of dichloromethane:methanol:ammonia (92:8:0.4) to give the title compound (300 mg) as an oil. MS: 679 (MH$^+$).

$^1$H NMR (CDCl$_3$) δ=7.90 (1H, s), 7.45–7.20 (15H, m), 5.95–5.90 (2H, m), 4.50 (1H, br s), 4.45–4.20 (6H, m), 3.90 (2H, s), 3.70 (1H, br s), 3.65–3.55 (2H, m), 3.35 (3H, s), 3.05–2.80 (3H, m), 2.10–1.80 (2H, m), 1.50–1.30 (2H, m). Analysis: Found C, 64.35, H, 6.16, N, 13.63; C$_{38}$H$_{43}$N$_7$O$_5$.0.5H$_2$O.0.33CH$_2$Cl$_2$ requires C, 64.38, H, 6.29, N, 13.71%.

The title compound was prepared by a similar method to example 3 using (2R,3R,4S,5R)-2-{2-(2-aminoethyl)-6-[(2,2-diphenylethyl)amino]-9H-purin-9-yl}-5-(methoxymethyl)-tetrahydro-3,4-furandiol (example 11) (200 mg, 0.40 mmol), phenylsulfonyl chloride (70 mg, 0.40 mmol) and triethylamine (0.15 ml, 1.08 mmol). The compound was purified by column chromatography on silica gel eluting with a solvent system of dichloromethane:methanol (95:5) to give the title compound (145 mg) as a powder. MS: 645 (MH$^+$).

$^1$H NMR (CDCl$_3$) δ=7.90 (1H, s), 7.80–7.75 (2H, m), 7.50–7.45 (1H, m), 7.45–7.20 (12H, m), 6.45–6.35 (1H, m), 5.95–5.90 (1H, m), 5.75 (1H, br s), 5.30 (1H, s), 4.50–4.15 (6H, m), 3.70–3.55 (2H, m), 3.45–3.35 (6H, m), 3.15–3.10 (1H, m), 3.00–2.85 (2H, m). Analysis: Found C, 60.77, H, 5.66, N, 12.96; C$_{33}$H$_{36}$N$_6$O$_6$S.0.25H$_2$O requires C, 61.05, H, 5.67, N, 12.94%.

Example 59

N-(tert-Butyl)-3-[({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)amino]propanamide

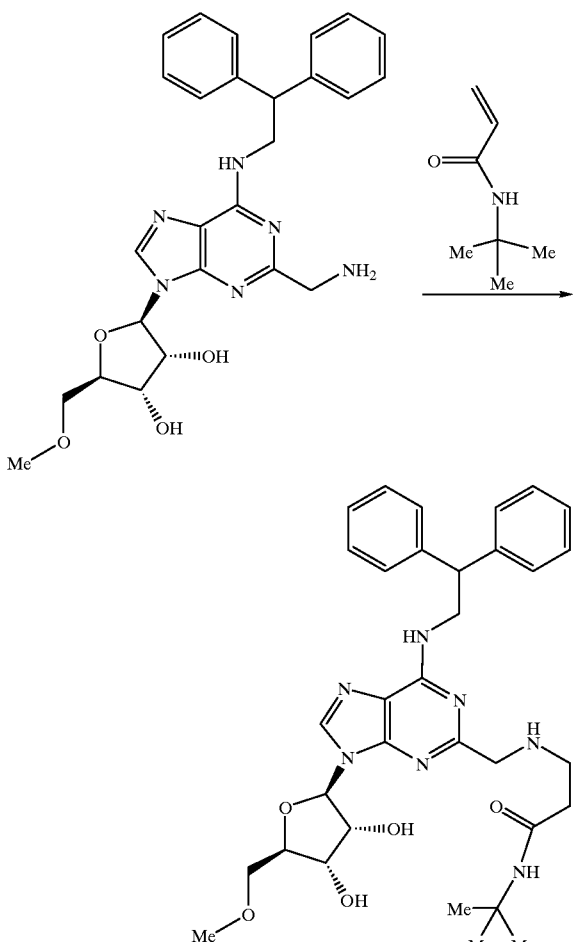

(2R,3R,4S,5R)-2-{2-(Aminomethyl)-6-[(2,2-diphenylethyl)amino}-9H-purin-9-yl]-5-(methoxymethyl)tetrahydro-3,4-furandiol (example 1) (250 mg, 0.48 mmol) was dissolved in stirred methanol (10 ml) and N-(tert-butyl) acrylamide (62 mg, 0.48 mmol) added. The reaction mixture was stirred for 24 hr at room temperature and then heated at reflux for 120 hr, at which time all solvent had evaporated. The residual reaction mixture was dissolved in dichloromethane and the solvent removed under reduced pressure, this procedure was repeated twice more and then the product purified by column chromatography on silica gel eluting with a solvent gradient of dichloromethane:methanol:ammonia (94:4:0.2) increasing in polarity to (93:7:0.3) to give the title compound (143 mg) as a foam. MS: 618 (MH+).

$^1$H NMR (CDCl$_3$) δ=7.95 (1H, s), 7.35–7.20 (10H, m), 6.15 (1H, br s), 5.95 (1H, s), 5.65 (1H, br s), 4.60–4.50 (2H, m), 4.40–4.25 (4H, m), 4.00–3.85 (2H, m), 3.75–3.70 (1H, m), 3.65–3.60 (1H, m), 3.35 (3H, s), 3.00–2.90 (1H, m), 2.90–2.80 (1H, m), 2.40–2.35 (2H, m), 1.30 (9H, s).

Example 60

(2R,3R,4S,5R)-2-{2-{2-[(1-Benzhydryl-3-azetidinyl)amino]ethyl}-6-[(2,2-diphenylethyl)amino]-9H-purin-9-yl}-5-(methoxymethyl)tetrahydro-3,4-furandiol

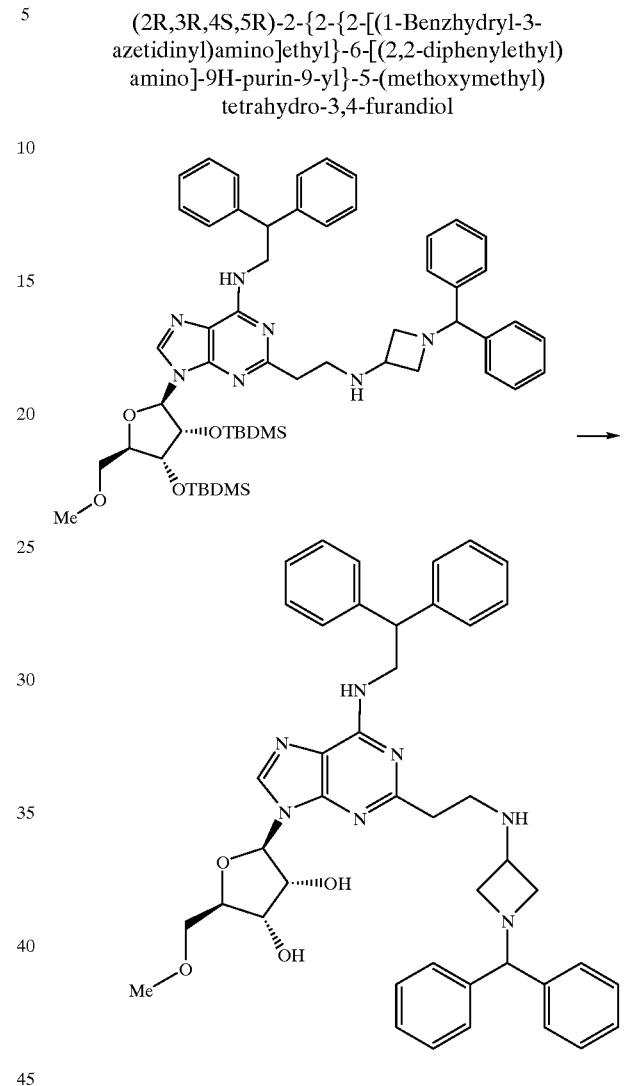

The title compound was prepared by a similar method to example 38 using 2-{2-[(1-benzhydryl-3-azetidinyl)amino]ethyl}-9-[(2R,3R,4R,5R)-3,4-bis{[tert-butyl(dimethyl)silyl]oxy}-5-(methoxymethyl)tetrahydro-2-furanyl]-N-(2,2-diphenylethyl)-9H-purin-6-amine (130 mg, 0.14 mmol) (preparation 38) and a 1 molar solution of tetra-n-butylammonium fluoride in tetrahydrofuran (0.4 ml, 0.4 mmol). The compound was purified by column chromatography on silica gel eluting with a solvent gradient of dichloromethane:methanol:ammonia (95:5:0.5) increasing in polarity to (90:10:1) to give the title compound (70 mg) as a foam. MS: 726 (MH+).

$^1$H NMR (CDCl$_3$) δ=7.95 (1H, s), 7.40–7.15 (20H, m), 5.95–5.90 (1H, m), 5.70 (1H, s), 4.50–4.45 (1H, m), 4.40–4.30 (5H, m), 4.25 (1H, br s), 3.65–3.45 (6H, m), 3.30 (3H, s), 3.00–2.90 (4H, m), 2.90–2.80 (2H, m).

Example 61

(2R,3R,4S,5R)-2-(6-[(2,2-Diphenylethyl)amino]-2-{[(2-methoxyethyl)amino]methyl}-9H-purin-9-yl)-5-(methoxymethyl)tetrahydro-3,4-furandiol

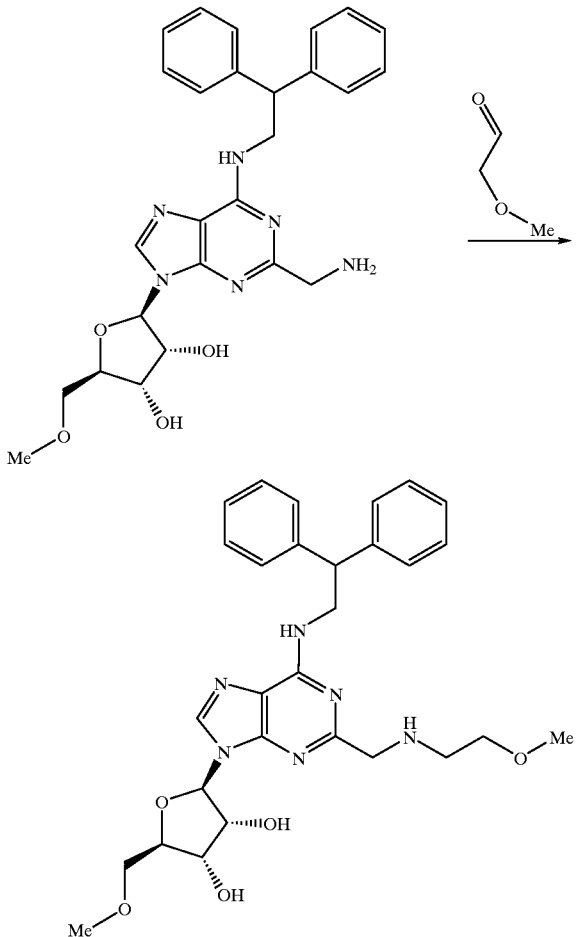

The title compound was prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (320 mg, 0.63 mmol) (example 1), 2-methoxyacetaldehyde (53 mg, 0.63 mmol) and sodium triacetoxyborohydride (210 mg, 0.95 mmol) in tetrahydrofuran (22 ml). The product was purified by column chromatography on silica gel eluting with a solvent system of dichloromethane:methanol:ammonia (92:8:0.4) to give the title compound (125 mg) as a foam. MS: 548 (MH$^+$).

$^1$H NMR (CDCl$_3$+trace of trfluoroacetic acid) δ=9.10 (1H, s), 7.35–7.20 (10H, m), 6.25–6.00 (1H, m), 4.70–4.25 (8H, m), 3.90–3.85 (1H, m), 3.85–3.75 (2H, m), 3.65–3.60 (1H, m), 3.50–3.45 (2H, m), 3.45–3.35 (6H, m).

Example 62

(2R,3R,4S,5R)-2-{6-[(2,2-Diphenylethyl)amino]-2-[(isobutylamino)methyl]-9H-purin-9-yl}-5-(methoxymethyl)tetrahydro-3,4-furandiol and

Example 63

(2R,3R,4S,5R)-2-{2-[(Diisobutylamino)methyl]-6-[(2,2-diphenylethyl)amino]-9H-purin-9-yl}-5-(methoxymethyl)tetrahydro-3,4-furandiol

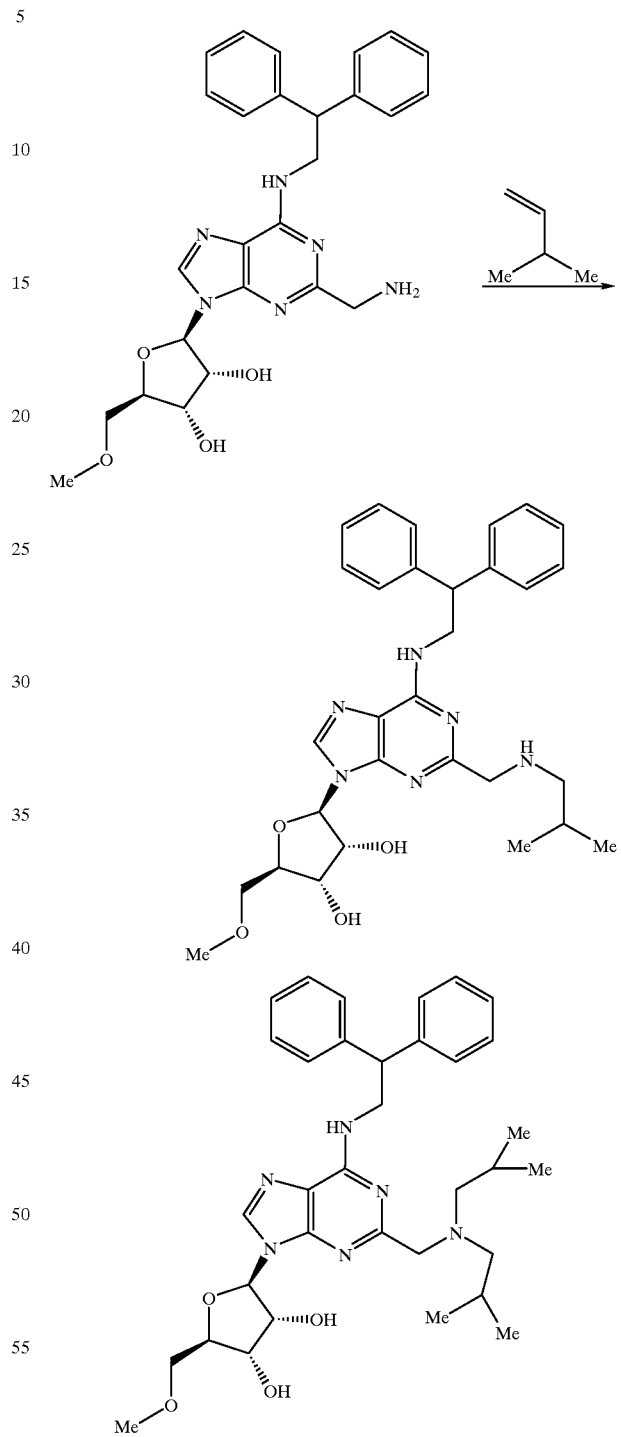

The title compounds were prepared by a similar method to example 5 using (2R,3R,4S,5R)-2-{2-(aminomethyl)-6-[(2,2-diphenylethyl)amino}-9H-purin-9-yl}-5-(methoxymethyl)tetrahydro-3,4-furandiol (310 mg, 0.6 mmol) (example 1), 2-methylpropanal (44 mg, 0.6 mmol) and sodium triacetoxyborohydride (200 mg, 0.9 mmol). The products were purified by column chromatography on silica gel eluting with a solvent system of dichloromethane:methanol:ammonia (96:4:0.4) to give example 63 (45 mg) as a foam and then with a solvent system of dichloromethane:methanol:ammonia (93:7:0.3) to give example 62 (144 mg) as a foam.

Data for EXAMPLE 62:

MS: 547 (MH+).

$^1$H NMR (CDCl$_3$) δ=7.90 (1H, s), 7.35–7.20 (10H, m), 6.00–5.95 (1H, m), 5.80 (1H, br s), 4.40–4.25 (6H, m), 3.90 (2H, s), 3.65–3.55 (2H, m), 3.35 (3H, s), 2.55–2.45 (2H, m), 1.90–1.80 (1H, m), 1.00–0.90 (6H, m). Analysis: Found C, 64.13, H, 6.93, N, 14.83; $C_{30}H_{38}N_6O_4 \cdot 0.5H_2O \cdot 0.17CH_2Cl_2$ requires C, 64.08, H, 6.92, N, 14.86%.

Data for EXAMPLE 63:

MS: 603 (MH+).

$^1$H NMR (CDCl$_3$) δ=7.90 (1H, s), 7.35–7.20 (10H, m), 6.90 (1H, s), 5.85–5.75 (2H, m), 4.45–4.25 (6H, m), 3.70 (2H, s), 3.60–3.50 (2H, m), 3.30 (4H, s), 2.35–2.25 (4H, m), 1.85–1.75 (2H, m), 0.90–0.80 (12H, m).

Example 64

(2R,3R,4S,5R)-2-(6-[(2,2-Diphenylethyl)amino]-2-{[(1-methyl-4-piperidinyl)amino]methyl}- 9H-purin-9-yl)-5-(hydroxymethyl)tetrahydro-3,4-furandiol

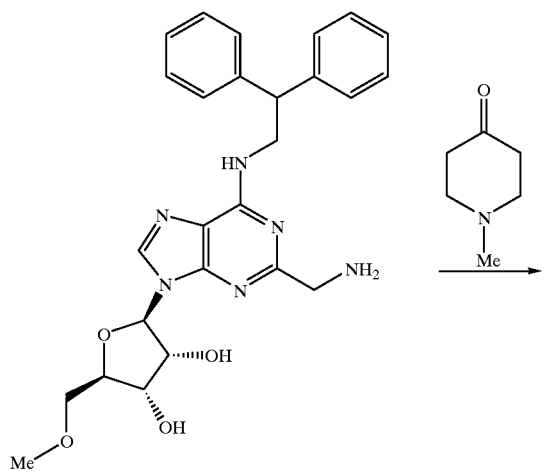

Sodium triacetoxyborohydride (162 mg, 0.76 mmol) was added to a stirred solution of (2R,3R,4S,5R)-2-{2-(aminomethyl)-6-[(2,2-diphenylethyl)amino]-9H-purin-9-yl}-5-(methoxymethyl)tetrahydro-3,4-furandiol (250 mg, 0.51 mmol) (example 1), 1-methyl-4-piperidinone (52 mg, 0.46 mmol) and acetic acid (30 mg, 0.5 mmol) in tetrahydrofuran (20 ml). The reaction mixture was stirred for 24 hr at room temperature. The solvent was then removed under reduced pressure and the residue partitioned between dichloromethane (30 ml) and saturated aqueous sodium hydrogen carbonate solution (10 ml). The aqueous layer was discarded and the organic layer washed with water (10 ml), separated and the solvent removed under reduced pressure to give a residue which was purified by column chromatography on silica gel eluting with a solvent gradient of dichloromethane:methanol:ammonia (90:10:0.5) increasing in polarity to (85:15:0.75) to give the title compound contaminated with example 1. The mixture was treated with diethyl ether (10 ml) and the solid filtered off. This solid was treated with diethyl ether (10 ml) and then filtered. The diethyl ether filtrates were combined and the solvent removed under reduced pressure to give the title compound (60 mg) as a solid. MS: 589 (MH+).

$^1$H NMR (CDCl$_3$) δ=7.90 (1H, s), 7.35–7.20 (10H, m), 5.95–5.90 (1H, m), 5.85 (1H, br s), 4.45–4.20 (6H, m), 3.90 (2H, s), 3.70–3.55 (2H, m), 3.35 (3H, s), 2.90–2.80 (2H, m), 2.60–2.50 (1H, partially obscured by OH peaks, m), 2.30 (3H, s), 2.10–2.00 (2H, m), 2.00–1.80 (2H, m), 1.65–1.50 (2H, m).

Example 65

(2R,3R,4S,5R)-2-(6-[(2,2-Diphenylethyl)amino]-2-{[(4-methoxycyclohexyl)amino]methyl}- 9H-purin-9-yl)-5-(methoxymethyl)tetrahydro-3,4-furandiol

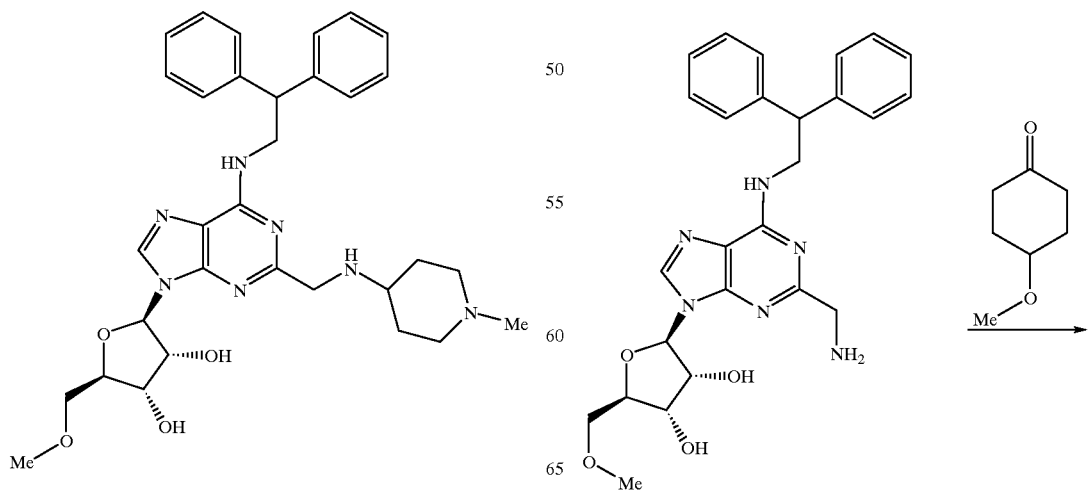

81
-continued

82

Example 66

(2R,3R,4S,5R)-2-{2-{[4,4-Dimethylcyclohexyl)amino]methyl}-6-[(2,2-diphenylethyl)amino]-9H-purin-9-yl}-5-(methoxymethyl)tetrahydro-3,4-furandiol

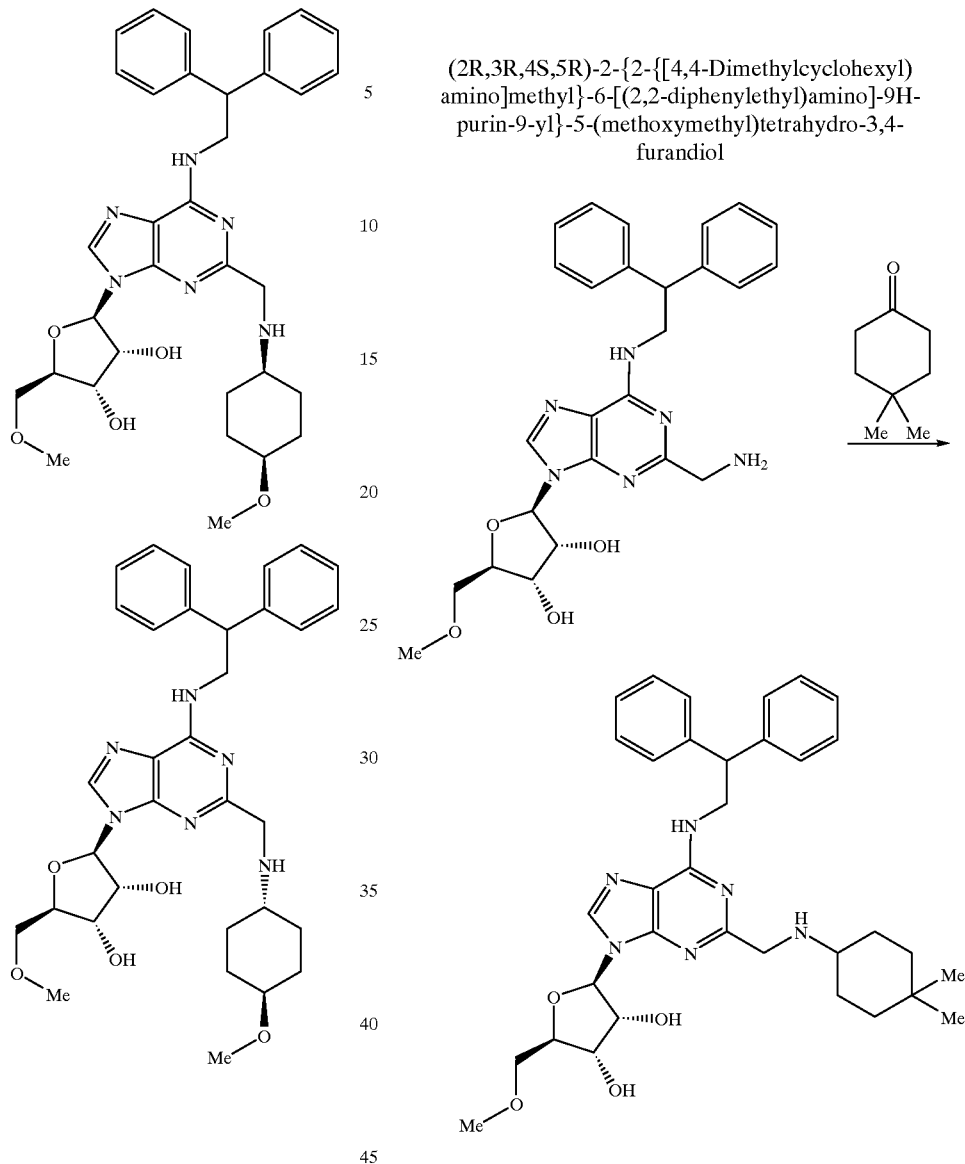

The title compound was prepared by a similar method to example 6 using (2R,3R,4S,5R)-2-{2-(aminomethyl)-6-[(2,2-diphenylethyl)amino}-9H-purin-9-yl}-5-(methoxymethyl)tetrahydro-3,4-furandiol (400 mg, 0.78 mmol) (example 1), sodium triacetoxyborohydride (260 mg, 1.23 mmol), 4-methoxycyclohexanone (100 mg, 0.78 mmol) (J. Am. Chem. Soc. 5190, 89, 1967) and acetic acid (56 mg, 0.93 mmol) in tetrahydrofuran (30 ml). The product was purified by column chromatography on silica gel eluting with a solvent system of dichloromethane:methanol:ammonia (94:6:0.3) to give the title compound as a mixture (3:2 ratio) of diastereoisomers (118 mg) as a foam. MS: 603 (MH$^+$).

$^1$H NMR (CDCl$_3$) δ=7.85 (1H, s), 7.35–7.15 (10H, m), 5.95–5.90 (1H, m), 5.75 (1H, br s), 4.40–4.20 (6H, m), 3.95–3.85 (2H, m), 3.65–3.50 (2H, m), 3.35–3.25 (6.6H, m), 3.15–3.10 (0.4H, m), 2.70–2.60 (0.6H, m), 2.60–2.50 (0.4H, m), 2.05–1.95 (2H, m), 1.90–1.80 (1H, m), 1.65–1.50 (2H, m), 1.50–1.40 (1H, m), 1.25–1.15 (2H, m).

The title compound was prepared by a similar method to example 6 using (2R,3R,4S,5R)-2-{2-(aminomethyl)-6-[(2,2-diphenylethyl)amino}-9H-purin-9-yl}-5-(methoxymethyl)tetrahydro-3,4-furandiol (330 mg, 0.67 mmol) (example 1), sodium triacetoxyborohydride (214 mg, 1.01 mmol), 4,4-dimethylcyclohexanone (85 mg, 0.67 mmol) and acetic acid (48 mg, 0.80 mmol) in tetrahydrofuran (30 ml). The product was purified by column chromatography on silica gel eluting with a solvent system of dichloromethane:methanol:ammonia (92:8:0.4) to give the title compound (216 mg) as a foam. MS: 602 (MH$^+$).

$^1$H NMR (CDCl$_3$) δ=7.90 (1H, s), 7.35–7.20 (10H, m), 5.95–5.90 (1H, m), 5.80 (1H, br s), 4.40–4.20 (6H, m), 3.90 (2H, br s), 3.65–3.55 (2H, m), 3.30 (3H, s), 2.50–2.45 (1H, m), 1.80–1.70 (2H, m), 1.45–1.30 (4H, m), 1.20–1.10 (2H, m), 0.90–0.85 (6H, m). Analysis: Found C, 65.94, H, 7.12, N, 13.77; C$_{34}$H$_{44}$N$_6$O$_4$.0.5H$_2$O.0.17H$_2$O requires C, 65.77, H, 7.32, N, 13.46%.

Example 67

(2R,3R,4S,5R)-2-{2-{2-[(Cyclopropylmethyl)amino]ethyl}-6-[(2,2-diphenylethyl)amino]-9H-purin-9-yl}-5-(methoxymethyl)tetrahydro-3,4-furandiol

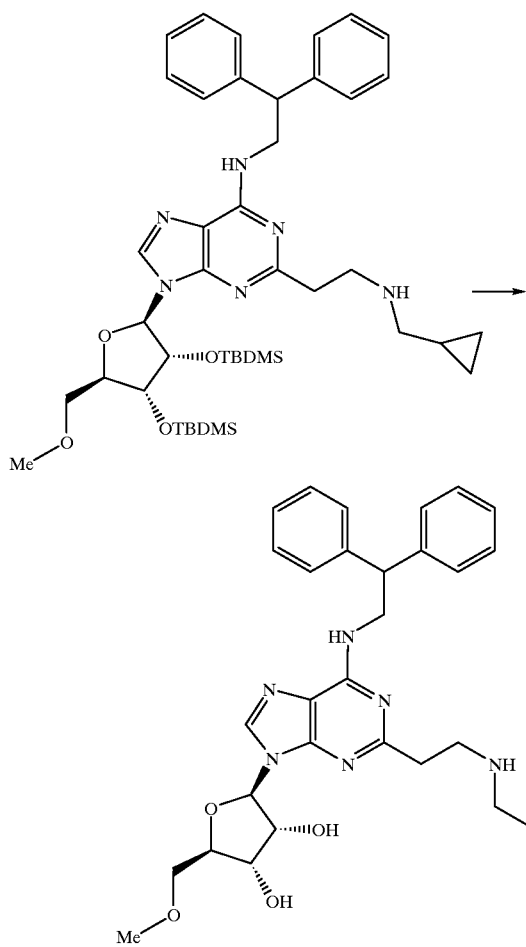

The title compound was prepared by a similar method to example 38 using the compound of preparation 40 (190 mg, 0.21 mmol) and tetra-n-butyl ammonium fluoride (0.6 ml of a 1 molar solution in tetrahydrofuran, 0.6 mmol) in tetrahydrofuran (3 ml). The product was purified by column chromatography on silica gel eluting with a solvent system of dichloromethane:methanol (97:3) increasing in polarity to dichloromethane:methanol:ammonia (95:5:0.5) to give the title compound (79 mg) as a foam. MS: 559 (MH+).

$^1$H NMR (CDCl$_3$) δ=7.90 (1H, s), 7.35–7.15 (10H, m), 5.95–5.90 (1H, m), 5.70 (1H, br s), 4.45–4.40 (1H, m), 4.40–4.30 (4H, m), 4.30–4.20 (1H, br s), 3.65–3.55 (2H, m), 3.40–3.30 (3H, s), 3.10–3.00 (2H, m), 3.00–2.95 (2H, m), 2.50–2.45 (2H, m), 0.95–0.85 (1H, m), 0.45–0.40 (2H, m), 0.10–0.05 (2H, m).

Example 68

(2R,3R,4S,5R)-2-[2-[(Cyclohexylamino)methyl]-6-(phenethylamino)-9H-purin-9-yl]-5-(methoxymethyl)tetrahydro-3,4-furandiol

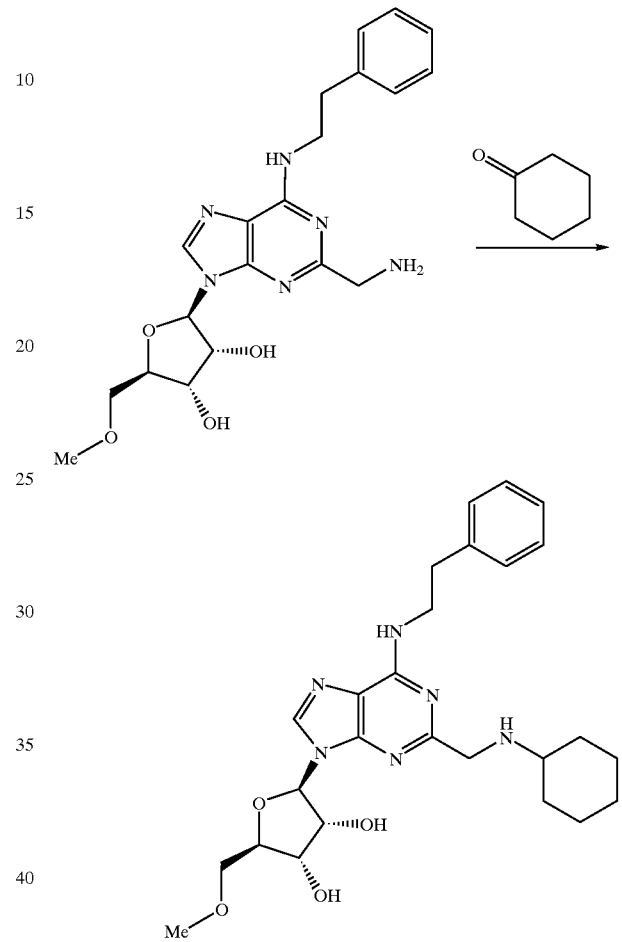

Sodium triacetoxyborohydride (154 mg, 0.72 mmol) was added to a stirred solution of (2R,3R,4S,5R)-2-[2-(aminomethyl)-6-(phenethylamino)-9H-purin-9-yl]-5-(methoxymethyl)tetrahydro-3,4-furandiol (200 mg, 0.48 mmol) (preparation 48), acetic acid (30 mg, 0.48 mmol) and cyclohexanone (45 mg, 0.46 mmol). The reaction mixture was stirred for 24 hr at room temperature and the solvent then removed under reduced pressure. The residue was then azeotroped with dichloromethane before purification by column chromatography on silica gel eluting with a solvent system of dichloromethane:methanol:ammonia (93:7:0.3) to give the title compound (110 mg) as a viscous oil. MS: 497 (MH+).

$^1$H NMR (CDCl$_3$) δ=7.95 (1H, s), 7.35–7.20 (5H, m), 6.00–5.90 (2H, m), 4.40–4.30 (2H, m), 4.30–4.20 (1H, m), 4.00–3.85 (4H, m), 3.70–3.55 (2H, m), 3.35 (3H, s), 3.00–2.90 (2H, m), 2.60–2.50 (1H, m), 2.00–1.90 (2H, m), 1.80–1.60 (3H, m), 1.35–1.15 (5H, m). Analysis: Found C, 60.88, H, 7.15, N, 16.25; C$_{26}$H$_{36}$N$_6$O$_4$·0.25H$_2$O·0.17CH$_2$Cl$_2$ requires C, 60.91, H, 7.19, N, 16.31%.

Example 69

N-{[9-[(2R,3R,4S,5R)-3,4-Dihydroxy-5-(methoxymethyl)tetrahydro-2-furanyl]-6(phenethylamino)-9H-purin-2-yl]methyl}benzenesulfonamide

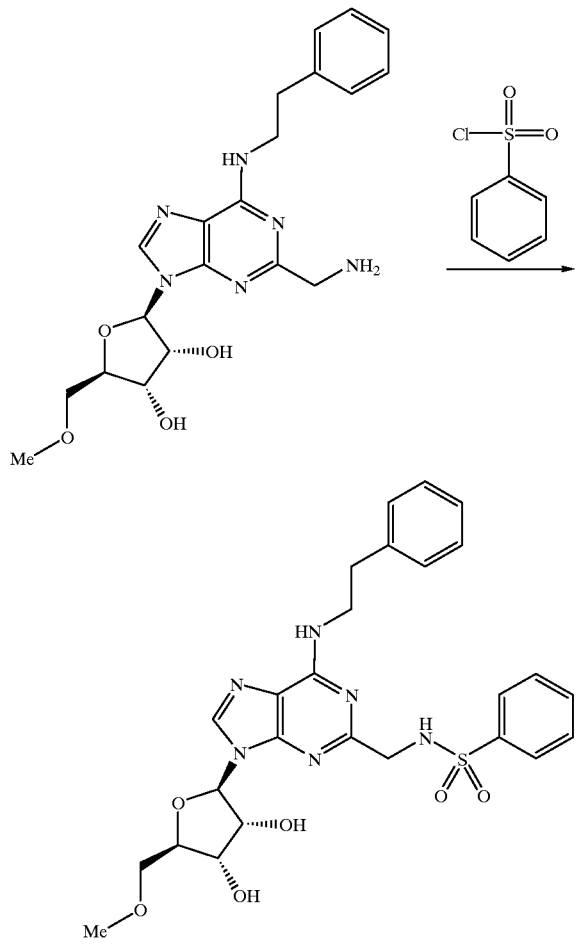

Phenylsulfonylchloride (57 mg, 0.33 mmol) was added to a stirred solution of (2R,3R,4S,5R)-2-[2-(aminomethyl)-6-(phenethylamino)-9H-purin-9-yl]-5-(methoxymethyl)tetrahydro-3,4-furandiol (150 mg, 0.36 mmol) (preparation 48) and triethylamine (110 mg, 1.08 mmol) in tetrahydrofuran (24 ml). The reaction mixture was stirred for 30 min at room temperature and then the solvent was removed under reduced pressure. The residue was azeotroped with dichloromethane and then purified by column chromatography on silica gel eluting with a solvent system of dichloromethane:methanol (95:5) to give the title compound (180 mg) as a foam. MS: 577 (MNa$^+$).

$^1$H NMR (CDCl$_3$) δ=7.95 (1H, s), 7.90–7.80 (2H, m), 7.50–7.20 (8H, m), 5.95–5.85 (3H, m), 5.20 (1H, br s), 4.50 (2H, s), 4.35–4.30 (1H, m), 4.30–4.20 (2H, m), 3.85 (2H, br s), 3.70–3.55 (2H, m), 3.35 (3H, s), 3.25 (1H, s), 3.00–2.90 (2H, m). Analysis: Found C, 55.06, H, 5.41, N, 14.63; C$_{26}$H$_{30}$N$_6$O$_6$S.0.17CH$_2$Cl$_2$ requires C, 55.26, H, 5.37, N, 14.77%.

Example 70

(2R,3R,4S,5R)-2-{2-[2-(Benzylamino)ethyl]-6-[(2,2-diphenylethyl)amino]-9H-purin-9-yl}-5-(methoxymethyl)tetrahydro-3,4-furandiol

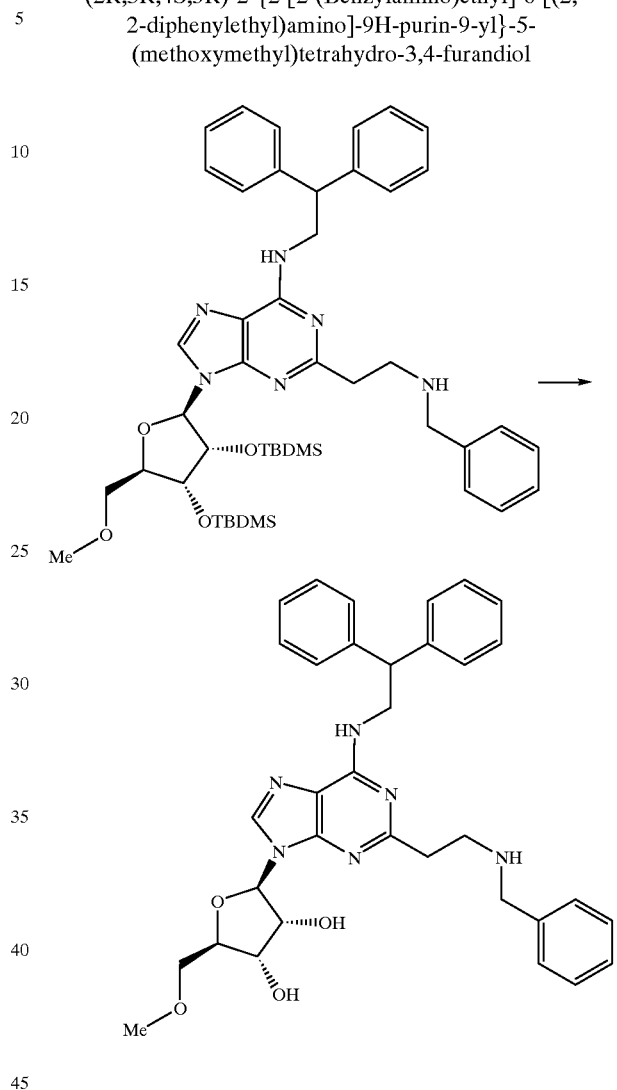

The title compound was prepared by a similar method to example 38 using N-benzyl-N-(2-{9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}ethyl)amine (360 mg, 0.44 mmol) (preparation 39) and a 1 molar solution of tetrabutylammonium fluoride in tetrahydrofuran (0.92 ml, 0.92 mmol). The product was purified by column chromatography on silica gel eluting with a solvent gradient of dichloromethane:methanol (93:7) increasing in polarity to dichloromethane:methanol:ammonia (90:10:1) to give the title compound (162 mg) as a foam. MS: 596 (MH$^+$).

$^1$H NMR (CDCl$_3$) δ=7.90 (1H, s), 7.40–7.20 (15H, m), 5.95–5.90 (1H, m), 5.75 (1H, br s), 4.40–4.15 (6H, m), 3.80 (2H, s), 3.65–3.50 (2H, m), 3.35 (3H, s), 3.15–2.95 (4H, m). Analysis: Found C, 67.22, H, 6.57, N, 13.75; C$_{34}$H$_{38}$N$_6$O$_4$.0.67H$_2$O requires C, 67.33, H, 6.48, N, 13.86%.

Example 71

6-[({9-[(2R,3R,4S,5R)-3,4-Dihydroxy-5-(methoxymethyl)tetrahydro-2-furanyl]-6-[(2,2-diphenylethyl)amino]-9H-purin-2-yl}methyl)amino]nicotinonitrile

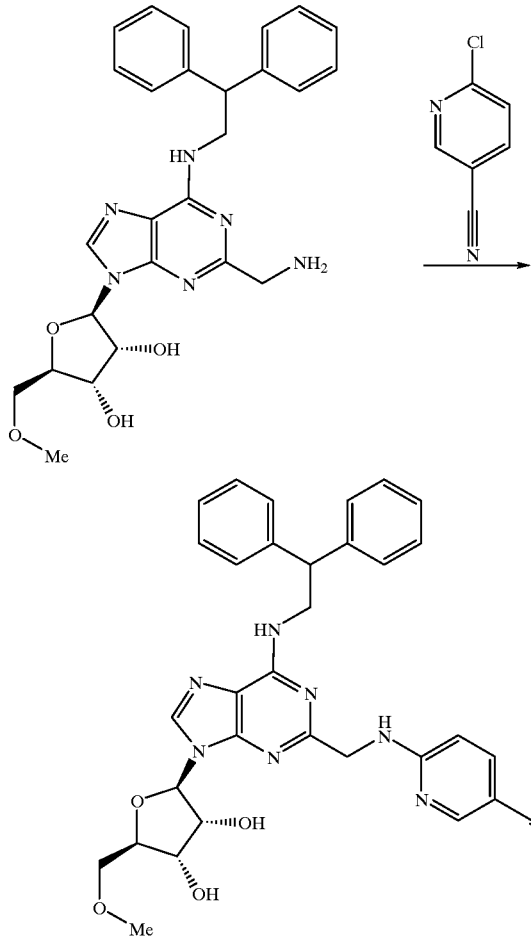

Example 72

(2R,3R,4S,5R)-2-(6-[(2,2-Diphenylethyl)amino]-2-{[(1-methyl-4-piperidinyl)oxy]methyl}-9H-purin-9-yl)-5-(methoxymethyl)tetrahydro-3,4-furandiol

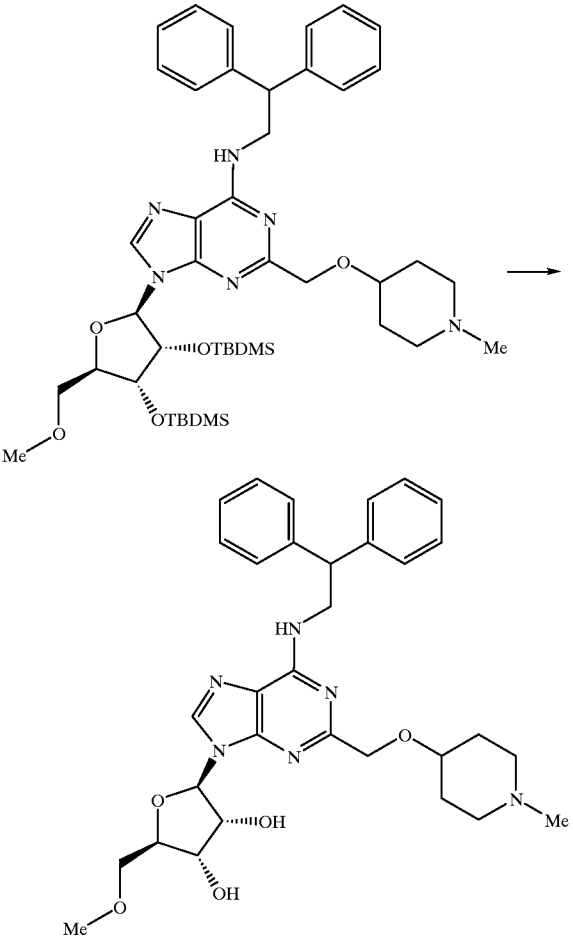

6-Chloronicotinonitrile (78 mg, 0.56 mmol) was added to a stirred solution of (2R,3R,4S,5R)-2-{2-(aminomethyl)-6-[(2,2-diphenylethyl)amino}-9H-purin-9-yl}-5-(methoxymethyl)tetrahydro-3,4-furandiol (250 mg, 0.51 mmol) (example 1) and triethylamine (57 mg, 0.56 mmol) in N-methyl-2-pyrrolidinone (10 ml). The reaction mixture was heated at 120° C. for 24 hr. The reaction mixture was then partitioned between water and ethyl acetate. The ethyl acetate layer was separated, washed with brine and dried with anhydrous magnesium sulfate. The solvent was removed under reduced pressure to give a residue that was purified by column chromatography on silica gel eluting with a solvent system of dichloromethane:methanol (95:5) to give material that was still impure and hence re-purified by column chromatography on silica gel eluting with a solvent system of ethyl acetate:methanol (90:10) to give a yellow oil which was treated with pentane to give the title compound (47 mg) as a solid. MS: 594 (MH+).

$^1$H NMR (CDCl$_3$) δ=8.40 (1H, s), 7.95 (1H, s), 7.55–7.50 (1H, m), 7.40–7.20 (10H, m), 6.45–6.40 (1H, m), 6.25 (2H, br s), 5.95–5.85 (2H, m), 5.50 (1H, br s), 4.60 (2H, br s), 4.50–4.45 (1H, m), 4.40–4.20 (5H, m), 3.65–3.55 (2H, m), 3.35 (3H, s), 3.10 (1H, s).

N-(9-[(2R,3R,4R,5R)-3,4-Bis{[tert-butyl(dimethyl)silyl]oxy}-5-(methoxymethyl)tetrahydro-2-furanyl]-2-{[(1-methyl-4-piperidinyl)oxy]methyl}-9H-purin-6-yl)-N-(2,2-diphenylethyl)amine (68 mg, 0.08 mmol) (preparation 49) was dissolved in stirred tetrahydrofuran (10 ml), then acetic acid (0.2 ml, 0.2 mmol) added followed by a 1 molar solution of tetra-n-butylammonium fluoride (0.2 ml, 0.2 mmol). The reaction mixture was stirred at room temperature for 1 hr and then more 1 molar solution of tetrabutylammonium fluoride (0.5 ml, 0.5 mmol) was added. The reaction mixture was stirred for another hour and then partitioned between saturated aqueous sodium hydrogen carbonate solution and ethyl acetate. The ethyl acetate phase was separated, washed with brine and dried with anhydrous sodium sulfate. This was evaporated to give a clear oil which was purified by column chromatography on silica gel eluting with a solvent gradient of dichloromethane:methanol (95:5) increasing in polarity to dichloromethane:methanol:ammonia (90:10:1) to give the title compound (20 mg) as a foam. MS: 589 (MH+).

$^1$H NMR (CDCl$_3$) δ=7.95 (1H, s), 7.40–7.15 (10H, m), 5.95–5.90 (1H, m), 5.85 (1H, br s), 4.60 (2H, s), 4.50–4.20 (8H, m), 3.65–3.55 (3H, m), 3.30 (3H, s), 2.85–2.75 (2H, m), 2.30–2.15 (5H, m), 2.05–1.95 (2H, m), 1.85–1.75 (2H, m).

Example 73

N-Benzyl-{9-[(2R,3R,4S,5R)-3,4-dihydroxy-5-(methoxymethyl)tetrahydro-2-furanyl]-6-[(2,2-diphenylethyl)amino]-9H-purin-2-yl}methanesulphonamide

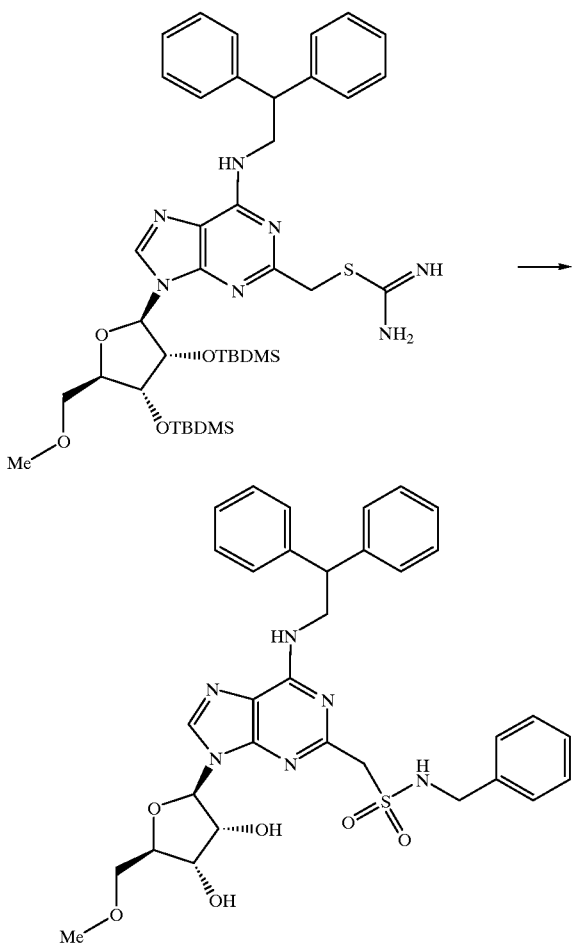

A stirred suspension of 2-({[amino(imino)methyl]sulfanyl}methyl)-9-[(2R,3R,4S,5R)-3,4-dihydroxy-5-(methoxymethyl)tetrahydro-2-furanyl]-6-[(2,2-diphenylethyl)amino]-9H-purine (0.75 g, 0.97 mmol) (preparation 50) in ice cold water (20 ml) was saturated with chlorine gas and stirred for 1 hr. The orange coloured solid that formed was filtered off, washed with water and dried. The solid was dissolved in stirred dichloromethane (20 ml), then triethylamine (190 mg, 1.93 mmol) and benzylamine (0.16 ml, 1.44 mmol) were added. The reaction mixture was stirred for 24 hr at room temperature and then the solvent was removed under reduced pressure to give a residue that was partitioned between diethyl ether and 1 molar hydrochloric acid. The diethyl ether layer was separated and the solvent removed under reduced pressure to give a solid which was dissolved in stirred tetrahydrofuran and a 1 molar solution of tetrabutylammonium fluoride in tetrahydrofuran (2.9 ml, 2.9 mmol) added. The solution was stirred for 1 hr and then the solvent removed under reduced pressure to give a residue that was partitioned between ethyl acetate and saturated aqueous sodium hydrogen carbonate solution. The ethyl acetate layer was separated and the solvent removed under reduced pressure to give a residue that was purified by column chromatography on silica gel eluting with a solvent gradient of dichloromethane:methanol (97:3) increasing in polarity to dichloromethane:methanol:ammonia (95:5:0.5). This material was re-purified by column chromatography on silica gel eluting with a solvent gradient of dichloromethane:methanol (97:3) increasing in polarity to dichloromethane:methanol:ammonia (95:5:0.5) to give the title compound (63 mg) as a foam. MS: 645 (MH$^+$).

$^1$H NMR (CDCl$_3$) δ=7.85 (1H, br s), 7.40–7.20 (15H, m), 5.90–5.80 (2H, m), 4.55–4.15 (10H, m), 3.65–3.50 (2H, m), 3.35–3.25 (3H, m). Analysis: Found C, 60.37, H, 5.62, N, 12.74; $C_{33}H_{36}N_6O_6S \cdot 0.66H_2O$ requires C, 60.36, H, 5.68, N, 12.80%.

Example 74

Potassium N-({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)-2-methyl-1-propanesulfamate

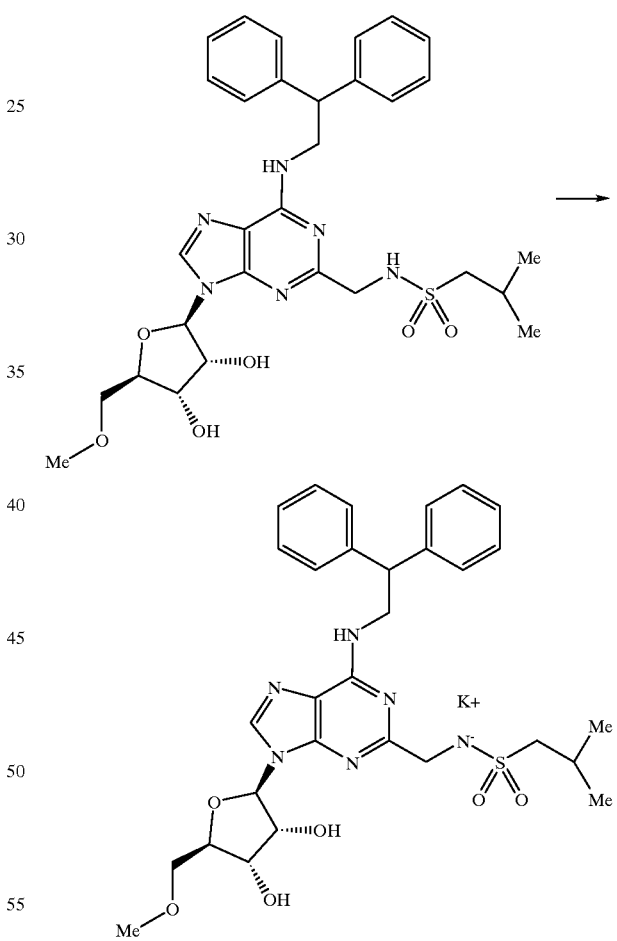

N-({9-[(2R,3R,4S,5R)-3,4-dihydroxy-5-(methoxymethyl)tetrahydro-2-furanyl]-6-[(2,2-diphenylethyl)amino]-9H-purin-2-yl}methyl)-2-methyl-1-propanesulfonamide (example 15) (1.9 g, 3.11 mmol) was dissolved into isopropyl alcohol (20 ml) and a 4 molar solution of potassium hydroxide (0.9 ml, 3.11 mmol) added. The isopropyl alcohol was removed by evaporation under reduced pressure and more isopropyl alcohol (20 ml) added to the residue, then the solvent removed under reduced pressure again. The residue was suspended in isopropyl alcohol (160 ml) and then the suspension heated under reflux for 1 hr. The resulting suspension was allowed to cool and then filtered. The white solid was washed with a little isopropyl alcohol and then dried. This gave the title compound (1.5 g) as a white crystalline solid m.p. 231° C.

$^1$H NMR (d$_6$ DMSO) δ=8.05 (1H, s), 7.35–7.20 (8H, m), 7.20–7.10 (2H, m), 5.95–5.85 (1H, m), 4.65–3.90 (11H possibly HOD in DMSO, m), 3.60–3.40 (2H, m), 3.25 (3H, s), 2.55 (2H partly obscured by D$_5$H DMSO), 2.05–1.90 (1H, m), 0.90–0.80 (6H, m). Analysis: Found C, 5–4.62, H, 5.75, N, 12.56; C$_{30}$H$_{37}$N$_6$O$_6$SK.0.5H$_2$O requires C, 54.78, H, 5.82, N, 12.78%.

boiled off from the solution until a gum started to appear and then more isopropyl alcohol was added. The resulting white crystalline solid was filtered off, dried and then recrystallized from hot ethanol to give the title compound (40 mg) as a white powder. M.p. 161–163° C.

$^1$H NMR (d$_6$ DMSO) δ=8.25 (1H, s), 7.90 (1H, s), 7.35–7.20 (8H, m), 7.20–7.10 (2H, m), 5.95–5.85 (1H, m), 4.65–4.50 (2H, m), 4.15–4.05 (2H, m), 4.05–3.95 (2H, m), 3.85 (2H, s), 3.60–3.45 (2H, m), 3.25 (3H, s), 3.05–2.85 (4H, m), 2.45–2.30 (2H, m), 2.05–1.90 (2H, m), 1.65–1.45 (2H, m), 1.05–0.95 (6H, m). Analysis: Found C, 58.06, H, 6.82, N, 12.31; C$_{34}$H$_{43}$N$_7$O$_4$.C$_4$H$_6$O$_6$.H$_2$O requires C, 58.23, H, 6.82, N, 12.51%.

Example 75

(2R,3R,4S,5R)-2-(6-[(2,2-Diphenylethyl)amino]-2-{[(1-isopropyl-4-piperidinyl)amino]methyl}-9H-purin-9-yl)-5-(methoxymethyl)tetrahydro-3,4-furandiol (2S,3S)-2,3-dihydroxybutanedioate

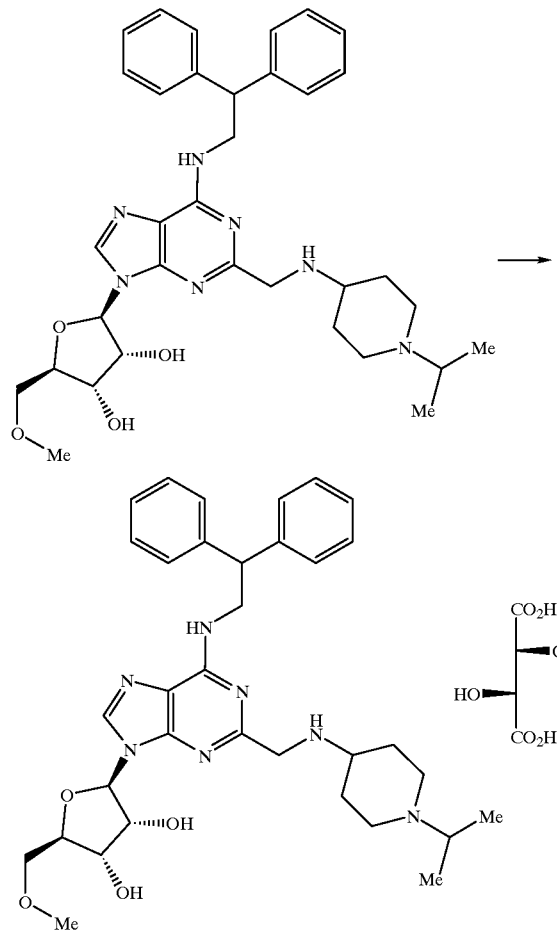

A solution of (2S,3S)-2,3-dihydroxybutanedioic acid (49 mg, 0.33 mmol) in isopropyl alcohol (1 ml) was added to a stirred solution of [((2R,3R,4S,5R)-2-(6-[(2,2-diphenylethyl)amino]-2-{[(1-isopropyl-4-piperidinyl)amino]methyl}-9H-purin-9-yl)-5-(methoxymethyl) tetrahydro-3,4-furandiol (200 mg, 0.33 mmol) (example 16) in isopropyl alcohol (1 ml). This resulted in the formation of a thick precipitate, which was dissolved by the addition of dichloromethane and isopropyl alcohol. The solvent was Example 76

(2R,3R,4S,5R)-2-{2-[(Benzylsulfanyl)methyl]-6-[(2,2-diphenylethyl)amino]-9H-purin-9-yl}-5-(methoxymethyl)tetrahydro-3,4-furandiol

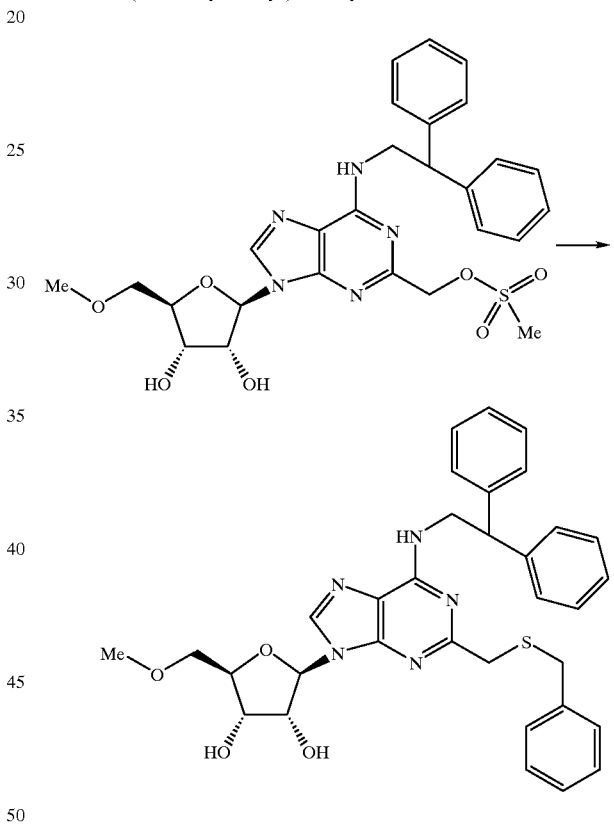

{9-[(2R,3R,4S,5R)-3,4-Dihydroxy-5-(methoxymethyl) tetrahydro-2-furanyl]-6-[(2,2-diphenylethyl)amino]-9H-purin-2-yl}methyl methanesulfonate (300 mg, 0.53 mmol) (preparation 25) was dissolved in stirred dichloromethane (4 ml) and phenylmethanethiol (0.13 ml, 1.05 mmol) and triethylamine (0.15 ml, 1.05 mmol) added. The reaction mixture was stirred for 48 hr at room temperature and then the solvent removed under reduced pressure. The residue was partitioned between methanol (100 ml) and hexane (100 ml) and the methanol layer washed with a further amount of hexane (100 ml). The solvent was then removed under reduced pressure from the methanol layer. The residue was purified by column chromatography on silica gel eluting with a solvent system of ethyl acetate:hexane (3:2) increasing in polarity to ethyl acetate:methanol (98:2). This gave title compound (100 mg) as a foam. MS: 599 (MH$^+$).

$^1$H NMR (CDCl$_3$) δ=7.90 (1H, s), 7.35–7.10 (15H, m), 6.30 (1H, br s), 5.95–5.85 (2H, m), 4.50–4.25 (6H, m), 3.80 (2H, s), 3.75 (2H, s), 3.65–3.50 (2H, m), 3.45 (1H, br s), 3.30 (3H, s).

The following Preparations illustrate the preparation of certain starting materials used in the preceding Examples.

Preparation 1

(3aR,4R,6R,6aR)-4-Methoxy-6-(methoxymethyl)-2,2-dimethyltetrahydrofuro[3,4-d][1,3]dioxole

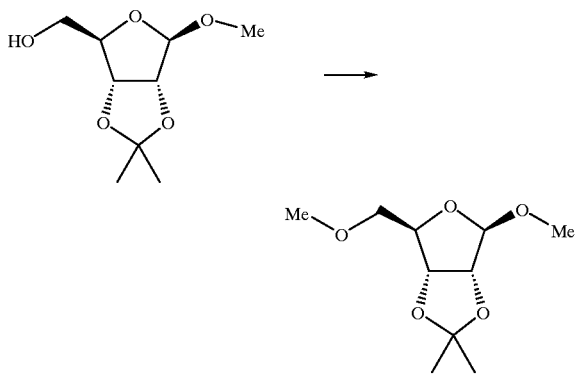

A stirred solution of [(3aR,4R,6R,6aR)-6-methoxy-2,2-dimethyltetrahydrofuro[3,4-d][1,3]dioxol-4-yl]methanol (J. Heterocycl. Chem., 13 1966, 485) (43.1 g, 0.21 mol) in dry tetrahydrofuran (400 ml), at 0° C. and under an atmosphere of nitrogen, was carefully treated with sodium hydride, (7.7 g of an 80% dispersion in mineral oil, 0.26 mol). The resultant mixture was warmed to room temperature and stirred for 1 hr. The reaction mixture was cooled to 0° C. and a solution of methyl iodide (15.8 m, 0.25 mol) in dry tetrahydrofuran (30 ml) added slowly. The resultant mixture was stirred for a further 30 min at 0° C. and then at room temperature for 24 hr. Water (1000 ml) was added carefully and the mixture extracted with diethyl ether (3×500 ml). The combined organic extracts were washed with brine, dried with anhydrous magnesium sulfate, filtered and the solvent removed under reduced pressure. The residue was purified by column chromatography on silica gel eluting with a solvent system of diethyl ether:pentane (1:4), to afford the title compound as an oil (36.5 g).

$^1$H-NMR (CDCl$_3$) δ=4.95 (1H, s), 4.65 (1H, d), 4.55 (1H, d), 4.30 (1H, t), 3.45–3.35 (5H, m), 3.30 (3H, s), 1.45 (3H, s), 1.30 (3H, s).

Preparation 2

(2R,3R,4S,5R)-2-Methoxy-5-(methoxymethyl)tetrahydro-3,4-furandiol and (2S,3R,4S,5R)-2-methoxy-5-(methoxymethyl)tetrahydro-3,4-furandiol

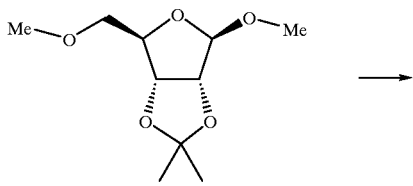

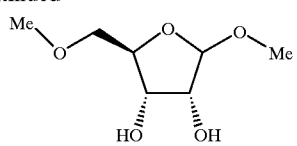

A stirred solution of (3aR,4R,6R,6aR)-4-methoxy-6-(methoxymethyl)-2,2-dimethyl tetrahydrofuro[3,4-d][1,3]dioxole (preparation 1) (36.5 g, 0.17 mol) in methanol (180 ml) at 0° C. was treated with 2 molar hydrochloric acid (180 ml) and stirred at room temperature for 24 hr. Solid sodium hydrogen carbonate (40 g) was added portion wise to neutralise the solution (pH 7) before solvent removal under reduced pressure. The residue was dissolved in dichloromethane and the solution dried with anhydrous magnesium sulfate, filtered and the solvent removed under reduced pressure to afford the title compound as an oil and as a mixture of anomers (25.7 g).

$^1$H-NMR (CDCl$_3$) δ=4.95 (0.25H, d), 4.85 (0.75H, d), 4.20 (0.75H, m), 4.15–4.00, (2H, m), 3.95 (0.25H, m), 3.60–3.45 (3H, m), 3.45–3.30 (5H, m), 2.85 (0.25H, d), 2.60 (1H, m), 2.45 (0.75H, d).

Preparation 3

(2R,3R,4R,5R)-4-(Benzoyloxy)-5-methoxy-2-(methoxymethyl)tetrahydro-3-furanyl benzoate and (2R,3R,4R,5S)-4-(benzoyloxy)-5-methoxy-2-(methoxymethyl)tetrahydro-3-furanyl benzoate

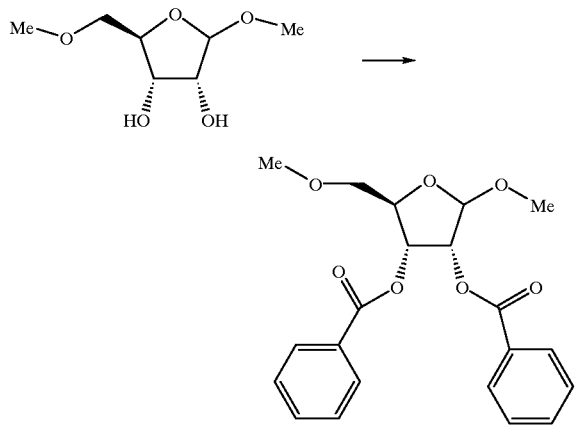

A stirred solution of (2R,3R,4S,5R)-2-methoxy-5-(methoxymethyl)tetrahydro-3,4-furandiol and (2S,3R,4S,5R)-2-methoxy-5-(methoxymethyl)tetrahydro-3,4-furandiol (preparation 2) (25.7 g, 0.14 mol) and pyridine (44 ml, 0.54 mol) in dry dichloromethane (350 ml) was treated with benzoyl chloride (40 ml, 0.34 mol) at 0° C. and the resultant mixture then stirred at room temperature for 24 hr. The solvent was removed under reduced pressure and the residue partitioned between diethyl ether and water. The layers were then separated and the aqueous layer extracted with diethyl ether:pentane (1:1). The combined organic layers were washed with water, brine, dried with anhydrous magnesium sulfate, filtered and the solvent removed under reduced pressure. The residue was purified by column chromatography on silica gel eluting with a gradient system of dichloromethane:diethyl ether (9:1) gradually changing to dichloromethane:diethyl ether (4:1) to afford the title compound as an oil and as a mixture of anomers (5–4.5 g).

$^1$H-NMR (CDCl$_3$) δ=8.05 (0.75H, d), 8.00 (1.25H, d), 7.95 (2H, dd), 7.60–7.20, (6H, m), 5.65–5.58 (1.75H, m), 5.40 (0.25H, d), 5.30–5.22 (0.25H, m), 5.15 (0.75H, s), 4.584.50 (0.75H, m), 4.45 (0.25H, m), 3.75–3.70 (1.25H, m), 3.70–3.60 (0.75H, m), 3.50–3.40 (6H, m).

Preparation 4

(2R,3R,4R,5S)-5-(Acetyloxy)-4-(benzoyloxy)-2-(methoxymethyl)tetrahydro-3-furanyl benzoate and (2R,3R,4R,5R)-5-(acetyloxy)-4-(benzoyloxy)-2-(methoxymethyl)tetrahydro-3-furanyl benzoate

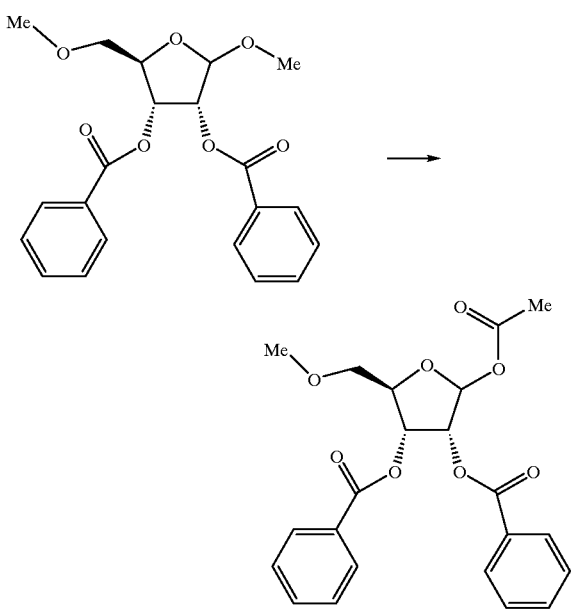

A stirred solution of (2R,3R,4R,5R)-4-(benzoyloxy)-5-methoxy-2-(methoxymethyl)tetrahydro-3-furanyl benzoate and (2R,3R,4R,5S)-4-(benzoyloxy)-5-methoxy-2-(methoxymethyl) tetrahydro-3-furanyl benzoate (preparation 3) (53.2 g, 0.14 mol) in dichloromethane (600 ml) at 0° C. was treated slowly with acetic anhydride (34 ml, 0.36 mol), acetic acid (16.5 ml, 0.29 mol) and concentrated sulphuric acid (1 ml, 18.8 mmol). The resultant mixture was stirred at room temperature for 24 hr. The reaction mixture was then diluted with water (1000 ml), solid sodium hydrogen carbonate (80 g) added portion wise to neutralise the solution (pH 7) and the mixture stirred for a further 2 hr. Dichloromethane (500 ml) and water (500 ml) were added to the reaction mixture and the layers were separated. The aqueous layer was then extracted with dichloromethane, and the combined organic layers washed with brine, dried with anhydrous magnesium sulfate, filtered and the solvent removed under reduced pressure to afford the title compound as an oil and as a mixture of anomers (57.5 g).

$^1$H-NMR (CDCl$_3$) δ=8.10 (1H, d), 8.00 (1H, d), 7.95–7.80 (2H, m), 7.60–7.25, (6H, m), 6.65 (0.5H, s), 6.40, (0.5H, s), 5.80–5.70 (1.5H, m), 5.55 (0.5H, m), 4.60 (1H, m), 3.80–3.60 (2H, m), 3.45 (3H, d), 2.15 (1.5H, s), 2.10 (1.5H, s).

Preparation 5

2,6-Dichloro-9-tetrahydro-2H-pyran-2-yl-9H-purine

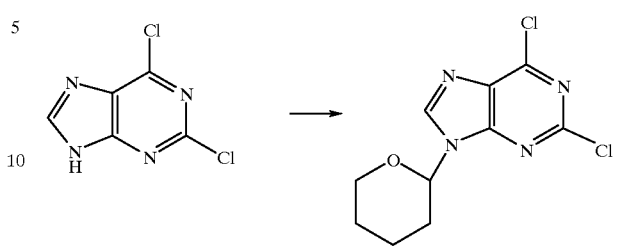

2,6-Dichloro-9H-purine (20 g, 0.11 mol) and 4-toluenesulphonic acid monohydrate (0.2 g) were dissolved in stirred ethyl acetate (300 ml), the mixture heated to 50° C. and a solution of 2,3dihydropyran (12.6 ml, 0.14 mol) in ethyl acetate (50 ml) added slowly over 30 min. The reaction mixture was then cooled to room temperature and water (100 ml) added and the pH of the solution adJusted to 7 with a saturated aqueous solution of sodium hydrogen carbonate. The layers were separated and the organic layer washed sequentially with water and brine, dried with anhydrous magnesium sulfate, filtered and the solvent removed under reduced pressure. The residue was dissolved in pentane and the solvent removed under reduced pressure again. This was then repeated, to afford the title compound as a slightly impure white solid (30.9 g).

$^1$H-NMR (CDCl$_3$) δ=8.30 (1H, s), 5.75 (1H, dd), 4.25–4.15 (1H, m), 3.85–3.70 (1H, m), 2.20–1.60 (6H, m).

Preparation 6

2-Chloro-N-(2,2-diphenylethyl)-9-tetrahydro-2H-pyran-2-yl-9H-purin-6-amine

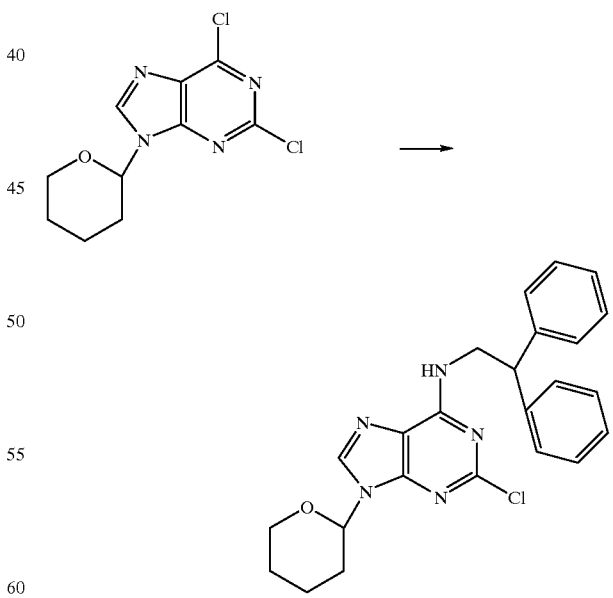

A stirred solution of 2,6-dichloro-9-tetrahydro-2H-pyran-2-yl-9H-purine (preparation 5) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture heated at reflux for 3 hr. The solvent was removed under reduced pressure, the residue dissolved in ethyl acetate and the solvent removed under reduced pressure. The residue was purified by column chromatography on silica gel eluting with a gradient system of ethyl acetate:hexane (40:60) gradually changing to ethyl acetate:hexane (60:40) to afford the title compound as a foam (49.7 g).

¹H-NMR (CDCl₃) δ=7.95–7.75 (1H, br s), 7.35–7.15 (10H, m), 5.80–5.70 (1H, br s), 5.65 (1H, d), 4.35 (1H, m), 4.30–4.18 (1H, brs), 4.10 (1H, d), 3.70 (1H, t), 2.05–1.95 (2H, m), 1.95–1.80 (1H, m), 1.80–1.55 (3H, m).

Preparation 7

N-(2,2-Diphenylethyl)-2-(methylsulfanyl)-9-tetrahydro-2H-pyran-2-yl-9H-purin-6-amine

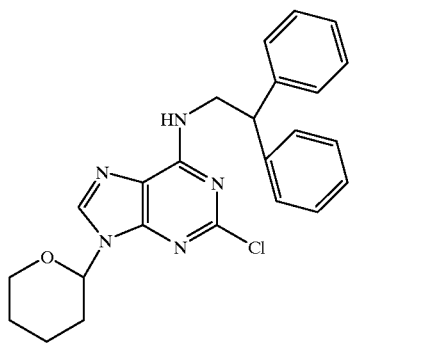

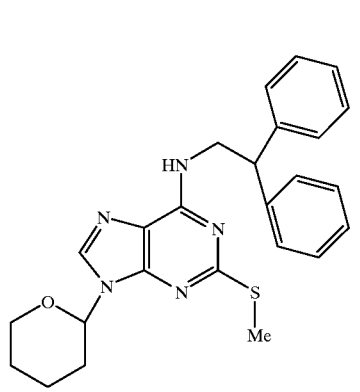

A stirred solution of 2-chloro-N-(2,2-diphenylethyl)-9-tetrahydro-2H-pyran-2-yl-9H-purin-6-amine (preparation 6) (49.7 g, 0.11 mol) in dry N,N-dimethylformamide (200 ml) was treated with sodium thiomethoxide (10 g, 0.14 mol) and the resulting mixture heated under an atmosphere of nitrogen at 100° C. for 1.5 hr. The mixture was then stirred at room temperature for 72 hr and then reheated to 100° C. for a further 2 hr. The reaction mixture was then cooled and diluted with water (1000 ml). A suspension was formed which was extracted with diethyl ether (×2). The combined organic extracts were washed sequentially with water and brine, dried with anhydrous magnesium sulfate, filtered and the solvent removed under reduced pressure. The residue was dissolved in diethyl ether and the solvent removed under reduced pressure. This procedure was then repeated using pentane to afford the title compound as a foam (48.9 g).

¹H-NMR (CDCl₃) δ=7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

Preparation 8

N-(2,2-Diphenylethyl)-2(methylsulfonyl)-9-tetrahydro-2H-pyran-2-yl-9H-purin-6-amine

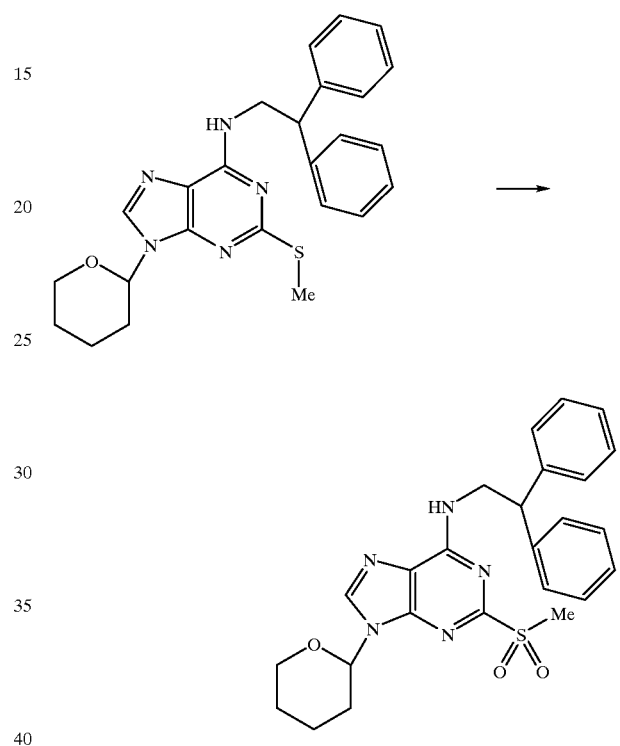

A solution of oxone® (potassium peroxymonosulphate) (44 g, 71.7 mmol) in water (200 ml) was added drop wise over 2 hr to a stirred solution of N-(2,2-diphenylethyl)-2-(methylsulfanyl)-9-tetrahydro-2Hpyran-2-yl-9H-purin-6-amine (preparation 7) (25 g, 56.2 mmol) and sodium hydrogen carbonate (20 g, 238 mmol) in acetone (1000 ml) and water (250 ml). The resultant mixture was stirred at room temperature for 24 hr, filtered and the residue washed with acetone. The acetone was removed from the filtrate under reduced pressure and the resulting aqueous residue extracted with ethyl acetate and then dichloromethane. The combined organic extracts were washed with brine, dried with anhydrous magnesium sulfate, filtered and the solvent removed under reduced pressure. The residue was triturated with diethyl ether, the mixture filtered and the collected material washed with diethyl ether and pentane, then dried to afford the title compound as a white solid (20.32 g).

¹H-NMR (CDCl₃) δ=8.00 (1H, s), 7.35–7.15 (10H, m), 6.05–5.95 (1H, br s), 5.75 (1H, d), 4.40–4.35 (1H, m), 4.35–4.20 (2H, brs), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

Preparation 9

6-[(2,2-Diphenylethyl)amino]-9-tetrahydro-2H-pyran-2-yl-9H-purine-2-carbonitrile

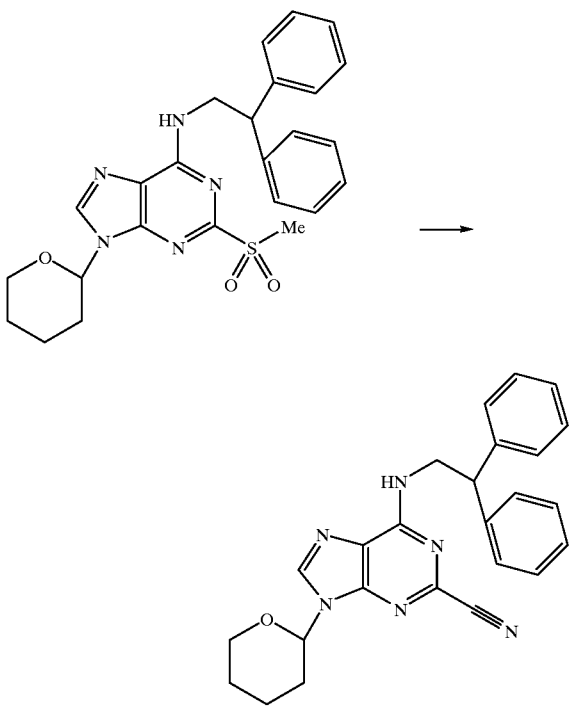

A stirred solution of N-(2,2-diphenylethyl)-2-(methylsulfonyl)-9-tetrahydro-2H-pyran-2-yl-9H-purin-6-amine (preparation 8) (20.1 g, 42.1 mmol) in dry N,N-dimethylformamide (100 ml) was treated with potassium cyanide (5.5 g, 84.6 mmol) and the mixture heated at 120° C. for 24 hr under a nitrogen atmosphere. The mixture was then cooled to room temperature, poured into water (1000 ml) and stirring continued for a further 1 hr. The resultant solid was slowly filtered and washed several times with water, then dissolved in dichloromethane. The solution washed with water, dried with anhydrous magnesium sulfate, filtered and the solvent removed under reduced pressure. The residue was then dissolved in diethyl ether and the solvent removed under reduced pressure (repeated) to afford the title compound as an oil (17 g).

$^1$H-NMR (CDCl$_3$) δ=8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 10

6-[(2,2-Diphenylethyl)amino]-9H-purine-2-carbonitrile

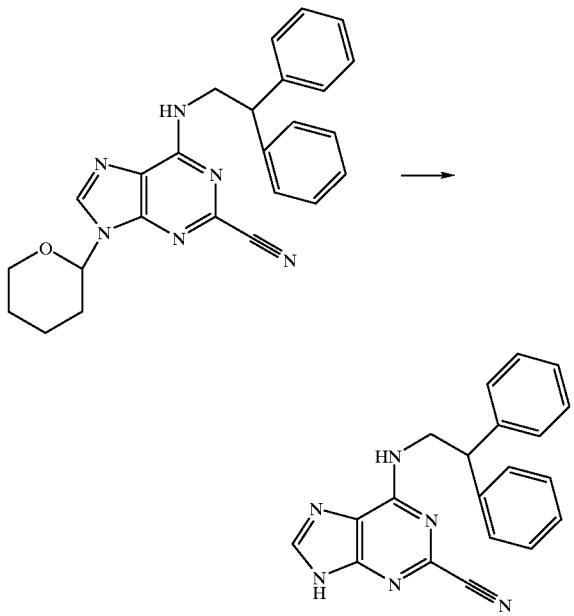

A stirred solution of 6-[(2,2-diphenylethyl)amino]-9-tetrahydro-2H-pyran-2-yl-9H-purine-2-carbonitrile (preparation 9) (17 g, 40.1 mmol) in ethanol (850 ml), was treated with 2 molar hydrochloric acid (50 ml) and the mixture stirred at room temperature for 24 hr. The solvent was then removed under reduced pressure, the residue dissolved in ethanol and the solvent removed under reduced pressure (repeated). The residue was triturated with diethyl ether, the mixture filtered and the collected material washed with diethyl ether and pentane, then dried to afford the title compound as a solid (14.3 g). MS: 341 (MH$^+$)

$^1$H-NMR (d$_6$ DMSO) δ=8.30 (1H, s), 8.20–8.05 (1H, br s), 7.40–7.10 (10H, m), 4.60–4.40 (1.4H, m), 4.20–4.00 (1.6H, m). Analysis: Found C, 70.37, H, 4.70, N, 24.58; C$_{20}$H$_{16}$N$_6$. requires C, 70.57, H, 4.74, N, 24.69%.

Preparation 11

(2R,3R,4R,5R)-4-(benzoyloxy)-5-{2-cyano-6-[(2,2-diphenylethyl)amino]-9H-purin-9-yl}-2-(methoxymethyl)tetrahydro-3-furanyl benzoate

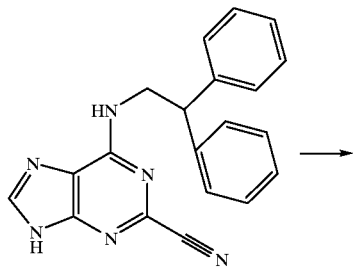

101
-continued

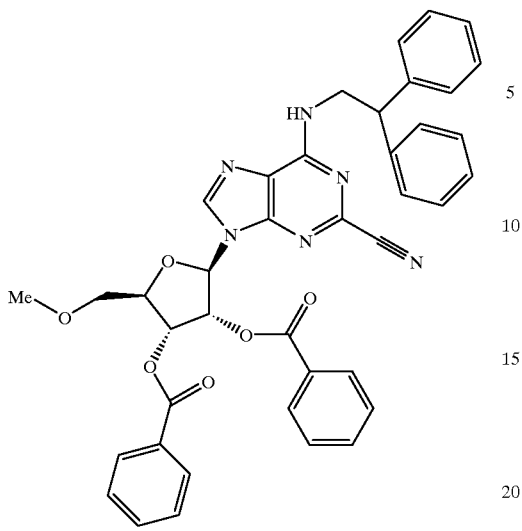

A stirred mixture of 6-[(2,2-diphenylethyl)amino]-9H-purine-2-carbonitrile (preparation 10) (5 g, 14.7 mmol), ammonium sulphate (200 mg, 1.8 mmol) and 1,1,1,3,3,3-hexamethyidisilazane (100 ml) was heated at 130° C. for 24 hr. Further portions of ammonium sulphate (200 mg, 1.8 mmol) and 1,1,1,3,3,3-hexamethyldisilazane (100 ml) were then added and the mixture heated at 130° C. for a further 4 hr. The solvent was then removed under reduced pressure and the residue dissolved in acetonitrile. The solvent was again removed under reduced pressure and the residue redissolved in acetonitrile (10 ml) to give solution A.

In a separate reaction vessel, a stirred solution of (2R,3R,4R,5S)-5-(acetyloxy)-4-(benzoyloxy)-2-(methoxymethyl)tetrahydro-3-furanyl benzoate and (2R,3R,4R,5R)-5-(acetyloxy)-4-(benzoyloxy)-2-(methoxymethyl)tetrahydro-3-furanyl benzoate (preparation 4) (6.2 g, 14.9 mmol) and bismuth tribromide (350 mg, 0.78 mmol) in dichloromethane (100 ml) was treated with bromotrimethylsilane (8 ml, 60.6 mmol) under an atmosphere of nitrogen and the mixture stirred at room temperature for 10 min. The solvent was removed under reduced pressure and the residue dissolved in acetonitrile. The solvent was again removed under reduced pressure and the residue redissolved in acetonitrile (10 ml) to give solution B. Solution A was then added to stirred solution B and the mixture stirred at room temperature for 24 hr. The mixture was then partitioned between saturated aqueous sodium hydrogen carbonate and ethyl acetate. The layers were separated and the aqueous layer extracted with ethyl acetate. The combined organic layers were washed with brine, dried with anhydrous magnesium sulfate, filtered and the solvent removed under reduced pressure. The residue was purified by column chromatography on silica gel eluting with a gradient system of ethyl acetate:pentane (2:3) gradually changing to ethyl acetate::pentane (2:1) to afford the title compound as a white foam (6.26 g). MS: 695 (MH$^+$)

$^1$H-NMR (CDCl$_3$) δ=8.35 (1H, s), 8.05 (2H, d), 7.95 (2H, d), 7.65–7.20 (16H, m), 6.60 (1H, d), 6.05–5.90 (3H, m), 4.60 (1H, s), 4.40–4.20 (3H, m), 3.80 (2H, s), 3.55 (3H, s).

102
Preparation 12

9-[(2R,3R,4S,5R)-3,4-Dihydroxy-5-(methoxymethyl)tetrahydro-2-furanyl]-6-[(2,2-diphenylethyl)amino]-9H-purine-2-carbonitrile

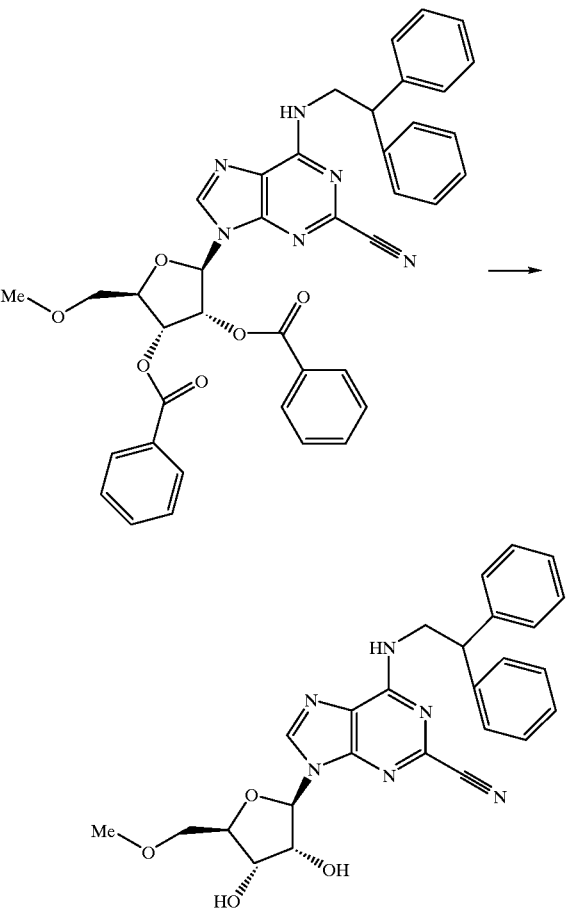

A solution of (2R,3R,4R,5R)-4-(benzoyloxy)-5-{2-cyano-6-[(2,2-diphenylethyl)amino]-9H-purin-9-yl}-2-(methoxymethyl)tetrahydro-3-furanyl benzoate (preparation 11) (6.75 g, 9.72 mmol) in methanol (300 ml) saturated with ammonia gas was stirred at room temperature for 72 hr. The solvent was removed under reduced pressure, the residue dissolved in dichloromethane and the solvent removed under reduced pressure (repeated). The residue was purified by column chromatography on silica gel eluting with a gradient system of dichloromethane:methanol (98:2) gradually changing to dichloromethane:methanol (96:4). The residue was triturated with diethyl ether, filtered, washed with diethyl ether and dried to afford the title compound as a solid (2.20 g). MS: 487(MH$^+$).

$^1$H-NMR (CDCl$_3$) δ=8.15 (1H, s), 7.40–7.20 (10H, m), 6.05 (1H, br s), 6.00 (1H, d), 4.60 (1H, m), 4.45 (1H, m), 4.40–4.20 (4H, m), 3.75–3.55 (2H, m), 3.40 (3H, s), 3.00 (1H, m). Analysis: Found C, 63.84, H, 5.22, N, 17.16; C$_{26}$H$_{26}$N$_6$O$_4$. requires C, 64.19, H, 5.39, N, 17.27%.

Preparation 13

Methyl 9-[(2R,3R,4S,5R)-3,4-dihydroxy-5-(methoxymethyl)tetrahydro-2-furanyl]-6-[(2,2-diphenylethyl)amino]-9H-purine-2-carboxylate

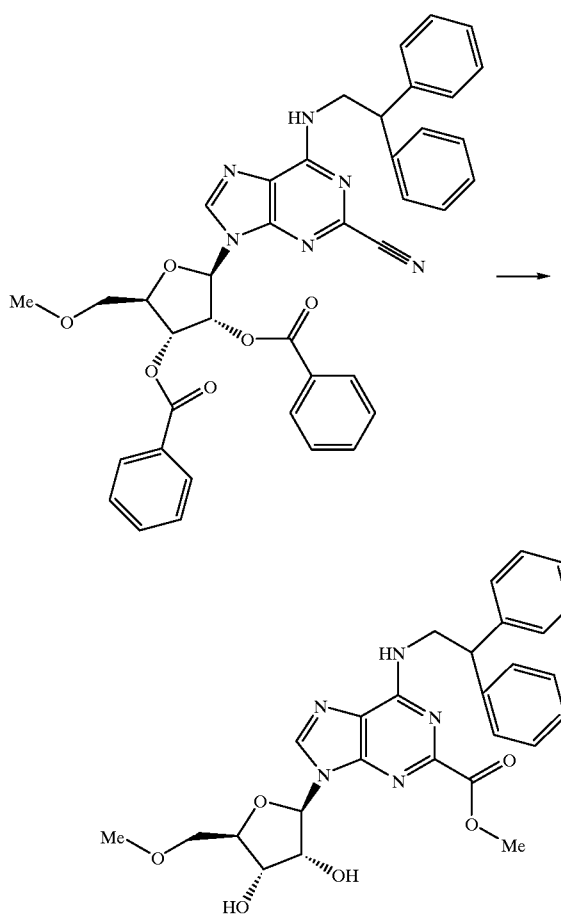

Preparation 14

Methyl 9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purine-2-carboxylate

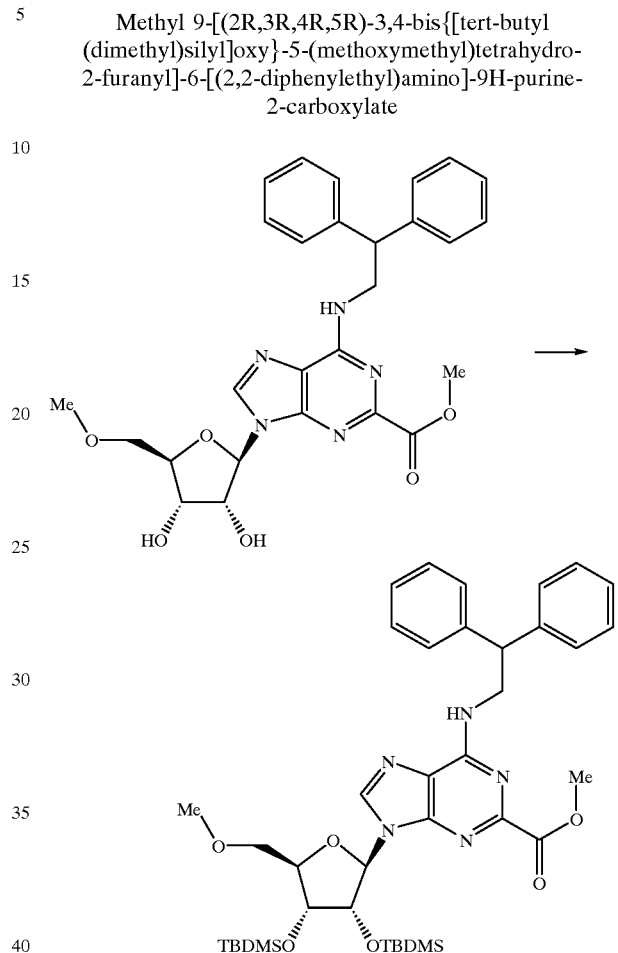

Sodium methoxide (0.69 g, 12.7 mmol) was added to a stirred solution of (2R,3R,4R,5R)-4-(benzoyloxy)-5-{2-cyano-6-[(2,2-diphenylethyl)amino]-9H-purin-9-yl}-2-(methoxymethyl) tetrahydro-3-furanyl benzoate (8.85 g, 12.7 mmol) (preparation 11) in methanol (150 ml) and the mixture stirred at 60° C., under a nitrogen atmosphere, for 3 hr. The solvent was removed under reduced pressure and tetrahydrofuran (80 ml) and 2 molar hydrochloric acid (50 ml) added. The mixture was stirred for 90 minutes before carefully adding solid sodium hydrogen carbonate (9 g) to neutralise the solution (pH 7). The resulting mixture was then partitioned between ethyl acetate and water, the aqueous layer separated and extracted with more ethyl acetate. The combined organic solutions were washed with brine and dried with anhydrous magnesium sulfate. The solvent was removed under reduced pressure and the residue purified by column chromatography on silica gel eluting with a gradient system of ethyl acetate changing to ethyl acetate:methanol (95:5) to afford the title compound as a foam (4.55 g).

$^1$H-NMR (CDCl$_3$) δ=8.19 (1H, s), 7.20–7.38 (10H, m), 6.27 (1H, d), 5.99 (1H, br s), 5.89 (1H, br s), 4.30–4.60 (5H, m), 4.06 (1H, s), 3.95 (3H, s), 3.64 (2H, dd), 3.38 (3H, s).

Methyl 9-[(2R,3R,4S,5R)-3,4-dihydroxy-5-(methoxymethyl)tetrahydro-2-furanyl]-6-[(2,2-diphenylethyl)amino]-9H-purine-2-carboxylate, (1.48 g, 3 mmol) (preparation 13), imidazole (0.82 g, 12 mmol) and tert-butyl(chloro)dimethylsilane (1.36 g, 9 mmol) were dissolved in anhydrous N,N-dimethylformamide (15 ml) and the solution stirred at room temperature for 18 hr. The resulting mixture was then partitioned between ethyl acetate and water, the organic phase washed with brine and the combined organic solutions dried with anhydrous sodium sulfate. The solvent was removed under reduced pressure and the residue purified by column chromatography on silica gel eluting with a gradient system of hexane:ethyl acetate (13:1) changing to hexane:ethyl acetate (2:1) to afford the title compound as an oil (1.52 g). MS: 749 (MH$^+$).

$^1$H-NMR (CDCl$_3$) δ=8.36 (1H, s), 7.18–7.38 (10H, m), 6.03 (1H, d), 5.98 (1H, br s), 4.20–4.50 (5H, m), 3.99 (3H, s), 3.83 (1H, dd), 3.62 (1H, dd), 3.43 (3H, s), 0.89 (18H, d), 0.02–0.13 (12H, m).

Preparation 15

{9-[(2R,3R,4R,5R)-3,4-Bis{[tert-butyl(dimethyl)silyl]oxy}-5-(methoxymethyl)tetrahydro-2-furanyl]-6-[(2,2-diphenylethyl)amino]-9H-purin-2-yl}methanol

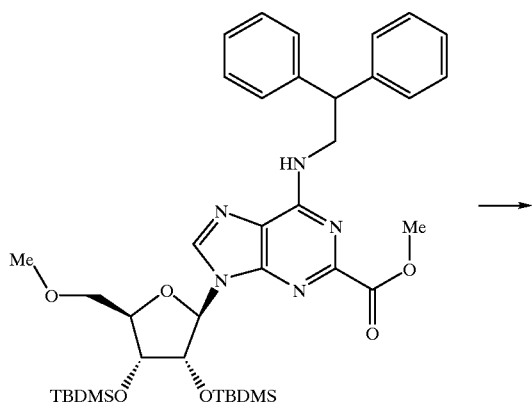

A stirred solution of methyl 9-[(2R,3R,4R,5R)-3,4-bis{[tert-butyl(dimethyl)silyl]oxy}-5- (methoxymethyl)tetrahydro-2-furanyl]-6-[(2,2-diphenylethyl)amino]-9H-purine-2-carboxylate (7.2 g, 9.64 mmol) (preparation 14) in dry diethyl ether (150 ml) was treated with trimethyl borate (0.11 ml, 0.97 mmol) and lithium borohydride (212 mg, 9.64 mmol) and the mixture heated at reflux for 1 hr under a nitrogen atmosphere. The mixture was then cooled to room temperature, water (100 ml) carefully added and stirring continued for 10 minutes. The organic phase was separated, washed with brine and dried with anhydrous sodium sulfate. The solvent was removed under reduced pressure and the residue purified by column chromatography on silica gel eluting with a gradient system of diethyl ether:pentane (1:1) changing to diethyl ether:pentane (3:1) to afford the title compound as an oil (5.17 g). MS: 721 (MH+).

$^1$H-NMR (CDCl$_3$) δ=8.19 (1H, s), 7.20–7.36 (10H, m), 5.95 (1H, d), 5.85 (1H, br s), 4.69 (2H, s), 4.15–4.50 (6H, m), 3.75–3.87 (2H, m), 3.59 (1H, dd), 3.42 (3H, s), 0.91 (9H, s), 0.87 (9H, s), 0.01–0.12 (12H, m).

Preparation 16

{9-[(2R,3R,4R,5R)-3,4-Bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate

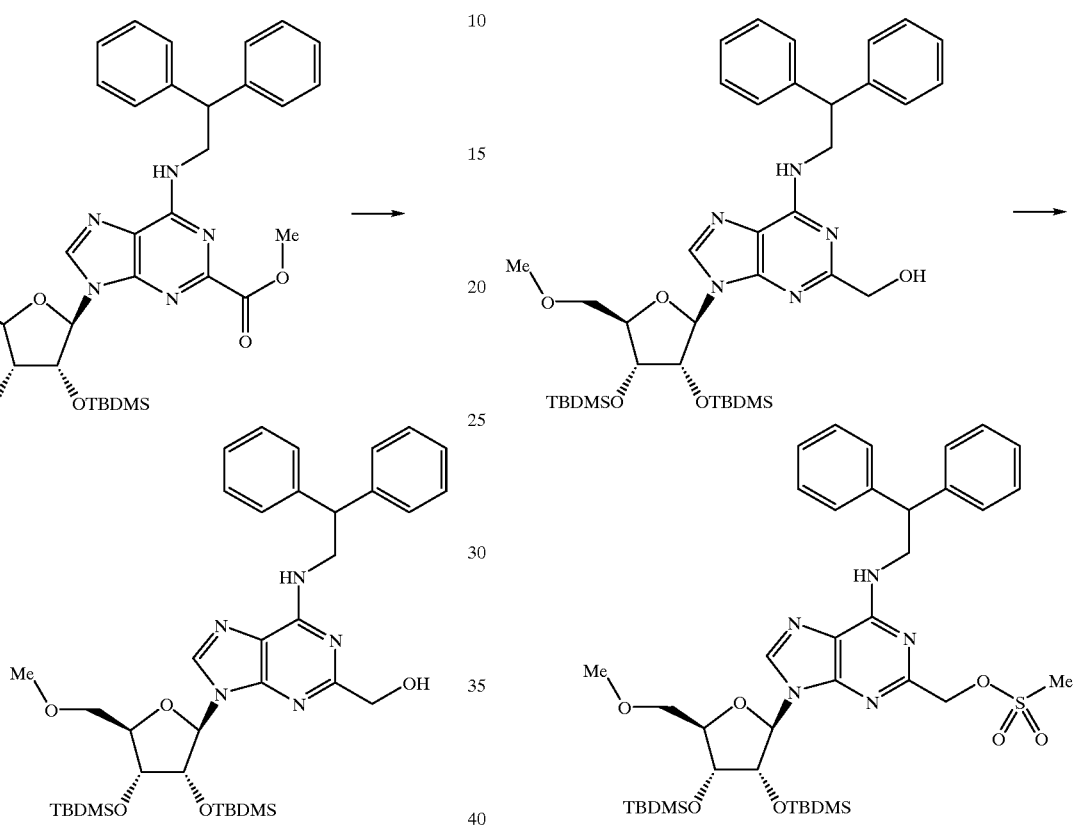

Methanesulfonyl chloride (0.6 ml, 7.7 mmol) was slowly added to a stirred solution of {9-[(2R,3R,4R,5R)-3,4-bis{[tert-butyl(dimethyl)silyl]oxy}-5- (methoxymethyl)tetrahydro-2-furanyl]-6-[(2,2-diphenylethyl)amino]-9H-purin-2-yl}methanol (4.22 g, 5.87 mmol) (preparation 15) and triethylamine (1.2 ml, 8.62 mmol) in dichloromethane (50 ml) and the mixture stirred at room temperature for 30 minutes. Triethylamine (1 ml, 7.2 mmol) and methanesulfonyl chloride (0.5 ml, 6.4 mmol) were then added and stirring continued for a further 15 minutes. The solvent was removed under reduced pressure and the residue purified by column chromatography on silica gel eluting with a gradient system of ethyl acetate:pentane (1:3) changing to ethyl acetate:pentane (1:1) to afford the title compound as a gum (4.52 g). MS: 820 (MNa+).

$^1$H-NMR (CDCl$_3$) δ=8.20 (1H, s), 7.20–7.46 (10H, m), 5.96 (1H, d), 5.70 (1H, br s), 5.25 (2H, s), 4.50 (1H, t), 4.17–4.40 (4H, m), 3.79 (1H, dd), 3.60 (1H, dd), 3.44 (3H, s), 3.10 (3H, s), 0.92 (9H, s) 0.86 (9H, s), 0.01–0.10 (12H, m).

Preparation 17

2-{9-[(2R,3R,4R,5R)-3,4-Bis{[tert-butyl(dimethyl)silyl]oxy}-5-(methoxymethyl)tetrahydro-2-furanyl]-6-[(2,2-diphenylethyl)amino]-9H-purin-2-yl}acetonitrile

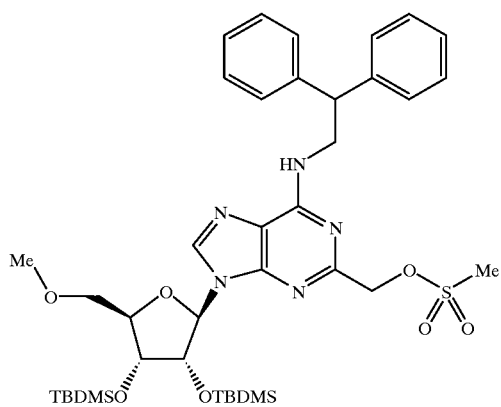

A stirred solution of {9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate (3.0 g, 3.76 mmol) (preparation 16) in anhydrous N,N-dimethylformamide (20 ml) was treated with potassium cyanide (0.37 g, 5.69 mmol) and heated to 65–70° C. for 3 hr. The mixture was cooled to room temperature and partitioned between diethyl ether and water. The organic phase was separated and the aqueous phase extracted again with diethyl ether. The combined organic solutions were then washed with brine, dried with anhydrous magnesium sulfate and the solvent removed under reduced pressure. The residue was purified by column chromatography on silica gel eluting with a solvent system of diethyl ether:pentane (1:1) to afford the title compound as a foam (2.2 g). MS: 751 (MNa$^+$).

$^1$H-NMR (CDCl$_3$) δ=8.15 (1H, s), 7.20–7.36 (10H, m), 5.90 (1H, d), 5.70 (1H, br s), 4.58 (1H, t), 4.18-4.43 (4H, m), 4.90 (2H, s), 3.80 (1H, dd), 3.62 (1H, dd), 3.43 (3H, s), 0.90 (9H, s), 0.85 (9H, s), 0.01–0.09 (12H, m).

Preparation 18

N-{2-(2-Aminoethyl)-9-[(2R,3R,4R,5R)-3,4-bis{[tert-butyl(dimethyl)silyl]oxy}-5-(methoxymethyl)tetrahydro-2-furanyl]-9H-purin-6-yl}-N-(2,2-diphenylethyl)amine

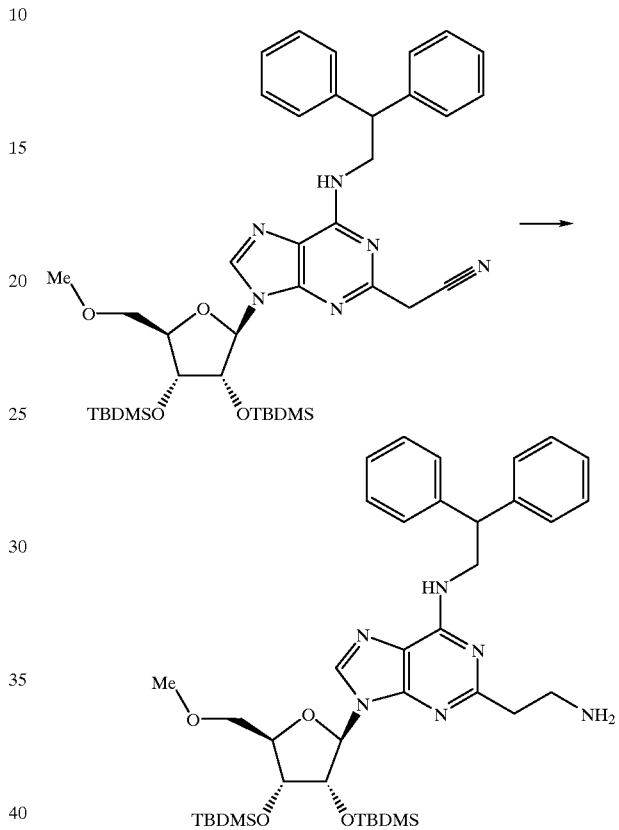

A solution of 2-{9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}acetonitrile (1.9 g, 2.6 mmol) (preparation 17) in ethanol (40 ml) saturated with ammonia gas was treated with Raney Nickel (400 mg), pressurised to 414 kPa (60 psi) with hydrogen in a sealed vessel and stirred at room temperature for 4 days. The mixture was then filtered through Arbocel (trade mark) and the residue washed with ethanol. The solvent was removed under reduced pressure from the filtrate, the residue dissolved in pentane and the solvent again removed under reduced pressure to give the title compound as a powder (1.08 g). MS: 733 (MH$^+$).

$^1$H-NMR (CDCl$_3$) δ=8.11 (1H, s), 7.20–7.35 (10H, m), 5.94 (1H, d), 5.51 (1H, br s), 4.50 (1H, t), 4.30–4.42 (3H, m), 4.19 (1H, q), 3.79 (1H, dd), 3.60 (1H, dd), 3.41 (3H, s), 3.19 (2H, br s), 2.86 (2H, br t), 0.92 (9H, s), 0.87 (9H, s), 0.05 (12H, m).

Preparation 19

N-(2-{9-[(2R,3R,4R,5R)-3,4-bis{[tert-butyl (dimethyl)silyl]oxy}-5-(methoxymethyl)tetrahydro-2-furanyl]-6-[(2,2-diphenylethyl)amino]-9H-purin-2-yl}ethyl)-N-(1-ethylpropyl)amine

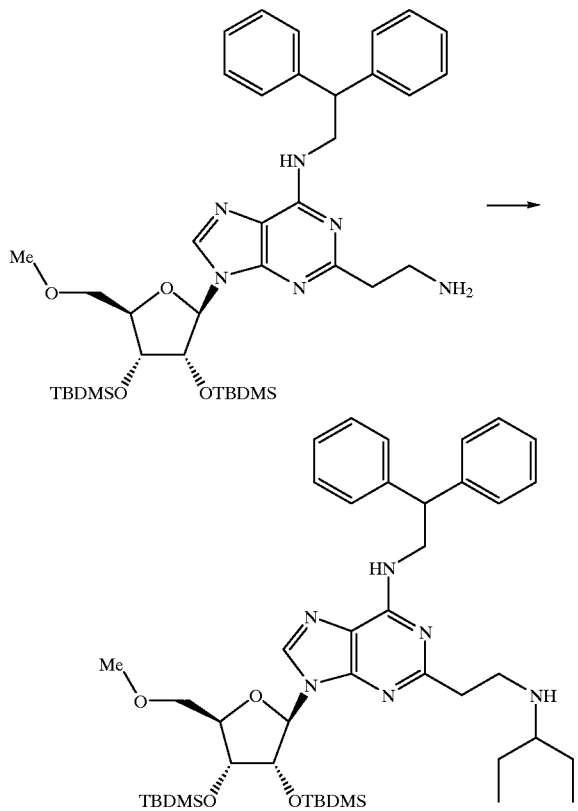

Sodium triacetoxyborohydride (105 mg, 0.51 mmol) and glacial acetic acid (24 mg, 0.40 mmol) were added to a stirred solution of N-{2-(2-aminoethyl)-9-[(2R,3R,4R,5R)-3,4-bis{[tert-butyl(dimethyl)silyl]oxy}-5-(methoxymethyl) tetrahydro-2-furanyl]-9H-purin-6-yl}-N-(2,2-diphenylethyl)amine (250 mg, 0.34 mmol) (preparation 18) and diethyl ketone (58 mg, 0.68 mmol) in dichloromethane (15 ml) and the resulting mixture stirred under an atmosphere of nitrogen gas at room temperature overnight. Additional portions of diethyl ketone (30 mg, 0.35 mmol) and sodium triacetoxyborohydride (60 mg, 0.29 mmol) were then added and stirring continued at room temperature for a further 24 hr. The mixture was diluted with ethyl acetate (20 ml) and washed sequentially with saturated aqueous sodium hydrogen carbonate solution, brine and water. The organic phase was separated and dried with anhydrous sodium sulfate. The solvent was removed under reduced pressure and the residue purified by column chromatography on silica gel eluting with dichloromethane:methanol:ammonia (96:4:0.4) to give the title compound (250 mg) as a gum. MS: 803 (MH$^+$).

$^1$H-NMR (CDCl$_3$) δ=8.10 (1H, s), 7.19–7.35(10H, m), 5.92 (1H, d), 5.49 (1H, br s), 4.16–4.50 (6H, m), 3.78 (1H, dd), 3.58 (1H, dd), 3.22 (3H, s), 2.97–3.11 (4H, m), 2.40 (1H, t), 1.38–1.48 (4H, m), 0.91 (9H, s), 0.86 (9H, s), 0.84 (6H, m), 0.04 (12H, t).

Preparation 20

4-[1-2,2,2-Trifluoroacetyl)-4-piperidinyl] benzenesulfonyl chloride

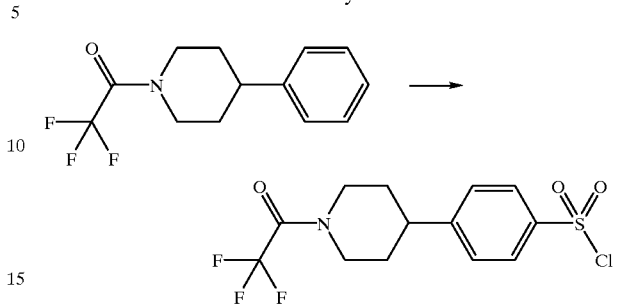

Chlorosulfonic acid (56 ml, 0.85 mol) was added dropwise to a stirred solution of 2,2,2-trifluoro-1-(4-phenyl-1-piperidinyl)-1-ethanone (preparation 31) (34 g, 0.13 mol) in dichloromethane (500 ml) at −15° C. The reaction mixture was then allowed to warm to room temperature and then stirred for 48 hr. The resulting mixture was then poured into ice water and more dichloromethane (500 ml) was added. The organic phase was separated, dried with anhydrous magnesium sulfate and the solvent removed under reduced pressure to give the title compound (41 g) as a brown oil.

$^1$H NMR (CDCl$_3$) δ=8.00–7.95 (2H, m), 7.50–7.40 (2H, m), 4.80–4.65 (1H, m), 4.25–4.15 (1H, m), 3.40–3.20 (1H, m), 3.05–2.80 (2H, m), 2.10–1.95 (2H, m), 1.80–1.60 (2H, m).

Preparation 21

Tetrahydro-2H-pyran-4-ylmethanesulfonyl chloride

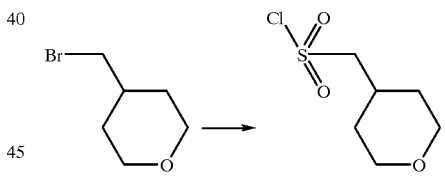

A stirred solution of 4-(bromomethyl)tetrahydro-2H-pyran (1.7 g, 9.4 mmol) (preparation 28) and sodium sulfite (4.78 g, 18.0 mmol) in a mixture of 1,4-dioxan (8 ml) and water (8 ml) was heated at reflux for 24 hr. The reaction mixture was allowed to cool and then left to stand for 72 hr. The solvent was removed under reduced pressure and the residue azeotroped with toluene three times. Thionyl chloride (17 ml) and a couple of drops of N,N-dimethylformamide were added and the resulting mixture stirred and heated under reflux for 1 hr. The thionyl chloride was removed under reduced pressure and the residue partitioned between ethyl acetate and water. The organic layer was washed with water and brine then dried with anhydrous magnesium sulfate. The solvent was removed under reduced pressure to give the title compound (830 mg) as an oil.

$^1$H NMR (CDCl$_3$) δ=4.00–3.90 (2H, m), 3.65–3.60 (2H, m), 3.50–3.40 (2H, m), 2.50–2.35 (1H, m), 1.90–1.80 (2H, m), 1.60–1.40 (2H, m).

Preparation 22

2-Amino-N,N-diisopropylacetamide

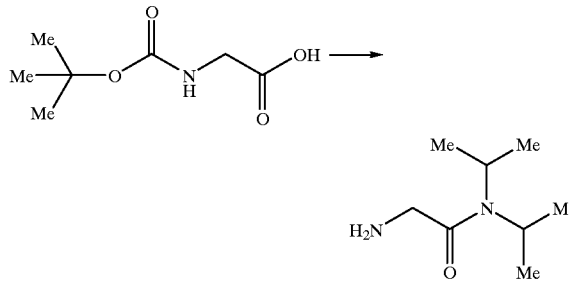

Trimethylacetylchloride (1.8 g, 15 mmol) was added to a stirred solution of 2-[(tert-butoxycarbonyl)amino]acetic acid (2.6 g, 15 mmol) and triethylamine (5 ml, 36 mmol) in dichloromethane (30 ml) at 0° C. The reaction mixture was stirred for 10 min and then N-ethyl-N-isopropyl-2-propanamine (2.5 ml, 18 mmol) was added. The reaction was allowed to warm to room temperature and stirred for 24 hr. The solvent was removed under reduced pressure and the residue taken up into a mixture of methanol (30 ml) and water (5 ml). Concentrated hydrochloric acid (10 ml) was added and the solution stirred for a further 3 hr. The reaction solvent was reduced to a low volume under reduced pressure, water (20 ml) was added and the solution adjusted to a basic pH (>7) by addition of solid potassium carbonate. The aqueous phase was extracted with dichloromethane (×4). The dichloromethane extracts were combined, dried with anhydrous magnesium sulfate and the solvent removed under reduced pressure to give the title compound (0.729) as an oil. MS: MH+ 159.

$^1$H NMR (CDCl$_3$) δ=3.90–3.70 (1H, m), 3.60–3.40 (1H, m), 3.35 (2H, s), 1.50–1.30 (6H, m), 1.30–1.10 (6H, m).

Preparation 23

N-9-[(2R,3R,4R,5R)-3,4-Bis{[tert-butyl(dimethyl)silyl]oxy}-5-(methoxymethyl)tetrahydro-2-furanyl]-2-{2-[(cyclohexylmethyl)amino]ethyl}-9H-purin-6-yl)-N-(2,2-diphenylethyl)amine

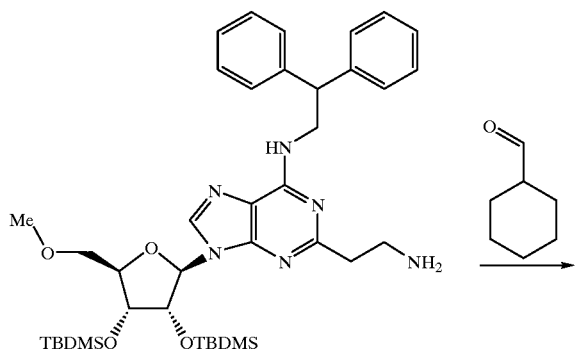

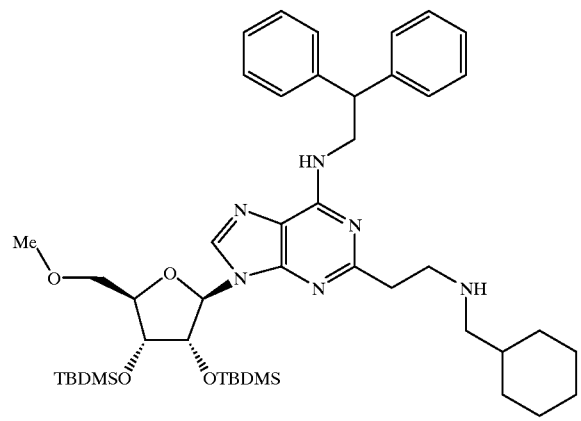

N-{2-(2-Aminoethyl)-9-[(2R,3R,4R,5R)-3,4-bis{[tert-butyl(dimethyl)silyl]oxy}-5-(methoxymethyl)tetrahydro-2-furanyl]-9H-purin-6-yl}-N-(2,2-diphenylethyl)amine (275 mg, 0.38 mmol) (preparation 18) and cyclohexanecarbaldehyde (42 mg, 0.38 mmol) were stirred together in dichloromethane (10 ml) for 2 min prior to the addition of sodium triacetoxyborohydride (120 mg, 0.57 mmol). The reaction mixture was stirred for 24 hr at room temperature and then ethyl acetate (70 ml) added. The solution was washed with saturated aqueous hydrogen carbonate, water and brine, then the solvent removed under reduced pressure to give a residue which was purified by column chromatography on silica gel eluting with dichloromethane:methanol:ammonia (97:3:0.3). This gave the title compound (215 mg) as a gum. MS: 829 (MH+).

$^1$H NMR (CDCl$_3$) δ=8.10 (1H, s), 7.35–7.15 (10H, m), 5.95–5.90 (1H, m), 5.50 (1H, br s), 4.50–4.45 (1H, m), 4.40–4.25 (4H, m), 4.20–4.15 (1H, m), 3.80–3.75 (1H, m), 3.60–3.55 (1H, m), 3.45 (3H, s), 3.10–3.00 (4H, m), 2.50–2.45 (2H, m), 1.75–1.40 (7H, m), 1.25–1.05 (4H, m), 0.95–0.85 (18H, m), 0.10–0.00 (12H, m).

Preparation 24

2-[(Benzyloxy)methyl]-9-[(2R,3R,4R,5R)-3,4-bis{[tert-butyl(dimethyl)silyl]oxy}-5-(methoxymethyl)tetrahydro-2-furanyl]-N-(2,2-diphenylethyl)-9H-purin-6-amine

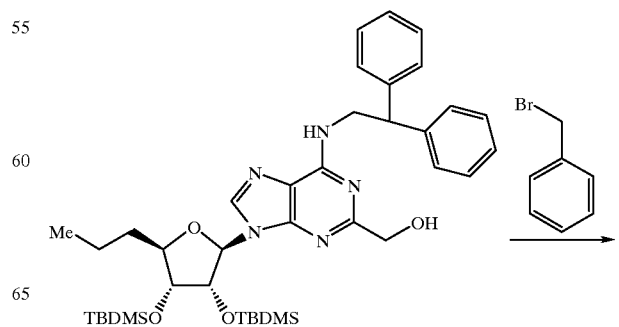

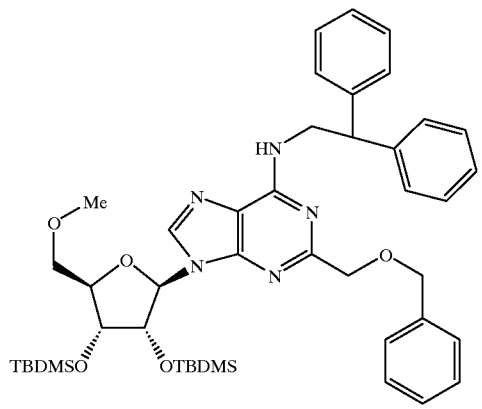

Sodium hydride (23 mg of an 80% dispersion in mineral oil, 0.76 mmol) was added to a stirred solution of {9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methanol (550 mg, 0.76 mmol) (preparation 15) in tetrahydrofuran (3 ml). The reaction mixture was stirred at room temperature for 10 min and then benzyl bromide (0.117 ml, 1 mmol) added. The reaction mixture was stirred for a further 24 hr and then the solvent removed under reduced pressure. The residue was purified by column chromatography on silica gel eluting with a gradient system of hexane:ethyl acetate (3:1) rising in polarity to (2:1) to give the title compound (65 mg) as a gum. MS: 832 (MNa$^+$).

$^1$H NMR (CDCl$_3$) δ=8.15 (1H, br s), 7.45–7.40 (2H, m), 7.30–7.15 (13H, m), 6.00–5.95 (1H, m), 5.70 (1H, br s), 4.75–4.60 (4H, m), 4.50–4.45 (1H, m), 4.40–4.30 (4H, m), 4.20–4.15 (1H, m), 3.80–3.75 (1H, m), 3.60–3.55 (1H, m), 3.40 (3H, s), 0.95–0.80 (18H, m), 0.50–0.00 (12H, m).

Preparation 25

{9-[(2R,3R,4S,5R)-3,4-Dihydroxy-5-(methoxymethyl)tetrahydro-2-furanyl]-6-[(2,2-diphenylethyl)amino]-9H-purin-2-yl}methyl methanesulfonate

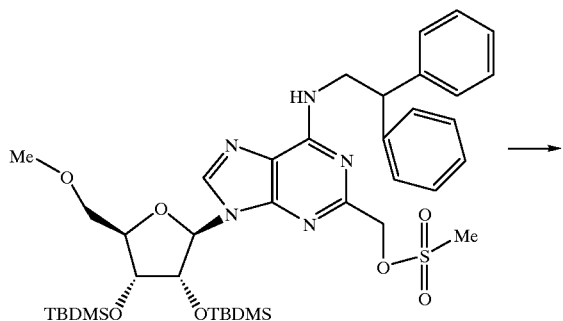

{9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate (240 mg, 0.3 mmol) (preparation 16) was dissolved in stirred tetrahydrofuran (1 ml) and a 1 molar solution of tetra-n-butylammonium fluoride in tetrahydrofuran (0.6 ml, 0.6 mmol) added. The reaction mixture was stirred at room temperature for 24 hr. The solvent was removed under reduced pressure and the residue purified by column chromatography on silica gel eluting with a gradient system of dichloromethane:methanol (95:5) increasing in polarity to dichloromethane:methanol (90:10). This gave the title compound (140 mg) as a foam. MS: 570 (MH$^+$).

$^1$H NMR (CDCl$_3$) δ=7.95 (1H, s), 7.40–7.20 (10H, m), 5.95–5.80 (2H, m), 5.70 (1H, m), 5.30 (2H, m), 4.55–4.20 (6H, m), 3.65–3.50 (2H, m), 3.30 (3H, s), 3.10 (3H, s), 3.05 (1H, s).

Preparation 26 tert-Butyl trans-4-(benzylamino)cyclohexylcarbamate

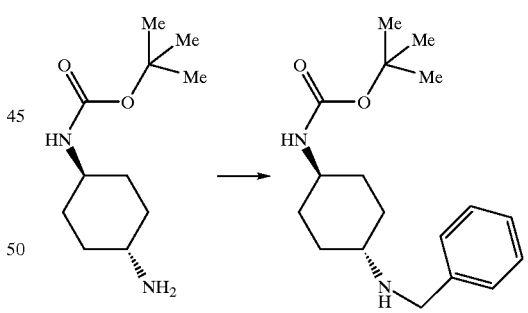

The title compound was prepared by a similar method to example 5 from tert-butyl trans-4-aminocyclohexylcarbamate (1.0 g, 4.7 mmol) (J. Org. Chem. 8811, 61, 1996), benzaldehyde (530 mg, 5 mmol) and sodium triacetoxyborohydride (2.0 g, 9.4 mmol). The product was purified by column chromatography on silica gel eluting with a solvent system of dichloromethane:methanol:ammonia (95:5:0.5) to give the title compound (0.73 g) as a solid.

$^1$H NMR (CDCl$_3$) δ=7.35–7.20 (5H, m), 4.35 (1H, br s), 3.80 (2H, s), 3.40 (1H, br s), 2.50–2.40 (1H, m), 2.05–1.90 (4H, m), 1.45 (9H, s), 1.30–1.05 (4H, m).

Preparation 27

N-(trans-4-Aminocyclohexyl)benzylamine

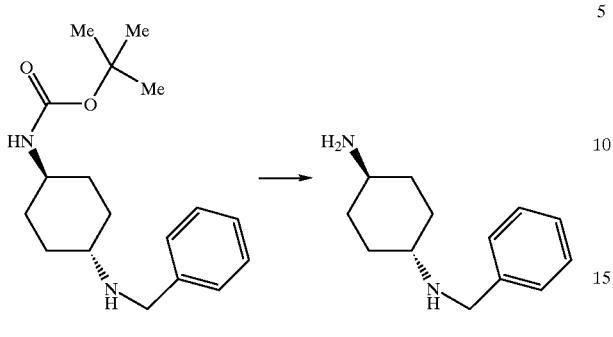

A stirred solution of tert-butyl trans-4-(benzylamino) cyclohexylcarbamate (730 mg, 3.6 mmol) (preparation 26) in dichloromethane (20 ml) was saturated with hydrogen chloride gas. The reaction mixture was stirred at room temperature for 2 hr and the solvent removed under reduced pressure to give a residue which was triturated with diethyl ether. The resulting solid was dissolved in water and solid sodium hydrogen carbonate added. The aqueous mixture was then extracted with ethyl acetate followed by dichloromethane. The organic extracts were combined, the solvent removed under reduced pressure and the residue purified by column chromatography on silica gel eluting with a solvent system of dichloromethane:methanol:ammonia (95:5:0.5) to give the title compound (530 mg) as a gum.

$^1$H NMR (CDCl$_3$) δ=7.35–7.20 (5H, m), 3.80 (2H, s), 2.70–2.60 (1H, m), 2.50–2.40 (1H, m), 2.00–1.90 (2H, m), 1.90–1.80 (2H, m), 1.25–1.05 (4H, m).

Preparation 28

4-(Bromomethyl)tetrahydro-2H-pyran

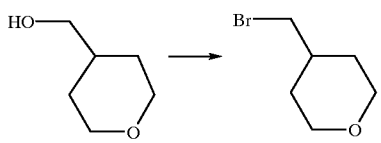

Triphenylphosphine (3.93 g, 15 mmol) was added to a stirred ice-cold solution of tetrahydro-2H-pyran-4-ylmethanol (1.16 g, 10 mmol) (WO 96/07410) and carbon tetrabromide (4.97 g, 15 mmol) in dichloromethane (50 ml). The reaction temperature was allowed to rise to room temperature and then the reaction mixture was stirred at room temperature for 24 hr. The solvent was removed under reduced pressure and the residue purified by column chromatography on silica gel eluting with a gradient system of hexane rising in polarity to hexane:ethyl acetate (9:1) to give the title compound (1.7 g) as an oil.

$^1$H NMR (CDCl$_3$) δ=4.05–3.95 (2H, m), 3.45–3.25 (4H, m), 2.00–1.70 (3H, m), 1.40–1.20 (2H, m).

Preparation 29

N-(9-[(2R,3R,4R,5R)-3,4-Bis{[tert-butyl(dimethyl) silyl]oxy}-5-(methoxymethyl)tetrahydro-2-furanyl]-2-{[2-(1-piperidinyl)ethoxy]methyl}-9H-purin-6-yl)-N-(2,2-diphenylethyl)amine

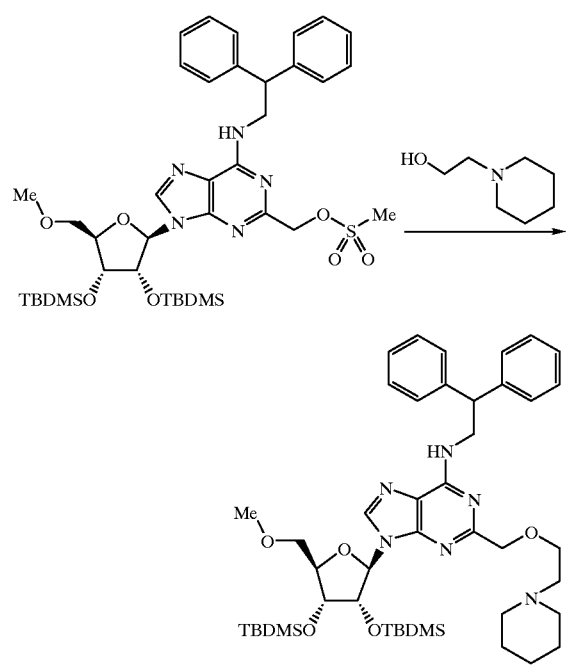

Sodium hydride (24 mg of an 80% dispersion in mineral oil, 0.81 mmol) was added to a stirred solution of {9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate (500 mg, 0.63 mmol) (preparation 16) and 2-(1-piperidinyl)-1-ethanol (105 mg, 0.81 mmol) in tetrahydrofuran (5 ml). The reaction mixture was stirred for 24 hr at room temperature and then heated at reflux for a further 8 hr. The reaction mixture was then poured into cold water and extracted with ethyl acetate. The organic phase was separated, washed with brine and dried with anhydrous sodium sulfate. The solvent was then removed under reduced pressure to give a residue which was purified by column chromatography on silica gel eluting with a solvent system of dichloromethane:methanol (95:5) to give the title compound (101 mg) as an oil. MS: 833 (MH$^+$).

$^1$H NMR (CDCl$_3$) δ=8.15 (1H, s), 7.35–7.15 (10H, m), 6.00–5.95 (1H, m), 5.65 (1H, br s), 4.60 (2H, s), 4.50–4.45 (1H, m), 4.45–4.30 (4H, m), 4.20–4.15 (1H, m), 3.85–3.75 (3H, m), 3.60–3.55 (1H, m), 3.45 (3H, s), 2.75–2.40 (6H, m), 1.70–1.50 (4H, m), 1.50–1.35 (2H, m), 0.95–0.80 (18H, m), 0.10–0.00 (12H, m).

Preparation 30

2-{9-[(2R,3R,4S,5R)-3,4-Dihydroxy-5-(methoxymethyl)tetrahydro-2-furanyl]-6-[(2,2-diphenylethyl)amino]-9H-purin-2-yl}acetonitrile

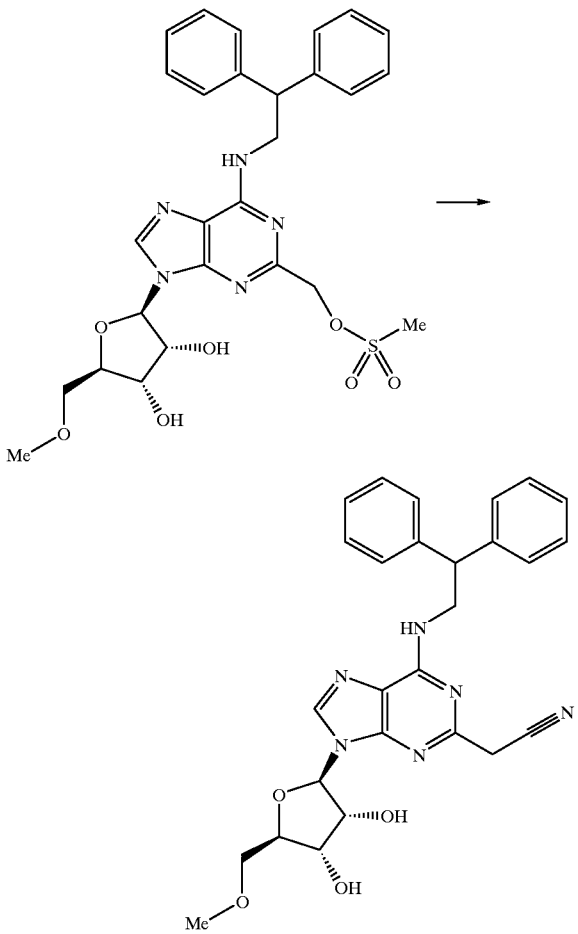

Potassium cyanide (22 mg, 0.33 mmol) was added to a stirred solution of {9-[(2R,3R,4S,5R)-3,4-dihydroxy-5-(methoxymethyl)tetrahydro-2-furanyl]-6-[(2,2-diphenylethyl)amino]-9H-purin-2-yl}methyl methanesulfonate (130 mg, 0.22 mmol) (preparation 25) in N,N-dimethylformamide (3 ml). The reaction mixture was heated to 70° C. for 1.5 hr, allowed to cool to room temperature and then partitioned between diethyl ether and water. The aqueous layer was washed with diethyl ether. The combined organic solutions were washed with brine and dried with anhydrous magnesium sulfate. The solvent was removed under reduced pressure to give a residue that was purified by column chromatography on silica gel eluting with a solvent system of dichloromethane:methanol (97:3). This gave the title compound (70 mg) as a powder. MS: 523 (MNa$^+$).

$^1$H NMR (CDCl$_3$) δ=7.90 (1H, s), 7.40–7.20 (10H, m), 5.90–5.80 (2H, m), 5.40 (1H, s), 4.60–4.55 (1H, m), 4.50–4.20 (5H, m), 3.95 (2H, s), 3.65–3.50 (2H, m), 3.30 (3H, s), 3.05 (1H, s). Analysis: Found C, 63.47, H, 5.71, N, 16.11; C$_{27}$H$_{28}$N$_6$O$_4$·0.5H$_2$O requires C, 63.64, H, 5.75, N, 16.49%.

Preparation 31

2,2,2-Trifluoro-1-(4-phenyl-1-piperidinyl)-1-ethanone

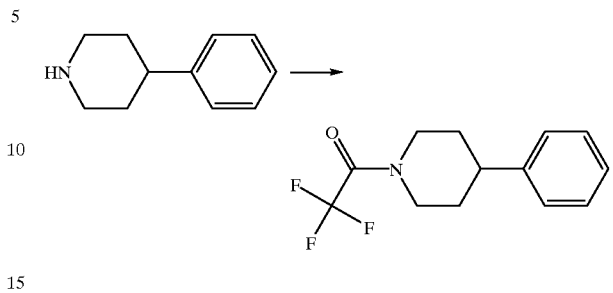

Trifluoroacetic anhydride (32.6 g, 0.155 mol) was slowly added to a stirred solution of 4-phenylpiperidine (25 g, 0.155 mol) and N-methylmorpholine (15.6 g, 0.155 mol) in dichloromethane (250 ml) at between –10° C. and –15° C. The reaction mixture was allowed to warm to room temperature and then stirred for a further 24 hr. The reaction mixture was then washed with water (100 ml), dried with anhydrous magnesium sulfate and the solvent removed under reduced pressure to give a residue which was purified by column chromatography on silica gel eluting with hexane:ethyl acetate (7:3) to give the title compound (34.5 g) as a gum.

$^1$H NMR (CDCl$_3$) δ=7.40–7.15 (5H, m), 4.75–4.60 (1H, m), 4.25–4.10 (1H, m), 3.30–3.15 (1H, m), 2.90–2.70 (2H, m), 2.05–1.90 (2H, m), 1.80–1.60 (2H, m),

Preparation 32 tert-Butyl trans-4-[(methylsulfonyl)amino]cyclohexylcarbamate

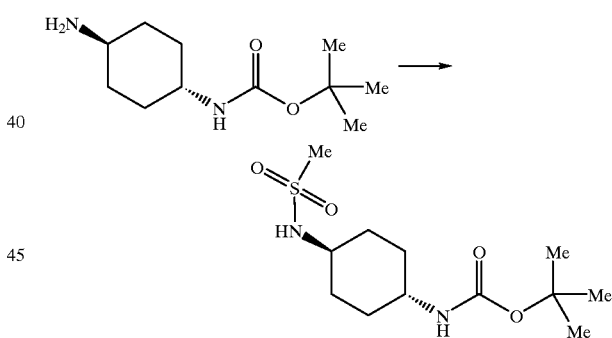

Methanesulfonyl chloride (0.56 g, 4.7 mmol) was added to a stirred solution of tert-butyl trans-4-aminocyclohexylcarbamate (J. Org. Chem. 8811, 61, 1996) (1.0 g, 4.7 mmol) and N-ethyl-N-isopropyl-2-propanamine (0.67 g, 0.52 mmol) in dichloromethane (30 ml). The reaction mixture was stirred for 30 min at room temperature and then partitioned between ethyl acetate (300 ml) and water (100 ml). The organic layer was washed twice with 1 molar aqueous citric acid solution and then with a saturated aqueous solution of sodium hydrogen carbonate, dried with anhydrous sodium sulfate and the solvent removed under reduced pressure to give a residue that was triturated with diethyl ether to give the title compound (0.99 g) as a white solid.

$^1$H NMR (CDCl$_3$) δ=4.35 (1H, br s), 4.15–4.10 (1H, m), 3.40 (1H, br s), 3.30–3.20 (1H, m), 2.95 (3H, br s), 2.10–2.00 (4H, m), 1.40 (9H, s), 1.40–1.15 (4H, m).

Preparation 33

N-(trans-4-Aminocyclohexyl)methanesulfonamide

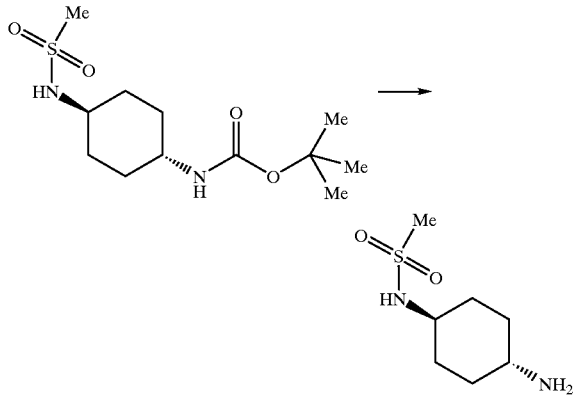

A stirred solution of tert-butyl trans-4-[(methylsulfonyl)amino]cyclohexylcarbamate (990 mg, 3.39 mmol) (preparation 32) in dichloromethane (25 ml) at room temperature was saturated with hydrogen chloride gas. The reaction mixture was stirred at room temperature for 2 hr and the solvent then removed under reduced pressure to give a colourless solid. The solid was triturated with diethyl ether and then suspended in ethyl acetate and exposed to ultrasonic agitation for 5 min. The remaining solid was filtered off to give the title compound (0.6 g) as a solid.

$^1$H NMR (d$_6$ DMSO) δ=8.15–7.95 (3H, br s), 7.05–7.00 (1H, m), 3.10–3.00 (1H, m), 3.00–2.80 (4H, m), 1.95–1.80 (4H, m), 1.45–1.15 (4H, m).

Preparation 34

N-(2-{9-[(2R,3R,4R,5R)-3,4-Bis{[tert-butyl(dimethyl)silyl]oxy}-5-(methoxymethyl)tetrahydro-2-furanyl]-6-[(2,2-diphenylethyl)amino]-9H-purin-2-yl}ethyl)-N-(2-methoxyethyl)amine

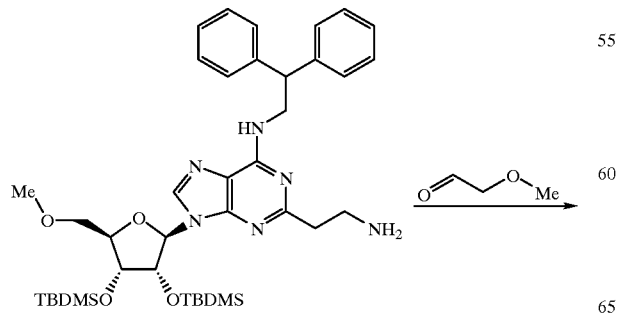

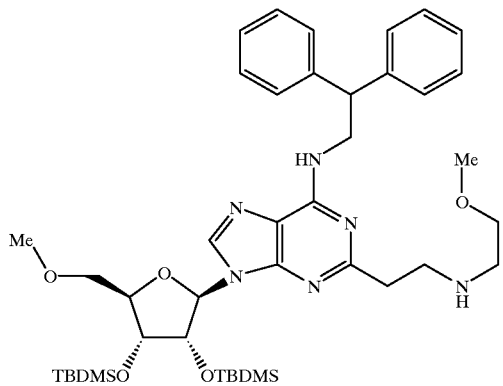

The title compound was prepared by a similar method to preparation 23 from the compound of preparation 18 (250 mg, 0.34 mmol), sodium tracetoxyborohydride (120 mg, 0.56 mmol) and 2-methoxyacetaldehyde (28 mg, 0.33 mmol). The compound was purified by column chromatography on silica gel eluting with a solvent system of dichloromethane:methanol:ammonia (95:5:0.5) to give the title compound (155 mg) as a foam. MS: 791 (MH$^+$).

$^1$H NMR (CDCl$_3$) δ=8.10 (1H, s), 7.35–7.20 (10H, m), 5.95 (1H, s), 5.50 (1H, br s), 4.50–4.45 (1H, m), 4.40–4.25 (4H, m), 4.20–4.15 (1H, m), 3.80–3.75 (1H, m), 3.60–3.55 (1H, m), 3.50–3.45 (2H, m), 3.40 (3H, s), 3.30 (3H, s), 3.15–2.95 (4H, m), 2.90–2.80 (2H, m), 0.95–0.85 (18H, m), 0.10–0.00 (12H, m).

Preparation 35

N-(9-[(2R,3R,4R,5R)-3,4-Bis{[tert-butyl(dimethyl)silyl]oxy}-5-(methoxymethyl)tetrahydro-2-furanyl]-2-{[cyclohexyl(methyl)amino]methyl}-9H-purin-yl)-N-(2,2-diphenylethyl)amine

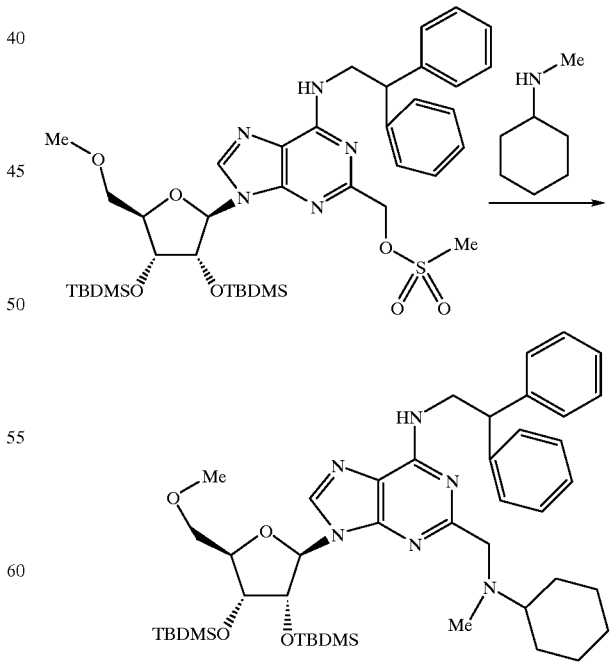

N-Cyclohexyl-N-methylamine (30 mg, 0.27 mmol) was added to a stirred solution of {9-[(2R,3R,4R,5R)-3,4-bis{

[tert-butyl(dimethyl)silyl]oxy}-5-(methoxymethyl)
tetrahydro-2-furanyl]-6-[(2,2-diphenylethyl)amino]-9H-
purin-2-yl}methyl methanesulfonate (150 mg, 0.19 mmol)
(preparation 16) and potassium carbonate (60 mg, 0.44
mmol) in acetonitrile (10 ml). The reaction mixture was
heated under reflux for 1 hr and then partitioned between
diethyl ether and water. The organic phase was removed and
the aqueous phase extracted with more diethyl ether. The
combined organic layers were washed with brine and dried
with anhydrous magnesium sulfate. The solvent was
removed under reduced pressure to give a residue which was
purified by column chromatography on silica gel eluting
with ethyl acetate. This gave the title compound (140 mg) as
a foam. MS: 815 (MH+).

$^1$H NMR (CDCl$_3$) δ=8.15 (1H, s), 7.35–7.20 (10H, m),
6.00–5.95 (1H, m), 5.55 (1H, br s), 4.55–4.50 (1H, m),
4.45–4.30 (4H, m), 4.25–4.15 (1H, m), 3.85–3.70 (3H, m),
3.60–3.55 (1H, m), 3.45 (3H, s), 2.65–2.40 (4H, m),
2.05–1.95 (2H, m), 1.80–1.75 (2H, m), 1.35–1.00 (6H, m),
0.95–0.85 (18H, m), 0.10–0.00 (12H, m).

Preparation 36

8-2-Pyridinyl)-1,4-dioxa-8-azaspiro[4.5]decane

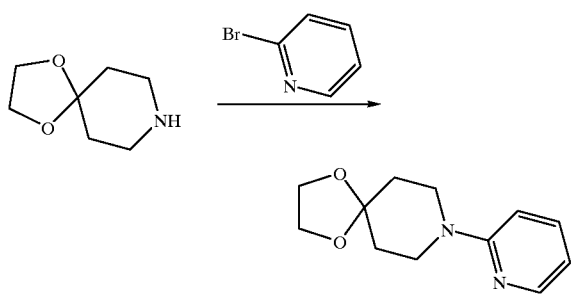

Potassium carbonate (700 mg, 5 mmol), 1,4dioxa-8-
azaspiro[4.5]decane (1.43 g, 10 mmol) and 2-bromopyridine
(1.58 g, 10 mmol) were stirred and heated together in
N,N-dimethylformamide (10 ml) at 125° C. for 4 hr. The
reaction mixture was then poured into water and extracted
with ethyl acetate. The organic phase was separated, washed
with water and dried over solid potassium carbonate and the
solvent removed under reduced pressure to give the title
compound (1.1 g) as an oil.

$^1$H NMR (CDCl$_3$) δ=8.20–8.10 (1H, m), 7.45–7.40 (1H,
m), 6.70–6.60 (1H, m), 6.60–6.50 (1H, m), 3.95 (4H, s),
3.70–3.60 (4H, m), 1.80–1.70 (4H, m).

Preparation 37

1-(2-Pyridinyl)-4-piperidinone

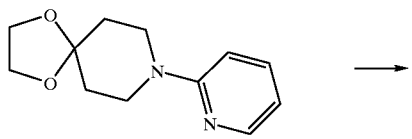

-continued

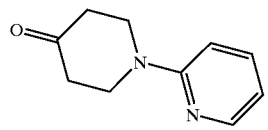

A solution of 8-(2-pyridinyl)-1,4-dioxa-8-azaspiro[4.5]
decane (23 g, 0.1 mol) (preparation 36) in 10% w/v sulphu-
ric acid was stirred at room temperature for 8 hr. The
reaction mixture was cooled in ice and then the solution
adjusted to pH>7 with 0.88 ammonia. The solution was
extracted with diethyl ether and the solvent removed from
the organic extracts under reduced pressure to give the title
compound (14.7 g) as an oil.

$^1$H NMR (CDCl$_3$) δ=8.25–8.20 (1H, m), 7.60–7.50 (1H,
m), 6.80–6.75 (1H, m), 6.75–6.65 (1H, m), 4.00–3.90 (4H,
m), 2.60–2.45 (4H, m).

Preparation 38

2-{2-[(1-Benzhydryl-3-azetidinyl)amino]ethyl}-9-
[(2R,3R,4R,5R)-3,4-bis{[tert-butyl(dimethyl)silyl]
oxy}- 5-(methoxymethyl)tetrahydro-2-furanyl]-N-
(2,2-diphenylethyl)-9H-purin-6-amine

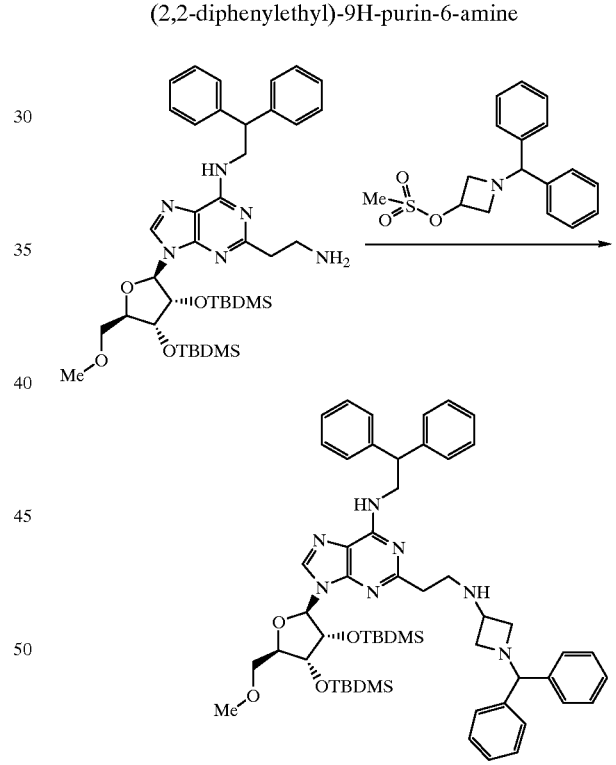

1-Benzhydryl-3-azetidinyl methanesulfonate (90 mg,
0.28 mmol) and potassium carbonate (50 mg, 0.36 mmol)
were added to a stirred solution of N-{2-(2-aminoethyl)-9-
[(2R,3R,4R,5R)-3,4-bis{[tert-butyl(dimethyl)silyl]oxy}-5-
(methoxymethyl)tetrahydro-2-furanyl]-9H-purin-6-yl}-N-
(2,2-diphenylethyl)amine (200 mg) (preparation 18) in
acetonitrile (3 ml). The reaction mixture was heated at reflux
for 5 hr and then allowed to stand at room temperature for
a further 24 hr. The resulting mixture was partitioned
between ethyl acetate and water. The ethyl acetate layer was
separated and the aqueous layer extracted with more ethyl acetate. The combined organic solutions were washed with brine and dried with anhydrous magnesium sulfate. The solvent was removed under reduced pressure and the residue purified by column chromatography on silica gel eluting with a solvent system of dichloromethane:methanol:ammonia (98:2:0.2) to give the title compound (135 mg) as a foam. MS: 955 (MH$^+$).

$^1$H NMR (CDCl$_3$) δ=8.10 (1H, s), 7.40–7.35 (4H, m), 7.30–7.10 (16H, m), 5.95–5.90 (1H, m), 5.50 (1H, br s), 4.50–4.45 (1H, m), 4.40–4.20 (5H, m), 4.20–4.15 (1H, m), 3.80–3.75 (1H, m), 3.60–3.45 (4H, m), 3.40 (3H, s), 3.05–2.90 (4H, m), 2.70–2.65 (2H, m), 0.90–0.85 (18H, m), 0.05–0.00 (12H, m).

Preparation 39

N-Benzyl-N-(2-{9-[(2R,3R,4R,5R)-3,4-bis{[tert-butyl(dimethyl)silyl]oxy}-5-(methoxymethyl)tetrahydro-2-furanyl]-[(2,2-diphenylethyl)amino]-9H-purin-2-yl}ethyl)amine

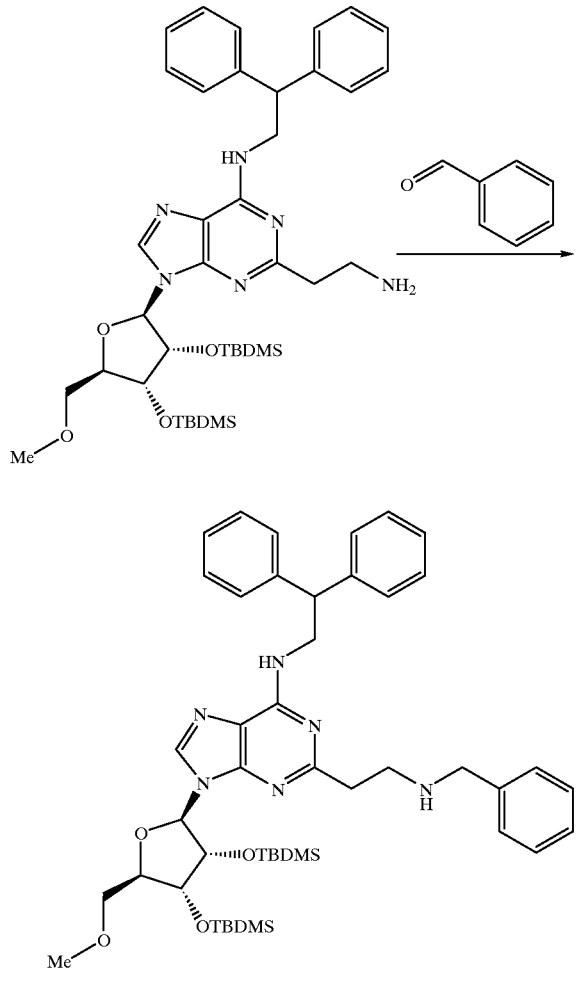

The title compound was prepared by a similar method to example 5 from N-{2-(2-aminoethyl)-9-[(2R,3R,4R,5R)-3,4-bis{[tert-butyl(dimethyl)silyl]oxy}-5-(methoxymethyl)tetrahydro-2-furanyl]-9H-purin-6-yl}-N-(2,2-diphenylethyl)amine (430 mg, 0.58 mmol) (preparation 18), benzaldehyde (65 mg, 0.61 mmol) and sodium triacetoxyborohydride (270 mg, 1.27 mmol) in tetrahydrofuran (15 ml). The product was purified by column chromatography on silica gel eluting with a solvent gradient of dichloromethane rising in polarity to dichloromethane:methanol:ammonia (95:5:0.5) to give the title compound (360 mg) as a foam. MS: 825 (MH$^+$).

$^1$H NMR (CDCl$_3$) δ=8.10 (1H, s), 7.40–7.15 (15H, m), 5.95–5.90 (1H, m), 5.60 (1H, br s), 4.50–4.45 (1H, m), 4.40–4.15 (5H, m), 3.85 (2H, s), 3.80–3.75 (1H, m), 3.60–3.55 (1H, m), 3.40 (3H, s), 3.20–3.00 (4H, m), 0.95–0.85 (18H, m), 0.10–0.00 (12H, m).

Preparation 40

N-(9-[(2R,3R,4R,5R)-3,4-Bis{[tert-butyl(dimethyl)silyl]oxy}-5-(methoxymethyl)tetrahydro-2-furanyl]-2-{2-[(cyclopropylmethyl)amino]ethyl}-9H-purin-6-yl)-N-(2,2-diphenylethyl)amine

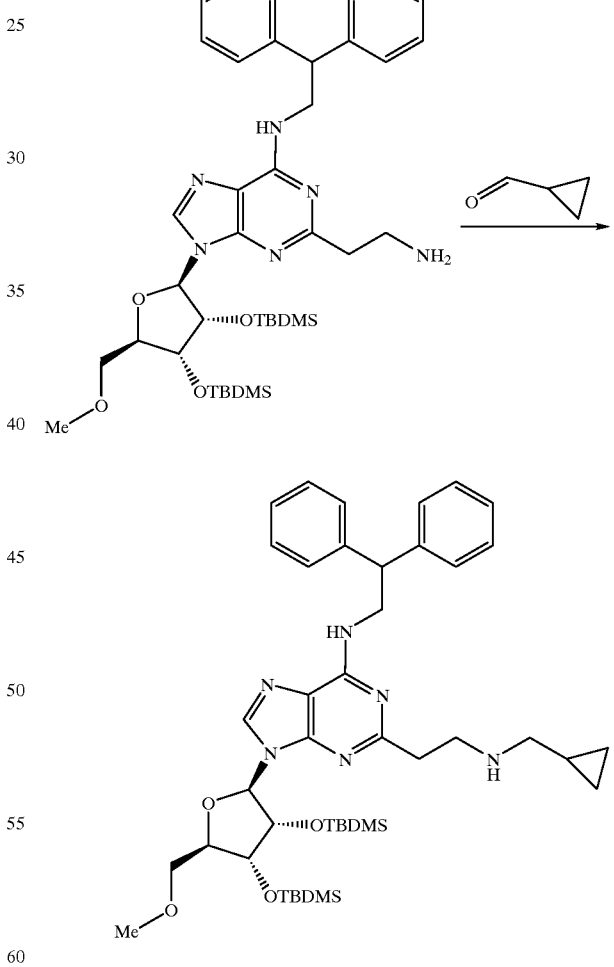

The title compound was prepared by a similar method to example 5 from N-{2-(2-aminoethyl)-9-[(2R,3R,4R,5R)-3,4-bis{[tert-butyl(dimethyl)silyl]oxy}-5-(methoxymethyl)tetrahydro-2-furanyl]-9H-purin-6-yl}-N-(2,2-diphenylethyl)amine (430 mg, 0.58 mmol) (preparation 18), cyclopropanecarbaldehyde (45 mg, 0.64 mmol) and sodium triacetoxyborohydride (270 mg, 1.27 mmol) in tetrahydrofuran (10 ml). The product was purified by column chromatography on silica gel eluting with a solvent gradient of dichloromethane rising in polarity to dichloromethane:methanol:ammonia (95:5:0.5) to give the title compound (360 mg) as a gum. MS: 788 (MH⁺).

¹H NMR (CDCl₃) δ=8.10 (1H, s), 7.35–7.20 (10H, m), 5.95–5.90 (1H, m), 5.55 (1H, br s), 4.50–4.45 (1H, m), 4.40–4.25 (4H, m), 4.20–4.15 (1H, m), 3.80–3.75 (1H, m), 3.60–3.55 (1H, m), 3.40 (3H, s), 3.20–2.90 (4H, m), 2.50–2.45 (2H, m), 0.95–0.85 (19H, m), 0.45–0.40 (2H, m), 0.10–0.05 (14H, m).

Preparation 41

2-Chloro-N-phenethyl-9-tetrahydro-2H-pyran-2-yl-9H-purin-6-amine

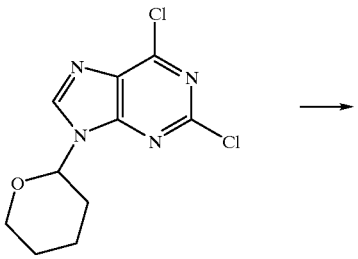

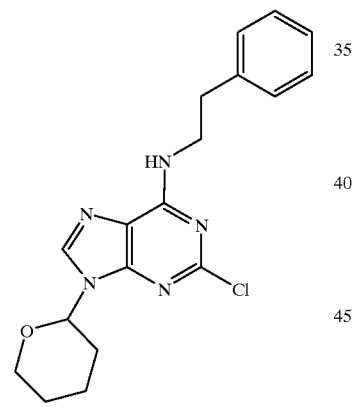

Phenethylamine (7.0 g, 58.4 mmol) was added to a stirred solution of 2,6-dichloro-9-tetrahydro-2H-pyran-2-yl-9H-purine (14.5 g, 53.1 mmol) (preparation 5) and triethylamine (21 g, 212.5 mmol) in acetonitrile (200 ml). The reaction mixture was stirred for 3 hr at room temperature and then more phenethylamine (1 g, 8.3 mmol) was added. The reaction mixture was stirred for a further 1 hr and then the solvent was removed under reduced pressure to give a residue which was partitioned between diethyl ether (500 ml) and water (250 ml). The diethyl ether layer was washed with more water (300 ml). The solvent was removed from the organic phase under reduced pressure to give a residue which was purified by column chromatography on silica gel eluting with diethyl ether to give the title compound (17.9 g) as a white solid.

¹H NMR (CDCl₃) δ=7.90 (1H, br s), 7.35–7.20 (5H, m), 5.90 (1H, br s), 5.70–5.65 (1H, d), 4.20–4.10 (1H, m), 3.90 (1H, br s), 3.80–3.70 (1H, m), 3.00–2.95 (2H, m), 2.10–2.00 (2H, m), 2.00–1.85 (1H, m), 1.85–1.60 (3H, m).

Preparation 42

2-(Methylsulfanyl)-N-phenethyl-9-tetrahydro-2H-pyran-2-yl-9H-purin-6-amine

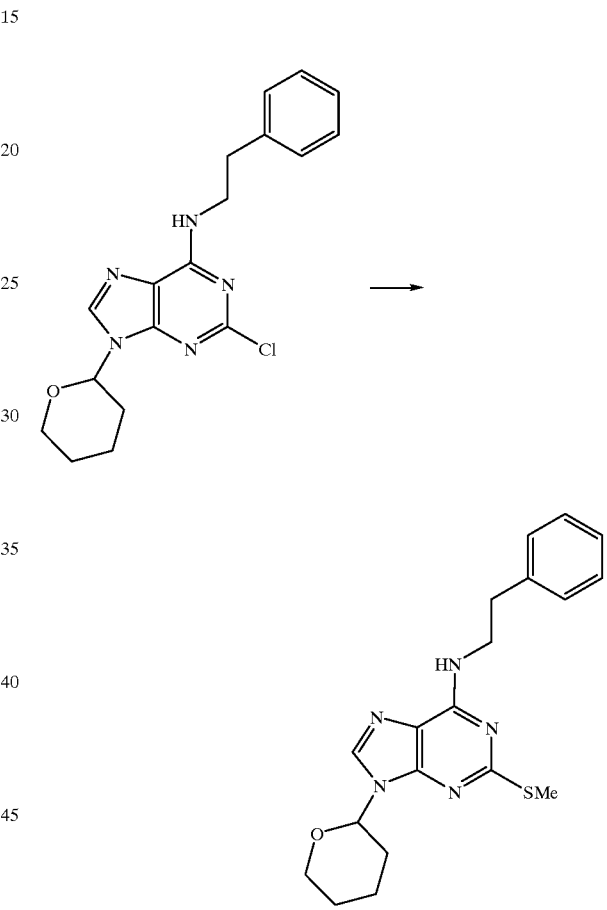

The title compound was prepared by a similar method to preparation 7 from 2-chloro-N-phenethyl-9-tetrahydro-2H-pyran-2-yl-9H-purin-6-amine (17.5 g, 49 mmol) (preparation 41) and sodium thiomethoxide (7.2 g, 75 mmol). This gave the title compound (16.7 g) as a white solid.

¹H NMR (CDCl₃) δ=7.80 (1H, s), 7.35–7.20 (5H, m), 5.80–5.60 (2H, m), 4.20–4.10 (1H, m), 3.90 (2H, br s), 3.80–3.70 (1H, m), 3.00–2.90 (2H, m), 2.60 (3H, s), 2.15–1.90 (3H, m), 1.85–1.60 (3H, m).

Preparation 43

2-(Methylsulfonyl)-N-phenethyl-9-tetrahydro-2H-pyran-2-yl-9H-purin-6-amine

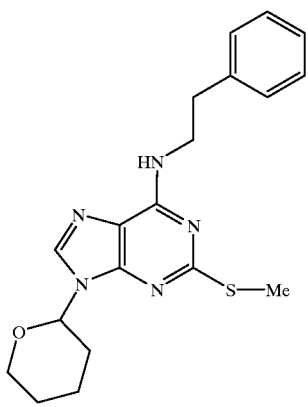

The title compound was prepared by a similar method to preparation 8 from 2-(methylsulfanyl)-N-phenethyl-9-tetrahydro-2H-pyran-2-yl-9H-purin-6-amine (16.7 g, 45 mmol) (preparation 42), Oxone (trade mark) (42.0 g, 136 mmol) and solid sodium hydrogen carbonate (20 g, 238 mmol). This gave the title compound (21.4 g) as a white solid. MS: 402 (MH$^+$).

$^1$H NMR (CDCl$_3$) δ=8.10 (1H, s), 7.35–7.20 (5H, m), 6.20 (1H, br s), 5.80–5.75 (1H, m), 4.20–4.10 (1H, m), 3.95 (1H, br s), 3.80–3.70 (1H, m), 3.30 (3H, s), 3.05–2.95 (2H, m), 2.20–1.60 (6H, m).

Preparation 44

6-(Phenethylamino)-9-tetrahydro-2H-pyran-2-yl-9H-purine-2-carbonitrile

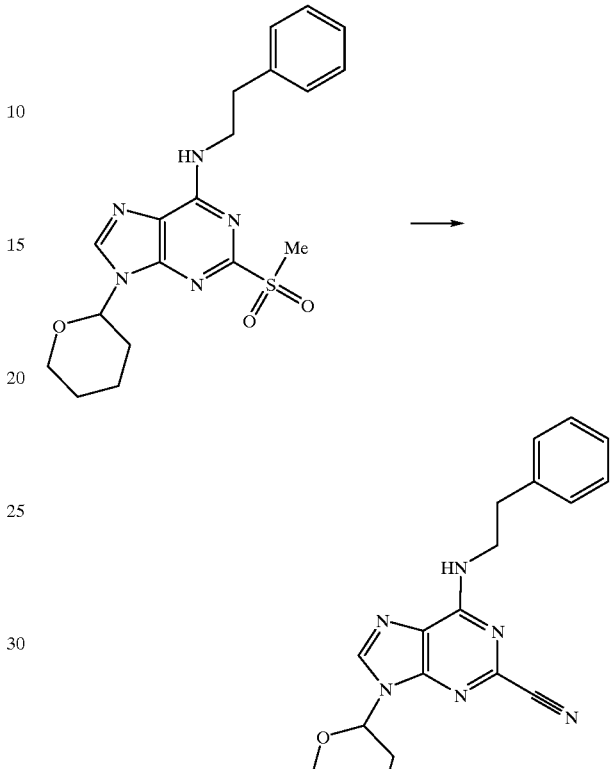

Potassium cyanide (5.6 g, 86.2 mmol) was added to a stirred solution of 2-(methylsulfonyl)-N-phenethyl-9-tetrahydro-2H-pyran-2-yl-9H-purin-6-amine (21.0 g, 43.1 mmol) (preparation 43) in N,N-dimethylformamide (100 ml). The reaction mixture was heated at 110° C. for 74 hr with extra potassium cyanide being added at 44 hr (3.3 g, 50.8 mmol) and 68 hr (1.2 g, 18.5 mmol). The reaction mixture was allowed to stand at room temperature for 70 hr, then poured into water (500 ml), extracted with diethyl ether (1000 ml) and the aqueous layer washed with diethyl ether (500 ml). The combined organic layers were washed with water (3×500 ml). The solvent was removed under reduced pressure from the combined organic layers to give a residue which was purified by column chromatography on silica gel eluting with a gradient system of dichloromethane:methanol (99:1) to give the title compound (10.2 g) as a brown solid. MS: 349 (MH$^+$).

$^1$H NMR (CDCl$_3$) δ=8.05 (1H, s), 7.35–7.20 (5H, m), 6.05 (1H, br s), 5.75–5.65 (1H, m), 4.20–4.10 (1H, m), 3.90 (1H, br s), 3.80–3.70 (1H, m), 3.05–2.90 (2H, m), 2.20–1.60 (6H, m).

Preparation 45

6-(Phenethylamino)-9H-purine-2-carbonitrile

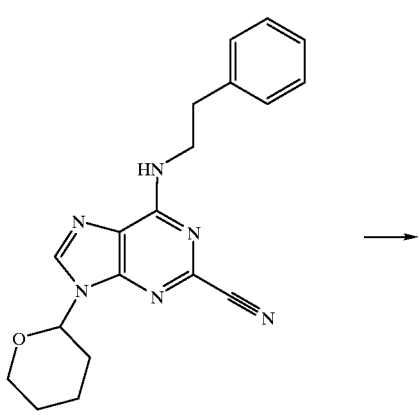

2 Molar hydrochloric acid (10 ml) was added to a stirred solution of 6-(phenethylamino)-9-tetrahydro-2H-pyran-2-yl-9H-purine-2-carbonitrile (10.2 g, 27.6 mmol) (preparation 44) in ethanol (250 ml) at 60° C. The solution was allowed to cool to room temperature and the white solid that had been formed filtered off. After drying, this gave the title compound (6.1 g) as a white crystalline solid. MS: 265 (MH$^+$).

$^1$H NMR (d$_6$ DMSO) δ=8.40–8.20 (2H, m), 7.35–7.10 (5H, m), 3.75–3.60 (2H, m), 2.95–2.85 (2H, m).

Preparation 46

(2R,3R,4R,5R)-4-(Benzoyloxy)-5-[2-cyano-6-(phenethylamino)-9H-purin-9-yl]-2-(methoxymethyl)tetrahydro-3-furanyl benzoate

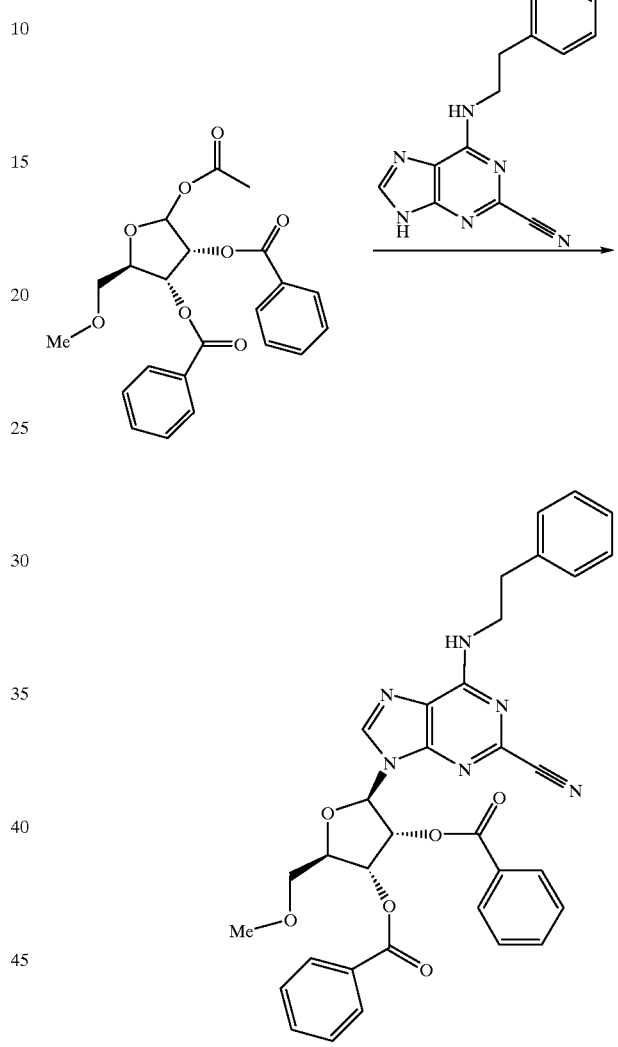

The title compound was prepared by a similar method to preparation 11 using 6-(phenethylamino)-9H-purine-2-carbonitrile (3.8 g, 11.2 mmol) (preparation 45), (2R,3R, 4R,5S)-5-(acetyloxy)-4-(benzoyloxy)-2-(methoxymethyl) tetrahydro-3-furanyl benzoate and (2R,3R,4R,5R)-5-(acetyloxy)-4-(benzoyloxy)-2-(methoxymethyl)tetrahydro- 3-furanyl benzoate (preparation 4) (6 g, 14.5 mmol), ammonium sulfate (200 mg, 1.2 mmol), 1,1,1,3,3,3-hexamethyidisilazane (150 ml), bromotrimethylsilane (8 ml, 177 mmol), acetonitrile (80 ml), dichloromethane (80 ml) and bismuth tribromide (0.35 g, 0.24 mmol). The product was purified by column chromatography on silica gel eluting with a solvent system of dichloromethane:methanol (99.5:0.5). This gave the title compound (7.9 g) as a white foam. MS: 619 (MH+).

$^1$H NMR (CDCl$_3$) δ=8.35 (1H, s), 8.05–8.00 (2H, m), 7.95–7.90 (2H, m), 7.65–7.20 (11H, m), 6.65–6.60 (1H, m), 6.05–5.90 (3H, m), 4.60 (1H, s), 3.95–3.80 (4H, m), 3.55 (3H, s), 3.00–2.90 (2H, m).

Preparation 47

9-[(2R,3R,4S,5R)-3,4-Dihydroxy-5-(methoxymethyl)tetrahydro-2-furanyl]-6-(phenethylamino)-9H-purine-2-carbonitrile

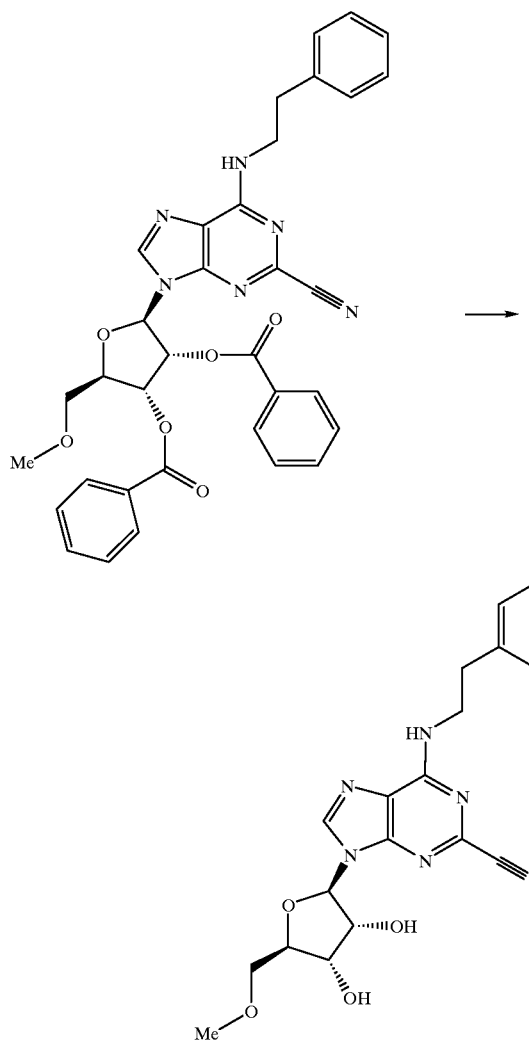

(2R,3R,4R,5R)-4-(Benzoyloxy)-5-[2-cyano-6-(phenethylamino)-9H-purin-9-yl]-2-(methoxymethyl)tetrahydro-3-furanyl benzoate (8.0 g, 19.5 mmol) (preparation 46) was dissolved in a saturated ethanolic solution of ammonia (300 ml). The solution was allowed to stand at room temperature for 24 hr, then re-saturated with ammonia gas and allowed to stand for a further 48 hr. The solvent was then removed under reduced pressure and dichloromethane added to the residue. The dichloromethane was then removed under reduced pressure and more dichloromethane (50 ml) added. The insoluble material was filtered off and dried. This was found to be the title compound (3.1 g) which was a solid.

$^1$H NMR (d$_6$ DMSO) δ=8.60–8.45 (2H, m), 7.30–7.15 (5H, m), 5.90–5.85 (1H, m), 5.55–5.50 (1H, m), 5.30–5.25 (1H, m), 4.55–4.50 (1H, m), 4.15–4.00 (2H, m), 3.70–3.65 (1H, m), 3.65–3.50 (2H, m), 3.30 (3H+HOD in DMSO, s), 2.95–2.90 (2H, m).

Preparation 48

(2R,3R,4S,5R)-2-[2-(Aminomethyl)-6-(phenethylamino)-9H-purin-9-yl]-5-(methoxymethyl)tetrahydro-3,4-furandiol

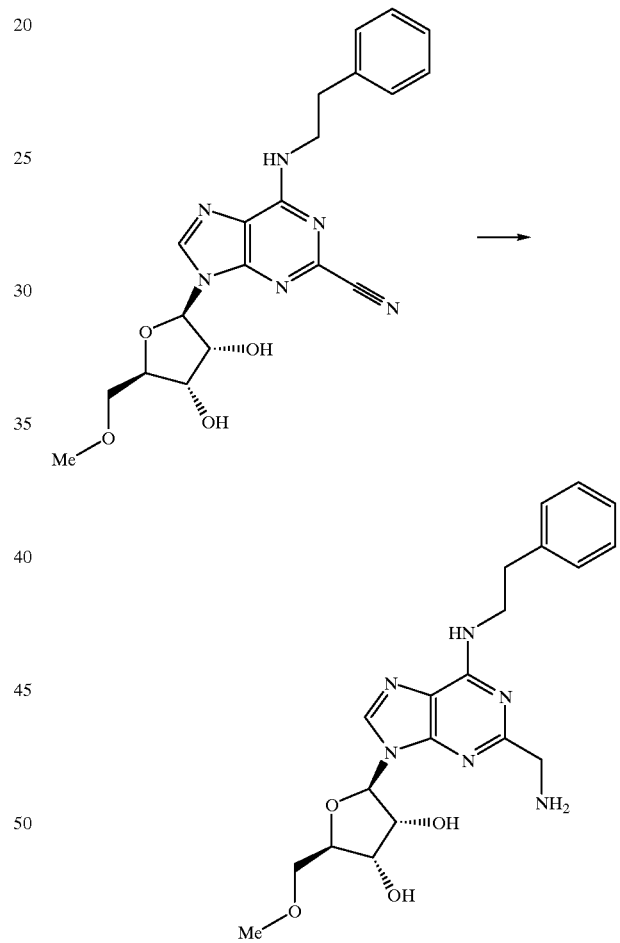

A solution of 9-[(2R,3R,4S,5R)-3,4-dihydroxy-5-(methoxymethyl)tetrahydro-2-furanyl]-6-(phenethylamino)-9H-purine-2-carbonitrile (2.9 g, 7.07 mmol) (preparation 47) in ethanol (300 ml), saturated with ammonia gas, was treated with 5% palladium on charcoal (1.0 g), pressurised to 1034 kPa (150 psi) with hydrogen gas in a sealed vessel and stirred at room temperature for 48 hr. The reaction mixture was filtered through Arbocel (trade mark) and the solvent removed under reduced pressure. The residue was dissolved in dichloromethane and the solvent removed under reduced pressure to give a product that was purified by column chromatography on silica gel eluting with a solvent system of dichloromethane:methanol:ammonia (92:8:0.4) to give the title compound (1.7 g) as a foam. MS: 416 (MH+)

1H NMR (d$_6$ DMSO) δ=8.20 (1H, br s), 7.70 (1H, br s), 7.30–7.15 (5H, m), 5.90–5.85 (1H, m), 5.45 (1H, br s), 5.25 (1H, s), 4.60 (1H, s), 4.15–4.10 (1H, m), 4.00–3.95 (1H, m), 3.75–3.60 (3H, m), 3.60–3.45 (2H, m), 3.30–3.25 (3H+HOD in DMSO, s), 2.95–2.90 (2H, m).

Preparation 49

N-(9-[(2R,3R,4R,5R)-3,4-Bis{[tert-butyl(dimethyl)silyl]oxy}-5-(methoxymethyl)tetrahydro-2-furanyl]-2-{[(1-methyl-4-piperidinyl)oxy]methyl}-9H-purin-6-yl)-N-(2,2-diphenylethyl)amine

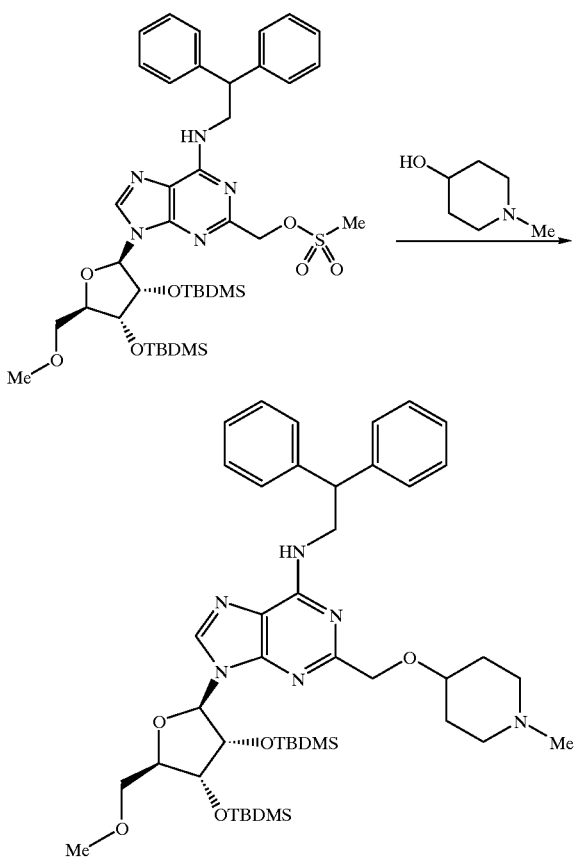

Sodium hydride (42 mg of an 80% dispersion in mineral oil, 1.4 mmol) was added to a stirred solution of {9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purin-2-yl}methyl methanesulfonate (preparation 16) (540 mg, 0.7 mmol) and 1-methyl-4-piperidinol (160 mg, 1.4 mmol) in tetrahydrofuran (10 ml). The reaction mixture was heated at reflux for 24 hr and then the solvent removed under reduced pressure to give a residue which was purified by column chromatography on silica gel eluting with dichloromethane:methanol (95:5) to give the title compound (68 mg). MS: 818 (MH+).

$^1$H NMR (CDCl$_3$) δ=8.20 (1H, s), 7.35–7.10 (10H, m), 6.00–5.95 (1H, m), 5.65 (1H, br s), 4.60 (2H, s), 4.50–4.10 (6H, m), 3.80–3.70 (1H, m), 3.70–3.50 (2H, m), 3.40 (3H, s), 3.40–3.30 (2H, m), 2.80–2.70 (2H, m), 2.30–2.20 (5H, m), 2.05–1.95 (2H, m), 0.95–0.80 (18H, m), 0.10–0.00 (12H, m).

Preparation 50

2-({[Amino(imino)methyl]sulfanyl}methyl)-9-[(2R,3R,4R,5R)-3,4-bis{[tert-butyl(dimethyl)silyl]oxy}-5-(methoxymethyl)tetrahydro-2-furanyl]-6-[(2,2-diphenylethyl)amino]-9H-purine

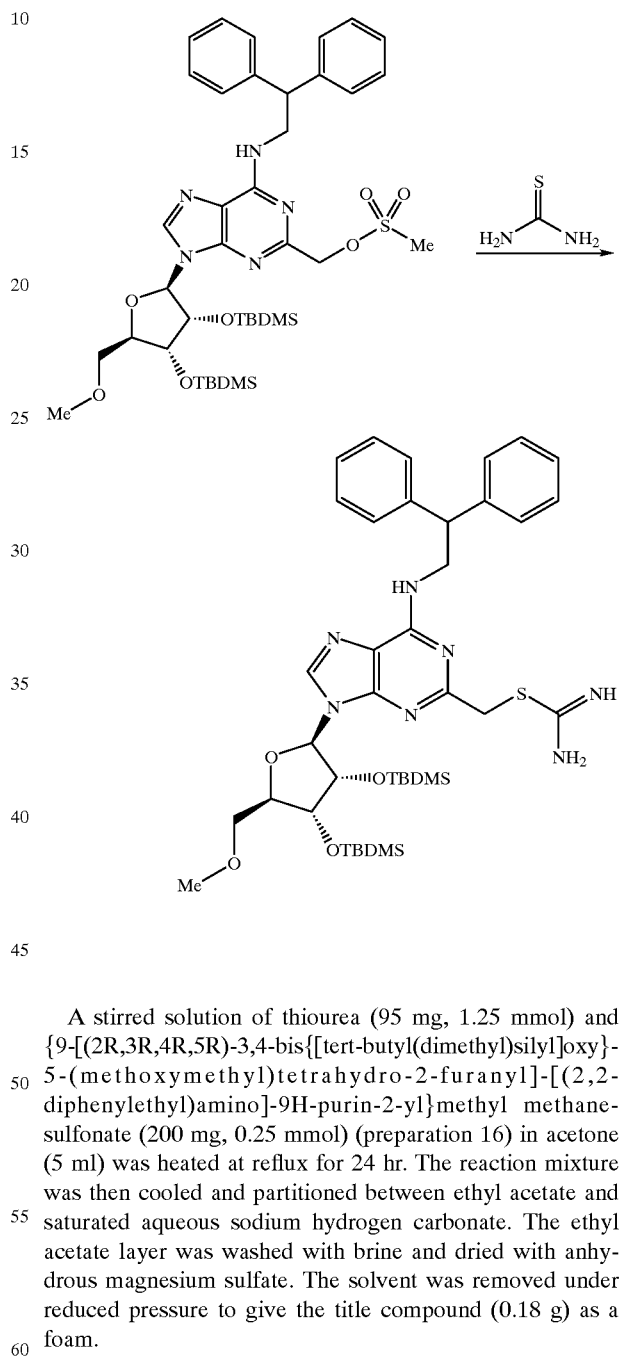

A stirred solution of thiourea (95 mg, 1.25 mmol) and {9-[(2R,3R,4R,5R)-3,4-bis{[tert-butyl(dimethyl)silyl]oxy}-5-(methoxymethyl)tetrahydro-2-furanyl]-[(2,2-diphenylethyl)amino]-9H-purin-2-yl}methyl methanesulfonate (200 mg, 0.25 mmol) (preparation 16) in acetone (5 ml) was heated at reflux for 24 hr. The reaction mixture was then cooled and partitioned between ethyl acetate and saturated aqueous sodium hydrogen carbonate. The ethyl acetate layer was washed with brine and dried with anhydrous magnesium sulfate. The solvent was removed under reduced pressure to give the title compound (0.18 g) as a foam.

$^1$H NMR (CDCl$_3$) δ=8.10 (1H, s), 7.30–7.20 (10H, m), 7.20–7.10 (2H, m), 5.85–5.80 (2H, m), 4.40–4.35 (1H, m), 4.35–4.30 (1H, m), 4.25–4.20 (1H, m), 4.20–4.00 (4H, m), 3.70–3.65 (1H, m), 3.55–3.50 (1H, m), 3.35 (3H, m), 0.85–0.75 (18H, m), 0.05 and −0.10 (12H, m).

Preparation 51

2-{9-[(2R,3R,4S,5R)-3,4-Dihydroxy-5-(methoxymethyl)tetrahydro-2-furanyl]-6-[(2,2-diphenylethyl)amino]-9H-purin-2-yl}acetic acid

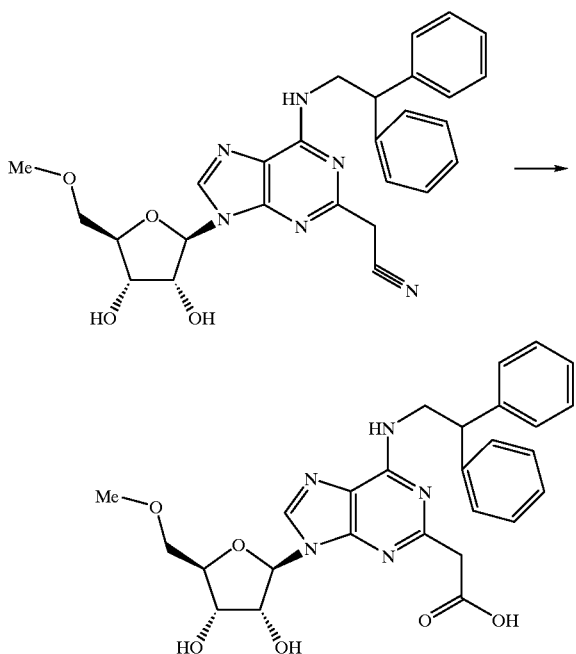

A stirred solution of 2-{9-[(2R,3R,4S,5R)-3,4-dihydroxy-5-(methoxymethyl)tetrahydro-2-furanyl]-6-[(2,2-diphenylethyl)amino]-9H-purin-2-yl}acetonitrile (preparation 30) (1.5 g, 3 mmol) in methanol (30 ml) and an aqueous 1 molar solution of sodium hydroxide (10 ml) was heated at reflux for 24 hr. The methanol was then removed under reduced pressure and the residual liquid diluted with more water and washed twice with ethyl acetate. The aqueous phase was acidified to pH<7 with a 1 molar aqueous citrc acid solution and then extracted twice with ethyl acetate. The extracts were combined, washed with brine and dried with anhydrous magnesium sulfate. The residue, after removal of the solvent under reduced pressure, was dissolved into diethyl ether and the solvent removed again twice under reduced pressure to give the title compound (1.25 g) as a foam. MS: 518 (M–H$^+$).

$^1$H NMR (CDCl$_3$) δ=8.00 (1H, s), 7.40–7.10 (10H, m), 6.20 (1H, br s), 5.95 (1H, s), 4.50–4.10 (6H, m), 3.90 (2H, m), 3.70–3.50 (2H, m), 3.30 (3H, s).

PHARMACOLOGICAL ACTIVITY

All the compounds prepared in the Examples section were tested for their ability to inhibit neutrophil function by the method described on pages 21 and 22 and they all demonstrated submicromolar IC$_{50}$ values in this assay.

What is claimed is:

1. A compound of formula (I):

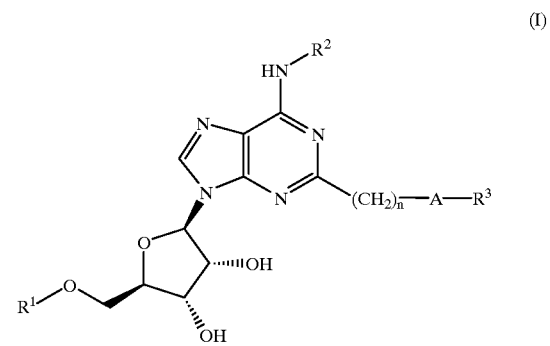

wherein

R$^1$ is alkyl or cyclopropylmethyl;

R$^2$ is phenyl-alkylene or naphthyl-alkylene, said alkylene chain being optionally further substituted by phenyl or naphthyl, each phenyl or naphthyl being optionally substituted by one or more substituents each independently selected from alkyl, alkoxy, halo and cyano;

n is 1 or 2;

A is NR$^a$, NR$^a$C(O), NR$^a$C(O)NR$^a$, NR$^a$C(O)O, OC(O)NR$^a$, C(O)NR$^a$, NR$^a$SO$_2$, SO$_2$NR$^a$, O, S or SO$_2$;

R$^a$ is H, alkyl or benzyl optionally ring-substituted by one or more substituents each independently selected from alkyl, alkoxy, halo and cyano;

R$^3$ is a group of the formula —(CH$_2$)$_p$—R$^p$—B;

p is 0, 1 or 2;

R$^p$ is a bond, alkylene, cycloalkylene, phenylene or naphthylene, said cycloalkylene, phenylene and naphthylene each being optionally substituted by one or more substituents each independently selected from alkyl, alkoxy, halo and alkoxyalkylene;

B is (i) H, —NR$^b$R$^b$, R$^b$R$^b$N-alkylene, —OR$^b$, —COOR$^b$, —OCOR$^b$, —SO$_2$R$^b$, —CN, —SO$_2$NR$^b$R$^b$, —NR$^b$COR$^b$, —NR$^b$SO$_2$R$^b$ or —CONR$^b$R$^b$, in which each R$^b$ is the same or different and is selected from H, alkyl, phenyl and benzyl, provided that, (a) when B is —OCOR$^b$, —SO$_2$R$^b$, —NR$^b$COR$^b$ or —NR$^b$SO$_2$R$^b$, then the terminal R$^b$ is not H, and, (b) R$^p$ is a bond, p is 0 and B is H only when A is NR$^a$, NR$^a$C(O)NR$^a$, OC(O)NR$^a$, C(O)NR$^a$, SO$_2$NR$^a$, O or S, (ii) an optionally-substituted, fully- or partially-saturated or -unsaturated, mono- or bicyclic, heterocyclic group, which is linked to R$^p$ by a ring carbon atom, or (iii) N-linked azetidinyl, pyrrolidinyl, piperidinyl, piperazinyl or morpholinyl, each optionally substituted by one or more alkyl substituents, with the proviso that —(CH$_2$)$_p$—R$^p$— is not —CH$_2$—; and where A is NR$^a$, C(O)NR$^a$, OC(O)NR$^a$ or SO$_2$NR$^a$, R$^a$ and R$^3$ taken together with the nitrogen atom to which they are attached can form an azetidine, pyrrolidine, piperidine or piperazine ring, optionally substituted by one or more alkyl substituents:

or a pharmaceutically acceptable salt or solvate thereof.

2. A compound as claimed in claim 1 wherein

R$^1$ is C$_1$–C$_6$ alkyl or cyclopropylmethyl;

R$^2$ is phenyl-(C$_1$–C$_6$)-alkylene or naphthyl-(C$_1$–C$_6$)-alkylene, said C$_1$–C$_6$ alkylene chain being optionally further substituted by phenyl or naphthyl, each phenyl or naphthyl being optionally substituted by one or more substituents each independently selected from $C_1$–$C_6$ alkyl, $C_1$–$C_6$ alkoxy, halo and cyano;

n is 1 or 2;

A is $NR^a$, $NR^aC(O)$, $NR^aC(O)NR^a$, $NR^aC(O)O$, $OC(O)NR^a$, $C(O)NR^a$, $NR^aSO_2$, $SO_2NR^a$, O, S or $SO_2$;

$R^a$ is H, $C_1$–$C_6$ alkyl or benzyl optionally ring-substituted by one or more substituents each independently selected from $C_1$–$C_6$ alkyl, $C_1$–$C_6$ alkoxy, halo and cyano;

$R^3$ is a group of the formula —$(CH_2)_p$—$R^p$—B;

p is 0, 1 or 2;

$R^p$ is a bond, $C_1$–$C_6$ alkylene, $C_3$–$C_7$ cycloalkylene, phenylene or naphthylene, said $C_3$–$C_7$ cycloalkylene, phenylene and naphthylene each being optionally substituted by one or more substituents each independently selected from $C_1$–$C_6$ alkyl, $C_1$–$C_6$ alkoxy, halo and $C_1$–$C_6$ alkoxy-$C_1$–$C_6$-alkylene;

B is
(i) H, —$NR^bR^b$, $R^bR^bN$—$(C_1$–$C_6)$-alkylene, —$OR^b$, —$COOR^b$, —$OCOR^b$, —$SO_2R^b$, —CN, —$SO_2NR^bR^b$, —$NR^bCOR^b$, —$NR^bSO_2R^b$ or —$CONR^bR^b$, in which each $R^b$ is the same or different and is selected from H, $C_1$–$C_6$ alkyl, phenyl and benzyl, provided that,
(a) when B is —$OCOR^b$, —$SO_2R^b$, —$NR^bCOR^b$ or —$NR^bSO_2R^b$, then the terminal $R^b$ is not H, and,
(b) $R^p$ is a bond, p is 0 and B is H only when A is $NR^a$, $NR^aC(O)NR^a$, $OC(O)NR^a$, $C(O)NR^a$, $SO_2NR^a$, O or S,
(ii) an optionally-substituted, fully- or partially-saturated or -unsaturated, mono- or bicyclic, heterocyclic group, which is linked to $R^p$ by a ring carbon atom, or
(iii) N-linked azetidinyl, pyrrolidinyl, piperidinyl, piperazinyl or morpholinyl, each optionally substituted by one or more $C_1$–$C_6$ alkyl substituents, with the proviso that —$(CH_2)_p$—$R^p$— is not —$CH_2$—; and where A is $NR^a$, $C(O)NR^a$, $OC(O)NR^a$ or $SO_2NR^a$, $R^a$ and $R^3$ taken together with the nitrogen atom to which they are attached can form an azetidine, pyrrolidine, piperidine or piperazine ring, each optionally substituted by one or more $C_1$–$C_6$ alkyl substituents.

3. A compound as claimed in claim 1 or 2 wherein in the definition of B, said optionally-substituted, fully- or partially-saturated or -unsaturated, mono- or bicyclic, heterocyclic group, which is linked to $R^p$ by a ring carbon atom, has from 4 to 12 ring atoms each independently selected from C, N, O and S.

4. A compound as claimed in claim 3 wherein in the definition of B, said optionally-substituted, fully- or partially-saturated or -unsaturated, mono- or bicyclic, heterocyclic group, which is linked to $R^p$ by a ring carbon atom, has from 4 to 10 ring atoms each independently selected from C, N, O and S.

5. A compound as claimed in claim 3 wherein in the definition of B, said optionally-substituted, fully- or partially-saturated or -unsaturated, mono- or bicyclic, heterocyclic group, which is linked to $R^p$ by a ring carbon atom, has ring atoms selected from 1 to 4 N atoms, 1 or 2 O and 1 or 2 S atoms, with the remaining ring atoms being C atoms.

6. A compound as claimed in claim 5 wherein in the definition of B, said optionally-substituted, fully- or partially-saturated or -unsaturated, mono- or bicyclic, heterocyclic group, which is linked to $R^p$ by a ring carbon atom, has from 1 to 4 ring N atoms, or 1 or 2 ring N atoms and 1 O or 1 S ring atom, or 1 O or 1 S ring atom, with the remaining ring atoms being C atoms.

7. A compound as claimed in any one of the preceding claims wherein said fully- or partially-saturated or -unsaturated, mono- or bicyclic, heterocyclic group, which is linked to $R^p$ by a ring carbon atom, is optionally substituted by one or more substituents each independently selected from $R^5$, —$OR^5$, halo, oxo, hydroxy, cyano, —$COR^5$, —COOH, —$COOR^5$, —$CONH_2$, —$CONHR^5$, —$CONR^5R^5$, amino, —$NHR^5$, —$NR^5R^5$, —$SO_2R^5$, —$SO_2NH_2$, —$SO_2NHR^5$, —$SO_2NR^5R^5$, —$NHCOR^5$, —$NR^5COR^5$, —$NHSO_2R^5$, —$NR^5SO_2R^5$ and pyridinyl,
wherein $R^5$ is $C_1$–$C_6$ alkyl, $C_3$–$C_7$ cycloalkyl, phenyl or naphthyl, each optionally substituted by $C_3$–$C_7$ cycloalkyl, $C_1$–$C_6$ alkoxy, halo, phenyl, naphthyl or benzylamino.

8. A compound as claimed in claim 1 wherein $R^1$ is $C_1$–$C_6$ alkyl.

9. A compound as claimed in claim 8 wherein $R^1$ is methyl.

10. A compound as claimed in claim 1 wherein $R^2$ is phenyl-$(C_1$–$C_6)$-alkylene, said $C_1$–$C_6$ alkylene chain being optionally further substituted by phenyl.

11. A compound as claimed in claim 10 wherein $R^2$ is 2-phenylethyl, said ethyl chain being optionally further substituted by phenyl.

12. A compound as claimed in claim 11 wherein $R^2$ is 2-phenylethyl or 2,2-diphenylethyl.

13. A compound as claimed in claim 12 wherein $R^2$ is 2,2-diphenylethyl.

14. A compound as claimed in claim 1 wherein A is $NR^a$, $NR^aC(O)$, $NR^aC(O)O$, $C(O)NR^a$, $NR^aSO_2$, $SO_2NR^a$, O, S or $SO_2$.

15. A compound as claimed in claim 14 wherein A is $NR^a$ or $NR^aSO_2$.

16. A compound as claimed in claim 1 wherein $R^a$ is H, $C_1$–$C_6$ alkyl or benzyl optionally ring-substituted by one or more $C_1$–$C_6$ alkoxy substituents.

17. A compound as claimed in claim 16 wherein $R^a$ is H, methyl, 2-methylprop-1-yl or methoxybenzyl.

18. A compound as claimed in claim 17 wherein $R^a$ is H, methyl, 2-methylprop-1-yl or 2-methoxybenzyl.

19. A compound as claimed in claim 1 or 2 wherein $R^3$ is H,
$C_1$–$C_6$ alkyl optionally substituted by $C_3$–$C_7$ cycloalkyl, $C_1$–$C_6$ alkoxy, amino, —NH($C_1$–$C_6$ alkyl), —N($C_1$–$C_6$ alkyl)$_2$, —$CONH_2$, —CONH($C_1$–$C_6$ alkyl), —CON($C_1$–$C_6$ alkyl)$_2$, phenyl (optionally substituted by halo, $C_1$–$C_6$ alkoxy, $C_1$–$C_6$ alkoxy-($C_1$–$C_6$)-alkylene, amino-($C_1$–$C_6$)-alkylene, cyano or piperidinyl (optionally substituted by $C_1$–$C_6$ alkyl, halo-($C_1$–$C_6$)-alkyl or halo-($C_1$–$C_6$)-alkanoyl)), piperidinyl or tetrahydropyranyl,
$C_3$–$C_7$ cycloalkyl optionally substituted by $C_1$–$C_6$ alkyl, $C_1$–$C_6$ alkoxy, benzylamino or $C_1$–$C_6$ alkanesulphonamido,
phenyl optionally substituted by halo, $C_1$–$C_6$ alkoxy, $C_1$–$C_6$ alkoxy-($C_1$–$C_6$)-alkylene, amino-($C_1$–$C_6$)-alkylene or piperidinyl (optionally substituted by $C_1$–$C_6$ alkyl, halo-($C_1$–$C_6$)-alkyl or halo-($C_1$–$C_6$)-alkanoyl), or azetidinyl, pyridinyl, piperidinyl, tetrahydrothiopyranyl or 1,2,3,4-tetrahydroisoquinolinyl, each optionally substituted by $C_1$–$C_6$ alkyl, benzhydryl, halo-($C_1$–$C_6$)-alkanoyl, oxo, hydroxy, cyano, $C_1$–$C_6$ alkoxycarbonyl, benzoyl or pyridinyl.

20. A compound as claimed in claim 19 wherein $R^3$ is H, methyl, n-propyl, i-propyl, 2-methylprop-1-yl, 2,2-dimethylprop-1-yl, n-butyl, t-butyl, pentan-3-yl, cyclopentyl, cyclohexyl, 4-(isopropyl)cyclohexyl, cyclopropylmethyl, cyclohexylmethyl, 2-methoxyethyl, 2-dimethylaminoethyl, 2-(N,N-dimethylcarbamoyl)ethyl, N,N-(diisopropyl)carbamoylmethyl, 2-(N-t- butylcarbamoyl)ethyl, phenyl, benzyl, 4-chlorobenzyl, 2-methoxybenzyl, 3,4-dimethoxybenzyl, 4-(isopropoxy)benzyl, 2-methoxymethylbenzyl, 4-aminomethylbenzyl, 4-cyanobenzyl, 4,4-dimethylcyclohexyl, 4-methoxycyclohexyl, 4-benzylaminocyclohexyl, 4-methanesulphonamidocyclohexyl, 2-piperidinoethyl, 4-(piperidin-4-yl)phenyl, 4-(1-trifluoroacetylpiperidin-4-yl)phenyl, 1-benzhydrylazetidin-3-yl, 2,6-dimethylpyridin-3-yl, 5-cyanopyridin-2-yl, 1-methylpiperidin-4-yl, 1-(isopropyl)piperidin-4-yl, 1-t-butoxycarbonylpiperidin-4-yl, 1-benzoylpiperidin-4-yl, 1-(2-pyridinyl)piperidin-4-yl, 1,1-dioxotetrahydrothiopyran-4-yl, tetrahydropyran-4-ylmethyl, 5-methyl-1,2,3,4-tetrahydroisoquinolin-8-yl or 5-methyl-2-trifluoroacetyl-1,2,3,4-tetrahydroisoquinolin-8-yl.

21. A compound as claimed in claim 20 wherein $R^3$ is phenyl, cyclohexyl, 5-methyl-1,2,3,4-tetrahydroisoquinolin-8-yl, 2-methylprop-1-yl, i-propyl, 2-methoxybenzyl or N,N-(diisopropyl)carbamoylmethyl.

22. A compound as claimed in claim 1 or 2 wherein —A—$R^3$ is amino, isopropylamino, pentan-3-ylamino, 2-methylprop-1-ylamino, di(2-methylprop-1-yl)amino, N-cyclohexyl-N-methylamino, 2-methoxyethylamino, 2-(N, N-dimethylcarbamoyl)ethylamino, N,N-(diisopropyl)carbamoylmethylamino, 2-(N-t-butylcarbamoyl)ethylamino, cyclopentylamino, cyclohexylamino, 4,4-dimethylcyclohexylamino, 4-(isopropyl)cyclohexylamino, 4-methoxycyclohexylamino, cis-4-methoxycyclohexylamino, trans-4-methoxycyclohexylamino, 4-benzylaminocyclohexylamino, trans-4-benzylaminocyclohexylamino, 4-methanesulphonamidocyclohexylamino, trans-4-methanesulphonamidocyclohexylamino, cyclopropylmethylamino, cyclohexylmethylamino, benzylamino, 4-chlorobenzylamino, 2-methoxybenzylamino, di(2-methoxybenzyl)amino, 4-(isopropoxy)benzylamino, 3,4-dimethoxybenzylamino, 2-methoxymethylbenzylamino, 4-aminomethylbenzylamino, 4-cyanobenzylamino, 1-benzhydrylazetidin-3-ylamino, 2,6-dimethylpyridin-3-ylamino, 5-cyanopyridin-2-ylamino, 1-methylpiperidin-4-ylamino, 1-(isopropyl)piperidin-4-ylamino, 1-(t-butoxycarbonyl)piperidin-4-ylamino, 1-benzoylpiperidin-4-ylamino, 1-(pyridin-2-yl)piperidin-4-ylamino, 2-piperidinoethylamino, 1,1-dioxotetrahydrothiopyran-4-ylamino, benzamido, phenylacetamido, t-butoxycarbonylamino, methanesulphonamido, n-propylsulphonylamido, i-propylsulphonylamido, n-butylsulphonamido, 2-methylprop-1-ylsulphonamido, 2,2-dimethylprop-1-ylsulphonamido, 2-methoxyethylsulphonamido, phenylsulphonylamido, benzylsulphonamido, 4-(piperidin-4-yl)phenylsulphonylamido, 4-(1-trifluoroacetylpiperidin-4-yl)phenylsulphonylamido, tetrahydropyran-4-ylmethylsulphonamido, 5-methyl-1,2,3,4-tetrahydroisoquinolin-8-ylsulphonylamido, 5-methyl-2-trifluoroacetyl-1,2,3,4-tetrahydroisoquinolin-8-ylsulphonylamido, benzylaminosulphonyl, 2-(N,N-dimethylamino)ethoxy, benzyloxy, 2-piperidinoethoxy, 1-methylpiperidin-4-yloxy, phenylthio, benzylthio or benzylsulphonyl, or is 4-isopropylpiperidinocarbonyl.

23. A compound as claimed in claim 22 wherein —A—$R^3$ is phenylsulphonamido, cyclohexylamino, 5-methyl-1,2,3,4-tetrahydroisoquinolin-8-ylsulphonylamido, 2-methylprop-1-ylamino, i-propylamino, 2-methoxybenzylamino, N,N-(diisopropyl)carbamoylmethylamino or 2-methylprop-1-ylsulphonamido.

24. A pharmaceutical composition including a compound of the formula (I) or a pharmaceutically acceptable salt or solvate thereof, as claimed in claim 1, together with a pharmaceutically acceptable excipient, diluent or carrier.

25. A method of treatment of a mammal, including a human being, to treat a disease for which a A2a receptor agonist is indicated including treating said mammal with an effective amount of a compound of the formula (I) or with a pharmaceutically acceptable salt, solvate or composition thereof, as claimed in claim 1.

26. A compound of the formula

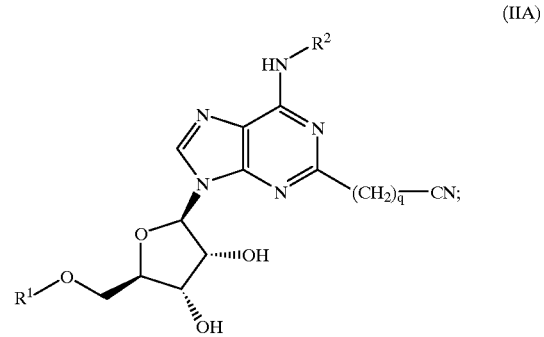

(IIA)

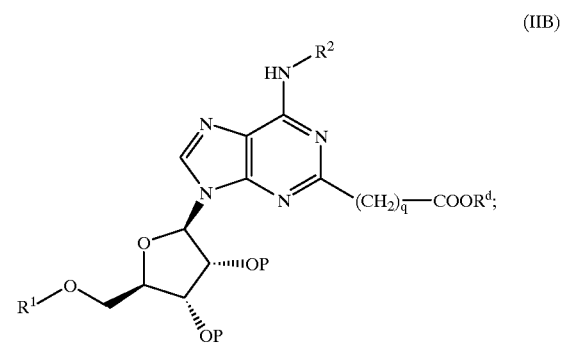

(IIB)

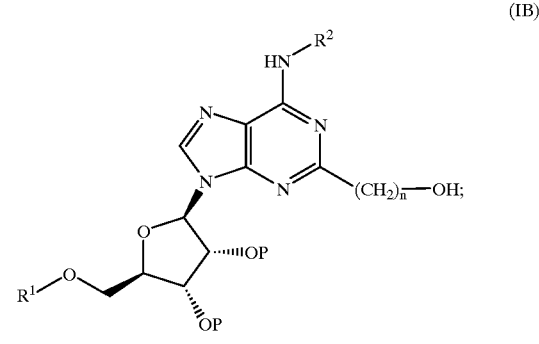

(IB)

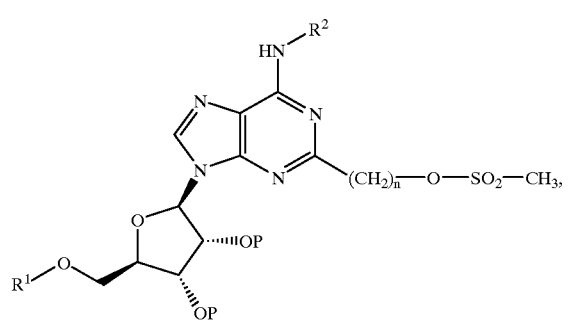

(XII)

or a deprotected form thereof, that is where P is replaced by H; or

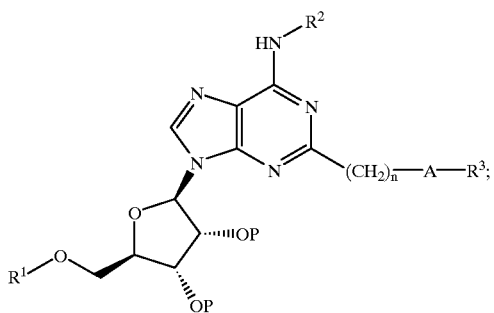

(XIII)

wherein q is n-1, $R^d$ is H or alkyl (preferably $C_1$–$C_6$ alkyl), P is a protecting group, and $R^1$, $R^2$, $R^3$ A and n are as defined in claim 1.

27. A process for the preparation of a compound of the formula (I) as claimed in claim 1, or a pharmaceutically acceptable salt or solvate thereof, which comprises (a) for a compound of the formula (I) wherein $R^1$, $R^2$, $R^3$, A and n are as defined in claim 1, deprotection of a compound of the formula

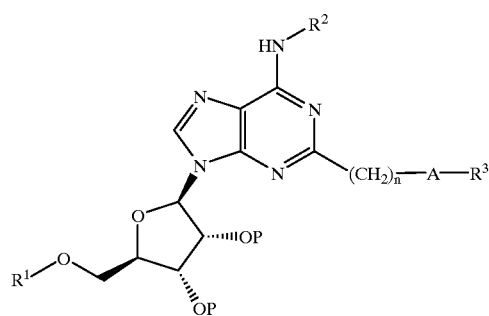

(XIII)

wherein P is a protecting group and $R^1$, $R^2$, $R^3$, A and n are as defined in claim 1;

(b) for a compound of the formula (I) wherein A is A is $NR^a$, $NR^aC(O)$, $NR^aC(O)NR^a$, $NR^aC(O)O$ or $NR^aSO_2$ and $R^a$, $R^1$, $R^2$, $R^3$ and n are as defined in claim 1, functional group interconversion of a compound of the formula

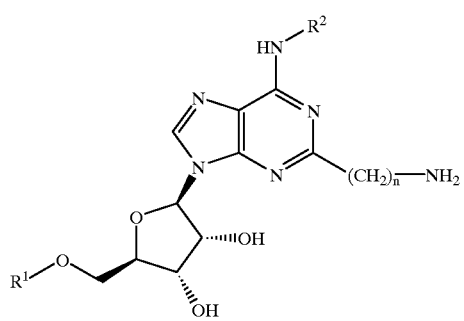

(IA)

wherein $R^1$, $R^2$ and n are as defined in claim 1, using an appropriate reagent such as an acylating, sulphonylating or alkylating agent, or a dicarbonate derivative, or by reductive amination;

(c) for a compound of the formula (I) wherein A is $NR^aSO_2$, $NR^a$, O or S and $R^a$, $R^1$, $R^2$, $R^3$ and n are as defined in claim 1, functional group interconversion of a compound of the formula (XII - Deprotected)

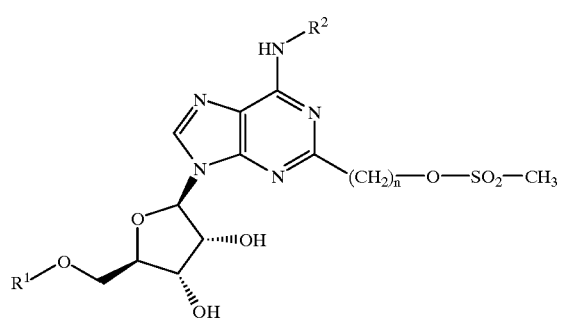

wherein $R^1$, $R^2$ and n are as defined in claim 1, using an appropriate reagent such as an alkoxide, thioalkoxide, thiol, sulphonamide derivative or amine: any one of said processes being optionally followed by conversion of the compound of the formula (I) to a pharmaceutically acceptable salt thereof.

28. A compound as claimed in claim 1 wherein $R^1$ is alkyl or cyclopropylmethyl;

$R^2$ is phenyl-alkylene or naphthyl-alkylene where the alkylene chain may be substituted with methyl, ethyl, phenyl or naphthyl;

n is 1 or 2; and

A is $NR^a$, $NR^aC(O)$, $NR^aC(O)NR^a$, $NR^aC(O)O$, $OC(O)NR^a$, $C(O)NR^a$, $NR^aSO_2$, $SO_2NR^a$, O, S or $SO_2$, in which $R^a$ is H or alkyl;

$R^3$ is a group of the formula —$(CH_2)_p$—$R^p$—B, wherein p is 0, 1 or 2;

$R^p$ is a bond, or is alkylene, optionally alkyl-substituted cycloalkylene, phenylene or naphthylene; and B is (i) H, —$NR^bR^b$, —$OR^b$, —$COOR^b$, —$OCOR^b$, —$SO_2R^b$, —CN, —$SO_2NR^bR^b$, —$NR^bCOR^b$ or —$CONR^bR^b$, in which each $R^b$ is the same or different and is selected from H and alkyl, provided that, (a) when B is —$SO_2R^b$ or —$NR^bCOR^b$, then the terminal $R^b$ is other than H, and, (b) $R^p$ is a bond, p is 0 and B is H only when A is $NR^a$, $NR^aC(O)NR^a$, $C(O)NR^a$, $SO_2NR^a$, O or S, or (ii) B is an optionally-substituted, fully or partially saturated or unsaturated mono- or bicyclic heterocyclic group, each of which is linked through a ring carbon atom;

or a pharmaceutically acceptable salt or solvate thereof.

* * * * *